(12) United States Patent
Kozhemyakin et al.

(10) Patent No.: US 6,368,788 B1
(45) Date of Patent: Apr. 9, 2002

(54) METHOD OF TREATING COMPLICATIONS IN IMMUNODEPRESSED STATES RESULTING FROM HIV INFECTION

(75) Inventors: Andrei L. Kozhemyakin; Nickolai V. Sinackevich; Sergey V. Seryi; Alexei M. Rakhilov; Vyacheslav G. Morozov; Vladimir Kh. Khavinson, all of St. Petersburg (RU)

(73) Assignee: Cytran, Inc., Kirkland, WA (US)

( * ) Notice: Subject to any disclaimer, the term of this patent is extended or adjusted under 35 U.S.C. 154(b) by 0 days.

(21) Appl. No.: 08/977,279

(22) Filed: Nov. 24, 1997

Related U.S. Application Data

(63) Continuation of application No. 08/452,411, filed on May 26, 1995, now Pat. No. 5,728,680, which is a continuation-in-part of application No. 08/278,463, filed on Jul. 21, 1994, now abandoned, which is a continuation-in-part of application No. 08/257,495, filed on Jun. 7, 1994, now abandoned, which is a continuation of application No. 07/783,518, filed on Oct. 28, 1991, now abandoned, which is a continuation-in-part of application No. 07/678,129, filed on Apr. 1, 1991, now abandoned.

(30) Foreign Application Priority Data

Dec. 30, 1987 (SU) .............................................. 4352833

(51) Int. Cl.[7] .......................... C12Q 1/70; G01N 33/53; A61K 38/00
(52) U.S. Cl. .............................. 435/5; 435/7.24; 514/9; 514/11; 514/19
(58) Field of Search ...................... 435/5, 7.24; 514/19, 514/9, 11

(56) References Cited

U.S. PATENT DOCUMENTS

| | | |
|---|---|---|
| 3,679,787 A | 7/1972 | Bergy et al. ................. 514/19 |
| 4,002,602 A | 1/1977 | Goldstein |
| 4,010,148 A | 3/1977 | Goldstein |
| 4,077,949 A | 3/1978 | Goldstein |
| 4,079,127 A | 3/1978 | Goldstein et al. |
| 4,116,951 A | 9/1978 | Wang |
| 4,120,951 A | 10/1978 | Goldstein |
| 4,133,804 A | 1/1979 | Bach et al. |
| 4,148,788 A | 4/1979 | Wang |
| 4,167,557 A | 9/1979 | Goldstein |
| 4,261,886 A | 4/1981 | Goldstein et al. |
| 4,264,571 A | 4/1981 | Goldstein et al. |
| 4,297,276 A | 10/1981 | Goldstein et al. |
| 4,339,427 A | 7/1982 | Goldstein et al. |
| 4,353,821 A | 10/1982 | Birr et al. |
| 4,374,828 A | 2/1983 | Folkers et al. |
| 4,377,511 A | 3/1983 | Lopukhin et al. |
| 4,388,234 A | 6/1983 | Horecker |

(List continued on next page.)

FOREIGN PATENT DOCUMENTS

| | | |
|---|---|---|
| CH | 659586 | 2/1982 |
| DE | 3421789 | 12/1988 |

(List continued on next page.)

OTHER PUBLICATIONS

Aliev et al. (1990) "Simulation of Thymus Dysfunction in Guinea Pigs by Using Immunomodulators" *Izv. Akad. Nauk. Az. SSR, Ser. Biol. Nauk.*, 1:73–80 (Chemical Abstracts 116(17), Abstract No. 171986U).

(List continued on next page.)

*Primary Examiner*—Hankyel Park
(74) *Attorney, Agent, or Firm*—Townsend and Townsend and Crew LLP

(57) ABSTRACT

Methods of treatment of subjects for decreasing cell mediated autoimmunity or humoral autoimmunity by administering an R'-Glu-Trp-R" pharmaceutical preparation useful in subjects having autoimmune diseases.

14 Claims, 8 Drawing Sheets

U.S. PATENT DOCUMENTS

| | | | |
|---|---|---|---|
| 4,389,343 A | 6/1983 | Horecker | |
| 4,395,404 A | 7/1983 | Low et al. | |
| 4,396,605 A | 8/1983 | Birr | |
| 4,426,324 A | 1/1984 | Meienhofer | |
| 4,427,783 A | 1/1984 | Newman et al. | |
| 4,428,938 A | 1/1984 | Kisfaludy et al. | |
| 4,442,031 A | 4/1984 | Felix et al. | 514/19 |
| 4,466,918 A | 8/1984 | Birr et al. | 514/19 |
| 4,470,926 A | 9/1984 | Birr et al. | 514/19 |
| 4,500,450 A | 2/1985 | Seipke et al. | 514/19 |
| 4,504,415 A | 3/1985 | Felix et al. | 514/19 |
| 4,505,853 A | 3/1985 | Goldstein et al. | 514/19 |
| 4,517,119 A | 5/1985 | Felix et al. | 514/19 |
| 4,526,717 A | 7/1985 | Seipke et al. | 514/19 |
| 4,571,336 A | 2/1986 | Houck et al. | 514/19 |
| 4,579,840 A | 4/1986 | Hahn | 514/19 |
| 4,599,231 A | 7/1986 | Milich et al. | 514/19 |
| 4,612,365 A | 9/1986 | Birr et al. | 514/19 |
| 4,614,731 A | 9/1986 | Horecker | 514/19 |
| 4,621,135 A | 11/1986 | Trainin et al. | 514/19 |
| 4,634,682 A | 1/1987 | Erickson et al. | 514/19 |
| 4,659,694 A | 4/1987 | Horecker | 514/19 |
| 4,696,915 A | 9/1987 | Horecker | 514/19 |
| 4,699,898 A | 10/1987 | Gottlieb | 514/19 |
| 4,711,952 A | 12/1987 | Kasafirek et al. | 514/19 |
| 4,722,999 A | 2/1988 | Handschumacher et al. | 514/19 |
| 4,751,216 A | 6/1988 | Gottlieb | 514/19 |
| 4,752,602 A | 6/1988 | Lipsky et al. | 514/19 |
| 4,814,434 A | 3/1989 | Goldfarb | 514/19 |
| 4,826,680 A | 5/1989 | Jaeger | 514/19 |
| 4,904,643 A | 2/1990 | Brunetti et al. | 514/19 |
| 4,910,296 A | 3/1990 | Birr et al. | 514/19 |
| 4,946,945 A | 8/1990 | Wojdani | 514/19 |
| 4,983,387 A | 1/1991 | Goldstein et al. | 514/19 |
| 5,070,076 A | 12/1991 | Morozov et al. | 514/19 |
| 5,143,903 A | 9/1992 | Polita et al. | 514/19 |
| 5,538,951 A * | 7/1996 | Morozov et al. | 514/19 |
| 5,569,585 A * | 10/1996 | Goodwin et al. | 435/6 |
| 5,728,680 A | 3/1998 | Morozov et al. | 514/19 |

FOREIGN PATENT DOCUMENTS

| | | | |
|---|---|---|---|
| EP | 0 164 654 | | 4/1985 |
| FR | 2583982 | | 2/1988 |
| RU | 8906134 | * | 7/1989 |
| SU | 989772 | | 9/1982 |
| SU | 1045456 | | 6/1983 |
| SU | 1090348 | | 1/1984 |
| SU | 1103392 | | 3/1984 |
| SU | 1105202 | | 4/1984 |
| SU | 1112606 | | 5/1984 |
| SU | 1156652 | | 1/1985 |
| SU | 1169655 | | 4/1985 |
| SU | 1187824 | | 7/1985 |
| SU | 1193585 | | 7/1985 |
| SU | 1197643 | | 8/1985 |
| SU | 1197674 | | 8/1985 |
| SU | 1235029 | | 2/1986 |
| SU | 1261665 | | 6/1986 |
| SU | 1298979 | | 11/1986 |
| SU | 1349041 | | 7/1987 |
| SU | 1383548 | | 11/1987 |
| SU | 1398863 | | 2/1988 |
| SU | 1417242 | | 4/1988 |
| SU | 1438044 | | 7/1988 |
| SU | 1470290 | | 12/1988 |
| SU | 1473142 | | 12/1988 |
| SU | 1522485 | | 7/1989 |
| SU | 1522486 | | 7/1989 |
| SU | 1522925 | | 7/1989 |
| SU | 1218521 | | 2/1993 |
| SU | 1436305 | | 2/1993 |
| SU | 1441928 | | 2/1993 |
| SU | 944191 | | 3/1993 |
| SU | 1417244 | | 3/1993 |
| SU | 1448443 | | 3/1993 |
| SU | 1077089 | | 4/1993 |
| SU | 1158201 | | 4/1993 |
| SU | 1227198 | | 4/1993 |
| WO | SU88/00255 | | 12/1988 |
| WO | WO 89/06134 | | 7/1989 |
| WO | WO 90/06945 | | 6/1990 |
| WO | WO 92/17191 | | 10/1992 |
| WO | WO 93/08815 | | 5/1993 |
| WO | WO 94/20063 | | 9/1994 |
| WO | WO 95/03067 | | 2/1995 |
| WO | WO 97/12625 | | 4/1997 |

OTHER PUBLICATIONS

Anisimov et al. (1982) *Mechanisms of Ageing and Development*, 19:245–258.

Anisimov et al. (1989) *Mechanisms of Ageing and Development*, 49:245–257.

Belokrylov et al. (1978) *Bulletin of Experimental Biology*, No. 7, 84:56–58.

Belokrylov et al. (1977) *Bulletin of Experimental Biology*, No. 7, 86:51–53.

Bespaluv et al. (1989) *Eksp. Onkol.*, Chemical Abstracts III, Abstract No. 146389R, 11(4) 23–6 (Russ).

Cytomedins (Bulletin), Apr. 13, 1990, Russia.

Demidov et al. (1991) "Effects of Thymus Preparations and Antituberculous Drugs on Immunological Reactivity and the Course of Tuberculous Process in Experimental Animals", *Probl. Tuberk.*, 12:52–54 (Chemical Abstracts 116(17), Abstract No. 165824Y).

Gavrilenko et al. (1982) *Bulletin of Experimental Biology*, No. 4, 93:39–40.

Goldstein et al. (1972) *Proc. Natl. Acad. Sci. USA*, 69:1800–1803.

Grigoriants et al. (1991) "Immunocorrection in the Combined Treatment of Patients with Osteomyelitis Developing Following Combined Injuries to the Maxillofacial and Craniocerebral Areas", *Stomatologiia (Mosk)*, 5:53–54 (Medline Abstract No. 92188368).

Iakovlev et al. (1991) "The Biochemical And Immunological Indices in the Rehabilitation Period of the Victims of the Accident on The Komsomolets Atomic Submarine", *Voen. Med. ZH*, 9:28–33 (Medline Abstract No. 92101433).

Khmel'nitskii et al. (1991) "Morphofunctional Charateristics of the Immunocompetent System in Hypotrophy and Its Correction By Thymogen", *Arkh. Patol.* 53:24–27 (Medline Abstract No. 92171772).

Khmel'nitskii et al. (1983), *Bulletin of Experimental Biology*, No. 6, 95:123– 124.

Kuznik et al. (1982), *Bulletin of Experimental Biology*, No. 9, 94:27–29.

Kusnik et al. (1981) *Bulletin of Experimental Biology*, No. 9, 92:264–266.

Low et al. (1981) *Proceedings of the National Academy of Science*, 78:1162– 1166.

Rodionov et al., (1991) "Natural Killer Activity in Patients with Chronic Dermatoses", *Vestn. Dermatol. Venerol.* 5:4–6, (Biological Abstract vol. 92, Abstract No. 100385).

Rodionov et al. (1990) "The Immunocorrective Therapy of Pyoderma Caused by Staphylococci Multiply Resistant to Antibiotics", *Vestn. Dermatol. Venerol*, 1:42–45 (Medline Abstract No. 90224329).

Solov'ev et al. (1977) *Bulletin of Experimental Biology*, No. 9, 84:355–358.

Solov'ev et al. (1983) *Bulletin of Experimental Biology*, No. 6, 95:123–124.

"Thymogen" (Bulletin), Nov. 11, 1989, published by Cytomed (Leningrad).

Werner, G. H. et al. (1986) "Immunomodulating peptides," *Experientia*, 42:521– 531.

Yakovlev et al., (1990) *Resistance Stress Regulation*, Nauka Publishers (Leningrad), pp. 90–93, 174–205.

Two brochures in Russian (no English translation).

Aliev, M.G. et al., "Simulation of thymus disfunction in guinea pigs by using immunomodulators" *Chem. Abstracts* 116:664 Abstract No. 171986u (1992).

*ASM News* 56:368 (1990).

Belokrylov, G. et al., "Ability of some amino acids incorporated into protein to stimulate the thymus–dependent immune response" *Eksp. Biol. Medit.* 102:51–53 (1986).

Bespalov, V.G. et al., "Inhibiting effect of thymogen, a synthetic analog of thymalin, on the development of esophagus and forestomach tumors induced by N– nitrososarcosine ethyl ester in rats" *Chem. Abstracts* 111:23 Abstract No. 146389r (1989).

Declaration of John S. Sundsmo (Aug. 23, 1995) with Exhibits.

Gee, N.S. and Kenny, A.J., "Proteins of the kidney microvillar membranes" *Biochem. J.* 246:97–102 (1987).

Jaroff, L. "Stop that Germ!" *Time*, pp. 56–64 (May 23, 1988).

Pettit, G.R., in: Synthetic Peptides, vol. 3, Academic Press, NY, pp. 130, 134, 143, 424, 427, 429, and 434 (1975).

Remington's Pharmaceutical Sciences, Mack Publishing Co., Easton, PA, pp. 996– 997, 1465–1469, 1553–1557 (1980).

Sandström, E.G. and Kaplan, J.C., "Antiviral therapy in AIDS: Clinical pharmacological properties and therapeutic experience to date" *Drugs* 34:372–390 (1987).

Sievertsson, H. et al., "Synthesis of Di– the tripeptides and assay in Vivo for activity in the thyrotrol releasing hormone and the luteinizing releasing hormone systems" *J. Med. Chem.* 15(1):8–11 (1971).

Rodionov et al, Vest N. Dermoatol. Venerol, 1:42–43, 1990.*

Stites & Terr, Basic & Clinical Immunology, Prentice Hall, Norwalk, 1991, p. 272–281.*

Brostoff et al, Clinical Immunol. Growen Med. Pub., London, 1991, p. 30.10.*

Van der Zeijst et Al, J. Exp. Med, 1978, 147:1253–1266.*

Ivanov et al., "Clinical Case: Diagnosis and Treatment of HIV–Infection," *Medical Military Journal*, 2:1990, p. 49, 1990.

Fox, J. L., No winners against AIDS, Bio/Tech, vol. 12, p. 128, see entire page, Feb. 1994.*

* cited by examiner

METHOD OF TREATING COMPLICATIONS IN IMMUNODEPRESSED STATES RESULTING FROM HIV INFECTION

Continuing data as claimed by applicant: This application is a CON of 08/452,411 May 26, 1995 U.S. Pat 5,728,680 which is a CIP of 08/278,463 Jul. 21, 1994 ABN which is a CIP of 08/257,495 Jun. 7, 1994 ABN which is a CON of 07/783,518 Oct. 28, 1991 ABN which is a CIP of 07/678,129 Apr. 1, 1991 ABN.

FEDERALLY SPONSORED RESEARCH OR DEVELOPMENT

Not applicable

FIELD OF THE INVENTION

The present invention relates generally to pharmaceutical compositions containing peptides having immunomodulating properties and more particularly to pharmaceutical compositions of tryptophan-containing dipeptides and methods of use thereof.

BACKGROUND OF THE INVENTION

The lymphoid system performs critical functions in animals and man that include preventing and combating infection, and surveillance and immune elimination of tumor cells. Loss of immune function leads to an immunocompromised status that can predispose the host to serious and life-threatening disease. Functional abnormalities may be present in any of the elements that participate in mediating an immune response, e.g., cellular or humoral elements such as granulocytes, lymphocytes, complement, antibody, or cytokines.

Immune deficiency may result from many different etiologies including hereditary genetic abnormalities (e.g., Chediak-Higashi Syndrome, Severe Combined Immunodeficiency, Chronic Granulomatous Disease, DiGeorge Syndrome) exposure to radiation, chemotherapy, heavy metals or insecticides; or, acquired as a result of bacterial, viral, parasitic or fungal infection.

The immune system is normally regulated by cellular and soluble elements and loss of regulatory control may result in autoimmune disease, e.g., multiple sclerosis, rheumatoid arthritis, systemic lupus erythematosus, Sjogren's syndrome, and insulin-dependent type I diabetes. Conventional immunosuppressive drugs that are used to treat autoimmune diseases have generalized and non-specific effects on the immune system that can predispose infection and increase the risk of malignancy. Methods to compensate for decreased innate resistance to infection following radiation or chemotherapy are therefore of great therapeutic value.

Thymus tissue extracts affecting proliferation and/or differentiation of T-lymphocytes have been reported, including, e.g., "thymosine" (1), "thymaline (2), "T-activine" (3), "thymosin-$\alpha_1$ (4), "thymosin fraction 5" (a heat-stable fraction isolated from calf thymus extracts), and others. Commonly tissue extracts exist as complex mixtures that include polypeptides, e.g., several peptides have been isolated from Thymosin fraction 5, such as Thymosin alpha, (28 amino acids, U.S. Pat. No. 4,079,127), Thymosin beta$_4$ (44 amino acids, Low, et al., PNAS, 28,1162–1166 (1981)), Thymosin bet$_8$ (39 amino acids, U.S. Pat. No. 4,389,343) and Thymosin beta9(41 amino acids, U.S. Pat. No 4,389,343). Thymosin-$\alpha_1$ fragments and dimers have also been described in U.S. Pat. Nos. 4,396,605; 4,470,926; 4,612, 365; and 4,910,296.

Widespread use of purified tissue extract fractions in medical practice has been hindered by variability of preparations, low yields, lack of highly purified and characterized reproducible sources, and problems associated with preparing complex mixtures having standardized biological potency. In addition, complexity and variability of tissue extracts potentially affect stability, toxicity, and safety. Alternatively, synthesis of large biologically active polypeptides is at present difficult and expensive particularly under manufacturing conditions required for pharmaceutical preparations.

Alternatively, synthesis of large biologically active polypeptides is at present difficult and expensive, particularly under the manufacturing conditions required for pharmaceutical preparations.

T-lymphocytes participate in cellular and humoral immune responses triggered by binding of foreign molecules to lymphocyte cell surface receptors. The erythrocyte rosette receptor defined by the CD2 cell functions as both an intercellular adhesion molecule and a cell surface signal transduction molecule. CD2 reportedly binds PHA and is involved in PHA-mediated lymphocyte blastogenesis. Binding of anti-CD2 antibodies to the CD2 receptor is also reportedly able to trigger T-lymphocyte blastogenesis and this pathway of activation may be independent of the CD3/T-cell receptor complex. T-cell CD2 binding to LFA-3/CD58 may mediate intercellular adhesive binding of T-lymphocytes to B-lymphocytes and thymic epithelial cells. CD2 binding to CD59 and CD48 ligands may facilitate intercellular binding to other cell types. Lymphocyte cell surface CD4 and CD8 molecules define MHC class specificity of T-helper, T-suppressor and cytotoxic T-lymphocytes. (Paul, W. E. Ed. 1993. "Fundamental Immunology, 3rd. Edition", Raven Press, N.Y. pp.541–5.)

SUMMARY OF THE INVENTION

Methods have been discovered for treating immunocompromised subjects to increase one or more indicia of cell mediated immunity (CMI), humoral immunity, or innate resistance to infection, by administering pharmaceutical preparations of R'-Glu-Trp-R". The results of in vitro studies showed that L-Glu-L-Trp dipeptide increased expression of accessory molecules on the surface of thymocytes and mature T-lymphocytes as evidenced by i) increased E-rosette forming cells (E-RFC) in thymocyte cultures after incubation with dipeptide; ii) increased E-RFC in cultures of thymocytes from aged animals after incubation with dipeptide; and, iii) increased expression of OKT 4$^+$ in cultures of human peripheral blood T-lymphocytes from patients with secondary immunodeficiency syndromes following incubation with L-Glu-L-Trp. L-Glu-L-Trp dipeptide did not measurably upregulated CD8 expression on lymphocytes. Increased expression of CD2 and CD4 accessory molecules on T-lymphocytes is compatible with a heighten the state of innate or induced immunity to infection, e.g., by upregulating T-helper and cytotoxic T-lymphocytes to respond to lower levels of antigen. To test this hypothesis, in vivo studies were conducted in which the immunological effects of L-Glu-L-Trp dipeptide were tested in experimental animal models. L-Glu-L-Trp treatments mobilized and altered tissue distribution of lymphocytes in experimental animals, activated monocytes and increased phagocytic activity of granulocytes. Animal model studies in mice showed that treatments with L-Glu-L-Trp decreased incidence of mortality from acute bacterial infection with *E. coli, Pseudomonas aeruginosa,* and staphylococci. In irradiated guinea pigs and 5-fluorouracil (5-FU) immunosuppressed mice, L-Glu-L-Trp treatments increased the number of lymphocytes and T-lymphocytes in peripheral blood. When injected locally, L-Glu-L-Trp increased the activation state of resident tissue macrophages (as measured by NBT reduction); and, promoted neutrophil infiltration into the tissue in response to a sterile inflammatory mediator (proteose peptone). L-Glu-L-Trp treatments increased in vitro expression of CD4 (but not CD8) on lymphocytes isolated from patients with secondary immunodeficiency syndromes. Clinical studies showed increased indicia of CMI, humoral immunity or innate immunity in the following patients treated with L-Glu-L-Trp pharmaceutical preparations: namely, patients with acute and chronic infections including respiratory infections, pleuritis, pelvic inflammatory diseases, infections of leprosy, tuberculosis, staphylococcal pyoderma, Dengue fever, chronic viral hepatitis, Shigella dysentery, malaria, influenza, and tuberculosis. L-Glu-L-Trp treatments also i) alleviated certain clinical symptoms in patients with autoimmune disease and allergy; ii) decreased complication rates and increased lymphocyte counts in cancer patients following radiation therapy; iii) increased lymphocyte counts in individuals exposed to accidental environmental radiation and surgical thymectomy; and, iii) increased lymphocyte counts in patients with secondary immunodeficiency. L-Glu-L-Trp showed efficacy in both prophylactic and therapeutic protocols. L-Glu-L-Trp treatments also proved useful for alleviating certain symptoms of systemic toxicity in patients with acute bacterial, viral, and parasitic infections.

HIV-infected patients are one group of immunocompromised subjects that may benefit from treatments with R'-Glu-Trp-R", however, it is understood that such treatments are not intended as a cure for AIDS or ARC, but rather for possible use in treating complications of HIV-infection, e.g., opportunistic bacterial and viral infections.

Embodiments of the invention provide methods of treatment using R'-Glu-Trp-R" pharmaceutical preparations to induce a heightened state of cell mediated immunity, humoral immunity, or innate resistance to infection.

BRIEF DESCRIPTION OF THE FIGURES

FIG. 1 graphically depicts the results of studies in experimental animals designed to test an L-Glu-L-Trp prophylactic regimen for treating an acute gram negative bacterial infection, as described in EXAMPLE 32. L-Glu-L-Trp was administered intraperitoneally (ip) on a daily basis from day −3 to day +1 at dosages that spanned 5-logs of concentration (i.e., 0.01 µg/kg to 100 µg/kg). The bacterial challenge was administered on day 0. For combination treatments with antibiotics, the same five daily ip doses of L-Glu-L-Trp were administered along with five daily ip doses of the indicated antibiotics.

FIG. 2 graphically depicts the results of studies parallel to those described above in regard to "FIG. 1", but using *Pseudomonas aeruginosa* as the gram negative bacterial pathogen instead of *E. coli,* i.e., as described in EXAMPLE 33.

FIG. 3 graphically depicts the results of studies parallel to those described above in regard to "FIG. 1", but using staphylococci as a gram positive bacterial pathogen instead of *E. coli,* i.e., as described in EXAMPLE 34, below.

DETAILED DESCRIPTION OF THE INVENTION

Introduction

Figure 1A:
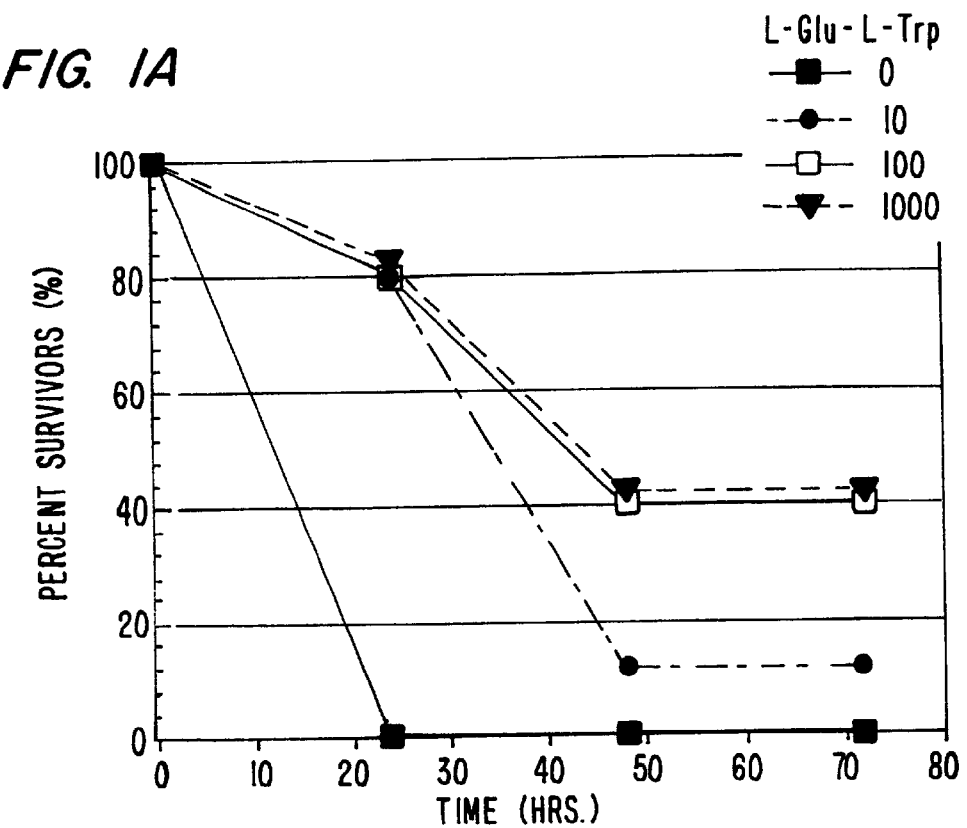
FIG. 1A graphically depicts the results of the prophylactic L-Glu-L-Trp treatment, i.e., expressed as the percentage of mice surviving (%) a peritoneal infection at 24, 48, or 72 hours after injection of an $LD_{100}$ dose of *E. coli*. Mice in the experimental group received the L-Glu-L-Trp treatment, while those in the control group did not.
Figure 1B:
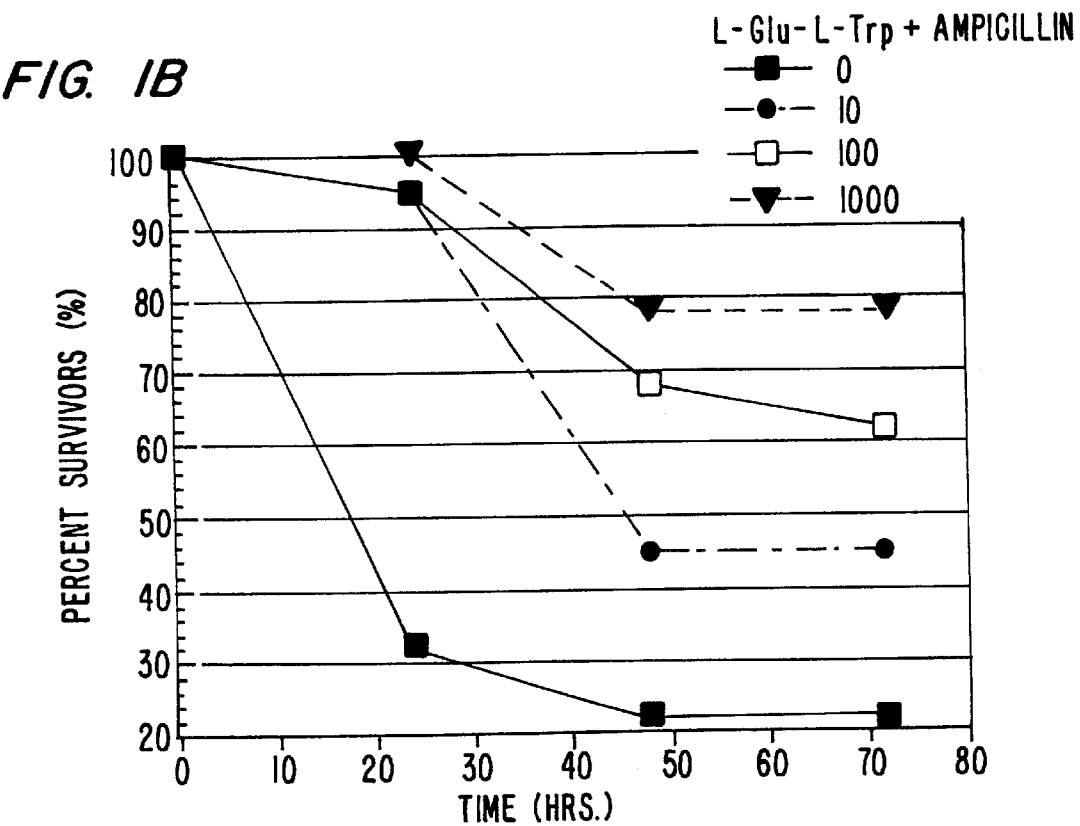
FIG. 1B graphically depicts the results of the prophylactic combination L-Glu-L-Trp and antibiotic treatment, i.e., expressed as the percentage mice surviving (%) an ip $LD_{100}$ challenge of *E. coli* at 24, 48, or 72 hours. Mice in the experimental group received the prophylactic course of combination therapy with L-Glu-L-Trp and ampicillin; mice in the control group were untreated; and, mice in the antibiotic control group were treated with only ampicillin (amp).
Figure 1C:
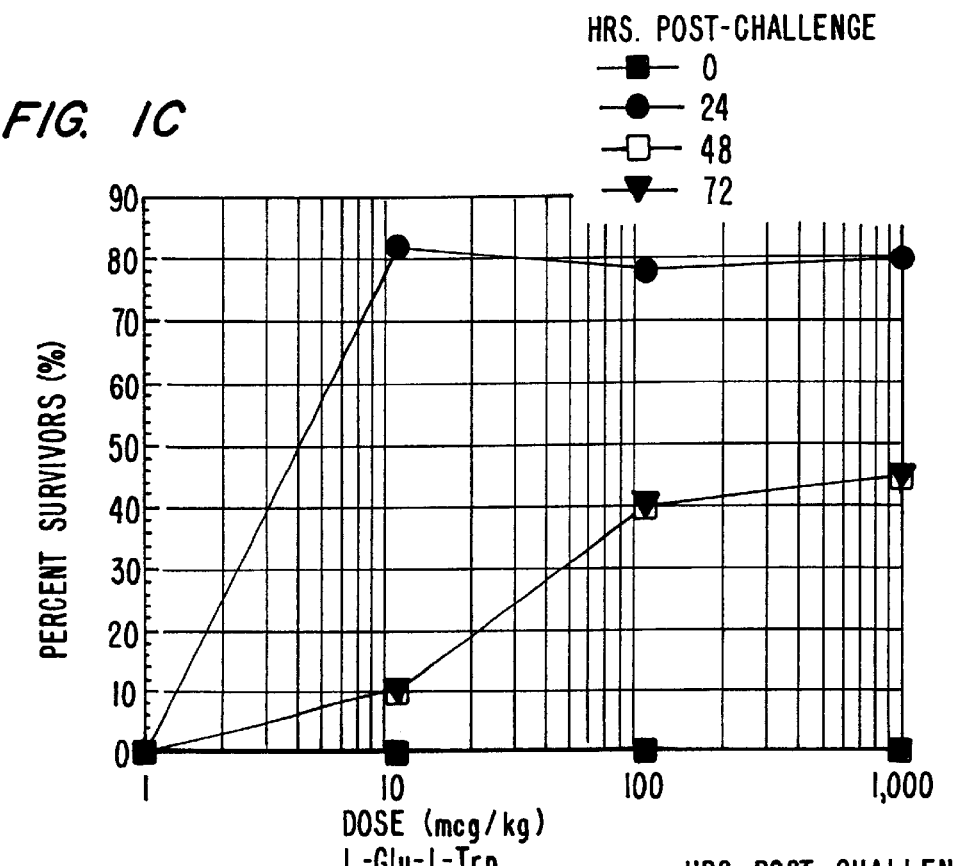
FIG. 1C graphically depicts the data presented in FIG. 1A, but plotted in a dose-response type fashion.
Figure 1D:
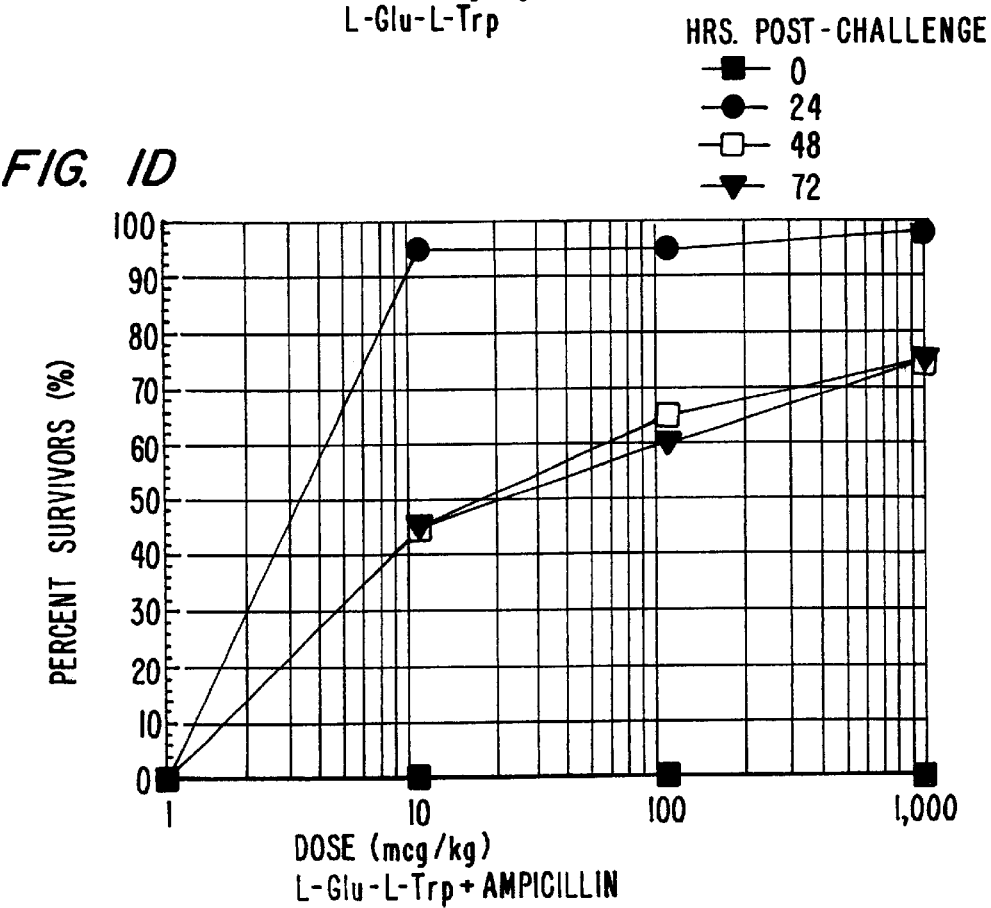
FIG. 1D graphically depicts the data presented in FIG. 1B, but plotted in a dose-response type fashion.
Figure 2A:
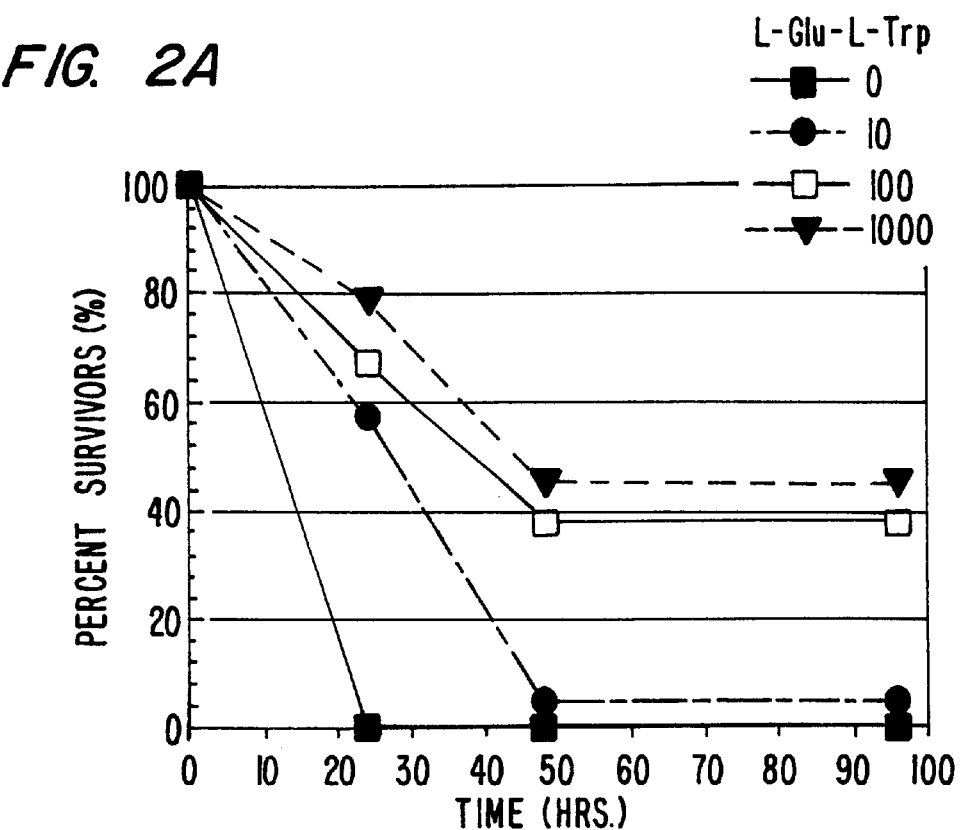
FIG. 2A graphically depicts the results of studies parallel to those described in regard to FIG. 1A, above, but using *Pseudomonas aeruginosa.* Mice in the experimental group received a prophylactic course of L-Glu-L-Trp treatment, while those in the control group did not.
Figure 2B:
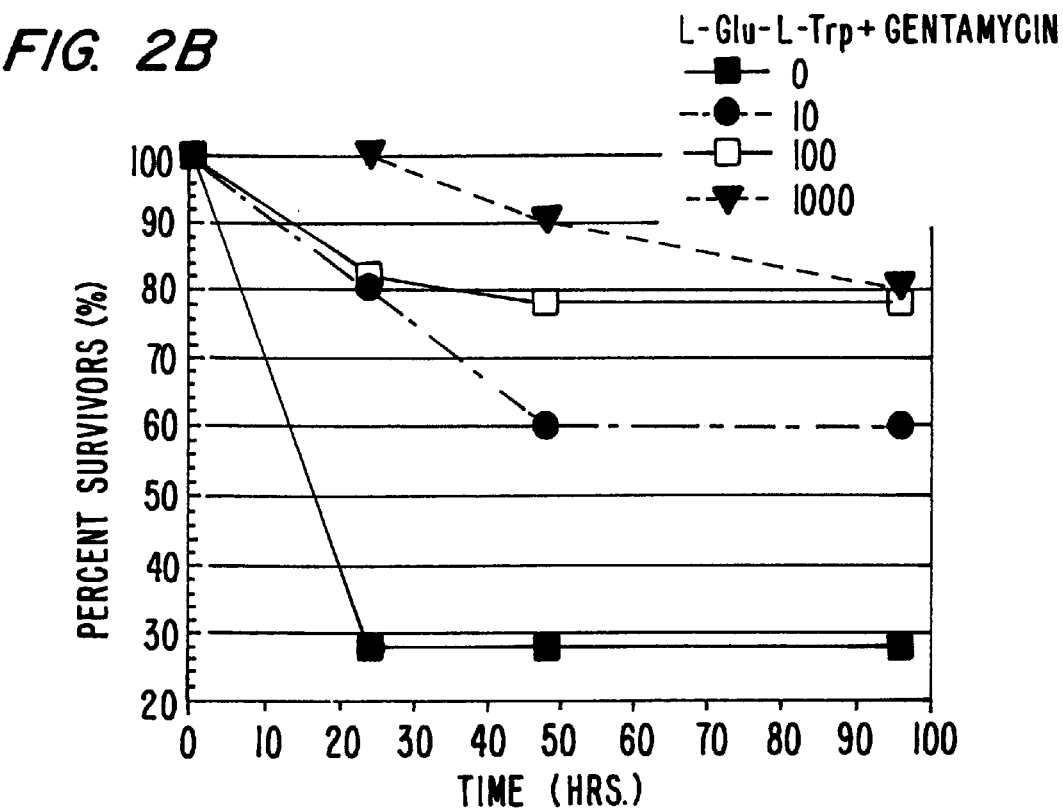
FIG. 2B graphically depicts the results of studies parallel to those described in regard to FIG. 1B, above, but using Pseudomonas aeruginosa. Mice in the experimental group received a prophylactic course of combination therapy using L-Glu-L-Trp and gentamicin; mice in the control group were untreated; and, mice in the antibiotic control group were treated with only Gentamycin (gen).
Figure 2C:
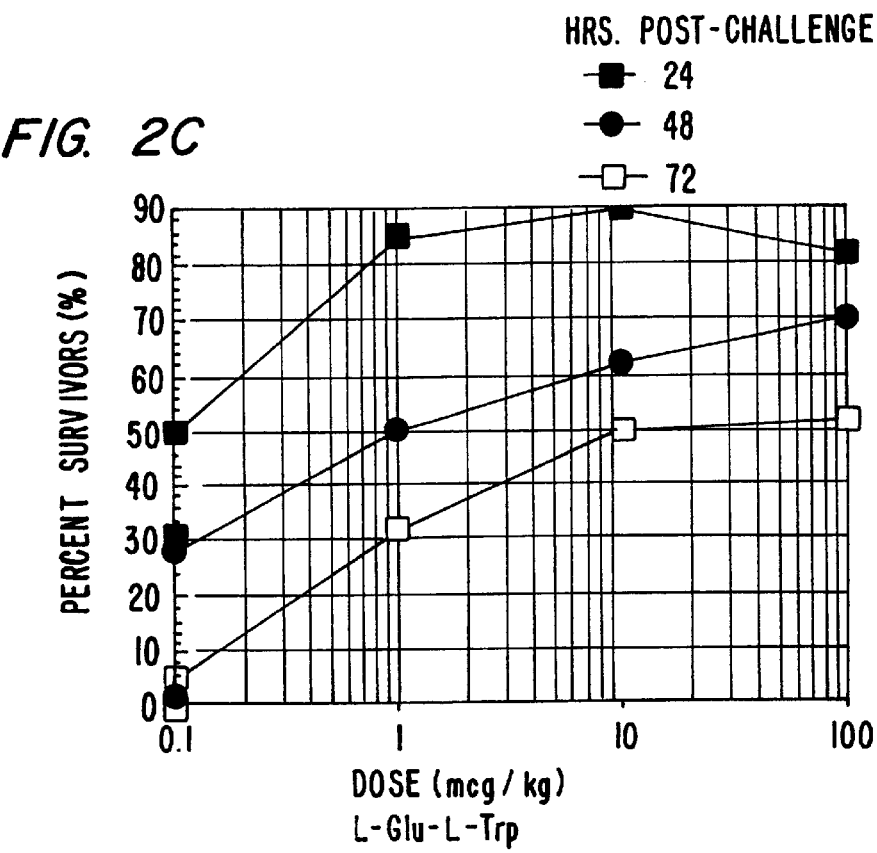
FIG. 2C graphically depicts the data presented in FIG. 2A plotted in a dose-response type fashion.
Figure 2D:
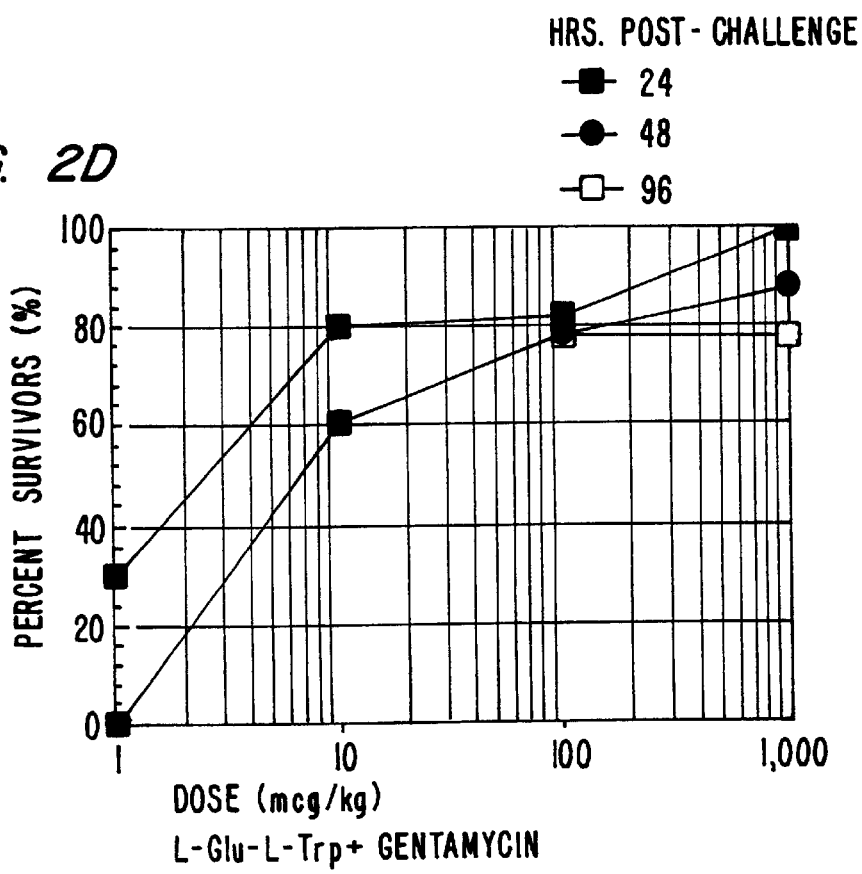
FIG. 2D graphically depicts the data presented in FIG. 2B plotted in a dose-response type fashion.

Thymalin was disclosed in U.S. Pat. No. 5,070,076 (Morozov, V. G. and V. K. Khavinson, 1991) as a mixture of polypeptides 80–90% of which have molecular sizes in the range of 600 to 6000 daltons and isoelectric points in the range of 3.5–6.7. The total mixture of polypeptides reportedly had a composition (mole % amino acid) as follows: Asp (5.8), Thr (5.7), Ser (5.7), Glu (6.2), Pro (10.1), Gly (8.6), Ala (10.7), Cys (3.4), Val (8.8), Met (trace), Ile (3.9), Leu (6.7), Tyr (2.4), Phe (3.2), His (2.9), and Lys (7.0). Isolation and purification led to eventual identification of several biologically active peptides including one peptide having a Glu-Trp sequence. Synthetic L-Glu-L-Trp peptides were discovered to exhibit biological activities in vitro and in certain animal model systems. The Pharmacologic Committee of the U.S.S.R. approved therapeutic use of L-Glu-L-Trp synthetic peptides on Jun. 19, 1990. In considering possible prior "use" and "art" issues it is valuable to consider the following noteworthy dates in opening-up of the former Soviet Socialist Republics: namely, Boris Yeltsin was elected President of the Russian Republic in June of 1991; on Aug. 24, 1991 Gorbachev resigned as General Secretary of the Communist Party and dissolved the Central Committee; and the last meeting of the Congress of Peoples Deputies took place in September of 1991 (David Remnick, "Lenins Tomb", Vintage Books, Random House, Inc., N.Y. 1994).

The results of studies disclosed in the Examples below show that L-Glu-L-Trp upregulates CD2 expression on T-lymphocytes in vitro and in vivo. Other studies show immunological effects of L-Glu-L-Trp on lymphocytes, mononuclear phagocytes, neutrophils, and on immunologic mediator pathways underlying expression of inflammation, allergy, endotoxic shock and cellular and humoral immunity.

As used herein the symbols for amino acids are according to the IUPAC-UB recommendations published in *Arch. Biochem. Biophys.* 115: 1–12, (1966) with the following single letter symbols for the amino acids:

| L, Leucine | V, Valine | Y, Tyrosine | D, Aspartic Acid |
|---|---|---|---|
| I, Isoleucine | P, Proline | W, Tryptophan | E, Glutamic Acid |
| M, Methionine | G, Glycine | N, Asparagine | K, Lysine |
| T, Threonine | A, Alanine | Q, Glutamine | R, Arginine |
| F, Phenylalanine | S, Serine | C, Cysteine | H, Histidine |

The symbols for protective groups used in peptide synthesis are described in Schrödex and Lübke, "The Peptides", Academic Press, N.Y. 1965, e.g., Boc for t-butyloxycarbonyl and Bzl for benzyl. Other abbreviations used are e.g., HPLC for high pressure liquid chromatography; TFA for trifluoroacetic acid; $K_D$ for dissociation constant; $K_a$ for association constant; $K_{eq}$ for equilibrium constant; f.a. for fatty acid; E for erythrocyte; E-RFC for E-rosette forming cell; EA for erythrocyte antibody; EAC for erytirocyte antibody complement; APC for antigen presenting cell; PHA for phytohemagglutinin; Con-A for Concanavalin-A; LPS for lipopolysaccharide; IL for interleukin; CSF for colony stimulating factor; IFN for interferon; CTL for cytotoxic T-lymphocyte; NK-cell for natural killer cell; BM for bone marrow; PBL for peripheral blood leukocyte; LN for lymph node; KLH for keyhole limpet hemocyanin; ELISA for enzyme linked immunosorbent assay; FIA for fluorescence immunoassay; TRF for time resolved florescence assay; RIA for radioimmunoassay; AST for hepatic alanyl-seryl transaminase enzyme; ALT for alanyl-leucyl transaminase; ATIII for antithrombin III; PTT for prothrombin time; FDP for fibrin degradation products; ARVI for acute respiratory viral infection; ip for intraperitoneal; im for intramuscular; sc for subcutaneous; id for intradermal; iv for intravenous; po for peros, i.e., oral; and, in for intranasal.

The present invention provides for a "Glu-Trp pharmaceutical preparation" comprising an R'-Glu-Trp-R" dipeptide, (e.g., L-Glu-L-Trp), or a cyclic form thereof according to Formula I, or a derivative or analogue thereof according to Formula II, or a multimeric form thereof according to Formula III, the latter including linear and branched multimers, cyclic forms, and cyclic polymers thereof. R'-Glu-Trp-R" is also referred to interchangeably as "EW", or "EW dipeptide", using the normal convention wherein the first named amino acid is the amino terminus and the last named amino acid is the carboxyl terminus. For convenience, all forms will be collectively referred to herein interchangeably as "the dipeptide", "EW dipeptide", "R'-Glu-Trp-R"", of which L-Glu-L-Trp is a representative and most preferred dipeptide.

Definitions

The following terms are intended to have meanings as follows: namely,

"Polypeptide" is intended to mean a serial array of amino acids of more than 16 and up to many hundreds of amino acids in length, e.g., a protein.

"CD2" is intended to mean the lymphocyte cell surface accessory molecule that is the homo- and heterotypic receptor that mediates binding of heterologous erythrocytes (e.g., rabbit or sheep erythrocytes) to lymphocytes to form E-rosettes (as disclosed in Paul, W. E. Ed. "Fundamental Immunology, 3rd. Edition, Raven Press, N.Y. at page 562 ; incorporated herein by reference). Lymphocytes having cell surface CD2, when capable of forming rosettes with rabbit erythrocytes are referred to herein as E-rosette forming cells, abbreviated E-RFC.

"$CD4^+$ lymphocyte" is intended to mean a lymphocyte having a plurality of cell surface CD4 molecules as evidenced by binding of an antibody specific for CD4 to the cell surface, e.g., monoclonal antibody OKT4 (Ortho Diagnostics, Piscataway, N.J.).

"$CD8^+$ lymphocyte" is intended to mean a lymphocyte having a plurality of cell surface CD8 molecules as evidenced by binding of an antibody specific for CD8 to the cell surface, e.g., monoclonal antibody OKT8 (Ortho Diagnostics, Piscataway, N.J.).

"Reticuloendothelial system" is intended to mean immune tissues containing macrophages, lymphocytes, reticular cells, mast cells, basophils, eosinophils, neutrophils, and the like. Representative components of the reticuloendothelial system include lymph nodes, spleen, thymus, bone marrow, lung, liver, epithelial tissues, lymphatic vessels, blood, and the like.

"Peripheral blood leukocytes", abbreviated PBL, are intended to mean the cellular components of the immune system in blood, e.g., lymphocytes, monocytes, eosinophils, basophils, neutrophils, plasma cells, mast cell precursors, and the like.

"Immune cell" is intended to encompass the cell types of the reticuloendothelial system, e.g., lymphocytes, mononuclear phagocytes, neutrophils, basophils, eosinophils, mast cells, plasma cells, reticular cells in the spleen, Langerhans cells and δγ-T cell receptor-bearing lymphocytes in the epithelia, Kupfer cells in the liver, and the like.

"Lymphocytes" are intended to encompass T-lymphocytes, (also referred to as T-cells), B-lymphocytes (also referred to as B-cells), natural killer-lymphocytes (NK-cells), cytotoxic T lymphocytes (CTL), T-helper lymphocytes, δγ-T-cell receptor bearing cells as well as precursors and activated derivatives thereof.

"Activated lymphocyte" is intended to mean that subset of lymphocytes which has been i) exposed to a stimulus, and ii) has been triggered to change from a metabolically-quiescent cell into a cell with increased protein synthesis and/or DNA and RNA synthesis and possibly cell division. Illustrative stimuli and triggering pathways leading to activated lymphocytes include interaction of T cell receptors with antigens, interaction of interleukin receptors with interleukins, interaction of growth factor receptors with growth factors, interaction of lymphocyte cell surface determinants with antibody (e.g., anti-CD2) or mitogens (e.g., PHA), and the like.

"Mononuclear phagocytes" are intended to mean cells of the monocyte/macrophage lineage including e.g., monocytes, macrophages, dendritic cells, reticular cells, Langerhans cells, and the like.

"Activated macrophage" is intended to mean a mononuclear phagocyte having an increased capacity for phagocytosis and intracellular killing of a microbe. Activated macrophages may be recognized, for example, by testing for phagocytic activity, biochemical markers (e.g., 5'-nucleotidase), or increased oxidative metabolism (e.g., increased ability to reduce nitrotetrazolium blue dye, NBT), and the like.

"Interleukin" is intended to mean an agent released by a first immune cell that affects a biological activity in a second immune cell. Representative interleukins include cytokines such as tumor necrosis factors (e.g., TNFα and TNFβ), IL-1, IL-2 (also known as T cell growth factor), IL-3, IL-4, IL-5, IL-6, IFN-γ and the like.

"Growth factor" is intended to mean an agent capable of stimulating an increase in cell number in a population of immune cells. Representative growth factors include granulocyte colony stimulating factor (G-CSF), macrophage colony stimulating factor (M-CSF), granulocyte/macrophage colony stimulating factor (GM-CSF), stem cell factor (SCF), and the like. Interleukins that have growth stimulatory activity are included as a subcategory within this usage, (e.g., IL-2, IL-3, IL-6 and the like), as are compounds having a mitogenic effect on immune cells (e.g., PHA, Con-A, LPS, and the like).

"Anti-microbial cellular and humoral immunity" is intended to mean that immunity which ameliorates, makes better, makes normal, or eliminates one or more clinical or laboratory indicia of disease produced by a microbe.

"Microbe" is intended to mean an agent that when multiplying in a subject causes a disease. Representative microbes include viruses, bacteria, mycoplasma, mycobacteria, parasites, rickettsia, dengue fever agent, prion disease agent, kuru kuru disease agent, and the like. Illustrative examples of genus and species of microbes in which the subject methods of the invention find uses include: gram positive bacteria (e.g., Staphylococcus, Streptococcus, Actinomyces, and the like), gram negative bacteria (e.g., Enterobacteriaceae, Bacillus, and the like), acid fast bacteria (e.g., *Mycobacterium tuberculosis, Mycobacterium intracellulare, Mycobacterium leprae, Mycobacterium avium, Mycobacterium bovis, Mycobacterium kansasii, Mycobacterium paratuberculosis*), and the like.

Representative examples of clinical indicia of disease include (but are not limited to) diagnostic manifestations such as redness and swelling, fever, malaise, lethargy, septicemia, pyogenic exudates, and the like. Representative diagnostic manifestations of disease have been classified and codified (International Classification of Diseases, ICD-9-CM, Washington, D.C. 1989).

Representative laboratory indicia of disease include (but are not limited to) "abnormal values" in measurements of i) neutrophil or lymphocyte counts in peripheral blood, ii) hematocrit, iii) serum alpha globulins or immunoglobulins, iv) expression of one or more cell surface accessory molecules on an immune cell, for example, molecules indicating a maturation state or activation state of either a T-lymphocyte (e.g., CD2, CD3, CD4, CD28, and the like) or a B-lymphocyte (e.g., B220, surface Ig, expression of rearrangement-recombinase activating genes in Rag 1 and Rag 2, and the like) or a mononuclear phagocyte (e.g., Ia/Mac-I expression, 5'-nucleotidase activity and the like), v) synthesis of one or more interleukins (e.g., IL-2, IL-1, TNF, TGF-β, IFN-γ, and the like), vi) synthesis of antibody specific for the subject microbe (e.g., using a diagnostic immunoassay format), vii) phagocytic activity in an in vitro assay with mononuclear phagocytes or neutrophils from the subject, and viii) splenic mass (e.g., as determined by CAT scan or sonography).

"Abnormal" as used herein refers to immune parameters of values that are outside of the range of values recorded in healthy individuals.

"Normalized" as used herein refers to changes in laboratory or clinical values that are, following treatment, returned to within the normal range of values recorded for normal healthy subjects.

"Cellular immunity" to a subject microbe is intended to mean that immunity which is conferred upon a host by immune cells and which, in an experimental animal model system, may be transferred from one animal to another using immune cells that are free of serum, and are free of B-lymphocytes and/or plasma cells producing an immunoglobulin specifically reactive with the subject microbe.

"Humoral immunity" to a subject microbe is intended to mean that immunity which is conferred upon a host by antibody and which, in an experimental animal model system, may be transferred from one animal to another using immune serum that contains antibody that is free of cells, or alternatively, may be transferred by B-lymphocytes and/or plasma cells that are producing antibody specifically reactive with the subject microbe.

"Innate resistance to infection" is used to mean that immunity which is preexistent in a host before exposure to a microbe such as e.g., that which is conferred by Langerhans cells and T-lymphocytes bearing γδ$^+$-T cell receptor molecules in epithelial tissues, or immune cells in biological fluids. In the context of the present disclosure the term is intended to encompass anti-microbial activities of neutrophils, monocytes, platelets, macrophages, dendritic cells, and Langerhans cells, and not the activities of serum proteins such as coagulation factors, complement, lysozyme and the like.

As used herein, the term "compromised host" is used interchangeably with "compromised subject" to refer to a patient who is at an increased risk of infectious complications because of a deficiency in any of his (or her) defense mechanisms, (e.g., skin barrier, mucous membrane barrier, innate immunity, humoral immunity, or cellular immunity). When her (or his) defect specifically involves elements of the immune response, they are termed herein "immunocompromised hosts" or "immunocompromised subjects". A subject without an immune defect and without a known deficiency in any defense mechanism is referred to herein interchangeably as "a normal healthy subject", an "immunocompetent host", or and "immunocompetent subject".

As used herein, the terms "modulator" and "modulating" mean the agent and process of altering a normal or compromised subject's resistance to infection, e.g., by increasing the flow of mucous, promoting wound healing of epithelial barriers and the like.

As used herein the terms "immunomodulator" and "immunomodulating" mean the agent and process of altering a normal or immunocompromised subject's immune system, as evidenced by a change in one or more laboratory measurements from a pre-treatment value to a post-treatment value and/or a change in the subject's ability to combat an infectious disease, and to heal tissue. Hence, immunomodulation as used herein means altering one or more cellular and/or humoral immune indices (clinical or laboratory) from a baseline pretreatment value to a different value. In one embodiment immunomodulation results in stimulation of cellular and/or humoral immunity in an immunodeficient subject, e.g., a subject exposed to accidental radiation, or treated with chemotherapy, radiation therapy, or thymectomy. In another embodiment immunomodulation results in depression of cellular and/or humoral immunity in a subject with a regulatory abnormality in the immune system, e.g., a subject with an autoimmune disease. The present invention encompasses both therapeutic methods of treating the immunodeficient, immunodepressed, or autoimmune states per se, as well as prophylactic therapies designed to stimulate cellular and/or humoral immunity to infectious agents and disease, as well as a treatment of infections, diseases or wounds, indirectly by enhancing the immune system. This includes enhancing or restoring the subject's immune system, as evidenced by measurable blood parameters and/or the patient's improved ability to combat infection or disease, and the ability to heal tissue. The infections may be caused by a variety of microbes, e.g., viruses, bacteria, mycobacteria, fungus, parasites and the like. Hence, immunomodulation encompasses improvement of the immune system due to an immunodeficient state (e.g., caused by removal of the thymus, exposure to radiation, or acquired during infection with a microbe). Furthermore, the present invention provides methods for modulating the immune system by lowering blood parameters and other indicia of an autoimmune state if these indicia are abnormally elevated. The present invention encompasses both prophylactic and therapeutic regimens.

"Subject in need thereof" is intended to mean a mammal having one or more clinical or laboratory indicia of a disease. The subject may exhibit clinical disease activity or may have a subclinical or latent infection. Subjects in need thereof include human and non-human primates, domestic animals, livestock, and the like, e.g., dogs, cats, rodents, birds, horses, cows, pigs and fish.

"'R'-Glu-Trp-R"' treatment" is intended to mean a method of delivering to a subject in need thereof a pharmaceutical preparation of R'-Glu-Trp-R", (or derivatives, multimers, analogues, cyclic forms and the like of Formulas I-E), with the aim of ameliorating, making better/making normal, one or more clinical or laboratory indicia of disease in the subject. The subject methods include delivering the preparation to a patient i) before the disease has been diagnosed, e.g., prophylactic protocols delivered with the aim of preventing development of the disease, as well as, ii) after the disease has been diagnosed, e.g., therapeutic protocols. That the subject treatments have fulfilled the intended aim of treating or preventing the microbial infection in the subject will be evident by a change (increase or decrease) or complete elimination of one or more clinical or laboratory indicia of disease as set forth above. Representative illness, diseases, and conditions have been classified and codified ("International Classification of Diseases; ICD-9-CM, Washington D.C., 1989). The methods of the invention find use in treatment of a variety of disease conditions where it is advantageous to stimulate an immune response. For example, embodiments of the invention find use in treating infections, e.g., for stimulating immunity against the microbe. Representative infections treatable by the methods of the invention include those caused by the following microbes: namely, Mycobacteria genus, gram negative bacteria (e.g., *E. coli*), gram positive bacteria (e.g., Staphylococci), Pseudomonas genus, Hemophilus genus, Mycoplasma genus, Pneumocystis genus, influenza, rhinovirus, HIV, and the like. Furthermore, the subject compositions may be used to aid healing of burns, wounds, open sores, sun exposure, local trauma, eczema, psoriasis, and the like. Other illustrative uses include healing bone fractures, lesions, periodontal and gingival diseases, obstetric and gynecologic diseases of the uterus and pregnancy, lymphatic infections and the like.

In one preferred embodiment an R'-Glu-Trp-R" pharmaceutical preparation is administered to an immunocompromised patient in an amount and for a time sufficient to increase, one or more indicia of either cell mediated immunity, humoral immunity, or innate resistance to infection, thereby effecting improvement in the clinical condition of the patient so treated. In an alternative preferred embodiment, an R'-Glu-Trp-R" pharmaceutical preparation is administered to a patient having an autoimmune disease in an amount and for a time sufficient to decrease, one or more indicia of either cell mediated immunity, humoral immunity, or innate resistance to infection, thereby effecting improvement in the clinical condition of the patient so treated.

The subject indicia of cell mediated immunity preferably include one or more measures of the number or percentage of immune cells in circulating peripheral blood of the subject, i.e., leukocytes, lymphocytes, monocytes, T-lymphocytes, B-lymphocytes, stem cells, $CD2^+$-lymphocytes, $CD4^+$-lymphocytes, $CD8^+$-lymphocytes, $CD19^+$-lymphocytes, plasma cells, neutrophils, stab neutrophils, segmented neutrophils, basophils, eosinophils, platelets, erythrocytes, and the like.

In the illustrative Examples, the R'-Glu-Trp-R" pharmaceutical preparations were administered in clinical tests according to the methods of the invention in an amount and for a time sufficient to increase the number of: human peripheral blood leukocytes by about 1.1-fold to about 1.6-fold (e.g., EXAMPLES 4, 6, and 19), lymphocytes of by about 1.1-fold to about 2.4-fold (e.g., EXAMPLES 3, 4, 6–7, 16, and 19), CD2+-lymphocytes by about 1.1-fold to about 2.6-fold (e.g., EXAMPLE 2), CD4'-lymphocytes by about 1.1 -fold to about 6.4-fold (e.g., EXAMPLES 2–4 and 16), CD8'-lymphocytes by about 1.1-fold to about 2.5-fold (e.g., EXAMPLES 3, 6, and 16), surface immunoglobulin positive B-lymphocytes by about 1.1-fold to about 1.6-fold (e.g., EXAMPLES 2–4, 6, 7, 16, 17 and 19), E-rosette forming T-lymphocytes by about 1.1 -fold to about 1.8-fold (e.g., EXAMPLES 4, 6, 9, 16, 19, 23 and 25), and the number of neutrophils by about 1.1-fold to about 1.4-fold (e.g., EXAMPLES 4 and 6).

In other illustrative Examples, the R'-Glu-Trp-R" pharmaceutical preparations were administered in clinical tests according to the methods of the invention in an amount and for a time sufficient to increase the ratio of the percentages of CD4+lymphocytes/CD8+ lymphocytes by about 1.1-fold to about 1.8-fold (e.g., EXAMPLES 2–4 and 25). In still other illustrative Examples, the R'-Glu-Trp-R" pharmaceutical preparations were administered in clinical tests according to the methods of the invention in an amount and for a time sufficient to increase the number of monocytes by about 1.1 -fold to about 1.4-fold (e.g., EXAMPLES 4 and 6).

In alternative embodiments the subject indicia of cell mediated immunity preferably included one or more measures of one or more activities of immune cells in circulation in the peripheral blood of the subject, e.g., an activity assay of cytokine (a.k.a. interleukin) integrin or adhesin synthesis by lymphocytes (e.g., IL-1, IL-2, IL-3, IL-4, IL-5, TNF-$\alpha$, TGF-$\beta$, IFN-$\alpha$, IFN-$\gamma$, integrin $\alpha_3\beta,\alpha_6\beta_4, \alpha_5\beta_1$ and the like), a lymphocyte blast transformation assay, an assay for a maturation or activation state or functional commitment of a T-lymphocyte (e.g., CD2, CD3, CD4, CD8, and the like) or monocyte (e.g., Ia/Mac-i), a monocyte phagocytosis assay (e.g., yeast or latex), a marker enzyme assay for an activation state of a macrophage or a neutrophil (e.g., 5'-nucleotidase enzyme, nonspecific acid esterase, nitrotetrazolium blue reduction and the like), an assay for a synthetic activity of the blood cells, an antibody dependent cellular cytotoxicity assay, a natural killer cell assay, a histological assay, an immunohistochemical assay, a cytofluorometric assay, and an enzyme-linked immunoassay.

In the illustrative Examples, the R'-Glu-Trp-R" pharmaceutical preparations were administered in clinical tests according to the methods of the invention in an amount and for a time sufficient to: (i) increase the percentage of blast transformed lymphocytes after addition of PHA mitogen or a Concanavalin-A mitogen by about 1.1-fold to about 1.9-fold (e.g., EXAMPLES 3, 6 and 18); (ii) increase the phagocytic index (i.e., ingested bacteria, yeast, or latex particles per phagocytic cell) by about 1.1-fold to about 1.8-fold (e.g., EXAMPLES 3 and 6); and (iii) increase NK activity on YAC-target cells of about 1.1-fold to about 1.5-fold (e.g., EXAMPLE 6).

Yet a third alternative embodiment of the subject indicia of cell mediated immunity preferably includes one or more measures of delayed type hypersensitivity, e.g., skin test diameter in response to a challenge with a bacterial, parasitic, or cellular antigen as determined by measuring induration at 36 hours after an intradermal injection of antigen. In the illustrative Examples, the R'-Glu-Trp-R" pharmaceutical preparations were administered in clinical tests according to the methods of the invention in an amount and for a time sufficient to increase the delayed type hypersensitivity skin test diameters in subjects so treated by about 1.1-fold to about 3.3-fold.

The subject indicia of humoral immunity preferably includes one or more measures of either the concentration of immunoglobulin IgG, IgA, IgM, IgD in a sample of a biological fluid (e.g., blood, plasma, saliva, and the like), or alternatively, a number or percentage of CD4+ T-helper lymphocytes, plasma cells, or B-lymphocytes in a sample of peripheral blood. The subject indicia of humoral immunity may most preferably include one or more measures of either the concentration of an antigen specific immunoglobulin that is capable of binding an antigen in an immunoassay.

In alternative embodiments the subject indicia of humoral immunity preferably include one or more measures of one or more activities of immune cells in circulation in the peripheral blood of the subject, e.g., an assay of immunoglobulin synthesis, an assay for a maturation or an activation state in a B-lymphocyte (e.g., B220, surface Ig, Rag 1, Rag 2, and the like), monocyte (e.g. IaMac-1), or T-helper lymphocyte (e.g., CD4). An alternative embodiment of the subject indicia of humoral immunity preferably includes one or more measures of immediate or Arthus type hypersensitivity, e.g., skin test diameter in response to a challenge with a bacterial, parasitic, or cellular antigen as determined by measuring erythema at 3–20 hours after subcutaneous injection of antigen).

The subject indicia of innate resistance to infection preferably include one or more measures of the concentration of a blood protein in a sample of biological fluid, i.e., an immunoglobulin (e.g., IgA or IgM), a lysozyme (e.g., salivary lysozyme), a cytoline (e.g., IL-2, IL-i, TNF and the like), an interferon (e.g., IFN-$\alpha_1$, IFN-$\alpha_2$, IFN-$\beta$, IFN-$\gamma$, and the like), a complement protein (e.g., C3, C3b, C3a, C5a, Factor B, and the like), a coagulation protein (e.g., fibrinogen, fibrin degradation products, von Willebrand's Factor (vWF), tissue factor, thrombospondin, platelet factor 4, and the like), a fibrinolytic system protein (e.g., plasminogen, tissue plasminogen activator, and the like), an enzyme inhibitor (e.g., anti-thrombin III, $\alpha_1$-antitrypsin, $\alpha_2$-macroglobulin, C3b-inactivator and the like), a bradykinin system protein, a hormone (e.g., insulin, a steroid hormone, and the like), and a receptor protein (e.g., a soluble CD4, or IL-1 or IL-2 receptor, and the like).

In the illustrative Examples, the R'-Glu-Trp-R" pharmaceutical preparations were administered in clinical tests according to the methods of the invention in an amount and for a time sufficient to decrease coagulation and/or to increase fibrinolysis. The decrease in coagulation was assayed in illustrative Examples by measuring: (i) the levels of coagulation enzyme inhibitors in peripheral blood i.e., anti-thrombin III, (abbreviated ATIII), $\alpha_1$-antitrypsin, and a Imacroglobulin; (ii) the levels of fibrin degradation fragments in blood; (iii) the clotting activities of blood, i.e., prothrombin time, (PT), PTT, citrated blood clotting time, and the like; and, (iv) the fibrinolytic activity of blood.

In alternative embodiments, the subject indicia of innate resistance to infection preferably include one or more measures of one or more activities of immune cells in circulation in the peripheral blood of the subject, e.g., an assay for lymphocytes (e.g., CD28), a maturation or an activation state in a B-lymphocyte (e.g., B220, surface Ig, Rag 1, Rag 2, and the like), monocyte (e.g., Ia/Mac-1), or T-helper or T-suppressor lymphocytes (e.g., CD4 and CD8, respectively), or complement receptors (eg. CR1, CR2, CR3, and the like).

The subject immunocompromised patients amenable to treatment by one or more of the embodiments of the invention include but are not limited to: (i) patients having a bacterial infection, viral infection, mycoplasma infection, parasitic infection, opportunistic infection, pneumocystis infection, cytomegalovirus infection, herpes virus infection, mycobacterium infection, or human immunodeficiency virus infection; (ii) patients exposed to radiation or one or more chemotherapeutic antiproliferative drugs; (iii) patients having a transplant, cancer or autoimmune disease, (i.e., see Frank, et al., Eds., "Sampter's Immunological Diseases", Little, Brown N.Y. 1994; sytemic lupus erythematosus, rheumatoid arthritis, Sjogren's syndrome, psoriasis, Epidermnolysis bullosa, or Type 1 insulin-dependent diabetes mellitus, (IDDM); (iv) patients having a primary or a secondary immune deficiency disease, (i.e., see Frank, et al., Eds., "Sampter's Immunological Diseases", Little, Brown, N.Y. 1994; (v) patients having a staphylococcal infection (e.g., pyoderma, furunculitis, cellulitis, eczema, acne vulgaris); (v) patients having gingivitis, dental caries, or periapical granulomas, (vi) patients having a gynecological infection, pelvic inflammatory disease (e.g., cervicitis, vaginitis, tubular or ovarian abscess or an adnexal abscess; (vii) patients having having lymphangitis or an infralymphatic infection, (viii) patients having an acute or chronic respiratory disease, upper airways disease, e.g., sinusitis or perisinusitis, rhinovirus or influenza infection, pleuritis, and the like); (ix) patients having chronic eye-ear-nose or throat infections (e.g., otitis media, conjunctivitis, uveitis or keratitis); (x) patients having bronchial allergy and/or asthma; (xi) patients having a chronic liver infection (e.g., chronic hepatitis); and (xii) patients who are at an increased relative risk of developing an infection or an autoimmune disease (e.g., relative of of patients with IDDM who are at an increased relative risk of developing the disease).

In one of the two alternative preferred embodiments of the invention, (above) an R'-Glu-Trp-R" pharmaceutical preparation is administered to a patient having an autoimmune disease in an amount and for a time sufficient to decrease, one or more indicia of either cell mediated autoimmunity (e.g. autoimmune T-lymphocytes), humoral autoimmunim (e.g., IgG or IgM rheumatoid factor, IgG or IgM binding nucleic acid antigens, and anti-erythrocyte antibodies), or nonspecific inflammation (e.g., complement or neutrophil mediated tissue destruction), thereby effecting improvement in the clinical condition of the patient so treated.

In the illustrative Examples, below, the R'-Glu-Trp-R" pharmaceutical preparations were administered in clinical tests according to the methods of the invention in an amount and for a time sufficient to: (i) decrease elevated polymorphonuclear leukocytes counts in peripheral blood by about 1.1-fold to about 1.7-fold; (ii) decrease elevated mononuclear phagocyte counts in peripheral blood by about 1.1-fold to about 1.3-fold; (iii) decrease elevated B-lymphocytes in peripheral blood about 1.1-fold to about 1.9-fold; (iv) decrease elevated CD4+T-lymphocyte counts in peripheral blood by about 1.1 -fold to about 1.3-fold; and (v) decrease spontaneously elevated blast transformation of lymphocytes induced by PHA or Concanavalin A of by about 1.1-fold to about 1.7-fold.

In still other preferred embodiments of the invention, an R'-Glu-Trp-R" pharmaceutical preparation is administered to a patient having a systemic toxicity (e.g., febrile, jaundiced, and the like), thereby effecting improvement in the clinical condition of the patient so treated. The R'-Glu-Trp-R" pharmaceutical preparation is administered at a dose and for a time sufficient to decrease the blood level of an acute phase protein in a sample of a biological fluid collected from the subject. Representative examples of acute phase proteins include prealbumin, orosomucoid, alpha,-antitrypsin, alpha2-macroglobulin, ceruloplasmin, complement C3, and transferrin.

In a preferred embodiment, a treatment regimen consists of administering a dose of about 10 μg per 1 killogram body weight to about 1 mg per 1 kg body weight daily over a period of I day to about 30 days to the subject. In preferred embodiments, the subject dose is administered either as a single daily intramuscular dose of the R'-Glu-Trp-R" pharmaceutical preparation, or as a single daily intranasal dose of the R'-Glu-Trp-R" pharmaceutical preparation. The subject dose is preferably formulated as an injectable, inhalant, nose drop, or mucosal spray solution containing about 0.001% to about 0.01% of the R'-Glu-Trp-R" pharmaceutical preparation. Alternatively, the formulation of the R'-Glu-Trp-R" pharmaceutical preparation may preferably be incorporated into a unit dose delivery form, e.g., a tablet, a suppository, a capsule, an eye film, or into a paste or ointment, e.g., a toothpaste, a dermal ointment, or water-soluble cream base. A most preferred unit dose form is for delivery of about 0.01 mg of the R'-Glu-Trp-R" pharmaceutical preparation.

In one preferred embodiment, an R'-Glu-Trp-R" pharmaceutical preparation is administered to an immunocompromised patient in an amount and for a time sufficient to increase one or more indicia of either cell mediated immunity, humoral immunity, or innate resistance to infection. The subject treatment of an immunocompromised patient is effective to improve the clinical condition of the patient so treated. In an alternative preferred embodiment, an R'-Glu-Trp-R" pharmaceutical preparation is administered to a patient having an autoimmune disease in an amount and for a time sufficient to decrease one or more indicia of either cell mediated immunity, humoral immunity, or innate resistance to infection. The subject indicia of cell mediated immunity, humoral immunity, or innate resistance to infection is determined by obtaining a sample of blood or tissue from the patient so treated and determining a number (or percentage of immune cells) or determining a functional activity of the immune cells in an in vitro assay. The frequency of the treatment and/or dosage of the R'-Glu-Trp-R" may be adjusted by the treating physician until the subject indicia of immunity is within a desired range. Treatment of an immunocompromised patient or patient with an autoimmune disease according to the method of the invention is effective to improve the clinical condition of the patient.

"Indicia of cell mediated immunity" is used herein to mean one or more measures of a number or percentage of immune cells in circulation in the peripheral blood of a subject treated according to the methods of the invention, e.g., a number or percentage of leukocytes, lymphocytes, monocytes, T-lymphocytes, B-lymphocytes, stem cells, CD 2+-lymphocytes, CD 4 -lymphocytes, CD 8 -lymphocytes, CD $19^+$ -lymphocytes, plasma cells, neutrophils, stab neutrophils, segmented neutrophils and the like.

Illustrative uses of the methods of the invention are disclosed in the Examples section, where an R'-Glu-Trp-R" pharmaceutical preparation was administered according to the methods of the invention in an amount and for a time sufficient to increase the number of: peripheral blood leukocytes by about 1.1-fold to about 1.4-fold (e.g. see EXAMPLES 6 and 19); lymphocytes by about 1.1-fold to about 1.7-fold (e.g. see EXAMPLES 6, 7, 16); CD $2^+$-lymphocytes by about 1.1-fold to about 2.2-fold (e.g. see EXAMPLE 2); CD $4^+$-lymphocytes by about 1.1 -fold to about 3.2-fold (e.g., see EXAMPLES 3, 4, and 16); CD $8^+$-lymphocytes by about 1.1-fold to about 1.8-fold (e.g., see EXAMPLES 3 and 6); cell-surface Ig+B-lymphocytes by about 1.1-fold to about 1.6-fold (e.g., see EXAMPLES 6, 7, 16, and 19); E-rosette forming T-lymphocytes by about 1.1-fold to about 1.8-fold (e.g., see EXAMPLES 4, 6, 7, 9 and 19); polymorphonuclear neutrophils by about 1.1-fold to about 1.3-fold (e.g., see EXAMPLES 4 and 6); and/or monocytes by about 1.1-fold to about 1.4-fold (e.g., see EXAMPLES 4 and 6).

In other Examples, an R'-Glu-Trp-R" pharmaceutical preparation was administered in an amount and for a time sufficient to increase the ratio of the numbers of CD $4^+$-lymphocytes/ CD $8^+$-lymphocytes by about 20% to about 40% from the pretreatment value (e.g., see EXAMPLES 2, 3 and 4; % increase=(ratio after treatment)-(ratio before treatment)/(ratio before treatment)). In still other Examples, an R'-Glu-Trp-R" pharmaceutical preparation was administered in an amount and for a time sufficient increase, (or in certain patient populations, to decrease), one or more measures of functional activity of immune cells selected from among: lymphocyte blastogenesis with PHA (phytohaemagglutinin) or Con A (concanavalin A); lymphocyte cytotoxic activity (e.g., CTL, ADCC, antibody dependent cytotoxicity, and NK cell cytotoxicity assay); monocyte phagocytic activity; differentiated or activated mononuclear phagocytes in tissues or peripheral blood (ie., identified using markers such as nonspecific acid esterase, 5'-nucleotidase, nitrotetrazolium blue reduction and the like); and, neutrophil phagocytic activity. In still other Examples, an R'-Glu-Trp-R" pharmaceutical preparation was administered in an amount and for a time sufficient to alleviate infection and decrease the level of potentially inflammatory cytokines (interleukins) produced by lymphocytes and monocytes (e.g., LMIR; EXAMPLES 3, 9, and 16). Monitoring efficacy of an R'-Glu-Trp-R" treatment by measuring increased or decreased interleukin production may vary dependent upon the particular disease state, patient condition, and cytokine measurement: e.g., IL-1, IL-2, IL-3, IL-4, IL-5, IL-6, TNFα, TGFβ, IFNα, IFNγ.

Other assays useful for monitoring efficacy of an R'-Glu-Trp-R" treatment may include measuring expression of cell-surface integrins on lymphocytes, mononuclear phagocytes, or neutrophils (e.g., $\alpha_3\beta_4$, $\alpha_3\beta_1$, $\alpha_5\beta_1$ and the like). Still other assays useful for monitoring efficacy of an R'-Glu-Trp-R" treatment may include measuring expression of a cell-surface marker assay for the maturational, activational or functional commitment state of a lymphocyte (e.g., CD 2, CD 3, CD 4, CD 8, CD 26, CD 45 and the like) or a monocyte (e.g., Ia/Mac-1).

Histological and immunohistochemical assays conducted with biopsy samples, and delayed type hypersensitivity skin test reactions are also useful for monitoring efficacy of an R'-Glu-Trp-R" treatment in certain patients (e.g., EXAMPLES 3 and 18). In the Examples section, an R'-Glu-Trp-R" pharmaceutical preparation was administered in clinical tests according to the methods of the invention in an amount and for a time sufficient to: (i) increase the percentage of blast transformed lymphocytes after addition of PHA or Con-A mitogen by about 1.1-fold to about 1.9-fold (e.g., see EXAMPLES 3, 6, and 18); (ii) increase the phagocytic index of mononuclear phagocytes by about 1.1-fold to about 1.8-fold (e.g., see EXAMPLES 3 and 6); (iii) increase NK activity on YAC-target cells by about 1. 1-fold to about 1.5-fold (e.g., see EXAMPLES 1 and 6 ); (iv) decrease endogenous cytokine production in an assay for leukocyte migration inhibition factor (LMIR) by about 40% to about 75% (e.g., see EXAMPLES 3, 9 and 16); and, (v) increase a delayed type hypersensitivity skin test diameter by about 1.1-fold to about 3.3-fold (e.g., see EXAMPLES 3 and 18).

"Indicia of humoral immunity" is used herein to mean one or more measures of a number or percentage of lymphocytes or plasma cells, and/or one or more immunoglobulin levels in a sample of peripheral blood from a subject treated according to the methods of the invention. In the latter case, the number or percentage of B-lymphocytes, plasma cells, surface Ig$^+$-lymphocytes, Fc-receptor lymphocytes, CD 19$^+$-lymphocytes, B220$^+$-lymphocytes, Rag-1$^+$- or Rag-2$^+$-lymphocytes and the like may be determined; and/or, the levels of IgA, IgD, IgG, IgM or IgE.

"Indicia of innate resistance to infection" is used herein to mean one or more measures of a number or percentage of immune cells or their biosynthetic products in a sample of tissue or blood in a tissue or blood sample of a subject treated according to the methods of the invention. In the latter case, "immune cells" include (but are not limited to) $\delta\gamma^+$-T-lymphocytes, neutrophils, mononuclear phagocytes, Mac-1$^+$-macrophages, reticular cells, dendritic cells, and the like; and, "biosynthetic products of immune cells" include (but are not limited to) immunoglobulins (e.g., IgA, IgD, IgE, IgM, IgG and the like), lysozymes (e.g., salivary lysozyme), interferons (e.g., IFN-$\alpha_1$, IFN-$\alpha_2$, IFN-β, IFN-γ and the like), complement proteins (e.g., C3, C3b,.C3a, C5a, Factor Bb and the like), coagulation proteins (e.g., fibrinogen, fibrin degradation products, vWF, tissue factor, thrombospondin, platelet factor 4, and the like), fibrinolytic proteins (e.g., plasminogen, tissue plasminogen activator, and the like), enzyme inhibitors (e.g., anti-thrombin III, $\alpha_1$-antitrypsin, $\alpha_2$-macroglobulin, C3b-inactivator and the like), arachidonic acid metabolites (e.g., prostaglandins, and the like), bradykinin system proteins, and receptors (e.g., soluble CD 4, IL-1 receptor, IL-2 receptor and the like).

Embodiments of the invention provide methods useful for treating a subject to induce a heightened state of antimicrobial cellular or humoral inmmunity by administering a pharmaceutical preparation of R'-Glu-Trp-R". Pharmaceutical preparations containing both R'-Glu-Trp-R" and a second agent are also envisaged, including a variety of different mixtures. The "subject in need of" the treatments of the invention are preferably man and domestic animals having one or more microbial infections that include, but are not limited to, subjects infected with the following infectious agents: bacteria, viruses, mycobacteria, parasites, opportunistic bacteria or viruses (e.g., pneumocystis, cytomegalovirus, herpes virus, mycoplasma, and the like). Representative examples of "subjects in need thereof" include the following: (i) individuals infected with human immunodeficiency virus and having a secondary opportunistic infection; (ii) individuals exposed to radiation and/or one or more chemotherapeutic agents (e.g., cancer patients); (iii) individuals undergoing immunosuppressive drug therapy (e.g., following transplantation or for treatment of an autoimmune disease such as Rheumatoid arthritis, Systemic lupus erythematosus, Type 1 insulin dependent diabetes (IDDM), Sjogren's syndrome, and the like); (iv) individuals having a primary or secondary immune deficiency disease; (v) individuals having a staphylococcal infection (e.g., pyoderma, furunculitis cellulitis, eczema, acne vulgaris) or psoriasis; (vi) individuals with gingivitis, dental caries, or periapical granulomas; (vii) individuals with lymphangitis or infralymphatic infection; (viii) individuals with acute or chronic respiratory disease, upper airways disease (e.g. sinusitis or perisinusitis, rhinovirus or influenza infection, bronchitis, pharyngitis, and the like), (ix) lower airways disease (e.g., pneumonia or pleuritis); (x) individuals with acute or chronic eye, nose or throat infections (e.g., otitis media, conjunctivitis, uveitis, or keratitis); (xi) individuals with bronchial allergy and/or asthma; (xii) patients having a chronic liver infection (e.g., hepatitis); and, (xiii) individuals at an increased relative risk of developing an infection or an autoimmune disease (e.g., relatives of a Type 1 IDDM patient).

"Immune deviation" is used herein to mean that the treatment method of the invention may be effective to change the effector elements involved in an ongoing immune response but the term as used herein does not mean effecting a quantitative increase or decrease in an ongoing immune response. Representative examples of immune deviation include affecting in the subject so treated (i) a change from an ongoing humoral immune response to a cell-mediated immune response, (ii) a change from an IgE-mediated immune response to an IgG-mediated immune response; (iii) a change from a first microbial antigen to a second microbial antigen; (iv) a change from a cytotoxic lymphocyte response to a macrophage mediated immune response; and, (v) a change from an autoimmune cytotoxic lymphocyte response to production of an IgG that blocks cytotoxic killing of tissue cells. The treatment methods of the invention may effect immune deviation in a treated subject. That immune deviation has been effected in the subject so treated may be determined by evaluating cell mediated and humoral immunity, prior to and after treatment.

As disclosed above, the "subject in need thereof" may be an immunocompromised subject such an individual have an underlying immunodeficiency syndrome occasioning frequent, recurrent, or intermittent microbial infections. Underlying patient syndromes include (but are not limited to) hereditary and acquired immunodeficiency syndromes such as primary immunodeficiency syndromes (e.g., DiGeorge Syndrome, Severe Combined Immunodeficiency Syndrome, Combined Immunodeficiency, X-linked lymphoproliferative disease); syndromes resulting from an underlying autoimmune disease (e.g., diabetes, systemic lupus erythematosus, Sjogrens syndrome); syndromes resulting from an underlying infection (e.g., HIV infection); syndromes resulting from a toxic reaction to a drug or a chemical; or secondary immunodeficiency disorders such as those disclosed in EXAMPLES 2–3, 12–13, 24, and 28.

The subject treatment methods of the invention preferably stimulate increased cellular, humoral or innate immunity, and thereby ameliorate or eliminate one or more "clinical or laboratory indicia of disease", e.g., redness and swelling, fever, malaise, septicemia, pyogenic exudates, and the like. The subject treatment methods of the invention may also restore one or more measurements of a "laboratory indicia of disease", i.e., changing a measurement value from an abnormal value to a more normal value; or alternatively, the subject treatments may increase a laboratory value above the normal range, i.e., to achieve an increased anti-microbial immunity. Representative examples of changes in a laboratory indicia of disease include (but are not limited to) the following: (i) decreasing an elevated neutrophil or lymphocyte count in a sample of peripheral blood into the normal range of values; (ii) increasing an abnormally low hematocrit; (iii) decreasing an elevated serum alpha globulin level in a serum sample (e.g., an acute phase reactant measurement); (iv) decreasing an elevated IgM immunoglobulin level or changing an $IgG_1/IgG_2$ ratio in a serum sample; (v) increasing abnormally low expression of one or more cell surface accessory molecules in a blood sample of immune cells (e.g., CD2, CD3, CD4, CD26, CD28, CD45, B220, surface Ig, Rag 1 and Rag 2, Ia/Mac-1 and the like), (vi) increasing biosynthesis of one or more interleukins (e.g., IL-2, IL-1, TNF, TGF-β, IFN-γ, and the like) in a sample of immune cells isolated from the subject; (vi) increasing biosynthesis of antibody specific for the subject microbe (e.g., using a diagnostic immunoassay format) in a serum sample; (vii) increasing phagocytic activity in an in vitro assay with mononuclear phagocytes or neutrophils from a sample of blood; (viii) decreasing an abnormally enlarged spleen or increasing a small spleen to more effectively combat infection (e.g., as determined by CAT scan or sonography); (ix) increasing the proportion of Fc-receptor bearing lymphoid cells in a spleen, thymus, and/or bone marrow sample; (x) increasing Fc-receptor bearing lymphoid cells in a sample of peripheral blood; (xi) increasing T-lymphocytes in a spleen biopsy specimen; (xii) increasing the number of neutrophils in a measured volume of a tissue infiltrate in response to an inflammatory agent; and/or (xiii) increasing the percentage of phagocytically active cells in a neutrophil infiltrate sample from the subject.

The subject methods of the invention find a variety of prophylactic and therapeutic uses in treatment of immune pathophysiologic conditions in man and domestic animals. In certain embodiments the methods of the invention find use during in vitro maintenance and expansion of bone marrow, peripheral blood leukocytes, $CD34^+$ lymphocytes, and other immune cells, such as may occur prior to autologous or allogenic bone marrow transplantation.

In one preferred embodiment, an R'-Glu-Trp-R" pharmaceutical preparation is administered to an individual with a diagnosed autoimmune disease in an amount and for a time sufficient to decrease one or more laboratory indicia of the disease state in the patient. Representative examples of the laboratory indicia include the following: (i) levels of IgG and/or IgM rheumatoid factor in patients with rheumatoid arthritis (RA); (ii) levels of anti-red cell antibodies in patients with Systemic lupus erythematosus (SLE); (iii) levels of complement activation fragments (e.g., C3a, C5a, C3b, SC5b-9, Bb and the like) in patients with IDDM, RA or SLE; (iv) levels of fibrin degradation fragments in patients with juvenile-onset RA; (v) levels of spontaneous lymphocyte blastogenesis in vitro (e.g., $^3$H-thymidine incorporation).

Illustrative uses of the subject treatment methods in several different patient populations effected: (i) a decrease of about 1.1-fold to about 1.7-fold in peripheral blood polymorphonuclear leukocyte counts from an elevated pretreatment value to a lower post-treatment value in patients with chronic staphylococcal infections and acute osteomyelitis (e.g., see EXAMPLES 6 and 16); (ii) a decrease of about 1.1-fold to about 1.3-fold in peripheral blood mononuclear phagocyte counts from an elevated pretreatment value to a lower post-treatment value in patients with chronic staphylococcal infections (e.g., see EXAMPLE 6); (iii) a decrease of about 1.1-fold to about 1.9-fold in B-lymphocytes from an elevated pretreatment value to a lower post-treatment value in patients with chronic staphylococcal or hepatitis infection (e.g., see EXAMPLES 6 and 23); and, (iv) a decrease of about 1.1-fold to about 1.3-fold in CD $4^+$-lymphocytes in peripheral blood from an elevated pretreatment value to a lower post-treatment value in patients with SLE (e.g., see EXAMPLE 6).

In another preferred embodiment, an R'-Glu-Trp-R" pharmaceutical preparation is administered to an individual exhibiting systemic toxicity, (e.g., febrile, jaundiced, alternating chills and fever), in an amount and for a time sufficient to decrease one or more laboratory indicia of the disease state in the patient. Representative examples of the laboratory indicia include measurements of fibrin degradation products (FDP), antithrombin-III, orosomucoid, prealbumin, alpha,-antitrypsin, alpha2-macroglobulin, ceruloplasmin, complement C3 and transferrin. In a preferred embodiment a treatment regimen according to the method of the invention consists of administering to the subject in need thereof a dose of about 10 μg per 1 kilogram of body weight to about 1 mg per 1 kg body weight once daily an each of about 1 day to about 30 days. In most preferred embodiments the subject dose is administered either as a single daily intramuscular dose, or as a single daily intranasal dose, of an R'-Glu-Trp-R" pharmaceutical preparation. In the latter case the subject dosage form is preferably either a sterile injectable solution, or inhalant, nose drop or mucosal spray solution containing about 0.001% weight to about 0.01% of the R'-Glu-Trp-R" pharmaceutical preparation. Alternatively, the formulation of the R'-Glu-Trp-R" pharmaceutical preparation may be in a unit dose delivery form, e.g., a tablet, capsule, suppository, eye film, paste or ointment. A most preferred unit dose form delivers about 0.01 mg of the R'-Glu-Trp-R" pharmaceutical preparation.

It is an object of the present invention to provide methods and R'-Glu-Trp-R" pharmaceutical compositions, (of which the dipeptide L-Glu-L-Trp, its analogues and derivatives, multimers and cyclized forms are representative examples), that have inmmunomodulatory activity for medical and veterinary uses, e.g. treatment of infections, diseases, wounds, burns, frost bites, and the like. It is also an object of the present invention to provide therapeutic methods for treatment of immunodepressed and immunodeficient states. It is yet another object of the present invention to provide methods for preventing and treating infections in a subject including opportunistic infection in an immunodeficient or immunodepressed subject.

In a representative prophylactic treatment regimen, the subject compositions of the invention are administered to a patient susceptible to, or otherwise at risk, for infection, anemia, or immune regulatory disorder that may be amenable to treatment by the subject methods of the invention in an amount defined as a "prophylactically effective dose." "Prophylactically effective dose" is used herein to mean an amount sufficient to protect the subject against development of a disease, wherein the amount will depend on the patient's state of health and weight, but will generally fall within the ranges described herein for therapeutic use. Prophylactic administration may be particularly desirable for hosts that have been exposed or at risk for exposure of infectious diseases, e.g. health-care workers, travelers, family members of infected individuals, immunosuppressed persons, and the like. The compositions of the present invention can be used for prophylaxis against common illnesses such as rhinoviruses, orthomyxoviruses, adenoviruses, a-hemolytic Streptococcus, a-Staphylococcus, and the like. The compositions of the present invention can be administered for surgical prophylaxis to lessen the risk of infectious complications. The compositions can also be used to inhibit organ rejection. Such organs can include skin, heart, lung, kidney, bone, liver, pancreas, tendon, and the like. The present compositions are particularly useful when used prophylactically to inhibit rejection of skin grafts.

In a representative therapeutic treatment regimen, a pharmaceutical preparation of the present invention is administered alone, or optionally with a second pharmaceutical agent, i.e., the latter two agent therapy is termed herein "combined therapy". In a combined therapy the subject R'-Glu-Trp-R" composition is preferably administered with one or more antibiotics, anti-viral compounds, or anti-fungal compounds, anti-parasitic agents, anti-inflammatory agent, or chemotherapeutic compounds. The subject compositions may be administered either in conjunction with the second treatment modalities, or separately, e.g., at different times or in different syringes or tablets. Often, the dose of the additional agents may be less than standard dosages (ie., because of the immunostimulatory effects of the subject compositions. Often, R'-Glu-Trp-R" is administered in a combined therapy with an anti-infective agent such as one or more antibiotics (i.e., anti-inflammatory agents, vaccines, antihistamines, immunomodulators, chemotherapeutic agents and the like. Illustrative combined treatments with R'-Glu-Trp-R" may include, e.g., anti-inflammatory agents such as Salicylates, Diclofenac Sodium, Etodolac, Fenoprofen Calcium, Flurbiprofen, Ibuprofen, Ketoprofen, Meclofenamate Sodium Monohydrate, Nabumetone, Naproxen, Napproxen Sodium, Oxaprozin, Phenylbutazone, Piroxicam, Sulindac, Tolmetin Sodium, Hydroxychloroquine Sulfate, Methotrexate, Penicillamine, Sulfasalazine, Aurothioglucose, Gold Sodium Thiomalate, Auranofin, Adrenal Corticosteroids, Azathioprine, Colchicine, Corticotropin, Fenoprofen Calcium, Allopurinol, Probenecid, Sulfinpyrazone, Probenecid, Colchicine, and the like; antihistamines such as e.g., Amino Alkylethers, Clemastine Fumarate, Tripelennamine Citrate, Tripelennamine Hydrochloride, Pyrilamine Maleate, Chlorpheniramine Maleate.

Illustrative combined treatments with R'-Glu-Trp-R" may include administration of a chemotherapeutic agent as the second agent. Representative chemotherapeutic agents so usefuil inlcude e.g., Chlorambucil, Cyclophosphamide, Ifosfamide, Mechlorethamine Hydrochloride, Melphalan, Thiotepa, Busulfan, Procarbazine Hydrochloride, Carmustine, Lomustine, Streptozocin, Cisplatin, Carboplatin, Dacarbazine, Altretamine, Mesna, Methotrexate, Leucovorin Calcium, Cytarabine, Floxuridine, Fluorouracil, Cladribine, Fludarabine, Mercaptopurine, Pentostatin, Thioguanine, Hydroxyurea, Bleomycin Sulfate, Dactinomycin, Daunorubicin Hydrochloride, Doxorubicin Hydrochloride, Idarubicin Hydrochloride, Mitomycin, Mitoxantrone Hydrochloride, Plicamycin, Vinblastine Sulfate, Vincristine Sulfate, Etoposide, Paclitaxel, Teniposide, Asparaginase, Prednisone, Prednisolone, Dexamethasone, Methylprednisolone, Diethylstilbestrol, Chlorotrianisene, Conjugated estrogen, Esterified estrogens, Estone, Ethinyl Estradiol, Estramustine Phosphate Sodium, Tamoxifen Citrate, Fluoxymesterone, Methyltestosterone, Testolactone, Testosterone Propinate, Flutamide, Goserelin Acetate, Leuprolide Acetate, Hydroxyprogesterone Caproate, Medroxyprogesterone Acetate, Megestrol Acetate, Aminoglutethimide, Mitotane, Aldesleukin, Interferon-$\alpha_{2a}$, BCG, Isotretinoin, Levamisole, Octreotide Acetate, Cyclophosphamide, Ifosfamide, Mechlorethamine Hydrochloride, Melphalan, Mesna, Busulfan, Carmustine, Lomustine, Nimustine, Semustine, Streptozocin, Cisplatin, Carboplatin, Iproplatin, Procarbazine Hydrochloride, Dacarbazine, Altretamine, Sodium Phosphate $P^{32}$, Chromic Phosphate $P^{32}$, Methotrexate, Methotresate Sodium, Methotrexate, Trimetrexate, Fluorouracil, Floxuridine, Azacitidine, Tegafur, Cladribine, Fludarabine Phosphate, Mercaptopurine, Pentostatin, Thioguanine, Tiazofurin, Hydroxyurea, Caracemide, Buthionine Sulfoximine, Eflomithine Hydrochloride, Mitoguazone, Phosphonoacetyl, Brequinar Sodium, Doxorubicin Hydrochloride, Idarubicin Hydrochloride, Epirubicin Hydrochloride, Menogaril, Razoxane, Bleomycin Sulfate, Dactinomycin, Mitomycin, Plicamycin, Didemnin B, Echinomycin, Deoxyspergualin, Mitoxantrone Hydrochloride, Amsacrine, Amonafide, Merbarone, Piroxantrone Hydrochloride, Vinblastine Sulfate, Vincristine Sulfate, Vindesine Sulfate, Etoposide, Teniposide, Paclitaxel, Homoharringtonine, Asparaginase, Mitotane, Estramustine Phosphate Sodiun, Tamoxifen Citrate, Leuprolide Acetate, Goserelin Acetate, Buserelin Acetate, Aminoglutethimide, Interferon Alfa-2a, Interferon Alfa-2b, Interferon Beta, Interleukin 2, Tumor Necrosis Factor, BCG Live, BCG Vaccine, Monoclonal Antibodies, Flavone Acetic Acid, Hexamethylene-Bis-Acetamide, Isotretinoin, Levamisole Hydrochloride, N-Methyfonnamide, Octreotide Acetate, and the like Representative uses of the subject methods of the invention in treating an immunocompromised subject include treatments designed to ameliorate clinical symptoms resulting from administration of chemotherapeutic compounds, e.g., during treatment of malignancy, graft-versus-host disease, autoimmune states, and the like. Autoimmune states in which treatment the methods of the present invention may prove useful include diseases such as rheumatoid arthritis, systemic lupus erythematosus, Reiter's Syndrome, psoriasis, ankylosing spondylitis, Sjögren's syndrome, sicca syndrome, mixed connective tissue disorder, multiple sclerosis, diabetes mellitus, and the like (see Frank, et al., Eds."Sampter's Immunological Diseases", Little, Brown, N.Y. 1994). The immunomodulating properties of the pharmaceutical compositions of the present invention provide a means for ameliorating, ie., making better/making normal, one or more symptoms of disease in a subject.

A variety of disease states may be treated by the subject methods of the invention. Infectious diseases may be treated. The infections may be bacterial, viral, fungal, or parasitic. The methods may be practiced in immunocompromised or immunocompetent hosts. Illustrative uses of the methods of the invention in treating patients with bacterial diseases are disclosed in the Examples section as follows: in treating patients with staphylococcal skin diseases (EXAMPLE 6); in treating patients with pelvic inflammatory diseases including complications of pregnancy, post-partem infections, and uterine infections (EXAMPLE 7); in treating patients with gastrointestinal diseases including Shigella dysentery (EXAMPLE 23); and, opportunistic infections (EXAMPLE 13).

Localized or disseminated infections may be treated by the present methods. The infections may be in any organ, tissue or body cavity, e.g., lungs, bone, kidney, central nervous system, heart, skin and soft tissues (e.g., post-traumatic infections), reproductive organs (orchitis, pelvic inflammatory diseases, and the like), liver, and the like. Illustrative uses of the subject methods in treatment of localized and disseminated infections are disclosed in the Examples section as follows: nose, ear and throat infections, sinusitis, pleuritis, pneumonia, and ophthalmic infections (EXAMPLES 4 and 11).

Representative uses of the subject methods of the invention include use in conjunction with a vaccine to enhance the immune response to the vaccine and provide a higher level of immunity and/or a prolonged anamnestic response. The subject R'-Glu-Trp-R" compositions can be administered prior to, simultaneously with, or following vaccination. Generally, the compositions will be administered prior to, or simultaneously with, vaccination. Representative examples of vaccines so useful include Viral Vaccines, Toxoids, Meningococcal Polysaccharide vaccine, Diphtheria Antitoxin, Tetanus, Prophylaxis, Tetanus Immune Globulin, Pertussis Vaccine, Measles Vaccine, Mumps Vaccine, Rubella Vaccine, PRP-D, Polysaccharide, PRP-OMP, Rabies Immune Globulin, BCG Vaccine, Cholera Vaccine, Meningococcal Polysaccharide Vaccine, Plague Vaccine, Smallpox vaccine, Vaccine Immune Globulin, Typhoid Vaccine, Yellow Fever Vaccine, Varicella-Zoster Immune Globulin, Botulism Antitoxin Trivalent, and Cytomegalovirus Immune Globulin.

Representative uses of the subject methods of the invention in treating bacterial infections in a combined treatment with an anti-infective agent such as an antibiotic, e.g., one or more penicillins, cephalosporins, aminoglycosides, macrolides, sulfa compounds, fluoroquinolones, or tetracyclines. In the latter case, the subject R'-Glu-Trp-R" compositions may be administered simultaneously with, or shortly before or after the chosen anti-infective agent. Representative pharmaceuticals that may be administered in conjunction with the subject dipeptide compositions in the methods of the invention include (but are not limited to) anti-infective agents such as e.g.: Penicillin G, Penicillin V, Methicillin, Nafcillin, Oxacillin, Cloxacillin, Dicloxacillion, Ampicillin, Amoxicillin, Bacampicillin, Cyclacillin, Carbenicillin Indanyl, Ticarcillin, Mezlocillin, Piperacillin, Cephalothin, Cefazolin, Cephapirin, Cephradine, Cephalexin, Cefadroxil, Cefamandole Nafate, Cefuroxime, Cefonicid, Ceforanide, Cefaclor, Cefoxitin, Cefotetan, Cefmetazole, Cefataxime, Ceftizoxime, Ceftriaxone, Ceftazidime, Cefoperazone, Moxalactam, Cefixime, Erythromycin, Stearate, Ethylsuccinate, Estolate, Lactobionate, Gluceptate, Azithromycin, Clarithromycin, Oxytetracycline, Demeclocycline, Doxycycline, Minocycline, Amikacin Sulfate, Gentamicin Sulfate, Intrathecal, Kanamycin Sulfate, Netilmicin Sulfate, Streptomycin Sulfate, Tobramycin Sulfate, Neomycin Sulfate, Sulfadiazine, Sulfamethizole, Sulfisoxazole, Sulfisoxazole Acetyl, Sulfamethoxazole, Trisulfapyrimidines, Phenazopyridine, Erythromycin, Ethylsuccinate, Trimethoprim, Ciprofloxacin, Ciprofloxacin Hydrochloride, Enoxacin, Lomefloxacin Hydrochloride, Norfloxacin, Ofloxacin, Vancomycin Hydrochloride, Teicoplanin, Rifampin, Metronidazole, Metronidazole Hydrochloride, Polmyxins, Bacitracin, Methenamine, Methenamine Hippurate, Methenamine Mandelate, Nitrofurantoin, Phenazopyridine Hydrochloride, Silver Nitrate, Acetic Acid, Domeboro Solution, m-Cresyl Acetate, Coly-Mycin S Otic, Cortisporin, Tridesilon, Ciclopiroxolamine, Clioquinol, Griseofulvin, Fulvicin, Grisactin, Grisactin Ultra, Grifulvin V, Halaprogin, Pyrithione zinc, Selenium sulfide, Tolnaftate, Undecylenic Acid, Naftfine, Terbinafind, Imidazole, Econazole, Ketoconazole, Miconaxole nitrate, Monistat-Derm, Oxiconazole nitrate, Sulconazole nitrate, Bis-triazoles, Intraconazole, Amphotericin B, Nystatin, Mycolstatin, Nilstat, Butoconazole, Clotrimazole, Ketoconazole, Miconazole nitrate, Tioconazold, Fluconazole, Intraconazole, Terconazole, Nystatin, Mycostatin, Nilstat, O-V Statin, Cantharidin, Interferon-$\alpha_{2a}$, Interferon-$\alpha_3$, Intralesional, Podophyllin Resin, Podofilox, Salicylic Acid, Benzylbenzoate, Crotamiton, Lindane, Malathion, Pernethrin, Phrethrins, Piperonyl Butoxide, Sulfur, Isoniazid, Pyrazinamide, Ethambutol, Capreomycin Sulfate, Cycloserine, Ethambutol Hydrochloride, Ethionamide, Clofazimine, Dapsone, Ethionamide, Itraconazole, Potassium Iodide Flucytosine, Chloroquine phosphate, Hydroxychloroquine phosphate, Chloroquine hydrochloride, Quinine sulfate, Pyrimethamine/sulfadoxine, Mefloquine, Quinidine gluconate, Dilozanide Furoate, Eflornithine Hydrochloride, Furazolidone, Iodoquinol, Melarsoprol, Metronidazole, Nifurtimox, Paramomycin Sulfate, Pentamidine Isethionate, Primaquine Phosphate, Quinine Sulfate, Sodium Stibogluconate, Meglumine Antimoniate, Trimetrexate Glucuronate, Pyrimethamine, Albendazole, Diethyclcarbamazine Citrate, Ivermectin, Mebendazole, Metrifonate, Niclosamide, Oxamniquine, Pyrantel Pamoate, Suramin Sodium, Thiabendazole, Cytarabine, Idoxuridine, Trifluridine, Vidarabine, Acyclovir, Zidovudine, Ribavirin, Bromovinyldeoxyuridine, Fluoroiodoaracytosine, Amantadine, Acemannan, Amphotericin B methyl, Ampligen, Castanospermine, Soluble CD4, Dextran sulfate, Dideoxycytidine, Dideoxyinosine, Didihydrodideoxythymidine, Foscarnet sodium, Fusidic acid, HPA-23, Isoprinosine, Penicillamine, Peptide T, Ribavirin, Rifabutin, Zidovudine, Interferon-$\alpha_{2b}$, Didanosine, Foscarnet Sodium, Zalcitabine, and the like.

Representative uses of the subject methods of the invention in a combined regimen for treating a mycobacterial infection includes administering the subject R'-Glu-Trp-R" composition and at least one anti-infective agent to a subject in need thereof. The mycobacterial infection may be localized or generalized, e.g., pulmonary and disseminated lesions of *Mytobacterium leprae* (e.g., as disclosed in EXAMPLE 18, below) or *Mycobacterium tuberculosis* (e.g., as disclosed in EXAMPLE 21, below). The subject methods may prove particularly usefuil in treating mycobacterial infection previously non-responsive to antibiotics. The anti-infective agent will generally be administered according to its standard dosage schedule. For example, treatment of *Mycobacterium tuberculosis* infections may comprise administering the dipeptides (or corresponding polymeric or cyclic forms) to the host in conjunction with standard therapy, such as isoniazid, rifampin, ethambutol, streptomycin, or pyrazinamide. These agents will generally be administered according to treatment protocols of the World Health Organization (Geneva, Switzerland) or Centers for Disease Control (Atlanta, Ga.). Treatment of *Mycobacterium leprae* infections may include administration of a composition of the present invention, as well as dapsone, rifampin, clofazimine, or ethionamide according to standard protocols as suggested by the World Health Organization (Geneva, Switzerland) or National Hansen's Disease Center (Carville, La.).

Representative uses of the subject methods in treating subjects with mycotic infections include treatments for patients having candidiasis (systemic or mucocutaneous), aspergillosis, blastomycosis, chromoblastomycosis, coccidio-mycosis, cryptococcosis, histoplasmosis, mucormycosis, paracoccidiodomycosis, pseudallescheriasis, or sporotichosis. The subject treatments for mycotic infections include combined therapeutic regimens in which the subject composition is administered with an anti-fungal agent, e.g., amphotericin B, flucytosine, ketoconazole, fluconazole, itraconazole, and the like, to a subject in need thereof.

Representative uses of the subject methods of the invention in treatment of viral infections include treatment of subjects having infections with HIV-1, HIV-2, cytomegalovirus, herpes viruses, HTLV-I, HTLV-II, hog cholera virus, distemper virus, feline sarcoma virus, hepatitis viruses, influenza virus, and Dengue virus. The subject methods include those in which the R'-Glu-Trp-R" compositions are administered in a combined treatment regimen with an anti-viral agent such as an interferon-$\alpha$, interferon-$\beta$, interferon-$\gamma$, interferon $\alpha_{2b}$, cytarabine, acyclovir, idoxuridine, vidarabine, ganciclovir, zidovudine, ribavirin, bromovinyldeoxyuridine, amantidine, foscarnet, dideoxyinosine, dideoxycytidine, azidothymidine, and the like. Illustrative treatments of subjects having viral infections are disclosed in the Examples section, as follows: patients having herpes infections (EXAMPLE 8); Dengue fever virus infections (EXAMPLE 20); influenza infections, vaccination, prophylaxis, and treatment of symptoms (EXAMPLE 4); hepatitis B virus infections (EXAMPLE 25); and HIV-1 infections (EXAMPLE 5).

Representative uses of the subject methods for treating subjects with parasitic infections includes patients having leishmaniasis, pneumocystis infections, giardiasis, trypanosomiasis, malaria, toxoplasmosis, coccidiosis, trichomoniasis, trichinosis, clonorchiasis, echinococcosis, dirofilariasis, and the like. The subject treatment methods with R'-Glu-Trp-R" are exemplified by methods disclosed below in which L-Glu-L-Trp compositions were administered in a combined treatment regimen with an anti-parasitic agent, e.g., with a quinine derivative in a patient with malaria (as illustrated in EXAMPLE 19).

Illustrative uses of the subject methods of the invention in treating clinical symptoms of immunodeficiency diseases, and symptoms of various bacterial, viral, or inflammatory diseases states are illustrated in the Examples section. The dose, route, and duration of administration of the R'-Glu-Trp-R" compositions can be determined by a skilled practitioner according to recognized and accepted methods of clinical practice, such as monitoring patient response to therapy (i.e., clinical indicia of disease) and/or laboratory test results (i.e., laboratory indicia of disease). In addition, methods for administration of R'-Glu-Trp-R" are disclosed in greater detail in the EXAMPLES section. It is routine in the practice of medicine for a physician to examine and treat patients with various infectious diseases, autoimmune diseases, or immunodeficiency diseases. Examples of infectious diseases include inner ear infections, sinus infections, urinary tract infections, pneumonia, bacterial endocarditis, osteomyelitis and the like. Examples of autoimmune diseases include Systemic lupus erythematosus, rheumatoid arthritis, multiple sclerosis, Type I diabetes, myasthenia gravis, Sjogren's syndrome, and the like. Examples of immunodeficiency diseases leading to immunocompromised hosts include primary and secondary immunodeficiency syndromes such as Wiscott-Aldrich syndrome and HIV-infection. Some syndromes are less severe than others. For example bacterial endocarditis can be life threatening, whereas inner ear infections are rarely life threatening. In deciding whether to use the subject methods of the invention in combination therapy e.g., with antibiotics or other biologically active agents (e.g., interferons or interleukins) to treat the particular syndrome, a physician will usually base the decision on knowledge of whether opportunistic bacterial, viral, or parasitic infections are commonly involved in subject syndrome. Such knowledge has been accumulated over decades, and is reported in the medical literature as well as medical texts. The timing of when to start the subject methods in combination or single agent therapy rests on the physician's clinical judgement. For life threatening infections, the physician will usually obtain the specimens for culture (e.g., for a throat or blood culture) and begin treatment with what has become standard empiric antibiotic therapy. Empiric therapy is a therapy designed to treat the most common or likely causative agent based on historic, demographic, and epidemiologic information. Empiric therapy may often include use of multiple therapeutic agents (e.g., more than one antibiotic and/or broad spectrum antibiotics) designed to cover a wide range of therapeutic possibilities. When laboratory test data are available (commonly about 48 hours for bacteriology or immunology tests and 3 to 7 days for virology tests) the choice of therapy may be adjusted to more particularly treat the disease (e.g., based on the results of in vitro antibiotic sensitivity testing). Because treatment of clinical syndromes is very often initiated empirically (before the causative agent or underlying condition has been identified), it would be very difficult if not impossible to test clinically a new therapeutic agent or method for one particular bacteria (e.g., staphylococcus). Rather, a new therapeutic method must be tested for a particular clinical syndrome. It is important to note that, for any given infectious syndrome, several different infectious agents or underlying conditions may be potential causative effectors of the disease. In the art of pharmaceutical drug development, preclinical studies of a therapy evaluate the therapy's effects on not just one infectious agent or condition, but on multiple agents or conditions of interest. The results of the various (sometimes equivocal) studies are weighed as to the benefits and risks of the particular therapy given the medical knowledge of the risks associated with a particular disease. It is common that not all patients with a syndrome are cured by a single therapy, but instead, that a subset of patients may exist wherein the therapy has a positive and favorable result. Examples of clinical syndromes in which subsets of patients may find favorable outcomes from the subject therapies of the invention are disclosed in the following several paragraphs.

Representative uses of the subject methods for treating an immunocompromised subject may alleviate symptoms such as susceptibility to one or more opportunistic bacterial or viral infections including those caused by Pneumocystis, cytomegalovirus, herpes virus, Staphylococcus, and the like. In one embodiment, a patient is administered an amount of R'-Glu-Trp-R" sufficient to induce an increase in either the total number of lymphocytes, T-lymphocytes, $CD4^+$-lymphocytes, $CD8^+$-lymphocytes, and the like. Illustrative examples of immunocompromised patients who may benefit from the subject treatment methods are provided in the Examples section including: i) patients with cancer following radiation therapy, i.e., breast cancer patients and patients with thoracic cavity tumors and other cancers after radiation therapy (EXAMPLE 3, Protocols A-C); ii) patients having occupational radiation exposure (EXAMPLE 12, Protocols A and B); and, iii) patients following adult thymectomy (EXAMPLE 24). Illustrative examples of other immunocompromised patients who may benefit from the subject treatment methods include patients having one or more temporary immune defects resulting from a chronic or acute infection patients having i) chronic bacterial infections with *M. leprae* or *M. tuberculosis* (EXAMPLES 18 and 21, respectively); ii) chronic hepatitis B virus infections (EXAMPLE 25, Protocol B); patients having pyelonephritis and prostatitis (EXAMPLE 17); osteomyelitis (EXAMPLE 16); and psoriasis (EXAMPLE 6).

Representative uses of the subject methods for treating a subject also include treatments designed to promote wound healing include treatments for, e.g., epithelial, mucosal, and bone defects. Illustrative examples of patients who may benefit from the subject treatment methods include patients having duodenal or gastric ulcers (EXAMPLE 23), bone fractures (EXAMPLE 16); and, epithelial defects including those resulting from leprosy (EXAMPLE 18), psoriasis, burns and frostbite (EXAMPLE 6).

Representative uses of the subject methods for treating a subject also include treatments designed to reduce systemic toxicity, e.g., manifested by symptoms of fever, chills, migraine headaches, muscle aches and the like. Illustrative examples of patients who may benefit from the subject treatment methods include patients having jaundice with systemic toxicity (EXAMPLE 25); toxemia associated with complications of pregnancy (EXAMPLE 7); and, fever, chills, and systemic toxicity associated with malarial infection or Dengue virus infection (EXAMPLES 19 and 20, respectively).

Representative uses of the subject methods for treating a subject also include treatments of patients with allergic disease states, including patients with acute respiratory allergic reactions, urticaria, hives, hay fever, asthma, and the like (EXAMPLES 14 and 22, below).

Representative uses of the subject methods for treating a subject also include treatments of patients with graft-versus-host disease. Bone marrow transplant patients may be treated according to the methods of the invention to lessen the immunoreactivity of the transplanted immunologically-active cells against the host tissue.

Representative uses of the subject methods for treating a subject also include treatments of patients with dental caries, gingivitis, and periodontitis. Illustrative uses of the subject methods in treatment of patients with gingivitis and periapical granulomas is disclosed in EXAMPLE 9 (Protocols A and C).

The pharmaceutical compositions of the invention are intended for parenteral, topical, subcutaneous, intramuscular, intrathecal, oral, intranasal, or local administration for prophylactic and/or therapeutic treatment. Preferably, the compositions of the present invention are administered intramuscularly or intranasally. The subject R'-Glu-Trp-R" compositions herein have the advantage of providing the desired effects at very low dosage levels and without toxicity. Thus, a purpose of therapy in an acute setting may be to rapidly increase the concentration of R'-Glu-Trp-R" in a tissue, e.g., by bolus intravenous injection or infusion. Alternatively, in other cases it may desirable to deliver R'-Glu-Trp-R" over a longer period of time.

The subject compositions containing R'-Glu-Trp-R" may be formulated in a manner that allows absorption into the blood stream. The present compositions are immunomodulators that induce changes at the cellular level that subsequently effect changes in cellular processes that no longer are dependent on the presence of the composition. So, in many instances it has been observed that the effects of the peptide are long-lasting, i.e., for weeks to months, despite the rather rapid degradation of the peptide, e.g., within minutes or hours. Although the subject R'-Glu-Trp-R" compounds are themselves water-soluble at the low concentrations in which they are usually employed, they are preferably used in the form of their acid or alkaline salts formed with pharmaceutically acceptable agents, e.g., acetic, citric, maleic, succinic acid, sodium, potassium, ammonium, or zinc (as disclosed in greater detail below). Freely-soluble salts of the subject R'-Glu-Trp-R" compositions may also be converted to salts of low solubility in body fluids, e.g., by modification with a slightly water-soluble pharmaceutically acceptable salt like tannic or palmoic acid, or by inclusion in a time-release formulation with covalently coupling to a larger carrier, or inclusion in timed-release capsule and the like.

The active dipeptide ingredient of the pharmaceutical preparations according to the present invention may be used as a free peptide or in the form of a water soluble pharmaceutically acceptable salt, such as a sodium, potassium, ammonium or zinc salt. It will be understood that the dipeptide may be administered with other active ingredients which independently impart an activity to the composition, such as, antibiotics, interferon, anesthetics, and the like. Pharmaceutically acceptable salts may be conveniently prepared from EW dipeptide or analogs by conventional methods. Thus, such salts may be, for example, prepared by treating EW dipeptide with an aqueous solution of the desired pharmaceutically acceptable metallic hydroxide or other metallic base and evaporating the resulting solution to dryness, preferably under reduced pressure in a nitrogen atmosphere. Alternatively, a solution of EW dipeptide may be mixed with an alkoxide to the desired metal, and the solution subsequently evaporated to dryness. The pharmaceutically acceptable hydroxides, bases, and alkoxides include those with cations for this purpose, including (but not limited to), potassium, sodium, ammonium, calcium, and magnesium. Other representative pharmaceutically acceptable salts include hydrochloride, hydrobromide, sulfate, bisulfate, acetate, oxalate, valarate, oleate, laurate, borate, benzoate, lactate, phosphate, tosulate, citrate, maleate, furmarate, succinate, tartrate, and the like.

For parenteral administration, the present invention provides pharmaceutical preparations which comprise a solution of a tryptophan-containing dipeptide, polymeric, multimeric, cyclic or derivative form thereof, dissolved in a pharmaceutically acceptable carrier, preferably an aqueous carrier. A variety of aqueous carriers may be used, e.g., water, buffered water, 0.4% saline, 0.3% glycine, and the like, including proteins and/or glycoproteins for enhanced stability, such as albumin, lipoprotein, globulin, and the like. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. It may be desirable to stabilize EW dipeptides, analogs, receptor fragments, and the like to increase their shelf life and pharmacokinetic half-life. Shelf life stability is improved by adding excipients such as: a) hydrophobic agents (e.g., glycerol); b) sugars (e.g., sucrose, mannose, sorbitol, rhamnose, xylose); c) complex carbohydrates (e.g., lactose); and/or d) bacteriostatic agents. Pharmacokinetic half-lifes of peptides are modified by coupling to carrier peptides, polypeptides, and carbohydrates by chemical derivatization (e.g., by coupling side chain or N- or C-terminal residues), or chemically altering the amino acid to another amino acid (as above). Pharmacokinetic half-lifes and pharmacodynamics may also be modified by: a) encapsulation (e.g., in liposomes); b) controlling the degree of hydration (e.g., by controlling the extent and type of glycosylation of the peptide); and, c) controlling the electrostatic charge and hydrophobicity of the peptide.

A presently most preferred formulation according to the instant invention is a solution for intramuscular injection containing about 0.001 to 0.01% by weight (0.0001–0.001 mg/kg body weight, or 10–100 μg active ingredient per 1 mL solvent).

The pharmaceutically acceptable vehicle for this injection form may be any pharmaceutically acceptable solvent such as 0.9% aqueous sodium chloride, distilled water, Novocaine solution, Ringer's solution, glucose solution, and the like. The dipeptide containing compositions according to the present invention may be administered with a compatible pharmaceutical suitable for parenteral administration (e.g., intravenous, subcutaneous, or intramuscular). The preparations may be subjected to conventional pharmaceutical operations, such as sterilization, and may contain adjuvants, such as preservatives, stabilizers, wetting agents and the like. The peptides in the present compositions are typically biologically active at a dose of about 0.5 μg/kg to about 10 μg/kg, preferably about 1 μg/kg to about 5 μg/kg. The concentration of the peptides in these pharmaceutical compositions can vary widely, i.e., from about 0.001% to as much as 15 or 20% by weight and will be selected primarily by fluid volumes, viscosities, etc., in accordance with the particular mode of administration selected. When utilized intramuscularly as an injection, the solution has the active ingredient in a therapeutically effective immunopotentiating amount of about 0.001 to 0.01% by weight. If prepared in the form of a tablet, capsule or suppository, it is preferred that the active ingredient be present in an amount of about 0.1 mg per tablet, suppository or capsule. In such form, the capsule, suppository or tablet may also contain other conventional excipients and vehicles such as fillers, starch, glucose, etc. In topical preparations, the peptides are generally contained in urea-based emollients, petroleum-based ointments, and the like at concentrations of about 0.1 to 10,000 parts per million, preferably about 1 to 1000 parts per million, and most preferably about 10 to 100 parts per million. Actual methods for preparing parenterally, orally, and topically administrable compounds will be known or apparent to those skilled in the art and are described in detail in, for example, Remington's Pharmaceutical Science, 17th ed., Mack Publishing Company, Easton, Pa. (1985), which is incorporated herein by reference.

Intramuscular and intranasal routes are preferred for administration of the subject R'-Glu-Trp-R" compositions. One preferred dosage of the subject composition for intramuscular administration is about 50 μg to 100 μg per dose for adults (for a 300 μg to 1000 μg total treatment therapy); for infants up to 1 year old about 10 μg per dose, for infants 1 to 3 years old about 10 μg to 20 μg per dose; for infants 4 to 6 years old about 20 μg to 30 μg per dose, for children 7 to 14 years old about 50 μg per dose. All of the foregoing dosages are useful for a treatment of 3 to 10 days, depending upon the immunodeficiency level. The treatment may be repeated as needed, usually within 1 to 6 months. In another preferred embodiment, a treatment dose of about 10 μg/kg to about 1 mg/kg of a pharmaceutical preparation of R'-Glu-Trp-R" is administered to a subject daily over a period of about 6 days to about 10 days, but optionally at the discretion of the attending physician, for up to about 30 days. In one preferred course of therapy, R'-Glu-Trp-R" is administered im daily at a dosage of 1–100 μg/kg for 5–7 days, followed by a 1–6 month intermission before repeating the same injection regimen.

The subject methods include those in which the R'-Glu-Trp-R" are administered by injection, e.g., by parenteral, intramuscular, intradermal, subcutaneous, and intraperitoneal injection. In a most preferred embodiment, the treatment dose is sufficient to increase a number or percentage of $CD2^+$ or Fc-receptor-bearing lymphocytes in peripheral blood or in a reticuloendothelial tissue, or to increase a number of immune cells in an inflammatory infiltrate, or to increase a proportion of phagocytically active cells in an inflammatory infiltrate.

For embodiments where the subject compositions of the invention is intended for treatment of an infectious disease in a subject, an amount is administered that is sufficient to cure or at least partially arrest the disease and its complications. An amount adequate to effect this therapeutic result in more than 50% of subjects so treated is defined as a "therapeutically effective dose." Amounts effective for this use will depend on the severity of the infection or disease and the weight and general state of the patient being treated, but generally range from about 0.1 mg/kg to about 5000 mg/kg host body weight of R'-Glu-Trp-R" dipeptide per day, more commonly about 0.2 mg/kg to about 1000 mg/kg host body weight of dipeptide per day, usually about 0.5 μg/kg to about 100 4μg/kg host body per day, more usually about 0.75 μg/kg to about 20 μg/kg host body weight per day, and preferably about 1 μg/kg to about 10 μg/kg host body weight per day. Maintenance dosages over a prolonged period of time may be adjusted as necessary. Typical total daily doses are about 50 to 100 μg in adults, about 50 μg in children 7–14 years of age, about 20–30 μg in children 4 to 6 years of age, about 10–20 μg in children 1–3 years of age and about 10 μg in children less than one year of age. The compositions may be administered once daily or more often as desired. Treatment of acute conditions generally will occur over about 3–10 days. Treatment of chronic conditions or prophylactic treatments have the same course, but can be repeated after as long as about 1–6 months or longer. In some instances, it may be desirable to administer the compositions intermittently on a daily basis for periods of about 2 to about 20 days, preferably about 3 to about 14 days, more preferably about 4 to about 10 days which are repeated at least about 15 days, preferably about 20 days or as much as about 1 to 6 months or more.

The route of delivery of R'-Glu-Trp-R" dipeptides and the like is determined by the disease and the site where treatment is required. For topical application it may be desirable to apply the dipeptide, analogs, agonists, and antagonists at the local site ((e.g., by placing a needle into the tissue at that site) or by placing an impregnated bandage during surgery); while for more advanced diseases it may be desirable to administer the compositions systemically. For other indications, the R'-Glu-Trp-R" dipeptides, analogs, agonists, antagonists, derivatives and the like may be delivered by intravenous, intraperitoneal, intramuscular, subcutaneous, intranasal, and intradernal injection, as well as, by intrabronchial instillation (e.g. with a nebulizer), transdermal delivery (e.g., with a lipid-soluble carrier in a skin patch), or gastrointestinal delivery (e.g., with a capsule or tablet).

In general, the acid addition salts of the subject R'-Glu-Trp-R", e.g., L-Glu-L-Lys, compositions with pharmaceutically acceptable acids will be biologically equivalent to the subject compositions themselves.

The preferred therapeutic compositions, inocula, routes, and dosages will vary with the clinical indication. For intramuscular injection, the inoculum is typically prepared from a dried peptide (or peptide conjugate) by suspending the peptide in a physiologically acceptable diluent such as water, saline, or phosphate-buffered saline. Some variation in dosage will necessarily occur depending upon the condition of the patient being treated, and the physician will, in any event, determine the appropriate dose for the individual patient. The effective amount of peptide per unit dose depends, among other things, on the body weight, physiology, and chosen inoculation regimen. A unit dose of peptide refers to the weight of peptide without the weight of carrier (when carrier is used). An effective treatment will be achieved when the concentration of R'-Glu-Trp-R" dipeptide, e.g., L-Glu-L-Trp, at a tissue site in the microenvironment of the cells approaches a concentration of $10^{-5}$ M to $10^{-9}$ M. Skilled practitioners can make use of clinical and laboratory indicia to monitor patient response to the subject therapy and adjust the dosage accordingly. Since the pharmacokinetics and pharmacodynamics of R'-Glu-Trp-R" dipeptides, agonists, antagonists, and the like will vary in different patients, a most preferred method for achieving a therapeutic concentration in a tissue is to gradually escalate the dosage and monitor the clinical and laboratory indicia. The initial dose, for such an escalating dosage regimen of therapy, will depend upon the route of administration. For intravenous administration, of R'-Glu-Trp-R" dipeptide with an approximate molecular weight of 200 to 400 daltons, an initial dosage of approximately 0.1 mg/kg body weight is administered and the dosage is escalated at 10-fold increases in concentration for each interval of the escalating dosage regimen.

For prophylactic uses against opportunistic infections in immunodeficient or immunodepressed patients, the intramuscular and/or intranasal single daily dose for adults may be from about 50 to 10μg, and for children about 10 μg to 50 μg per dose for treatment over 3 to 5 days.

For treatment of burns, frost bite, or other wounds, including chronic apical periodontitis, the dipeptide may be applied in about 100 μg doses as a paste or other suitable medium.

For ophthalmology, such as for treatment of infectious eye diseases, the dipeptide may be applied in single daily dosages of about 10 μg (over 4 to 1 days) or as installations into the conjunctival cavity at about 5 μg twice daily over about 4 to 5 days.

The dipeptide may be injected intramuscularly in an injection solution having a therapeutically effective immunomodulatory amount of about 0.001 to 0.01% by weight of the subject R'-Glu-Trp-R" composition. If presented in the form of a tablet, capsule or suppository, it is preferred that the active ingredient be present in an amount of about 0.1 mg per tablet, suppository or capsule. If presented in such form, the capsule, suppository or tablet may also contain other conventional excipients and vehicles such as fillers, starch, glucose, etc.

Conveniently, the subject R'-Glu-Trp-R" dipeptide is synthesized by any of a number of automated techniques that are now commonly available. Generally speaking, these techniques involve stepwise synthesis by successive additions of amino acids to produce progressively larger molecules. The amino acids are linked together by condensation between the carboxyl group of one amino acid and the amino group of another amino acid to form a peptide bond. To control these reactions, it is necessary to block the amino group of one amino acid and the carboxyl group of the other. The blocking groups should be selected for easy removal without adversely affecting the peptides, i.e., by racemization or by hydrolysis of the formed peptide bonds. Amino acids with carboxyl- groups (e.g., Asp, Glu) or hydroxylgroups (e.g., Ser, homoserine, and Tyr) also require blocking prior to condensation. A wide variety of procedures exist for synthesis of peptides, solid-phase synthesis usually being preferred. In this procedure an amino acid is bound to a resin particle, and the peptide generated in a stepwise manner by successive additions of protected amino acids to the growing chain. Modifications of the technique described by Merrifield are commonly used (Merrifield, R. B., *J. Am. Chem. Soc.*, 96: 2989–2993, 1964)). In an exemplary automated solid-phase method, peptides are synthesized by loading the carboxy- terminal amino acid onto an organic linker (e.g., PAM, 4-oxymethyl phenylacetamidomethyl) covalently attached to an insoluble polystyrene resin that is cross-linked with divinyl benzene. Blocking with t-Boc is used to protect the terminal amine, and hydroxyl- and carboxyl- groups are commonly blocked with 0-benzyl groups. Synthesis is accomplished in an automated peptide synthesizer (Applied Biosystems, Foster City, Calif., e.g., Model 430-A). Following synthesis the product may be removed from the resin and blocking groups removed using hydrofluoric acid or trifluoromethyl sulfonic acid according to established methods (Bergot, B. J. & S. N. McCurdy, *Applied Biosystems Bulletin* (1987)). A routine synthesis can produce 0.5 numole of peptide-resin. The yield following cleavage and purification is approximately 60 to 70%. For example, an amino and side chain protected derivative of an activated ester of Glx is reacted with side-group protected Trp, attached to the solid phase at its C-terminus. After elimination of the alpha-amino protecting group, the peptide may be cleaved from the solid phase or another amino acid added in a similar fashion. Additional amino acids are serially added in a similar fashion. The peptides are then cleaved by acid that also typically removes protecting groups. The peptides may then be isolated and lyophilized and stored for future use. Suitable techniques of peptide synthesis are described in detail in Stewart & Young, SOLID PHASE PEPTIDE SYNTHESIS, 2d edition, Pierce Chemical Company, 1984; and Tam, et al., *J Am. Chem. Soc.* 105:6442 (1983), both of which are incorporated herein by reference. Purification of the product peptides is accomplished, for example, by crystallizing the peptide from an organic solvent such as methyl-butyl ether, followed by dissolving in distilled water, and dialysis (if the molecular weight of the peptide is greater than about 500 daltons), thin layer chromatography, gel chromatography, lyophilization, or reverse HPLC (e.g., using a C18 column with 0.1% trifluoroacetic acid and acetonitrile as solvents) if the molecular weight of the peptide less than 500 daltons. Purified peptide is lyophilized is stored in a dry state until use. A representative R'-Glu-Trp-R" pharmaceutical preparation is the purified dipeptide L-Glu-L-Trp, which comprises a white powder (if lyophilized; otherwise, it is crystalline), soluble in water, DMF; insoluble in chloroform and ether. [$alpha2_D$=+12.6; C=0.5 $H_2O$. $R_f$=0.65 (butanol: acetic acid: water=3:1:1). UV (275±5nm, max). NMR (500MHz): 0.0001 mol/l of the peptide solution, Trp (3.17; 3.37; 4.57; 7.16; 7.24; 7.71; 7.49); Glu (1.90; 1.96; 2.21; 3.72)].

Typically an amino and side chain protected derivative of an activated ester of glutamic acid is reacted with protected L-tryptophan. After elimination of the protecting groups and conventional purification, such as by thin layer or GL chromatography, the peptide may be purified such as by, lyophilization, gel purification, and the like.

The compounds may be administered alone or formulated with pharmaceutically acceptable carriers, in either single or multiple doses. Suitable pharmaceutical carriers include inert solid diluents or fillers, sterile aqueous solutions, and various nontoxic organic solvents. Pharmaceutical compositions can be formed by combining R'-Glu-Trp-R" dipeptide with a pharmaceutically acceptable carrier and an optional antibiotic. The subject combination therapeutic agents can then readily be administered in a variety of dosage forms such as tablets, lozenges, syrups, injectable solutions, and the like. Combination therapeutic agents may also include R'-Glu-Trp-R" dipeptide, e.g., L-Glu-L-Trp, in the same unit dosage form. Pharmaceutical carriers can, if desired, contain additional ingredients such as flavorings, binders, excipients, and the like. Thus, for purposes of oral administration, tablets containing various excipients such as sodium citrate, calcium carbonate, and calcium phosphate may be employed along with various disintegrants such as starch, and preferably potato or tapioca starch, alginic acid, and certain complex silicates, together with binding agents such as polyvinylpyrrolidone, sucrose, gelatin, and acacia. Additionally, lubricating agents, such as magnesium stearate, sodium lauryl sulfate, and talc are often useful for tableting purposes. Solid compositions of a similar type may also be employed as fillers in salt and hard-filled gelatin capsules. Preferred materials for this purpose include lactose or milk sugar and high molecular weight polyethylene glycols. When aqueous suspensions of elixirs are desired for oral administration, the essential active R'-Glu-Trp-R" dipeptide therein may be combined with various sweetening or flavoring agents, colored matter or dyes, and if desired, emulsifying or suspending agents, together with diluents such as water, ethanol, propylene glycol, glycerin, and combinations thereof. For parenteral administration, solutions of R'-Glu-Trp-R", analogs, or receptor fragments in sesame or peanut oil or in aqueous polypropylene glycol may be employed, as well as sterile aqueous saline solutions of the corresponding water soluble pharmaceutically acceptable metal salts previously described. Such an aqueous solution should be suitably buffered if necessary and the liquid diluent first rendered isotonic with sufficient saline or glucose. These particular aqueous solutions are especially suitable for intravenous, intramuscular, subcutaneous, and intraperitoneal injection. The sterile aqueous media employed are all readily obtainable by standard techniques well known to those skilled in the art. Additionally, it is possible to administer the aforesaid compounds topically (e.g., through a placed catheter) using an appropriate solution suitable for the purpose at hand.

The following examples are provided to further elucidate the invention, but are not intended to restrict the invention in scope or spirit in any way. Experimental animal trials (disclosed herein in EXAMPLES 26–36) determined the effects of L-Glu-L-Trp at dosages of about 10 $\mu$g/kg to about 1 mg/kg on different lymphocyte subpopulations and lymphoid organs in vivo. The results of the studies disclosed in EXAMPLES 26–36 are summarized in TABLES A-D. The results indicate that in an experimental animal model, treatments with L-Glu-L-Trp at a dosage of about 0.1 mg/kg to about 1 mg/kg was effective i) to increase $CD2^+$ lymphocytes in peripheral blood by about 3-fold; ii) to increase Fc receptor bearing lymphoid cells in spleen and bone marrow (BM) by about 1.3-fold and about 1.7-fold, respectively (TABLE A); iii) to mobilize cells from the spleen and thymus into peripheral blood with resultant reduction in spleen and thymic mass (TABLE B); and, iv) to increase neutrophil infiltration into tissues in response to an inflammatory agent by about 2-fold with about a 1.7-fold increase in phagocytically active cells in the infiltrate (TABLE C).

TABLE A

| CD2+ and Fc-Receptor Lymphocytes in Treated Guinea Pigs | | |
|---|---|---|
| Lymphoid Organ | CD2 + L-Glu-L-Trp Treatment | Fc-receptor + L-Glu-L-Trp Treatment |
| Thymus | ns | ns |
| Spleen | ns | 1.7 × ↑ ($p < 0.05$) |
| LN | 32% ↓ ($p < 0.05$) | ns |
| BM | 50% ↓ ($p < 0.05$) | 1.3 × ↑ ($p < 0.05$) |
| PBL | 3 × ↑ ($p < 0.05$) | ns |

*ns, no statistically significant change; CD2+ lymphocytes (E-RFC), results presented in EXAMPLE 28 (TABLE 51), below; Fc-receptor lymphocytes (EA-RFC), results presented in EXAMPLE 29 (TABLE 52), below.

TABLE B

| Splenic and Thymic Mass in Treated Mice* | |
|---|---|
| Lymphoid Organ | L-Glu-L-Trp Treatment |
| Thymus | 44% ↓ ($p < 0.01$) |
| Spleen | 15% ↓ ($p < 0.05$) |

*ns, no statistically significant change; results presented in EXAMPLE 30 (TABLE 54), below.

TABLE C

Neutrophils Induced by a
Sterile Inflammatory Agent in Treated Mice*

| Neutrophil Index | L-Glu-L-Trp Treatment |
|---|---|
| Total cells X10$^6$ | 2 × ↑ ($p < 0.05$) |
| Phagocytic cells (%) | 1.7 × ↑ ($p < 0.05$) |
| Phagocytic Index | ns |

*ns, no statistically significant change; results presented in EXAMPLE 30 (TABLES 58–59), below.

The results shown in the Examples section, disclose effects of L-Glu-L-Trp treatments on lymphocytes, macrophages and neutrophils (EXAMPLES 26–31) as follows: i) activating anti-microbial activity of resident macrophages (EXAMPLE 30); ii) promoting of neutrophil infiltration into tissues in response to inflammatory agents (EXAMPLE 30); iii) stimulating formation of antibody forming cells in the spleen (EXAMPLE 31); iv) enhancing responsiveness of T-lymphocytes (EXAMPLES 26–30); v) mobilizing lymphocytes from lymph nodes (and from tissues) into peripheral blood and spleen (EXAMPLE 30); and, vi) mobilizing lymphocytes from bone marrow and thymus into peripheral blood (EXAMPLE 30). The observed respective immunologic effects of L-Glu-L-Trp are compatible with the interpretation that the subject treatments of the invention heighten the state of innate immunity to infection in a subject so treated.

In certain therapeutic uses it may prove useful to monitor dipeptide levels in bodily fluids while escalating the dose delivered to the patient. The representative R'-Glu-Trp-R" dipeptide, e.g., L-Glu-L-Trp, is non-mutagenic in vitro, non-toxic to human and guinea pig lymphocytes in vitro, non-toxic when in injected intraperitoneally into guinea pigs and mice, and without adverse effects in human preclinical trials, as disclosed in the EXAMPLES.

The amino acid sequence of the R'-Glu-Trp-R" dipeptide permits preparation of appropriate nucleotide sequences (e.g., by standard techniques), and incorporation of these sequences into bacterial, yeast, and insect plasmid DNA, as well as into mammalian cell viral vectors (e.g., retroviral vectors.) Expression systems that may be used to produce the peptides of the invention include prokaryotic, eukaryotic, yeast, and insect cells. It is presently believed likely that EW is a cytomedine released from hydrolysis of tissue polypeptides, at a rate homeostatically determined by tissue pH and enzymatic activity in the tissues. The present disclosure serves as a useful basis for constructing derivatized and covalently modified EW analogs, antagonists, and the like which can be screened and tested for biological activities. For example, EW may be used for preparation of an analog that is, e.g., a) covalently modified by adenylation, methylation, acylation, phosphorylation, uridylation, fatty-acylation, glycosylation, and the like; b) a sterioisomer of an L-Glu-L-Trp, e.g., replacing a D- for an L-sterioisomer, and the like; c) a derivative of EW, wherein one amino acid is substituted for another of like properties, ie., a neutral nonpolar amino acid for another neutral nonpolar (e.g., W replaced by S, T, Y, N, Q, or C), an acidic amino acid for another acid (e.g., E replaced by D), or a basic amino acid for another basic (e.g., K replaced R or H); d) a chemically modified form of EW, e.g., a C-terminal (or gamma-carboxyl) group modified to a carbonyl, or an N-terminal group modified to an amide, or N- or C-terminal extension with Sar or gamma-amino butyric acid (GABA); e) a chemically derivatized form of EW, e.g., covalent coupling of the IM peptide to a larger peptide (or polypeptide) carrier, or an N- or C-terminal extended peptide; or, f) replacing one amino acid with another of slightly different properties, e.g., changing the hydrophobicity of the dipeptide. Alternative methods for identifying the subject R'-X-Trp-R" dipeptides of the invention are disclosed in U.S. Ser. No. 08/370,838, incorporated herein by reference.

"Analog" is intended to mean a chemical compound according to Formula I–III, that mimics or improves on the electronic, steric, hydrophobic, and 3-dimensional space filling requirements of the groups in an EW dipeptide that are involved in binding to a cellular EW-receptor (e.g., alpha side chain residues, and/or the amino and carboxyl groups in L-Glu-L-Trp). Representative analogs include chemical mimetic compounds that are capable of antagonizing binding of EW to a ligand-receptor, i.e., antagonists (as defined below), and other ligands that are capable of binding to a ligand receptor and exerting effects similar to EW, i.e., agonists (as defined below).

"Agonist" as used herein means a chemically modified EW, or organic chemical molecule according to Formula I-III, that is capable of spacially conforming to the molecular space filled by an EW ligand and that is further capable of combining with the subject ligand receptors to initiate an action that is initiated by EW following binding to their specific ligand receptor(s) on cells in vitro or in vivo. Representative examples of actions initiated by EW may be: i) upregulation of lymphocyte cell surface determinants such as CD2, CD4, CD28, CD45, CD58, CD59, LFA 1, ICAM 1, ICAM 2, ICAM 3, and the like; ii) macrophage activation; iii) stimulating (or inhibiting) lymphocyte blastogenesis in response to antigen (or mitogen), iv) stimulating release of interleulins from lymphocytes (e.g., IL2, IHA, IL5, IL6, IL10, IFNγ, TGFβ, and the like); v) mobilization of intracellular calcium (e.g., through membrane calcium channels) and cAMP; vi) stimulating cell interactions between T-helper lymphocytes, B-lymphocytes and antigen presenting cells in initiation of primary and secondary humoral (antibody-mediated) immune responses; vii) stimulation of macrophages to increase their antibacterial and cytotoxic activities to microbial and mammalian target cells, and the like. Agonists possess binding affinity for ligand-receptor(s) and intrinsic activity for inducing the immune effects that are induced when EW bind to their ligand receptor. A screening assay for identifying a candidate R'-Glu-Trp-R" agonist, may consist of the following steps: (a) synthesizing a chemical mimetic compound, e.g., a compound of Formula I, II, or III; (b) introducing the compound into a T-cell rosette assay as a test article; and (c) determining that the test article has an activity substantially similar to the activity of L-Glu-L-Trp in the T-cell rosette assay.

"Antagonist" as used herein means a chemical molecule according to Formula I–III, that spacially conforms to the molecular space filled by EW and is further capable of combining with the subject ligand receptor(s), as set forth above, to inhibit, neutralize, impede or reverse, at least in part, an action initiated following binding of EW to the subject ligand receptor on a lymphocyte or a macrophage. A screening assay for identifying a candidate R'-Glu-Trp-R" antagonist analog, may consist of the following steps: (a) synthesizing a chemical mimetic compound, e.g., a compound of Formula I, II, or III; (b) introducing the analog into a T-cell rosette assay as a test article; and (c) determining that the test article inhibits the activity of L-Glu-L-Trp in the T-cell rosette assay.

Screening assays for analogs, e.g., antagonists and agonists, may include comparative testing of the subject test articles for biological activities exhibited by L-Glu-L-Trp in vivo in experimental animal model systems (e.g., Examples 1–44). Alternatively, it may prove convenient to monitor activities of the test agents in in vitro assays wherein L-Glu-L-Trp have been shown to exhibit biologic activity, e.g., changes in calcium flux or cyclic nucleotide levels, and changes in intracellular second messenger pathways triggered by the addition of L-Glu-L-Trp to lymphocytes. Biological activity of a compound according to Formula II or Formula III of Example 45 may for example be determined by testing for second messenger pathways triggered by receptor binding the subject compound. Second messenger pathways may be monitored, e.g., by testing intracellular levels of $Ca^{++}$, cAMP, cGMP, adenyl cyclase, tyrosine kinase, guanylate cyclase, protein kinase, phosphorylase A, protein kinase C; or, cellular release of interleukins, arachidonic acid metabolites, prostaglandins, and the like.

The present disclosure of significant biological effects of EW dipeptides on immune cells also serves as basis for isolating cell surface receptors binding EW, and for identifying other ligands in biological fluids which may bind to the subject receptors.

"Ligand" as used herein refers to a compound that is capable of filling the three-dimensional space in a receptor binding site so that electrostatic repulsive forces are minimized, electrostatic attractive forces are maximized, and hydrophobic and hydrogen bonding forces are maximized. L-Glu-L-Trp is a representative ligand. Ligands bind to their specific receptors in a specific and saturable manner. A candidate ligand may be tested to determine whether it is an analog by radiolabeling the candidate ligand and then testing whether its binding to lymphocytes is specifically and competitively inhibited in the presence of an excess (e.g., 1000-fold molar excess) of unlabeled L-Glu-L-Trp. Alternatively, a test may be conducted to determine whether the candidate ligand inhibits binding of radiolabeled L-Glu-L-Trp to lymphocytes. A positive test result in either assay may be taken as an indication that the candidate ligand is an analog. A negative test result in either assay is indeterminant.

"Ligand receptor" is used herein to refer to a receptor capable of binding a ligand, according to the definition above, in a specific and saturable manner. In an illustrative assay for identifying a ligand receptor in a sample of cells, a labeled ligand (e.g., a radiolabeled or biotin-labeled L-Glu-L-Trp) at a concentration from within the range of 0.1 nM to 10 mM, is incubated at room temperature, 37° C., and 4° C. with an aliquot of about $10^5$–$10^7$ cells. Following the incubation, the cells are washed (e.g., by centrifugation through an isobutylpthalate or sucrose cushion) and the amount of labeled ligand associated with the cell pellet is determined (e.g., by quantifying radioactivity or reacting the sample with enzymatically-labeled avidin, washing to remove unbound avidin, and then adding substrate to visualize the enzyme-bound-avidin-biotin receptor complex). The data obtained in this manner may be plotted in a Scatchard plot from which an association constant of the receptor for the ligand may be determined. The association constant for binding of a ligand (e.g., EW dipeptide) is about 0.01 nM to about 1 mM, and most preferably about 1 nM to about 50 $\mu$M. Affinity chromatography e.g., on solid phase resins containing immobilized EW dipeptide (EW-resin), may prove useful for preparing substantially purified preparations of the subject EW receptors and their fragments. Purified EW receptors and receptor fragments may be useful as pharmacological inhibitors, antagonists, and agonists of EW dipeptide binding in vivo. Receptor fragments may for example be isolated by affinity chromatography of crude cell and tissue hydrolysates on EW-resin columns, or alternatively, by binding the receptor to an EW-resin and then treating with one or more selected proteases to create EW receptor fragments which are either eluted from the column (i.e., non-ligand binding portions of the receptor), or remain ligand-binding portions which remain bound to the resin. The ligand-binding portions of the receptor may be eluted from the resin either by raising the salt concentration (e.g., to 1–4 M NaCl, or 0.5–2 M guanidine HCl) to negate electrostatic binding interactions, or by dropping the pH to induce a conformational change in the receptor fragment. The amino acid sequence of the EW receptor is conveniently determined by automated amino acid sequencing, and the sequence may be used to construct synthetic peptides, and nucleotide probes (e.g., degenerate probes) for cloning the subject EW receptor.

"Ligand-receptor fragments" is a term used to refer to portions of the subject ligand receptor that are smaller in size than a ligand receptor isolated from a natural source, e.g., tissue, biological fluids and the like. Fragments may be prepared from a ligand receptor isolated from a tissue and then subjected to proteolytic degradation or treatment with a chemical such as cyanogen bromide. In the latter case, the subject fragments of the receptor are conveniently purified before use, e.g., by reverse-phase HPLC or immunoaffinity chromatography. Alternatively, fragments of the ligand receptor may be prepared by expressing a portion of a nucleotide sequence of a genomic or cDNA clone capable of expressing the subject ligand receptor, e.g., a portion of ligand receptor nucleotide sequence in an expression plasmid or vector introduced into a cell, wherein the cell manufactures the subject receptor fragment and the fragment can be purified (as above). Fragments of the subject ligand receptor may be soluble in biological fluids and aqueous solutions and may bind EW with a greater or lesser $K_D$ than a complete (non-degraded) ligand receptor.

"Substantially purified" as used herein with respect to peptides refers to a preparation from a natural source that contains either a "peptide" (i.e., intended to mean about 2 to about 18 amino acids), a ligand according to criteria set forth above, or a ligand receptor or receptor fragment that is: i) enriched greater than about 50-fold from its concentration in a natural source material, and ii) contains less than 5% peptide or polypeptide impurities detectable by reverse-phase HPLC, SDS-PAGE, or immunoassay.

The disclosure herein of biological activities of EW dipeptides provides a basis for identifying and isolating proteins that either proteolytically inactivate EW dipeptides, or that alter binding of these dipeptides to EW receptors. "EW-peptidase" are used herein to refer to dipeptidylpeptidases capable of catalyzing hydrolysis of the glutarnyl-tryptophane peptide bond. The subject enzymes inactivate EW peptides and render them biologically inactive. EW-peptidases may conveniently be purified from tissues and cells using conventional purification methods (e.g. affinity chromatography on EW-resin columns, as above, alternatively, ion exchange and/or molecular sieve chromatography using FPLC or HPLC systems). Purification may be monitored using calorimetric or fluorescent EW peptide substrates, and protease test assays. The subject protease test assays may, in turn, prove useful for identifying natural and synthetic inhibitors of EW-peptidases. The subject EW dipeptidylpeptidase inhibitors may have biological effects similar to EW, since they may decrease proteolytic degradation of EW dipeptide and thus increase the biological half-life of a natural EW dipeptide arising endogenously within a tissue.

The present disclosure further provides a basis for diagnostic immunoassays, antibody reagents and the like for measuring levels of EW in biological fluids. While the subject EW dipeptides are relatively nonimmunogenic, (falling into the class of low molecular weight haptens), antibodies may be induced in experimental animals when they are conjugated to a carrier (e.g., KLH). Polyclonal and monoclonal antibodies to EW find uses in a variety of immunoassay formats for diagnostic monitoring the levels of the subject dipeptides in bodily fluids in health and disease. Representative immunoassay formats include: enzyme linked immunoabsorbent assays (ELISA), radioimmunoassays (RIA), fluorescence immunoassay (FIA), time-resolved fluorescence assays (TRF), and cascade assay formats that are routinely used in the art for increasing low-end sensitivity of assays. Individuals with high levels of EW dipeptide may be at decreased relative risk for infectious disease, while those with decreased levels may be at an increased relative risk. The EW dipeptide can be used as a positive and a negative control in the subject diagnostic assays. The subject assays may be assembled for use in a reagent immunoassay test kit. The antibodies disclosed herein specific for EW may be useful in a variety of competitive and non-competitive direct and indirect immunoassay formats as will be apparent to skilled artisans. The level of EW in a biological sample is commonly determined by comparison with positive and negative controls and assay calibrators.

The term "biological fluids" is used herein to mean tissue fluids (such as joint fluid, cerebrospinal fluid and the like), plasma and serum, fluids in body cavities (i.e., peritoneal fluid, lung lavage fluid, urogenital mucus secretions, and the like), urine, feces, sputum, sweat, and the like.

While not wishing to be tied to any particular molecular mechanisms of action, cytomedines are believed to interact with cellular receptors. Traditionally, cellular receptors have been believed to bind specific ligands with a specific affinity. Binding (or non-binding) of the ligand to the cellular receptor is believed to induce certain cellular functions. It is further believed that cytomedines interact with these cellular receptors. In addition to the ligand-binding site, however, the receptors apparently have separate cytomedine-binding sites. It is believed that receptor-cytomedine binding can alter the conformation of the ligand-binding site so as to increase the affinity of the receptor for the ligand, thereby altering the response of the cell to a particular concentration of ligand within the microenvironment of the cell. Different cytomedines and different cytomedine concentrations can have varying effects on the binding affinity between the receptor and the ligand. Situations may exist in which cytomedine ligands interact with cellular receptors that have secondary binding sites for molecules other than the cytomedine, and in this case, the cytomedinetreceptor interaction may alter the binding for the other molecule. For example, when the dipeptide Glu-Trp interacts with T cells, there is an increase in receptor binding affinity for CD48, CD58, or CD59, and an accompanying increase of intracellular cAMP concentrations in the cells. Increased intracellular cAMP in turn activates intracellular protein kinase activity that is an important signal transduction pathway for activating transcription and translation of proteins necessary for lymphocyte activation and progression of the cell division cycle from GWG, into mitosis.

Tryptophan-containing dipeptides (e.g., EW, DW, NW, AW, QW, IW, SW, TW, SW, TW, GW, HEW, HW, LW, VW, EWEW, GEW, EGW, EWKHG, EWKKHG, EW-NH-NH-GHK-NH$_2$, Ac-L-Glu-L-Trp-OH, Suc-EW, Cpr-EW, But-EW, L-Glu-D-Trp, D-Glu-L-Trp, D-Glu-D-Trp, RKDVW, RKEVW, RKEWY, RKEW, KEWY, KEVW, KEW, GWY, pEW, and the like) may constitute improved delivery vehicles for the amino acid tryptophan. Tryptophan is convertible by tissue hydroxylase enzymes, e.g., liver phenylalanine hydroxylase, into 5-hydroxy-tryptamine (ie., serotonin) and by mono-amino oxidase enzymes into 5-hydroxy-indol-acetic acid in the pathway to melatonin. Serotonin is capable of binding to beta-adrenergic receptors, adrenoreceptors, serotonergic receptors, e.g., on endothelial cells, vascular and bronchial smooth muscle, neural cells, platelets, lymphocytes, CD 4$^+$-lymphocytes, and myocardial cells. Metabolically modified EW, e.g., modified to glutamyl-serotonin, may be rapidly hydrolyzed to release serotonin into tissues and blood.

While not wishing to be tied to any particular mechanism of action, it is believed likely that the subject tryptophan-containing peptides reversibly associate with specific cellular EW receptors, one example being provided by the T-lymphocyte E-rosette receptor defined as the "CD2" cell surface determinant. It is believed likely that binding of EW dipeptide to CD2 (and other EW receptors) trigger: i) conformational changes in the receptor that signal up-regulation of adenylate cyclase and increased intracellular cAMP; and, ii) increased affinity of the CD2 receptors for binding of EW dipeptides. It is presently believed likely that L-Glu-L-Trp exerts its immunomodulatory effects by stimulating increased expression and/or affinity of CD2 molecules on T-lymphocytes and thymocytes, and binding of L-Glu-L-Trp to EW-receptors. It is considered likely that increases CD2 expression or binding affinity. Intracellular mechanisms triggered by dipeptide binding to the receptor may mediate: (a) changes in lymphocyte tissue distribution, i.e., mobilization of one or more subsets from lymphoid tissues into peripheral blood, (b) activation of one or more lymphocyte subsets; and/or (c) down- or up-regulation of the functional activity of one or more lymphocyte subsets. The changes induced at a cellular and molecular level by a tryptophane-containing dipeptide may result in immune deviation, wherein an immune response (i.e., cellular or humoral) directed toward one antigen is down-regulated and a response to a different antigen is up-regulated. As disclosed in the Examples section, increased T-lymphocyte counts in peripheral blood is a visible manifestation of the mobilization from lymphoid tissues induced by treatment with EW dipeptides. Increased cytokine production, e.g., as assayed by leukocyte migration inhibition response (LMIR), is another particular manifestation of activated T-lymphocytes. Activation of mononuclear phagocytes (e.g., monocytes) is manifested by increased phagocytic activity, e.g., phagocytosis of latex or staphylococci, and activation of granulocytes is manifested as increased cell numbers in inflammatory exudates as well as increased phagocytic activity. Effects of tryptophane-containing dipeptides on immunoresponsiveness of animals and man are disclosed in the Examples which follow. It is considered possible that the CD2 receptor on lymphocytes may bind serotonin.

EXAMPLE 1

Lack of Mutagenicity and Toxicity of L-Glu-L-Trp

Note that the Materials and Methods used in Examples 1–34, below, appear immediately following Example 46, i.e., at the end of the Examples section immediately before the citations.

Protocol A

Mutagenicity

On peripheral blood of human volunteers in vitro. Cell cultures were incubated and treated. As can be seen from Table 1, after 24 hrs. incubation at concentrations of 1 μg/mL and 100 μg/mL, there was statistically no mutagenic effect in these cultures.

TABLE 1

Analysis of Possible Chromosomal Damage in Human Peripheral Blood Lymphocytes

| Dose | Number of analysed metaphases | Metaphases chromosome aberrations # | Metaphases chromosome aberrations % | Index of reliability* (P) | Level of mutagenic effect (numbers) |
|---|---|---|---|---|---|
| Control | 1000 | 15 | 1.5 | — | — |
| L-Glu-L-Trp −1 μg/ml | 1000 | 15 | 1.5 | >0.05 | 0 |
| L-Glu-L-Trp −100 μg/ml | 1000 | 16 | 1.6 | >0.05 | 0 |

*p > 0.05, not statistically significant difference from control cell preparations.

Protocol B

Acute Toxicity Studies

Summary

L-Glu-L-Trp, when injected im at dosages calculated to be about 10,000-times the therapeutic dosage, was non toxic in mice, guinea pigs, chickens, and dogs as determined by monitoring general condition, behavior, movements, cardiac and respiratory physiology, and gross pathology.

Protocol C

Chronic Toxicity Studies

Summary:

L-Glu-L-Trp when injected daily as a single im or iv for a period of 30 days was without adverse effects as determined by monitoring behavior, feeding, body weight, coat condition, mucous membranes, red and white cell blood counts, cardiac and respiratory physiology, liver and kidney function, and gross pathology. Kidney function was determined by evaluation of diuresis after water-loading; for certain other experiments animals were sacrificed and examined after 10, 20, 30, and 60 days.

EXAMPLE 2

Accidental Radiation Induced Inmunodeficiency: Chernobyl

Background:

On Apr. 26, 1986 the largest nuclear catastrophe of our time took place at 1:24 a.m. local time, destroying the fourth reactor of the Chernobyl nuclear power plant (NPP). The reactor and its core were reportedly destroyed by an explosion causing two radioactive jet emissions of Iodine131 followed by Cesium$^{137}$ and gamma emissions (Milhaud, G., Biomedicine & Pharmacology 45(6):219–220 (1991)). The accident reportedly cause the deaths of 31 workers and firemen who intervened to bring the installation back under control, 203 individuals were hospitalized with acute radiation sickness, and more than 135,000 persons were evacuated from the 30 km zone immediately adjacent to the NPP. Initial optimism that there would be no residual after affects, were not justified. Studies of individuals exposed to radiation at the Chernobyl NPP have reported doses of whole body exposure at 0.1–0.5 Gy for individuals involved in the clean-up; 4–9 Gy for power plant workers (Yarilyn, A.A., et al., Intl. J. Radiation Biology 63(4):519–528 (1993)); and a range of 0.1–12.5 Gy for accidental exposure of different individuals in the 135,000 inhabitants within the 30 km zone surrounding the NPP (Barkhudarov, R. M., Vestnik Akademii Meditsinskikh Nauk.SSSR 8:3–9 (1991)); Gruzdev, et al., Radiobiologiia 32(1):3–18 (1992)) Russian physicians treating the exposed individuals reported a correlation between the numbers of lymphocytes in peripheral blood and the severity of the acute radiation sickness, with an initial drop in the average numbers of lymphocytes to 50% of normal by day 3–6 post-exposure (Suvorova, L. A., et al., Radiobiologiia 31 291–6 (1991)). Decreased lymphocyte counts are reportedly correlated with the severity of radiation sickness (Hirsh, E. F., et al., World J Surgery 16(5): 918–923 (1992)). Hematological data have also been used to construct an empincal dose curve for gamma radiation exposure at Chernobyl and values reported for 127 of the former residents range from 0.5 Gy to 12 Gy (Konchalovskii, M. V., et al., Meditsinskai Radiologiia 36(1): 29–33 (1991)). For reference, 10 Gy is a 100% bone marrow lethal dose of radiation in mice as determined 30 days post-exposure (Hendrickson, F. R., et al., CLINICAL ONCOLOGY, eds: Holleb, A. I., et al., Amer. Cancer Soc., Atlanta, Ga., p. 42 (1992))). Human exposure to 2 Gy of whole body irradiation daily for 2 days (4 Gy total), has been reported to result in decreased erythrocyte and granulocyte precursors in bone marrow. Daily exposure to 2 Gy whole body irradiation for 5 days (10 Gy total) has been reported to result in a total absence of undifferentiated and differentiated cellular forms and blast cells in the bone marrow with maximal depression of peripheral blood lymphocytes counts being evident at 10–15 days and cell counts approaching only 40% of normal. Reportedly, recovery generally occurs after 3–6 months. (Mettler, F. A., et al., MEDICAL EFFECTS OF IONIZING RADIATION, Grune & Stratton Inc., N.Y.;p. 165(1985)).

Approximately 120,000 former Chernobyl residents are currently reportedly being followed to determine long term effects of radiation exposure. In patients suffering from acute radiation sickness during the accident, immune defects have been reported three to five years later with decreased circulating T- and B-lymphocytes and increased levels of serum autoantibodies (Iarilin, A. A., et al., Radiobiologiia 32: 771–778 (1992)); Beliakov, I. M., et al., Radiobiologiia 32((30): 349–356 (1992)); decreased antibacterial immunity (Bidnenko, et al., Zhunal Mikrobiologii Epidemiologii I Immunologii 1: 33–36 (1992)); chromosomal aberrations in peripheral blood lymphocytes (Bochkov, N. P., et al., Meditsinskaia Radiologiia 36(7): 50–52 (1991)); elevated numbers of large undifferentiated cells in peripheral blood, increased neutrophil counts, and reduced numbers of lymphocytes and basophils (Liubchenko, et al., Laboratornoe Delo 8: 47–51 (1991)); increased morbidity from solid tumors (Behar, A., et al. J Environ. Pathol. Tox. & Oncology 10(6):281–285 (1991)); and, decreased monocyte phagocytic activity and humoral immunity (Iakovlev, N. I., et al., Akusherstvo I Ginekologiya11: 42–45 (1991)); Ivanov, A.A., et al., Akusherstvo I Ginekologiya 11:42–45 (1991)); Ivanov, A. A., et al., Gematologiya I Transfuziologiya 36(12):20–22 (1991)).

In geographic regions adjacent to Chernobyl, population epidemiologists reported increased rates of respiratory virus infection (in Kiev; Vozianov, A. F., et al., Vrachebnoe Delo 3: 14–17 (1991)), and increased tuberculosis mortality (in Byelorussian SSR; Kalechits, O. M., et al., Problemy Tuberkuleza 11: 14–16 (1990); Dvoirin, M. S., et al., Problemy Tuberkuleza 11: 12–14 (1990)).

Five years after the accident, experimental rats exposed for 30 days to ground radiation in the 30 km Chernobyl disaster zone reportedly received a cumulative body dose of 57 rads (1 Gy=100 rads) and exhibited aberrations in bone marrow metaphases and peripheral blood leukocyte counts (Izmozherova, et al., *Radiobiologiia* 32(4): 493–9 (1992)). It has been suggested that exposure to sublethal levels of radiation may cause premature aging of T-lymphocytes with lessened tumor surveillance activity (Davila, D. R., et al., *Int. J Radiation Biol.* 611: 123–133 (1992)); Sasaki, H., et al.,*J. Radiation Biol.* 32 (suppl.): 310–326 (1991)). $CD4^+$T-lymphocytes are reportedly more radiosensitive than $CD8^+$ (DeRuysscher, D., et al., *Eur. J Cancer* 28A(10): 1729–1734 (1992)); Ceschia, T., et al., *Radiologia Medica* 81(4): 532–536 (1991)).

The chief methods of therapy for individuals exposed to radiation in the Chernobyl zone were reported to be administration of antimicrobial drugs and fresh donor platelets (i.e., "Conventional Therapy", in Protocols A-E, below). Stem cell transplantation using allogeneic bone marrow reportedly showed limited efficacy (Baranov, A. E., et al., *Meditsinskaia Radiologiia* 36((3): 29–32 (1991)).

Summary Overview of Protocols A-E, below:

In all, 348 Chernobyl residents and workers were examined (20–50 years of age; 320 men and 28 women). The state of the immune systems in these individuals was determined in the field using peripheral blood samples and rosette-forming lymphocyte methods. In certain studies, patients were examined during hospitalization and T- and B-lymphocyte populations were determined using a flow cytometer and monoclonal antibodies specific for lymphocyte cell surface markers. Radiation exposure levels for the different patients were determined using dosimetry data obtained by the military in Chemobyl using a D-2-P dosimeter. The time course of the immunodepression in these subjects is summarized as follows: subjects in Protocol A, evaluated within the first few weeks after evacuation from Chernobyl showed peripheral blood leukocyte and lymphocyte counts that were only 60% of normal ("Before", TABLE 2). By 2 months (Protocol B) the lymphocyte counts in patients presenting for therapy had fallen to about 40% of normal ("Before, TABLE 3), but by six months (Protocols C; D) improvement was noted, ie., to 76% of normal ("Before", TABLE 5). Changes in total lymphocyte counts over the latter 6 month period were mirrored by increased numbers of $CD4^+$ lymphocytes (i.e., from 10% at 4–5 months (TABLE 4) to 43% at 6 months (TABLE 5); and $CD8^+$ T-lymphocytes (i.e., from 39% at 4–5 months to 71% at 6 months).

Immunomodulator therapy was initiated in 1986 with thymalin, (a mixture of thymic peptides, the preparation of which was disclosed by some of the instant inventors in DE 3,421,789, Morozov, V. G., et al., (1985)). Treatments were administered to patients presenting in the clinic within the first few weeks after the Chernobyl NPP accident, and again at 2 months, 4–5 months, and 6 months (Protocols A-D, below). Thymalin was administered prophylactically to a small group of workers who participated in sealing the roof of reactor III (Protocol E). In addition, the immunomodulatory synthetic peptide L-Glu-L-Trp was administered to certain patients at three years post-exposure (i.e., Protocol E, below).

Treatments with thymalin were administered as 5 daily injection of 10 mg. Treatments with L-Glu-L-Trp were administered as 5 daily im injections of 100 µg each. The effects of the treatments on leukocytes were monitored in the week following treatment by collecting samples of peripheral blood from the different patients.

Protocol A: early Values

The 42 patients described below, were tested for blood parameters the first few days to weeks after exposure to 0.2–0.5 Gy of environmental radiation in Chernobyl ("Before") and then again after a 5 days of thymalin therapy (daily doses of 10 mg im; "After"). A control group of 34 Chernobyl subjects received conventional therapy (i.e., antihistamines, multivitamins, and treatments for symptoms). The majority of the subjects in this trial protocol, upon clinical examination, presented with complaints of weakness, scratchy throat, cough, acute eye pain, and a metallic taste in the mouth. Upon examination, hyperemia of the fauces and conjunctiva was revealed. No pathology was identified in the internal organs on gross examination. It can be seen from the data in TABLE 2 that a response to the thymalin treatment was observed in the treatment population even at this early time after radiation exposure in Chernobyl.

TABLE 2

Thymalin Treatment of Chernobyl Subjects (X ± m):
Treatments Initiated Shortly after Accidental Radiation Exposure

| Laboratory Indicia[a] | Examination Group | | |
|---|---|---|---|
| | Healthy Normal Controls | Accidental Radiation Exposure | |
| | | Before | After Thymalin |
| Leukocytes, abs | 5.7 ± 0.3 | 3.8 ± 0.3* | 6.4 ± 0.8** |
| % Normal Value: | (100%) | (67%) | (112%) |
| Ratio Post-/Pre Treat[b]: | — | — | (1.68) |
| Lymphocytes, abs | 1.91 ± 0.12 | 1.15 ± 0.14* | 2.27 ± 0.16** |
| % Normal Value: | (100%) | (60%) | (119%) |
| Ratio Post-/Pre-Treat: | — | — | (1.97) |
| CD2-DR+, % | 30.8 ± 1.1 | 17.6 ± 2.0* | 31 ± 3** |
| CD2-DR+, abs | 0.59 ± 0.04 | 0.20 ± 0.03* | 0.69 ± 0.08** |
| % Normal Value: | (100%) | (34%) | (117%) |
| CD2, % | 50.6 ± 1.6 | 47 ± 4 | 50.9 ± 2.4 |
| CD2, abs | 0.98 ± 0.09 | 0.55 ± 0.08* | 1.13 ± 0.07** |
| % Normal Value: | (87%) | (56%) | (115%) |
| Ratio Post-/Pre-Treat: | — | — | (2.05) |
| E-RFC, % | 29.7 ± 2.5 | 29.8 ± 2.6 | 23.4 ± 2.6 |
| Ratio Post-/Pre-Treat: | — | — | (0.79) |
| LMIR with ConA, % | 66 ± 4 | 98 ± 9* | 60 ± 7** |
| CD19 (C3-receptor+), % | 22.8 ± 2.2 | 27.0 ± 2.8 | 30.5 ± 1.9 |
| CD19, abs | 0.47 ± 0.03 | 0.30 ± 0.05* | 0.68 ± 0.04** |
| % Normal Value: | (100%) | (64%) | (145%) |
| Ratio Post-/Pre-Treat: | — | — | (2.26) |
| IgM, g/l | 1.1 ± 0.4 | 0.51 ± 0.08* | 0.58 ± 0.10* |
| % Normal Value: | (100%) | (46%) | (53%) |
| IgG, g/l | 10.1 ± 0.9 | 8.6 ± 1.3 | 9.2 ± 0.7 |
| % Normal Value: | (100%) | (85%) | (91%) |
| IgA, g/l | 1.71 ± 0.16 | 2.07 ± 0.20 | 1.11 ± 0.09** |
| % Normal Value: | (100%) | (121%) | (65%) |
| C3, g/l | 0.57 ± 0.03 | 0.74 ± 0.07 | 0.68 ± 0.04 |

[a]abs, absolute cell no. × $10^9$/L;
[b]Post-/Pre-Treat = After-treatment value/Before-treatment value;
*statistically significant (p < 0.05) in comparison with the indices in healthy normal subjects;
**statistically significant (p < 0.05) in comparison with the data obtained prior to L-Glu-L-Trp treatment; LMIR-leukocyte migration inhibition response; abs-cell concentration presented as $10^9$/L.

The observed improvement in immune parameters (TABLE 2) was correlated with a material improvement in the ability of the treated subjects to perform work, and a reduction in the hyperemia of the mucosa. Non-treated subjects in the control group exhibited a continued decline in ability to perform work and reported headaches and insomnia.

Protocol B: Two Months of Therapy

Among the victims at the time of the Chernobyl accident, $1^{st}$–$3^{rd}$ degree acute radiation sickness was confirmed in 200 cases and, in addition, still other subjects received in excess of 0.8 Gy with clinical signs of radiation trauma. Examination of individuals in this latter group revealed indications of immune dysfunction. Twenty-three such adult patients, exposed to 1.0–3.0 Gy of radiation, were treated at 2 months, and again at 6 months post-exposure. The patients received 10 mg thymalin daily for 5–10 consecutive days by intramuscular injection. Twelve normal healthy individuals were evaluated in a control group to establish normal immune parameters. The results of the evaluation ("Before") and treatment ("After") at 2 months are shown in TABLE 3.

TABLE 3

Treatment of Radiation-Induced Immunodeficiency: Treatments with Thymalin at Two Months Post-Radiation Exposure (X ± m)

| | Examination Group | | |
|---|---|---|---|
| | Healthy | Accidental Irradiation | |
| Indicia[a] | Normal Control | Before | After Thymalin Treatment |
| Leukocytes, abs | 5.6 ± 0.8 | 3.5 ± 0.4* | 5.0 ± 1.2** |
| % Normal Value: | (100%) | (63%) | (89%) |
| Ratio Post-/Pre-Treat[b]: | — | — | (1.43) |
| Lymphocytes, abs | 1.98 ± 0.16 | 0.80 ± 0.24* | 1.9 ± 0.4** |
| % Normal Value: | (100%) | (40%) | (96%) |
| Ratio Post-/Pre-Treat: | — | — | (2.38) |
| CD2-DR+, % | 35.8 ± 0.9 | 21 ± 4* | 30.0 ± 1.2** |
| CD2-DR+, abs | 0.59 ± 0.04 | 0.16 ± 0.04* | 0.55 ± 0.06* |
| % Normal Value: | (100%) | (27%) | (93%) |
| CD2, % | 49.3 ± 1.5 | 32 ± 7 | 48.7 ± 1.8** |
| CD2, abs | 0.98 ± 0.09 | 0.55 ± 0.08* | 1.13 ± 0.08** |
| % Normal Value: | (100%) | (56%) | (115%) |
| Ratio Post-/Pre-Treat: | — | — | (2.05) |
| E-RFC, % | 30.2 ± 1.6 | 22.9 ± 1.9* | 27.4 ± 2.4 |
| Ratio Post-/Pre-Treat: | — | — | (1.19) |
| LMI with ConA, % | 65.0 ± 2.1 | 120 ± 17* | 90 ± 10 |
| CD19, % | 22.0 ± 1.7 | 32 ± 3* | 27 ± 4 |
| CD19, abs | 0.46 ± 0.03 | 0.26 ± 0.06* | 0.51 ± 0.10** |
| % Normal Value: | (100%) | (57%) | (110%) |
| Ratio Post-/Pre-Treat: | — | — | (1.96) |
| gM, g/L | 1.1 ± 0.4 | 0.87 ± 0.07 | 1.00 ± 0.10 |
| % Normal Value: | (100%) | (79%) | (91%) |
| IgG, g/L | 11.1 ± 0.9 | 10.2 ± 2.0 | 10.0 ± 1.0 |
| % Normal Value: | (100%) | (92%) | (90%) |
| IgA, g/L | 1.70 ± 0.10 | 1.5 ± 0.4 | 1.49 ± 0.19 |
| % Normal Value: | (100%) | (88%) | (88%) |

[a]abs, absolute cell no. × $10^9$/L;
[b]Post-/Pre-Treat = After-treatment value/Before-treatment value;
*statistically significant (p < 0.05) in comparison with the indices in healthy normal subjects;
**statistically significant (p < 0.05) in comparison with the data obtained prior to L-Glu-L-Trp therapy;
LMIR -leukocyte migration inhibition response; RFC -rosette-forming cells.

The results in TABLE 3 show a statistically significant increase in circulating leukocytes, lymphocytes, and CD2+ lymphocytes in peripheral blood following treatment with thymalin. No change in CD19+ peripheral blood B-lymphocytes was observed. Simultaneous with the restoration of immune system parameters in peripheral blood, subjects in the thymalin treated group exhibited a marked decline in symptoms associated with the asthenic syndrome. Clinical improvements induced by thymalin were maintained for 2–4 months post-therapy, after which the clinical condition of the patients again worsened. Control subjects receiving conventional treatment did not exhibit any statistically significant change in immune parameters.

Protocol C. Therapy at 4 and 6 Months Post-Exposure

Acute radiation sickness (ARS) was manifest at 2–6 months in many patients. Seven patients with ARS after exposure to 1.0–2.0 Gy of radiation in Chernobyl were treated at 4–5 months post-exposure with 100–150 mg thymalin daily for 10–15 days (1st course) followed by 10 mg thymalin once a week for a period of 18 months (2nd course). Immune parameters were evaluated before therapy, and immediately following the first and second courses of treatment (TABLE 4 The results presented in TABLE 4 show significant increases in the number of leukocytes, and CD2+-DR+- and CD3-lymphocytes after the first and second courses of therapy.

TABLE 4

Thymalin Therapy: 4–6 Months Post-Exposure (X ± m)

| | Time Interval of Examination | | |
|---|---|---|---|
| Indicia | Before Therapy | After 1st course of Thymalin | After the 2nd course of Thymalin |
| Leukocytes, abs[a] | 3.5 ± 0.5 | 4.7 ± 0.2* | 5.5 ± 0.3* |
| Ratio Post-/Pre Treat[b]: | (1.0) | (1.34) | (1.57) |
| Lymphocytes, abs | 1.0 ± 0.5 | 1.5 ± 0.4 | 1.9 ± 0.5* |
| Ratio Post-/Pre-Treat: | (1.0) | (1.5) | (1.9) |
| CD2-DR+, % | 12.8 ± 2.6 | 22.3 ± 0.5 | 29 ± 3* |
| CD2-DR+, abs | 0.13 ± 0.04 | 0.34 ± 0.05* | 0.56 ± 0.08* |
| Ratio Post-/Pre-Treat: | (1.0) | (2.6) | (4.3) |
| CD3, % | 24 ± 3 | 35 ± 4* | 46 ± 3* |
| CD3, abs | 0.26 ± 0.05 | 0.49 ± 0.06* | 0.89 ± 0.11* |
| Ratio Post-/Pre-Treat: | (1.0) | (1.9) | (3.4) |
| CD4, % | 7.1 ± 1.1 | 19.5 ± 1.7* | 24.1 ± 1.5* |
| CD4, abs | 0.07 ± 0.01 | 0.28 ± 0.03* | 0.45 ± 0.04* |
| Ratio Post-/Pre-Treat: | (1.0) | (4.0) | (6.4) |
| CD8, % | 17 ± 3 | 15.4 ± 2.3 | 22.3 ± 2.2* |
| CD8, abs | 0.16 ± 0.04 | 0.23 ± 0.03 | 0.40 ± 0.05* |
| Ratio Post-/Pre-Treat: | (1.0) | (1.4) | (2.5) |
| CD19, % | 12.2 ± 1.9 | 15.0 ± 2.8 | 21.1 ± 2.1* |
| CD19, abs | 0.14 ± 0.04 | 0.21 ± 0.06 | 0.39 ± 0.06* |
| Ratio Post-/Pre-Treat: | (1.0) | (1.5) | (2.8) |

*statistically significant (p < 0.05) in comparison with the indices prior to the first treatment;
[a]abs-cell concentration presented as $10^9$/L;
[b]ratio = post-treatment value/pre-treatment value.

Protocol D: 6 Months:

Periodic examiniations of patients revealed a subset of Chernobyl patients who received 1.0–3.0 Gy of radiation in Chernobyl and who subsequently exhibited great fluctuations in leukocyte counts. This subset of patients included 32 patients who were tested for blood parameters at 6 months, and then treated with Thymalin at a dosage of 10 mg daily for 10 consecutive days in the hopes of stabilizing immune parameters. Twenty other patients served as a control group, and they were treated using conventional methods. The results presented in TABLE 5 show marked decreases in T- and B-lymphocyte subpopulations in patients prior to therapy with reduced CD2-DR+-, CD2+-, CD3+-, and CD4+-lymphocyte counts and decreased levels of B-lymphocytes with surface immunoglobulin. Treatment with Thymalin resulted in statistically significant increases in the following lymphocyte subpopulations: CD2+-DR+-, CD2+-, CD3+-, CD4+ T-lymphocytes, and, CD19+- and surface Ig+-B-lymphocytes. The latter increases in lymphocyte subpopulations were not observed in peripheral blood samples from patients treated in the control group with the conventional therapy. CD8+-lymphocytes did not change reliably as a result of the thymalin treatment (TABLE 5).

TABLE 5

Thymalin Treatment of Acute Radiation Sickness:
Treatments 6 Months After the Chernobyl Accident (X ± m)

| Indices: | Normal Healthy Controls | Irradiated Subjects | | |
|---|---|---|---|---|
| | | Conventional Therapy | Thymalin Therapy: | |
| | | | Before | After |
| Lymphocytes, % | 33.9 ± 1.2 | 32.9 ± 2.4 | 29.2 ± 2.0 | 30.0 ± 1.8 |
| Lymphocytes, abs | 1.96 ± 0.06 | 1.49 ± 0.14* | 1.39 ± 0.13 | 1.52 ± 0.12* |
| % Normal Value: | (100%) | (76%) | (71%) | (78%) |
| Ratio Post-/Pre-Treat: | — | — | (0.9) | (1.02) |
| CD2, % | 53.6 ± 1.9 | 38.7 ± 2.7* | 32 ± 3* | 49 ± 3** |
| CD2, abs | 1.05 ± 0.05 | 0.56 ± 0.04* | 0.44 ± 0.04* | 0.75 ± 0.05** |
| % Normal Value: | (100%) | (53%) | (42%) | (71%) |
| Ratio Post-/Pre-Treat: | — | — | (0.79) | (1.34) |
| CD2-DR+, % | 30.8 ± 1.1 | 18.9 ± 1.6* | 19.7 ± 1.2* | 20.8 ± 1.6** |
| CD2-DR+, abs | 0.59 ± 0.04 | 0.30 ± 0.25* | 0.28 ± 0.02* | 0.31 ± 0.02** |
| % Normal Value: | (100%) | (51%) | (47%) | (53%) |
| CD3, % | 55.6 ± 1.9 | 39.0 ± 2.4* | 37 ± 5* | 53.4 ± 1.8** |
| CD3, abs | 1.09 ± 0.08 | 0.58 ± 0.04* | 0.51 ± 0.03* | 0.82 ± 0.04** |
| % Normal Value: | (100%) | (53%) | (47%) | (75%) |
| CD4, % | 35.3 ± 2.7 | 20.3 ± 1.3* | 18.9 ± 1.3* | 32.6 ± 1.4** |
| CD4, abs | 0.69 ± 0.05 | 0.30 ± 0.03* | 0.26 ± 0.03* | 0.50 ± 0.04** |
| % Normal Value: | (100%) | (43%) | (38%) | (72%) |
| Ratio Post-/Pre-Treat: | — | — | (0.9) | (1.67) |
| CD8, % | 21.3 ± 0.9 | 19.5 ± 1.5 | 17.5 ± 1.6 | 21.2 ± 1.8 |
| CD8, abs | 0.41 ± 0.03 | 0.29 ± 0.03 | 0.24 ± 0.03 | 0.32 ± 0.03 |
| % Normal Value: | (100%) | (71%) | (59%) | (78%) |
| Ratio Post-/Pre-Treat: | — | — | (0.8) | (1.10) |
| T4/T8 | 1.64 ± 0.12 | 1.04 ± 0.04* | 1.08 ± 0.10* | 1.54 ± 0.11** |
| LMI | 59.7 ± 1.7 | 106 ± 6* | 107 ± 6* | 72.7 ± 4.5** |
| CD19, % | 25.00 ± 0.12 | 18.2 ± 2.1* | 23 ± 3 | 26.7 ± 2.1 |
| CD19, abs | 0.49 ± 0.04 | 0.27 ± 0.03* | 0.31 ± 0.05* | 0.41 ± 0.03** |
| % Normal Value: | (100%) | (55%) | (63%) | (84%) |
| Ratio Post-/Pre-Treat: | — | — | (1.15) | (1.52) |
| B-Ig+, % | 13.8 ± 1.2 | 15.8 ± 1.3 | 16.2 ± 1.7 | 19.0 ± 1.3 |
| B-Ig+, abs | 0.29 ± 0.02 | 0.23 ± 0.03 | 0.23 ± 0.04 | 0.29 ± 0.03 |
| % Normal Value: | (100%) | (79%) | (79%) | (100%) |
| Ratio Post-/Pre-Treat: | — | — | (1.0) | (1.26) |
| B-IgM+, % | 6.4 ± 0.7 | 6.3 ± 0.8 | 5.4 ± 0.5 | 8.8 ± 0.7 |
| B-IgM+, abs | 0.12 ± 0.01 | 0.09 ± 0.01* | 0.08 ± 0.01* | 0.13 ± 0.02 |
| B-IgG+, % | 4.1 ± 0.5 | 7.8 ± 0.9* | 7.1 ± 0.8* | 6.4 ± 0.5 |
| B-IgG+, abs | 0.082 ± 0.008 | 0.098 ± 0.007 | 0.104 ± 0.008 | 0.100 ± 0.007 |
| B-IgA+, % | 2.20 ± 0.20 | 1.80 ± 0.15* | 1.70 ± 0.20* | 1.8 ± 0.3 |
| B-IgA+, abs | 0.038 ± 0.004 | 0.033 ± 0.004 | 0.024 ± 0.003 | 0.030 ± 0.002 |
| IgM, g/L | 1.15 ± 0.06 | 1.14 ± 0.08 | 1.20 ± 0.07 | 1.07 ± 0.09 |
| % Normal Value: | (100%) | (99%) | (104%) | (93%) |
| IgG, g/L | 11.5 ± 0.5 | 11.9 ± 1.0 | 11.7 ± 0.9 | 10.9 ± 1.1 |
| % Normal Value: | (100%) | (103%) | (102%) | (95%) |
| IgA, g/L | 1.9 ± 1.0 | 1.6 ± 0.8 | 1.6 ± 0.8 | 1.8 ± 0.9 |
| % Normal Value: | (100%) | (84%) | (84%) | (95%) |

[a]abs -cell concentration presented as 109/L;
[b]Post-/Pre-Treat Ratio = post-treatment value/pre-treatment value;
*statistically significant ($p < 0.05$) vs. the indices in healthy people;
**statistically significant ($p < 0.05$) vs. the data obtained before treatment; abs -cell concentration presented as $10^9$/L;
LMI -leukocyte migration inhibition.

Correlated with the observed improvements in immune parameters, clinical improvements were observed in the treated patients including a lack of infectious complications over the following two years of observation. Asthenic symptoms in 5 of the 7 treated patients were brought completely under control.

Protocol E: Prophylactic Administration Prior to Irradiation

A special investigation of the potential immunoprotective effects of thymalin was assessed in a group of 20 volunteers who worked on the roof of the Chernobyl NPP reactor m. These subjects were given 10 mg thymalin daily on each of the three days they worked in the 30 km high radiation zone, with treatments commencing one day before the work on the NPP. Twenty other volunteers were given glucose tablets, as a control. The volunteers received a dose of radiation equal to 0.25 +/−0.02 Gy over each of the 1–2 days they worked on the NPP. Immune parameters were evaluated before administering thymalin, and again on day 7 after the completion of the NPP work project. Volunteers who received the placebo demonstrated changes in the number of $CD2^+$-, $CD2$-$DR^+$-, and $CD8^+$-lymphocytes. In contrast, prophylactic treatment with thymalin prevented the latter changes in lymphocyte subpopulations.

Protocol F: 3 years: L-Glu-L-Trp Treatment

An increased incidence of cancer is one sequelae known to occur in subjects exposed to radiation, presumably because of decreased immune surveillance and elimination of tumor cells. At three years post-radiation exposure, preliminary evaluation of patients exposed to radiation at Chernobyl suggested lingering impaired immunity in 20% of the subjects as evidenced by reduced numbers of CD2-DR$^+$ lymphocytes and depressed leukocyte enzymes. An attempt to normalize immune parameters was attempted in 70 of the latter patients exposed 3 years previously to 0.2–0.5 Gy of radiation at Chernobyl. Evaluation of these 70 patients revealed decreased CD2$^+$-DR$^+$ cells (in 100% of the subjects), decreased surface IgM$^+$ B-lymphocytes (in 49% of the subjects), and nonspecific elevated cytokine production in response to Con-A mitogen in the LMIR assay (in 84% of subjects). In general, most of these patients exhibited clinical symptoms of secondary immunodeficiency and asthenic syndrome including cardiovascular alterations and changes in vital signs. The subjects were treated with L-Glu-L-Trp in an attempt to alleviate the immune defects. The treatment course consisted of daily doses of 100 μg L-Glu-L-Trp administered im for 3–5 days. Sixty three subjects, similarly exposed to radiation in Chernobyl were used as untreated controls. Mean peripheral blood CD2$^+$ lymphocyte counts following L-Glu-L-Trp treatment were restored to within the normal healthy range of values (TABLE 6), and a restoration of CD2$^+$ counts was observed in 85% of the cases. Improvement in the CD2$^+$ lymphocyte counts was accompanied by improvement in the general condition of the patients and disappearance of symptoms associated with the asthenic syndrome. Normalization of CD2$^+$ lymphocytes did not occur in untreated patients (TABLE 6).

TABLE 6

Indices of Cellular Immunity and Innate Immunity in Chernobyl Subject Receiving Treatment with L-Glu-L-Trp at 3 Years Post-Radiation Exposure

| | Laboratory Test Results | | |
|---|---|---|---|
| | Before | After | |
| Indicia | Therapy | Untreated | L-Glu-L-Trp |
| Leukocytes, abs | 5.8 ± 0.3 | 5.5 ± 1.0 | 5.6 ± 0.4 |
| Lymphocytes, abs | 2.0 ± 0.3 | 1.8 ± 0.23 | 2.1 ± 0.3 |
| CD2-DR+, % | 15 ± 3* | 18.4 ± 2.5 | 32 ± 3** |
| CD2-DR+, abs | 0.30 ± 0.06* | 0.34 ± 0.11 | 0.66 ± 0.10** |
| CD3, % | 67.7 ± 2.7* | 61 ± 3* | 59.2 ± 2.1** |
| CD3, abs: | 1.33 ± 0.05* | 1.12 ± 0.18 | 1.21 ± 0.15 |

TABLE 6-continued

Indices of Cellular Immunity and Innate Immunity in Chernobyl Subject Receiving Treatment with L-Glu-L-Trp at 3 Years Post-Radiation Exposure

| | Laboratory Test Results | | |
|---|---|---|---|
| | Before | After | |
| Indicia | Therapy | Untreated | L-Glu-L-Trp |
| CD4, % | 36.7 ± 2.6 | 38 ± 3 | 36.2 ± 1.7 |
| CD4, abs | 0.72 ± 0.05 | 0.70 ± 0.05 | 0.74 ± 0.08 |
| CD8, % | 29.7 ± 0.9* | 25.0 ± 2.7 | 23.2 ± 2.1** |
| CD8, abs | 0.56 ± 0.02* | 0.46 ± 0.06 | 0.48 ± 0.07** |
| T4/T8 | 1.24 ± 0.10* | 1.52 ± 0.13 | 1.58 ± 0.04** |
| LMI, % | 140 ± 30* | 107 ± 10** | 75 ± 6** |
| B-Ig+, % | 10.7 ± 0.3 | 11.2 ± 0.7 | 11.0 ± 0.3 |
| B-Ig+, abs | 0.21 ± 0.01 | 0.20 ± 0.05 | 0.23 ± 0.04 |
| B-IgM+, % | 3.0 ± 0.3* | 4.4 ± 0.3 | 4.1 ± 0.6* |
| B-IgM+, abs | 0.062 ± 0.002* | 0.08 ± 0.004 | 0.12 ± 0.003** |
| B-IgG+, % | 4.7 ± 0.9 | 4.6 ± 0.5 | 4.8 ± 0.5 |
| B-IgG+, abs | 0.059 ± 0.003 | 0.08 ± 0.006 | 0.09 ± 0.007 |
| B-IgA+, % | 2.3 ± 0.3 | 1.98 ± 0.09 | 1.9 ± 0.3 |
| B-IgA+, abs | 0.048 ± 0.006 | 0.04 ± 0.002 | 0.04 ± 0.002 |
| IgM, g/L | 0.53 ± 0.09* | 1.03 ± 0.13** | 1.06 ± 0.06** |
| IgG, g/L | 13.2 ± 1.1 | 11.3 ± 1.2 | 10.9 ± 1.3 |
| IgA, g/L | 0.82 ± 0.25* | 1.1 ± 0.3 | 1.2 ± 0.4* |

$^a$abs -cell concentration presented as 109/L;
$^b$Post-/Pre-Treat Ratio = post-treatment value/pre-treatment value;
*statistically significant (p < 0.05) vs. the indices in healthy people;
**statistically significant (p < 0.05) vs. the data obtained before treatment;
abs -cell concentration presented as 10$^9$/L;
LMI -leukocyte migration inhibition.

EXAMPLE 3

Radiotherapy-Induced Immunodeficiency

Protocol A Breast Cancer

Thirty six patients with breast cancer were treated with conventional radiation therapy (i.e., single doses of about 2–3 Gy daily for 10 days; total cumulative patient dose of 20–30 Gy). Following radiotherapy the patients were treated with L-Glu-L-Trp by injection of daily dosages im of 100 μg. The patients had been previously treated with radiation therapy (single doses 2 Gy; total dose 20–30 Gy). The results presented in TABLE 7, show that the L-Glu-L-Trp treatment restored indices of cellular immunity to normal values.

TABLE 7

Indices of Cellular Immunity and Innate Resistance in Breast Cancer Patients Before and After Radiotherapy, and After L-Glu-L-Trp (X ± m)

| Indices | Before Radiotherapy | After Radiotherapy | After L-Glu-L-Trp |
|---|---|---|---|
| Lymphocytes (×10$^9$/L) | 1.61 ± 0.18 | 0.79 ± 0.09* | 1.72 ± 0.21** |
| Ratio Post-Rad/Pre-Rad Value$^a$: | (1.0) | (0.5) | (1.1) |
| Ratio Post-Treat/Pre-Treat Value: | — | — | (2.18) |
| T-lymphocytes (×10$^9$/L) | 0.83 ± 0.07+ | 0.32 ± 0.03* | 0.92 ± 0.12** |
| Ratio Post-Rad/Pre-Rad Value: | (1.0) | (0.4) | (1.1) |
| Ratio Post-Treat/Pre-Treat Value: | — | — | (2.88) |
| "Active" T-lymphocytes (×10$^9$/L) | 0.49 ± 0.06 | 0.19 ± 0.03* | 0.52 ± 0.07** |
| Ratio Post-Rad/Pre-Rad Value: | (1.0) | (0.4) | (1.1) |
| Ratio Post-Treat/Pre-Treat Value: | — | — | (2.74) |
| T-helpers (OKT4+) (×10$^9$/L) | 0.30 ± 0.03 | 0.12 ± 0.01* | 0.39 ± 0.04** |
| Ratio Post-Rad/Pre-Rad Value: | (1.0) | (0.4) | (1.3) |

TABLE 7-continued

Indices of Cellular Immunity and Innate Resistance in Breast Cancer
Patients Before and After Radiotherapy, and After L-Glu-L-Trp (X ± m)

| Indices | Before Radiotherapy | After Radiotherapy | After L-Glu-L-Trp |
|---|---|---|---|
| Ratio Post-Treat/Pre-Treat Value: | — | — | (3.25) |
| T-suppressors (OKT8+) (×10$^9$/L) | 0.28 ± 0.04 | 0.16 ± 0.02* | 0.21 ± 0.03 |
| Ratio Post-Rad/Pre-Rad Value: | (1.0) | (0.6) | (0.8) |
| Ratio Post-Treat/Pre-Treat Value: | — | — | (1.31) |
| OKT4+/OKT8+ | 1.07 ± 0.09 | 0.75 ± 0.06* | 1.86 ± 0.17** |
| DTH[a] to tuberculin (mm) | 7.3 ± 0.4 | 2.6 ± 0.2* | 8.7 ± 0.6** |
| Ratio Post-Rad/Pre-Rad Value: | (1.0) | (0.4) | (1.2) |
| LMI[b] with ConA (%) | 68 ± 4 | 96 ± 7* | 71 ± 5** |
| Increase in no. E-RFC in vitro after incubation with L-Glu-L-Trp | 1.23 ± 0.15 | 1.19 ± 0.13 | 1.27 ± 0.14 |
| B-lymphocyte (Ig+) (×10$^9$/L) | 0.15 ± 0.02 | 0.11 ± 0.01 | 0.17 ± 0.02 |
| Ratio Post-Rad/Pre-Rad Value: | (1.0) | (0.7) | (1.1) |
| Ratio Post-Treat/Pre-Treat Value: | — | — | (1.55) |
| Granulocyte Phagocytic Index | 4.3 ± 0.3 | 2.06 ± 0.18* | 3.7 ± 0.2** |
| Granulocyte Cation Proteins | 1.58 ± 0.09 | 1.36 ± 0.08* | 1.49 ± 0.12 |
| C3-complement (g/L) | 0.75 ± 0.05 | 0.66 ± 0.04 | 0.68 ± 0.04 |

*statistically significant (p < 0.05) vs. the index before radiotherapy;
**statistically significant (p < 0.05) vs. the index after radiotherapy;
a)-Delayed Type Hypersensitivity skin reaction to tuberculin (mm diameter);
b)-Leukocyte Migration Inhibition;
c)-Sensitivity Index;
[a]Ratio post-radiation value/pre-radiation value, or the Ratio of the post-treatment (i.e., L-Glu-L-Trp) value/pre-treatment value.

Protocol B

Radiation and Chemotherapy

Diffuse alveolar damage and pulmonary disease is reportedly a common, important, and frequently unrecognized problem in patients receiving radiotherapy and chemotherapy (Doran, H. M., et al., *Histopathology* 18(3):211–219 (1991)). Alveolar damage and lung disease in cancer patients are important targets for therapeutic drug development.

Summary Overview:

A total of 246 patients were eventually entered into studies after receiving radiation and chemotherapy. L-Glu-L-Trp was administered to the patients in single 100 μg daily dose for each of 10 days during the period of chemotherapy. A control group constituted 158 similar patients (following radiation and chemotherapy), and these patients were treated in a conventional manner (i.e., chemotherapy and support therapy). Patients treated with L-Glu-L-Trp experienced normalization of immunological indices, and a decreased incidence and severity of post-operative complications including upper respiratory infections, nausea, and inflammations exacerbated by the radiation and chemotherapy, i.e., gastritis, cholecystitis, and the like. Immune parameters were periodically monitored over the next 4–6 months in the patients and decreased levels of lymphocytes or their subpopulations were used as clinical triggers for additional therapeutic intervention with L-Glu-L-Trp.

Protocol C

Tumor Therapy

Thymogen Use in Oncology Practice for the Combined Treatment of Patients with Thoracic Cavity Tumors:

Surgical removal of thoracic tumors was followed in 38 patients by focal radiation therapy and then a course of L-Glu-L-Trp therapy consisting of 5 daily im injections of 100 μg L-Glu-L-Trp each. Only radiation therapy (and supportive antibiotic therapy) was administered as a control to 56 patients. The clinical results that were recorded are summarized in TABLE 8.

TABLE 8

Clinical Complications in Oncology Patients Treated with Focal Radiation Therapy and then L-Glu-L-Trp

| Cancer | No. Patients | Radiation Route | Therapy Dose | Immuno-Therapy | Complications[a]: Total | Septic | Cardio-Pulm. | Mortality |
|---|---|---|---|---|---|---|---|---|
| Esophagus | 22 | 5–6 Gy/ | 20–30 Gy | 5 × im 100 μg | 2 | 1 | 1 | 0 |
| Stomach | 32 | 4 days | | None | 10 | 6 | 4 | 0 |
| Lung | 16 | 5–6 Gy/ | 20–30 Gy | 5 × im 100 μg | 1 | 0 | 0 | 0 |
| | 24 | 4 days | | None | 6 | 3 | 2 | 2 |

[a]Complications, "septic", septic shock; "cardio-pulm.", cardiopulmonary; "mortality", death.

In this trial treatment, L-Glu-L-Trp decreased the total number of complications (Total) as well as the number of cases of septicemia, cardiopulmonary complications, and mortality.

EXAMPLE 4

Respiratory Disease

Protocol A: Influenza Prophylaxis

Summary Overview:

A group of 452 persons were treated with daily dosages of 100 μg of L-Glu-L-Trp administered im on each of 5–10 consecutive days. A control group consisted of 250 untreated persons. The incidence of diagnosed respiratory diseases and influenza were recorded for both groups over the next four months. The results summarized in TABLES 9 and 10 show that the untreated group had a higher incidence of the respiratory disease, illness, hospitalization and disablement than the group treated with L-Glu-L-Trp.

TABLE 9

Prophylactic Treatment with L-Glu-L-Trp: Effect on the Incidence of Acute Respiratory Diseases and Influenza Illness (mean values)

| Indices | Treatment Group L-Glu-L-Trp | Control | Ratio Control/TX* |
|---|---|---|---|
| Sickness rate per 100 persons/month | 9.8 | 30.4 | 3.1 |
| Pneumonia rate/100 persons/month | 0.20 | 0.50 | 2.5 |
| Need for hospitalization, % | 30.6 | 44.9 | 1.7 |
| Average term of hospitalization, days | 6.2 | 8.8 | 1.4 |
| Overall incidence of lingering and complicated cases, % | 3.9 | 13.8 | 3.5 |
| Incidence of lingering and complicated cases for in-patients, % | 9.8 | 26.2 | 2.7 |
| Number of cases of temporary disablement per 100 persons/month | 4.1 | 7.0 | 1.7 |
| Number of days of temporary disablement per 100 persons/month | 26.5 | 57.6 | 2.2 |

*Ratio = Value Control/Value L-Glu-L-Trp treated.

Protocol B: Prophylaxis/Influenza- Athletes in Training:

Summary Overview:

The burden of heavy training loads under all conditions of inclement weather places the athlete at an increased risk of respiratory infection. L-Glu-L-Trp was administered to 89 young sportsmen (athletes). The control group consisted of 54 young students. L-Glu-L-Trp was administered intranasally daily as a single dose of 1 μg/kg on each of 3 consecutive days. L-Glu-L-Trp reduced the rate of upper respiratory infections and illness by 4-fold in the treatment group (i.e., as compared with the controls). In addition, those L-Glu-L-Trp treated individuals who did develop an infection had a far less severe course of infection (than in the control group) and the infections were without complications. Clinical improvement in the L-Glu-L-Trp treatment group was accompanied by the normalization of immunological indices.

Trial Population:

Students of the Children's and Youth's Sports School (47 boys; 42 girls) were evaluated. The athletic specialties included track and field, rowing, fencing, basketball and swimming. The control group consisted of 30 adolescent boys and 24 girls who did not engage in sports. The trial was conducted in the months of January and February and when acute respiratory infections were widespread in student populations.

Therapeutic Protocol:

L-Glu-L-Trp was introduced by intranasal instillation of 8–15 drops of a 0.01% solution daily for 3 days.

Laboratory Indices of Non-Specific Resistance:

The following measurements were taken to evaluate the state of non-specific resistance to infection in the trial and control populations: i) barrier properties of the skin and mucous membranes, ii) humoral factors of immunity (bactericidal activity of serum), iii) serum C3 levels, iv) numbers of neutrophils, their ability to phagocytose yeast, and cellular content of cationic proteins, v) number of T-lymphocytes (E-RFC), T-suppressor (OKT $8^+$) and T-helper cells (OKT $4^+$), vi) blastogenic responses of lymphocytes to PHA and Con-A (% blast cells), vii) number of B-lymphocytes (EA-RFC), viii) serum concentrations of IgM, IgG, and IgA (radial immunodiffusion), ix) serum levels of immune complexes, and x) levels of lysozyme in saliva. The results of these investigations are presented in summary form in TABLES 11–13.

TABLE 10

Incidence of Acute Respiratory Disease and Influenza In Recipients of Prophylactic L-Glu-L-Trp Treatments (mean values) as a Function of Time After Treatment

| Indices | Groups | 1st month | 2nd month | 3rd month | 4th month |
|---|---|---|---|---|---|
| Sickness rate/100 persons/month | L-Glu-L-Trp | 9.6 | 11.3 | 9.4 | 11.0 |
| | Control | 28.6 | 33.4 | 28.7 | 30.6 |
| Need for hospitalization, % | L-Glu-L-Trp | 27.0 | 27.1 | 28.3 | 28.3 |
| | Control | 41.2 | 50.8 | 48.8 | 39.0 |
| Average term of hospitalization, days | L-Glu-L-Trp | 6.2 | 6.2 | 6.2 | 7.0 |
| | Control | 9.3 | 8.4 | 10.2 | 11.0 |
| Number of cases of temporary disablement/100 persons/month | L-Glu-L-Trp | 3.8 | 7.3 | 3.4 | 3.6 |
| | Control | 6.9 | 10.2 | 7.5 | 5.6 |
| Number of days of temporary disablement/100 persons/month | L-Glu-L-Trp | 24.0 | 48.6 | 14.3 | 26.3 |
| | Control | 47.9 | 82.0 | 51.4 | 42.8 |

TABLE 11

Blood Hematology Values

| Index | Athletes Before | Athletes After L-Glu-L-Trp | Controls Before | Controls After L-Glu-L-Trp |
|---|---|---|---|---|
| Leukocytes: | | | | |
| $\times 10^9$/L: | 5.6 ± 0.2 | 6.1 ± 0.2 | 6.6 ± 0.9 | 5.6 ± 0.4 |
| % Normal Value: | (100%) | (109%) | (100%) | (97%) |
| Ratio Post-Treat/Pre-Treat Value: | — | (1.09) | — | (0.85) |
| Neutrophils: | | | | |
| %: | 46.5 ± 2.0 | 49.0 ± 1.5 | 51.5 ± 4.3 | 47.5 ± 2.9 |
| $\times 10^9$/L: | 2.70 ± 0.09 | 3.01 ± 0.2 | 3.57 ± 0.8 | 2.67 ± 0.3 |
| % Normal Value: | (100%) | (115%) | (100%) | (75%) |
| Eosinophils: | | | | |
| %: | 4.0 ± 0.6 | 4.2 ± 0.6 | 3.8 ± 0.6 | 4.0 ± 0.8 |
| $\times 10^9$/L: | 0.24 ± 0.03 | 0.23 ± 0.03 | 0.26 ± 0.06 | 0.22 ± 0.07 |
| % Normal Value: | (100%) | (96%) | (100%) | (85%) |
| Monocytes | | | | |
| %: | 8.2 ± 0.4 | 9.4 ± 0.5 | 9.5 ± 0.9 | 10.6 ± 1.2 |
| $\times 10^9$/L: | 0.43 ± 0.04 | 0.59 ± 0.05† | 0.66 ± 0.2 | 0.58 ± 0.07 |
| % Normal Value: | (100%) | (137%) | (100%) | (88%) |
| Lymphocytes: | | | | |
| %: | 38.5 ± 2.0 | 34.9 ± 4.7 | 34.9 ± 4.7 | 37.8 ± 2.9 |
| $\times 10^9$/L: | 2.14 ± 0.1 | 2.22 ± 0.1 | 2.09 ± 0.1 | 2.08 ± 0.2 |
| % Normal Value: | (100%) | (104%) | (100%) | (99%) |
| T-Lymphocytes: | | | | |
| %: | 66.4 ± 1.5 | 70.8 ± 1.4† | 69.0 ± 1.7† | 73.9 ± 1.7 |
| $\times 10^9$/L: | 1.43 ± 0.07 | 1.55 ± 0.08 | 1.45 ± 0.1 | 1.56 ± 0.1 |
| % Normal Value: | (100%) | (108%) | (100%) | (108%) |
| T-suppressor (CD8+) | | | | |
| %: | 6.3 ± 1.0 | 5.9 ± 0.7 | 3.6 ± 0.8 | 4.8 ± 1.0 |
| $\times 10^9$/L: | 0.14 ± 0.02 | 0.12 ± 0.02 | 0.08 ± 0.03 | 0.08 ± 0.05 |
| % Normal Value: | (100%) | (86%) | (100%) | (100%) |
| T-helper (CD4+): | | | | |
| %: | 51.6 ± 1.8 | 56.1 ± 1.3† | 49.6 ± 2.9 | 65.6 ± 2.0†† |
| $\times 10^9$/L: | 1.12 ± 0.07 | 1.25 ± 0.07 | 1.00 ± 0.1 | 1.36 ± 0.2 |
| % Normal Value: | (100%) | (112%) | (100%) | (136%) |
| B-Lymphocytes: | | | | |
| %: | 17.7 ± 0.8 | 13.6 ± 0.9†† | 22.4 ± 1.7 | 20.1 ± 1.5 |
| $\times 10^9$/L: | 0.39 ± 0.02 | 0.29 ± 0.02 | 0.48 ± 0.07 | 0.41 ± 0.05 |
| % Normal Value: | (100%) | (74%) | (100%) | (85%) |
| IgG (mg/mL) | 12.2 ± 0.8 | 10.2 ± 0.6 | 12.1 ± 0.7 | 12.6 ± 0.7 |
| % Normal Value: | (100%) | (84%) | (100%) | (104%) |
| IgM (mg/mL) | 1.1 ± 0.09 | 1.1 ± 0.07 | 1.3 ± 0.09 | 1.0 ± 0.02†† |
| % Normal Value: | (100%) | (100%) | (100%) | (77%) |
| IgA (mg/mL) | 1.3 ± 0.6 | 1.8 ± 0.1 | 1.8 ± 0.2 | 1.8 ± 0.2 |
| % Normal Value: | (100%) | (138%) | (100%) | (100%) |
| C3 (g/L) | 0.7 ± 0.02 | 0.8 ± 0.02†† | 1.1 ± 0.06 | 0.7 ± 0.03 |
| Serum Lysozyme (%) | 60.7 ± 1.8 | 60.2 ± 1.6 | 46.3 ± 1.5 | 50.6 ± 1.4†† |
| Serum β-Lysin (%) | 70.3 ± 3.6 | 57.6 ± 3.2†† | 49.8 ± 8.2 | 46.8 ± 5.4 |

†Post-treatment values statistically different than the pre-treatment values, $p < 0.05$;
††statistically different pre- to post-treatment values, i.e., $p < 0.01$.

The investigators concluded that the absolute number of leukocytes in athletes and controls was not significantly different prior to treatment. After treatment with L-Glu-L-Trp, no marked changes were observed in PBL, monocytes, lymphocytes, or lymphocyte subpopulations, despite some apparently statistically significant (but small) changes in the number of monocytes and the percentages of T-helper and B-lymphocytes.

Despite the lack of a significant effect on peripheral blood leukocytes, a statistically significant increase was reported in lysozyme activity in blood (TABLE 11) and saliva (TABLE 12) following treatment with L-Glu-L-Trp. In addition, the phagocytic index of neutrophils (i.e., number of yeast phagocytosed per cell) was increased (TABLE 13).

TABLE 12

Nonspecific Resistance to Infection: Salivary Lysozyme, IgA and IgM

| Group | Salivary Lysozyme (%) | Total Salivary IgA (g/L) | Salivary Secretory IgA (g/L) | Salivary IgM (g/L) |
|---|---|---|---|---|
| Athletes: | | | | |
| Before: | 63.8 ± 2.2 | 0.38 ± 0.03 | 0.05 ± 0.006 | 0.65 ± 0.06 |
| After L-Glu-L-Trp: | 68.7 ± 1.3† | 0.55 ± 0.05†† | 0.056 ± 0.004 | 0.65 ± 0.06 |
| Controls: | | | | |
| Before: | 54.1 ± 5.5 | 0.52 ± 0.1 | 0.055 ± 0.009 | 0.71 ± 0.06 |
| After L-Glu-L-Trp: | 63.5 ± 3.0 | 0.48 ± 0.1†† | 0.066 ± 0.009 | 0.73 ± 0.09 |

†statistical significance change from pre- to post-treatment at $p < 0.05$;
††$p < 0.01$

TABLE 13

Immune Function

| | Athletes | | Controls | |
|---|---|---|---|---|
| Functional Indices | Before | After L-Glu-L-Trp | Before | After L-Glu-L-Trp |
| Blasts w/PHA (%) | 34.3 ± 1.6 | 42.5 ± 2.5†† | 47.4 ± 6.2 | 34.1 ± 3.1 |
| Blasts w/Con-A (%) | 51.3 ± 3.9 | 53.4 ± 3.9 | 49.2 ± 5.7 | 66.8 ± 4.0†† |
| Phagocytosis (yeast) | 63.4 ± 1.5 | 73.3 ± 1.5†† | 64.8 ± 1.9 | 75.0 ± 1.7†† |
| Granulocyte Cationic Proteins | 1.4 ± 0.05 | 1.1 ± 0.04 | 0.95 ± 0.06 | 1.22 ± 0.1 |

†Post-treatment significantly different than the Pre-treatment values, i.e. $p < 0.05$;
††post-treatment significantly different that pre-treatment values, $p < 0.01$ Clinical Result:

In the two month period of the trial, the overall incidence of acute respiration in the students of the Children's and Youth's Sports School was 63.3% in a total school population of 367 adolescents. The rate of infection in the control group of school children not engaged in sports activities was 7.4% (4 children). Incidence of infection in the group of athletes treated with L-Glu-L-Trp was 24.7%.

The investigators concluded that under conditions of intense muscular activity in young athletes there appeared to be a decline in functional immune activity as evidenced by decreased LMIR, altered T-helper/T-suppressor ratios, decreased lymphocyte blast responsiveness to mitogens, decreased circulating B-lymphocytes, and decreased serum immunoglobulin levels. It was postulated that the presumed immune impairments might result from "insufficient maturity of T-cell populations." Treatments with L-Glu-L-Trp were seen as favorably affecting lysozymne levels, LMIR, IgA levels, and C3 levels (TABLE 31).

Protocol C: Prophylaxis Respiratory Infections-Polar Explorers:
Summary Overview L-Glu-L-Trp was administered prophylactically to 27 military volunteers with a goal of increasing the subjects' resistance to high-level solar UV radiation in Northern polar marine climates. The control group comprised 24 similarly occupied co-workers. L-Glu-L-Trp was administered intranasally at a dosage of 1 μg/kg daily on each of three consecutive days. Prophylactic treatment with L-Glu-L-Trp prevented the occurrence of upper respiratory infections in the treated group which occurred in their co-workers (i.e., the control group). Non-treated subjects exhibited decreases in peripheral blood immune parameters suggestive of immunosuppression.

Protocol D: Nose, Ear and Throat Infections
Summary Overview:

One hundred eighty six subjects (186) with diagnosed acute respiratory disease, including upper airway diseases and viral infections, were treated with L-Glu-L-Trp. A control group consisted of 87 untreated subjects. L-Glu-L-Trp was administered daily im or intranasally at a dosage of 100 μg on each of 3–7 consecutive days. Treatment with L-Glu-L-Trp resulted in a milder course of respiratory viral infections in the treatment group than in the control group. Clinically evident symptoms of infection were also decreased in the treated patients, including rhinorrhea, sore throat, fever, muscle aches, headaches, and ear pain. Secondary infectious complications were diminished in the treated individuals, and the length of time that medical follow-up was required was also diminished.

Protocol E: Influenza Treatments

One hundred fifty-six patients (156) with influenza were treated with 100 μg L-Glu-L-Trp im or 1 μg/kg intranasally on each of 5–10 consecutive days. A control group constituted with entry of 82 influenza patients who remained untreated. Treatments with L-Glu-L-Trp resulted in accelerated alleviation of symptoms associated with influenza infection, e.g., joint pain, muscle aches, fevers, chills, and upper respiratory symptoms.

Protocol F: Influenza Symptoms and Sinusitis

Summary Overview: Fifty-one patients (51) were treated daily for 3–10 days with either 100 μg L-Glu-L-Trp administered im, or 1 μg/kg administered intranasally. A control group of 24 similar patients remained untreated. Treatment with L-Glu-L-Trp resulted in reduced nasal mucous swelling, normalization of breathing, decreased volume of exudate from affected sinuses, and improved general condition and immune status. The L-Glu-L-Trp treatment decreased the total duration of patient treatment by up to 1.7-fold, i.e., as compared with the length of treatment required for patients in the control group.

Protocol G: Combination Therapy; Influenza Symptoms

Sixty-six (66) hospitalized patients between the ages 18–20 years with confirmed influenza infections were admitted into the trial. Of the patients, 12 were determined to be severely infected, and the remaining 54 seriously infected and in need of hospitalization. The patients were divided into two groups, 35 receiving conventional therapy (control), and the remaining 31 received daily injections of 100 μg L-Glu-L-Trp im on each of 3 consecutive days as an adjunct to the conventional ongoing therapy. The patients treated with L-Glu-L-Trp experienced a 3.5-times lower incidence of respiratory complications than the patients in the control group. Patients treated with L-Glu-L-Trp also showed a more rapid normalization of immune parameters, including leukocyte migration inhibition response (LMIR), blastogenic response to PHA and ConA, and levels of IgA and IgM.

Protocol H: Influenza with Immune Defects

A clinical trial was conducted in a group of 588 patients between the ages of 17–21 years all having a confirmed infection with Influenza A, (i.e., confirmation by either hemagglutination-inhibition or the presence of specific viral antigens). Three hundred fifteen of the patients (315) were ultimately hospitalized and determined to have significant immunological impairment related to their acute viral infection. Forty-nine patients (49) were treated using a combination therapy in which L-Glu-L-Trp was administered as an adjunct to the conventional support therapy. The results of this trial showed that L-Glu-L-Trp treatment reduced the percentage of patients with secondary complications (including pneumonia), and decreased the duration of pharyngitis, tracheitis, and the time over which therapy needed to be administered (TABLE 14). Coincident with the improvements in clinical symptoms was an observed increase in the percentage of T-helper lymphocytes, and a change in the T-helper/T-suppressor ratio (TABLE 14).

TABLE 14

| Treatment Regimen | Pharyngitis manifestations | Tracheitis manifestations | Length of Required Therapy |
|---|---|---|---|
| Combined Therapy: Conventional + L-Glu-L-Trp | 3.6 ± 0.3 days | 3.6 ± 0.3 days | 7.1 ± 0.3 days |
| Conventional Therapy Only | 4.8 ± 0.2 days | 4.0 ± 0.3 days | 8.3 ± 0.4 days |

| Treatment Regimen | Secondary (Pneumonia) Complications | Increase in T-helper Cells Percentage | T-helper/ T-suppressor Ratio |
|---|---|---|---|
| Combined Therapy: Conventional + L-Glu-L-Trp | 4.0% | 17% | 2.7 |
| Conventional Therapy Only | 9.1% | 7% | 1.8 |

A Protocol I: Influenza Therapy:

Summary Overview:

Forty-eight volunteers (48) were experimentally infected with influenza, then examined and treated daily by administration of L-Glu-L-Trp at a dosage of 100 $\mu$g im or 1 $\mu$g/kg intranasally over a period of 5–10 days. Thirty-four similarly infected volunteers (34) served as untreated controls. Treatment with L-Glu-L-Trp resulted in normalization of fever, reduction in toxic symptoms, and resolution of icterus jaundice). The hematological and immunological indices examined immediately following the period of treatment were restored to within the normal range.

Protocol J: Influenza:

Summary Overview

L-Glu-L-Trp was administered to 268 volunteers as an adjunct to flu vaccination. The control group consisted of 197 subjects receiving flu vaccination but not L-Glu-L-Trp. Flu vaccine was delivered by air pressure injection and L-Glu-L-Trp was administered daily at a dose of 50 $\mu$g im on each of 3 consecutive days. L-Glu-L-Trp treatment significantly decreased the incidence of sickness in the vaccinated subjects for a period of 12 months compared to controls who received flu-vaccination without L-Glu-L-Trp. In the event of flu, the course of the infection was noted to be less severe and the recovery more rapid when compared to controls.

Protocol K: Pleuritis:

Summary Overview:

Efficacy of L-Glu-L-Trp in combined antibiotic therapy was evaluated in twelve male patients (aged 18 to 45) with suppurative lung diseases that were poorly responsive to antibiotic therapy and accompanied by diffuse pleuritis, disseminated intravascular coagulation (DIC), pleural effusions, and fever. Laboratory tests revealed elevated white cell counts in peripheral blood, decreased lymphocyte counts (TABLE 17), elevated serum fibrin degradation products (FDP) and abnormally low serum antithrombin III (ATIII) levels (TABLE 15). L-Glu-L-Trp was administered to these patients as a treatment of nearly last resort, and as part of the ongoing (unsuccessful) regimen of broad spectrum antibiotic therapy: i.e., 200 $\mu$g of L-Glu-L-Trp was administered im daily over a period of 5–7 days. A dramatic change in the clinical picture was observed in all 12 patients: namely, fever ablated, the volume of pleural effusion decreased, incidences of DIC decreased then disappeared, examination of X-rays showed that infections were consolidated, laboratory tests showed decreases in peripheral blood leukocyte counts, FDP levels dropped, and ATIII levels increased to within the normal range. In addition, T-cell counts in peripheral blood increased and IgG, IgM, and IgA increased (TABLE 17) and C-reactive protein levels fell (TABLE 16). No allergic or adverse effects of L-Glu-L-Trp treatment were observed. The results of the laboratory tests conducted in this trial are summarized in TABLES 15–17.

TABLE 15

Hematology Values

| Indicia | Patients Before Therapy | After L-Glu-L-Trp Therapy |
|---|---|---|
| Clotting time (citrated whole blood-recalcified) | 116.2 ± 11.6 | 146.5 ± 28.2 |
| Kaolin-Cephalin clotting time | 54.1 ± 5.7 | 61.7 ± 6.1 |
| Fibrinogen Concentration (g/L) | 6.9 ± 1.6 | 4.7 ± 1.2 |
| FDP ($\mu$g/mL) | 156 ± 24.7 | 21.7 ± 0.8[†] |
| ATIII (% of normal) | 69.5 ± 21.2 | 98.3 ± 15.3 |
| Fibrinolytic Activity (min.) | 265.2 ± 54.0 | 181.2 ± 52.2 |

[†]Statistically different than the normal control values, i.e., $p < 0.05$.

TABLE 16

Blood Acute-Phase Protein Measurements

| Indicia | Patients Before Therapy | After L-Glu-L-Trp Therapy |
|---|---|---|
| C3 complement (mcg/mL) | 735 ± 46.8 | 918.9 ± 85.9[+] |
| Prealbumin (mcg/mL) | 267.5 ± 42.5 | 273.3 ± 40.7 |
| Ceruloplasmin ($\mu$g/mL) | 321 ± 34.8 | 295 ± 22.8 |
| Orosomucoid ($\mu$g/mL) | 1368.3 ± 181.7 | 1146.7 ± 147 |
| $\alpha$2-macroglobulin ($\mu$g/mL) | 1.8 ± 0.2 | 2.4 ± 0.2 |
| $\alpha$1-anti-trypsin ($\mu$g/mL) | 185.5 ± 15.6 | 96.0 ± 3.5 |
| C-reactive protein ($\mu$g/mL) | 36.8 ± 2.6 | 7.4 ± 2.5[†] |
| Transferrin ($\mu$g/mL) | 2.8 ± 0.8 | 3.2 ± 0.4 |

[†]Statistically different than the normal control values, i.e., $p < 0.05$.

TABLE 17

Laboratory Indicia of Disease Activity in Patients with Lung and Pleural Disease

| Indicia | Before Treatment | After L-Glu-L-Trp Treatment |
|---|---|---|
| T-Lymphocytes: ×10⁹/L:: | 0.46 ± 0.3 | 0.74 ± 0.08† |
| % Normal Value:: | (52%) | (83%) |
| B-Lymphocytes: ×10⁹/L: | 0.35 ± 0.01 | 0.46 ± 0.02† |
| % Normal Value: | (76%) | (100%) |
| IgG (mg/mL) | 153.2 ± 12.6 | 186.8 ± 31.8 |
| % Normal Value: | (114%) | (139%) |
| IgM (mg/mL) | 140.8 ± 32.2 | 131.2 ± 38.5 |
| % Normal Value: | (111%) | (103%) |
| IgA (mg/mL) | 153.4 ± 25.6 | 159.5 ± 12.3 |
| % Normal Value: | (156%) | (162%) |

†Statistically different than the normal control values, i.e., $p < 0.05$.

Protocol L: Pneumonia

Eight children with progressive destructive pneumonia were treated with L-Glu-L-Trp in combination with conventional antibiotic therapy. All patients presented at the hospital with marked manifestations of systemic toxicity, in serious condition, and all with respiratory impairment. In all cases there was also diagnosis of secondary immune deficiency and thrombohemorrhagic syndrome. L-Glu-L-Trp was administered daily at a dosage of 100 μm daily for 5 days. Laboratory tests were conducted to compare the pre- and post-treatment values with values recorded for normal healthy controls. A control population of children with pneumonia was treated with only the antibiotic therapy. The results of the laboratory analyses are presented in TABLES 18–20.

TABLE 18

Hematology Values

| Index | Normal Healthy Control | Patients Before Therapy | After L-Glu-L-Trp Combination Therapy |
|---|---|---|---|
| Whole blood clotting time (sec.) | 472 ± 18.4 | 360 ± 23.5 | 465 ± 16.2 |
| Clotting time (citrated whole blood-recalcified) | 142 ± 8.9 | 133.4 ± 4.3 | 129 ± 2.3 |
| Kaolin-Cephalin clotting time | 62 ± 4.1 | 51 ± 1.7 | 58 ± 1.2 |
| Prothrombin time | 22 ± 0.5 | 26 ± 0.2 | 22 ± 0.1 |
| Thrombotest | 41 ± 2.3 | 33 ± 1.2 | 33 ± 1.2 |
| Fibrinogen Concentration (g/L) | 4.51 ± 0.65 | 5.1 ± 0.2 | 4.2 ± 0.4 |
| FDP (μg/mL) | 128 ± 11.2 | 178 ± 13.5 | 96 ± 6.7 |
| ATIII (% of normal) | 83 ± 4.4 | 78 ± 1.8 | 85 ± 2.1 |
| Fibrinolytic Activity (min.) | 204 ± 16.3 | 245 ± 13.7 | 186 ± 11.5 |
| Hagemann Factor Dependent Fibrinolysis | 79 ± 10.7 | 118 ± 18.4 | 72 ± 6.8 |

Unfortunately no p-values were calculated for the data presented in TABLES 18–20 obtained in this foreign study. However, the findings presented in TABLE 18 suggested underlying thrombosis in this patient population with elevated levels of fibrin degradation products (FDP) and decreased levels of ATIII. L-Glu-L-Trp treatment apparently decreased the levels of fibrin degradation products, and increased serum ATIII levels. (Similar effects of L-Glu-L-Trp on FDP and ATIII were observed in studies of patients with disseminated intravascular coagulation resulting from pleuritis, Example 4, Protocol E, above.)

TABLE 19

Laboratory Indicia of Disease Activity in Children with Bacterial Pneumonia

| Marker | Normal Healthy Control | Before Therapy | After Combination L-Glu-L-Trp Therapy |
|---|---|---|---|
| Leukocytes ×10⁹/L: | 11.2 ± .01 | 13.3 ± .01 | 11.0 ± 0.01 |
| % Normal Value: | (100%) | (119%) | (98%) |
| Lymphocytes ×10⁹/L: | 0.31 ± 0.03 | 0.335 ± 0.002 | 0.36 ± 0.01 |
| % Normal Value: | (100%) | (108%) | (116%) |
| T-Lymphocytes: ×10⁹/L:: | 0.681 ± 0.09 | 0.9 ± 0.09 | 1.1 ± 0.01 |
| % Normal Value:: | (100%) | (132%) | (167%) |
| B-Lymphocytes: ×10⁹/L: | 0.482 ± 0.07 | 0.70 ± 0.05 | 0.84 ± 0.06 |
| % Normal Value: | (100%) | (145%) | (175%) |
| IgG (mg/mL) | 142 ± 9.8 | 133 ± 6.6 | 138 ± 5.6 |
| % Normal Value: | (100%) | (94%) | (97%) |
| IgM (mg/mL) | 171 ± 13.6 | 160 ± 6.9 | 153 ± 6.9 |
| % Normal Value: | (100%) | (94%) | (89%) |
| IgA (mg/mL) | 41 ± 5.2 | 60 ± 5.9 | 67 ± 4.8 |
| % Normal Value: | (100%) | (146%) | (163%) |

TABLE 20

Clinical Indicia of Disease Activity in Children with Bacterial Pneumonia

| Clinical Index | Conventional Antibiotic Therapy | L-Glu-L-Trp Combination Therapy |
|---|---|---|
| Duration Systemic Toxicity (days) | 10.7 ± 1.6 | 8.2 ± 0.9 |
| Patient Condition Stabilized (days) | 10.6 ± 2.0 | 6.8 ± 0.7 |
| Normalization of Body Temperature (days) | 20.5 ± 2.4 | 13.9 ± 1.7 |
| Favorable Resolution by X-ray (days) | 21.9 ± 3.1 | 19.3 ± 2.5 |
| Hemoglobin (g/L) | 106.0 ± 2.7 | 115.0 ± 1.6 |
| Erythrocyte Sedimentation Rate (mm) | 34.8 ± 4.8 | 26.2 ± 3.2 |
| Antibiotics Required (days) | 25.9 ± 2.0 | 21.4 ± 1.4 |
| Hospital Bed-Days | 42.3 ± 2.1 | 41.7 ± 1.5 |
| Mortality % | 1.2 | 0 |

Clinical Effects

L-Glu-L-Trp treated patients showed a normalization of body temperature more rapidly than control patients receiving conventional antibiotic therapy, and in patients with intrapulmonary infection, the infection resolved more rapidly than in controls, as evidenced by changes in lung opacity on chest X-ray.

EXAMPLE 5

It Acquired Immunodeficiency Syndrome

In separate studies, a total of 21 HIV-infected individuals were studied, including full-blown syndrome, prodromal, and pre-AIDS afflicted individuals who were treated with Thympentin. Thympentin and TPI are thymic gland peptide extracts previously disclosed in the scientific literature. Comparative studies reveal L-Glu-L-Trp to be more effective than TPI in restoring normal immunologic indices, T-cell functional activity, and T4/T8 ratios.

Method of Administration:

Sterile saline containing the sodium salt of L-Glu-L-Trp can be administered either im, or by intralymphatic, or intranasal routes each day for 5–10 consecutive days, and the treatments are repeated every 30 days.

Immunosuppressed individuals who have sustained radiation injuries (Examples 2 and 3,) were treated with L-Glu-L-Trp with excellent restoration of immunological indices. Therefore, L-Glu-L-Trp may benefit HIV infected individuals, and AIDS patients, by treating symptoms and complications resulting from the acute HIV viral infection and thereby reducing the need to use other medications with potentially toxic side effects.

L-Glu-L-Trp treatments stimulated innate immunity and anti-bacterial cellular immunity in experimental animals, see Examples below. Stimulation of the latter immune mechanisms in HIV infected (or AIDS) patients may result in a reduction in the incidence, duration, or severity of opportunistic infections including respiratory infections.

EXAMPLE 6

Dermatologic Diseases

Patients were entered into a large ongoing dermatology clinical trial protocol, the results of which are summarized in Protocols A-F, below.

Protocol A: Chronic Staphylococcal Pyoderma:
Summary Overview.

The total clinical trial population eventually under examination consisted of 159 patients with pyoderma, including furunculitis, cellulitis, and folliculitis. Trial Protocol A1, below, details some of the results obtained in this trial. Medications were administered either im or intranasally for 5 consecutive days. Peripheral blood immune indices were decreased prior to treatment and following treatment with L-Glu-L-Trp were restored to within the normal range. Treatments with L-Glu-L-Trp also resulted in a disappearance of skin manifestations and resolution of pyoderma in the treated patients. Clinical improvement was correlated with return of the immune parameters to within the normal range of values. In certain patients, L-Glu-L-Trp was also topically applied as a sterile saline solution of medication for a period of 5 to 10 days at a dosage of 1 μg/kg body weight.

Protocol A1: Chronic Staphylococcal Pyoderma:
Patient Population:

Efficacy of L-Glu-L-Trp in combined antibiotic therapy was evaluated in 59 patients (aged 18 to 56; 32 men and 27 women) with chronic pyoderma non-responsive to antibiotic therapy. The patients were divided into Group 1 (n=36; L-Glu-L-Trp combination therapy) and Group 2 (n=23; control), as described below. Diagnosis, at the time of clinical presentation, and the demographics of the patient population are summarized in TABLE 21. The length of illness for the patients in the trial ranged from 5 months to 16 years.

TABLE 21

| | Patient Population | | | | | | |
|---|---|---|---|---|---|---|---|
| | Total | Demographics | | | | | |
| Patient | No. | Male Ages: | | | Female Ages: | | |
| Diagnosis | Patients | 18–30 | 31–43 | 44–56 | 18–30 | 31–43 | 44–56 |
| Chronic relapsing osteofolliculitis | 3 | 1 | — | — | 1 | 1 | — |
| Volar eruptions | 1 | — | 1 | — | — | — | — |
| Papular-postular acne | 19 | 12 | — | — | 6 | 1 | — |
| Chronic relapsing folliculitis gravis | 1 | — | — | — | — | 1 | — |
| Chronic furunculitis | 11 | 1 | 2 | 1 | 4 | 1 | 2 |
| Abscess and indurative acne | 14 | 7 | — | — | 6 | 1 | — |
| Chronic relapsing hydradenitis | 1 | 1 | — | — | — | — | — |
| Chronic abscess pyoderma | 7 | 4 | 2 | — | — | — | 1 |
| Chronic ulcerative pyoderma | 2 | — | — | — | — | 2 | — |
| Totals: | 59 | 26 | 5 | 1 | 17 | 7 | 3 |

Group 1 consisted of 36 patients (18–56 years of age; 17 men and 19 women) who had been previously repeatedly treated with antibiotics without significant clinical effect. Staphylococci cultured from 14 patients showed broad spectrum resistance to 10 of 15 antibiotics tested. The length of illness was from 6 months to 16 years. Twenty-four of the patients (24) had a clinical history that included recurrence of one or more diseases, e.g., chronic tonsillitis, maxillary sinusitis, dental granuloma, periodontitis, pancreatitis, gastritis, gastric ulcers, chronic bronchitis, chronic prostatitis, otitis, etc. Staphylococci were isolated from dermal foci of infection in all 30 patients. The latter isolates were resistant to several antibiotics and in 14 patients, the staphylococci were multiple drug resistant, (i.e., resistant to 10 of the 15 antibiotics tested).

Group 2 (conventional treatment control) consisted of 23 patients with similar demographics and pyoderma diseases.
Therapeutic Protocols:

The patients in Group 1 were treated in a combination, two-stage therapy using antibiotics and L-Glu-L-Trp. Patients in Group 2 received only antibiotics and other palliative therapies.

Stage 1: In the first stage of the protocol, only L-Glu-L-Trp was administered in the hope of increasing host immune responsiveness and antibiotic sensitivity of the bacteria. At the conclusion of stage 1, staphylococci were isolated from the patients and tested for drug resistance. Based on the results of the antibiotic sensitivity testing, an antibiotic was selected for use in Stage 2, below.

Stage 2: In the second stage, both L-Glu-L-Trp and the selected antibiotic were administered in combination, and in certain cases a staphylococcal "autovaccine" was prepared and used to immunize the patients against their individual staphylococcal strain. The decision on the type of second stage therapy was made on a patient-by-patient basis after evaluating the effects of first stage therapy on B-lymphocytes, neutrophils, and IgM levels in circulation. If the latter indicators were significantly elevated then only combination therapy with L-Glu-L-Trp and antibiotic was administered in the second stage, however, if the indicators were not elevated, then autovaccine was administered in addition to the antibiotic and L-Glu-L-Trp therapy, i.e., in an attempt to boost an immune response to the bacteria.

Treatment Route:

L-Glu-L-Trp treatment was administered by two different routes: namely, im (Group 1A) and intranasally (Group 1B). Group 1A consisted of 17 patients (ie., 17 of the 36 patients in Group 1) who were treated with L-Glu-L-Trp by intramuscular injection of 100 µg daily for 5 days. Group 1B, the remaining 19 patients in Group 1, received L-Glu-L-Trp by intranasal instillation, daily for 5 days, of 1 mL of a 0.01% solution. (In pharmacokinetic studies of experimental animals, administration of labeled L-Glu-L-Trp by intranasal instillation resulted in rapid, i.e., minutes, appearance of label in peripheral blood.) Results obtained with Group 1A and Group 1B were not statistically different, so the data were combined for subsequent analysis and the data obtained with Groups 1A and 1B are presented together in tabular form below.

Antibiotics were administered according to established dosages and routes: i.e., penicillin, Ampicillin, oxacillin, tetracycline, erythromycin, garamycin; administered by intramuscular route. Antibiotics were chosen according to the antibiotic sensitivity of the Staphylococci isolated from the respective patients. (Antibiotic sensitivity was determined by testing staphylococcal isolates for their sensitivity in an antibiotic sensitivity doubling-dilution assay with the aid of the semi-automatic MIC-2000 system, Dynatech, USA).

Laboratory Test Results

Materials and methods used in these studies appear in the text immediately following EXAMPLE 34, below. Laboratory parameters of disease activity were monitored including, morning body temperature, leukocyte and differential blood cell counts, and immune parameters (TABLE 22). The mean values (+/− S.D.) recorded in Group 1A and 1B patient samples at the conclusion of Stage 2 of therapy are summarized in TABLE 22.

TABLE 22

Laboratory Indicia of Disease Activity in Patients with Chronic Pyoderma

| Marker | Normal Healthy Value | Conventional Treatment Control (n = 23) | L-Glu-L-Trp[a] Treatment (n = 36) |
|---|---|---|---|
| Leukocytes |  |  |  |
| ($\times 10^9$/L): | 6.71 ± 0.17 | 7.89 ± 0.36[†+] | 7.75 ± 0.33 |
| % Normal Value: | (100%) | (118%) | (115%) |
| Lymphocytes: |  |  |  |
| %: | 28 ± 0.6 | 29.4 ± 1.3 | 30.8 ± 1.4 |
| $\times 10^9$/L: | 2.01 ± 0.09 | 2.26 ± 0.12 | 2.41 ± 0.14 |
| % Normal Value: | (100%) | (112%) | (120%) |
| T-Lymphocytes: |  |  |  |
| %: | 61.4 ± 1.6 | 62.8 ± 1.9 | 69.3 ± 1.9* |
| $\times 10^9$/L:: | 1.70 ± 0.12 | 1.38 ± 0.08[†] | 1.68 ± 0.12* |
| % Normal Value:: | (100%) | (81%) | (99%) |
| T-helper: |  |  |  |
| (OKT4+) %: | 35.3 ± 2.7 | 13.7 ± 1.6[†] | 20.3 ± 2.9 |
| $\times 10^9$/L: | 0.65 ± 0.05 | 0.30 ± 0.03[†] | 0.46 ± 0.05* |
| % Normal Value:: | (100%) | (46%) | (71%) |
| T-suppressor: |  |  |  |
| (OKT8+) %: | 21.3 ± 0.9 | 17.9 ± 1.4 | 17.1 ± 1.9 |
| $\times 10^9$/L: | 0.41 ± 0.03 | 0.37 ± 0.04 | 0.39 ± 0.04 |

TABLE 22-continued

Laboratory Indicia of Disease Activity in Patients with Chronic Pyoderma

| Marker | Normal Healthy Value | Conventional Treatment Control (n = 23) | L-Glu-L-Trp[a] Treatment (n = 36) |
|---|---|---|---|
| % Normal Value: | (100%) | (90%) | (95%) |
| T4+/T8+ Ratio: | 1.64 ± 0.12 | 0.82 ± 0.17[†] | 1.32 ± 0.11* |
| B-Lymphocytes: |  |  |  |
| %: | 18.1 ± 1.4 | 13.5 ± 1.4 | 12.1 ± 1.5 |
| $\times 10^9$/L: | 0.49 ± 0.04 | 0.30 ± 0.04[††] | 0.28 ± 0.04 |
| % Normal Value: | (100%) | (61%) | (57%) |
| Surface Ig + B-Lym: |  |  |  |
| %: | 13.8 ± 1.2 | 16.1 ± 2.2 | 16.9 ± 1.7 |
| $\times 10^9$/L: | 0.29 ± 0.02 | 0.40 ± 0.07 | 0.34 ± 0.05 |
| % Normal Value: | (100%) | (138%) | (117%) |
| IgG (g/L) | 11.5 ± 0.50 | 14.1 ± 0.49[††] | 15.5 ± 0.73 |
| % Normal Value: | (100%) | (123%) | (135%) |
| IgM (g/L) | 1.15 ± 0.06 | 1.38 ± 0.17 | 1.25 ± 0.12 |
| % Normal Value: | (100%) | (120%) | (109%) |
| IgA (g/L) | 1.90 ± 0.08 | 2.38 ± 0.14[††] | 2.40 ± 0.18 |
| % Normal Value: | (100%) | (125%) | (126%) |
| C3 (g/L) | 0.84 ± 0.02 | 0.76 ± 0.01[††] | 0.77 ± 0.02 |
| % Normal Value: | (100%) | (90%) | (92%) |
| Imm. Cmplx. (Units) | 44.0 ± 1.6 | 39.6 ± 3.6 | 45.9 ± 4.9 |
| NK Activity (% cytotox.) | 45.07 ± 2.82 | 29.8 ± 3.35[†] | 45.18 ± 2.55* |
| Monocytes: |  |  |  |
| %: | 7.0 ± 0.28 | 6.14 ± 1.4 | 5.65 ± 0.40 |
| $\times 10^9$/L: | 0.55 ± 0.03 | 0.48 ± 0.03 | 0.43 ± 0.04 |
| % Normal Value: | (100%) | (87%) | (78%) |
| Neutrophils: |  |  |  |
| %: | 63.0 ± 1.1 | 61.1 ± 1.5 | 59.8 ± 1.5 |
| $10^9$/L: | 4.41 ± 0.18 | 4.98 ± 0.29 | 4.54 ± 0.25 |
| % Normal Value: | (100%) | (113%) | (103%) |
| Phagocytic Cells |  |  |  |
| $\times 10^9$/L: | 2.65 ± 0.06 | 2.19 ± 0.10[†] | 2.36 ± 0.27 |
| % Normal Value: | (100%) | (83%) | (89%) |
| Phag. Index | 4.92 ± 0.05 | 4.51 ± 0.58[†] | 5.31 ± 0.20** |
| Erythrocytes $\times 10^{12}$/L | — | 5.4 ± 0.7 | −5.2 ± 0.6 |
| Erythrocyte Sed. Rate (mm) | — | 13.2 ± 1.31 | 1.2 ± 1.4 |

[a]L-Glu-L-Trp therapy = 1st stage therapy with L-Glu-L-Trp only as described below under "Clinical Results";
[b]HSA, hemolytic *Staphylococcus aureus* antigen;
[†]Significant different between healthy/normal and pre-treatment values at the p <0.05 level;
[††]p < 0.01 level; or,
[†††]p < 0.001 level;
*Significant difference between patient pre- and post-treatment values at the p < 0.05 level;
**p < 0.01 level; or,
***p < 0.001 level, T-Lymphocytes:

The results presented in TABLE 22 show i) that patients with pyoderma have decreased peripheral blood T-lymphocytes, T4+-lymphocytes, and NK activity similar to those existent in certain immunodeficiency states; and, ii) that treatment with L-Glu-L-Trp stimulated an increase in peripheral T-lymphocytes, T4+ lymphocytes, the ratio of T4+/T8+ lymphocytes, and NK activity in peripheral blood to >70% of values recorded in peripheral leukocytes of normal healthy volunteers. Functional activity of peripheral T-lymphocytes, as measured by blastogenesis in response to stimulation with Con-A and PHA mitogens and HSA (hemolytic staphylococcal allergen) antigen, was also apparently depressed in chronic pyoderma patients and treatment with L-Glu-L-Trp increased blastogenesis to greater than (or near equal to) the levels produced by healthy volunteers (TABLE 23).

TABLE 23

Lymphocyte Blastogenic Activity:

| Blast Transformation (Antigen) | | Normal Healthy Values | Patients Before Therapy | After L-Glu-L-Trp Therapy |
|---|---|---|---|---|
| PHA | (%) | 35.9 ± 2.6 | 50.2 ± 2.7 | 40.2 ± 3.9 |
| Con-A | (%) | 49.4 ± 3.3 | 76.3 ± 4.9 | 58.3 ± 3.9 |
| HSA | (%) | 95.1 ± 5.7 | 114.5 ± 7.6 | 84.9 ± 5.5 |

(No mean values were significantly different than the Pre-treatment values, i.e. p > 0.05)

Multivariant analysis of the immune values and clinical results observed in these studies suggested a direct correlation between the length of staphylococcal infection and the blood levels and immune functions of T-lymphocytes. The results of this trial suggest that immunity mediated by T-lymphocytes may not express itself in chronic staphylococcal skin disease until >2.5–4 years after diagnosis of the infection, despite (or because of) treatment with conventional antibiotics and corticosteroid ointments. In this patient population, antibiotic resistance was apparently correlated with the development of a possible T-lymphocyte deficiency. Treating the patients' immunodeficiency with L-Glu-L-Trp was apparently correlated with a decrease in antibiotic resistance of the staphylococci isolated from the patients.

B-Lymphocytes

The results presented in TABLE 22, show decreased absolute B-lymphocyte levels and surface $Ig^+$ lymphocytes in the trial population, despite increased numbers of surface $IgG^+$ lymphocytes and increased serum levels of IgG and IgA in the peripheral blood samples. Following Stage 2 of L-Glu-L-Trp treatment, total B-lymphocyte counts did not change significantly, but the numbers of surface $IgG^+$ lymphocytes decreased, ie., from $0.37\pm0.075\times10^9$/L to $0.19\pm0.023\times10^9$/L (p<0.05) as compared to normal levels of $0.08\times0.008\times10^9$/L.

Phagocytic Activity:

The results presented in TABLE 22 show an increase in the number of Staphylococci ingested by each peripheral blood phagocytic cell (i.e., phagocytic index), a favorable functional characteristic commonly observed with "activated" macrophages and neutrophils.

In vitro studies:

In a separate in vitro study, lymphocytes from 26 patients of Group 1, above, were incubated in tissue culture medium containing 0.01% L-Glu-L-Trp (i.e., 100 µg/mL). An increase in the percentage of E-RFC was observed from 64.2±2.27% to 73.3±2.26% (p<0.01), $OKT4^+$ lymphocytes increased from 13.4±1.4% to 18.2±1.6% (p<0.05), but $OKT8^+$ lymphocytes did not change significantly, i.e., 17.2±1.7% to 17.9±1.4% (p>0.05). (Similar data showing increased OKT4 expression on T-lymphocytes treated in vitro with L-Glu-L-Trp is presented in other Examples, below.)

Clinical Results:

Stage 1: Clinical results recorded during the first stage of therapy (L-Glu-L-Trp only), included a short-lived aggravation of the dermal diseases in 20 of the 36 patients which occurred after the second day of L-Glu-L-Trp therapy. The aggravation was manifest as an "intensification of hyperemia and dermal infiltration around infected foci and an increase in the amount of purulent excretion". During continued administration of L-Glu-L-Trp the "phenomenon subsided" and "regenerative processes were strengthened". In the cutaneous lesions acceleration of scar tissue formation and re-epithelialization were observed. Bacterial isolates were tested for antibiotic sensitivity, and increased antibiotic sensitivity was recorded for isolates from certain patients. At the time of the trial it was thought possible that L-Glu-L-Trp treatment induced synthesis and release of anti-staphylococcal factor (ASF), a T-cell cytokine that reportedly increases the antibiotic sensitivity of antibiotic-resistant Staphylococci.

Staphylococci were isolated from patients before and after treatment in Stage 1 with L-Glu-L-Trp in order to determine whether a favorable reversal of T-lymphocyte immunodeficiency might lead to a change in the antibiotic sensitivity. The isolated bacterial colonies following Stage I were typed as follows: namely, in 16 patients *S. aureus,* in 34, *S. epidermidis,* in 2 saprophytic Staphylococci. In all cases the same types of Staphylococci were isolated following treatment with L-Glu-L-Trp, but in 4 patients the predominant Staphylococci in the isolates changed from *S. aureus* to *S. epidermidis* (n=2), and saprophytic Staphylococci (n=2). The results of testing patient isolates for antibiotic sensitivity are summarized in TABLE 24.

TABLE 24

Antibiotic Sensitivity of Patient Isolates

Mean Sensitivity (µg/mL)

| Antibiotic | Before Treatment | After Stage 1 Treatment |
|---|---|---|
| Penicillin | 9.45 ± 0.28 | 2.52 ± 0.70 |
| Bicillin-3 | 9.24 ± 0.53 | 2.42 ± 1.02 |
| Oxacillin | 5.11 ± 0.63 | 1.56 ± 0.45 |
| Ampicillin | 8.10 ± 0.49 | 2.64 ± 0.60 |
| Levomycetin | 9.17 ± 0.36 | 4.58 ± 0.67 |
| Streptomycin | 6.71 ± 0.59 | 3.39 ± 0.66 |
| Monomycin | 6.34 ± 0.55 | 2.01 ± 0.46 |
| Kanamycin | 6.32 ± 0.58 | 2.09 ± 0.54 |
| Gentamycin | 5.47 ± 0.92 | 1.32 ± 0.49 |
| Cisomycin | 3.46 ± 0.90 | 1.59 ± 0.58 |
| Ceporin | 5.69 ± 0.86 | 1.82 ± 0.67 |
| Cephamezine | 3.52 ± 0.94 | 1.33 ± 0.53 |
| Keflin | 4.49 ± 0.93 | 1.86 ± 0.69 |
| Kefzol | 4.61 ± 0.87 | 1.86 ± 0.93 |

The results presented in TABLE 24 show that the Staphylococci isolated from patients prior to therapy were relatively resistant to penicillin antibiotics, however the isolates were relatively sensitive in vitro to cephalosporins (i.e., Ceporin, Cephan, Keflin, and Kefiol), and certain aminoglycoside antibiotics (i.e., Cisomycin). Following treatment with L-Glu-L-Trp the Staphylococci isolated from the patients showed increased antibiotic-sensitivity to one, a few, or all antibiotics (noteworthy exceptions being penicillin, bicillin-3, and levomycetin). In certain cases more than a 100-fold increase in antibiotic sensitivity was observed. Thus, it may be concluded that while L-Glu-L-Trp did not completely eliminate penicillin resistance, the phenotype of multiple drug resistance (i.e., to antibiotics other than penicillin) was altered following treatment.

Stage 2: Clinical results recorded during the second stage of therapy (ie., with L-Glu-L-Trp and an antibiotic, pyrogenal, or autovaccine, above), are summarized in TABLE 25. The clinical findings included absence of suppuration from dermal infections, and absence of new eruptions of infected foci from the skin as well as complete cicatrization of ulcers and resolution of deep infiltrates. Peripheral blood leukocyte counts also returned to normal values by the end of the therapy and humoral immune activity also appeared to be increased as measured by the absolute levels of serum IgM.

TABLE 25

Clinical Results: Following Stage 2 of Treatment:

Number of Patients with Clinical Result:

| Patient Diagnosis | Recovered | Significantly Improved | Improved | No Effect | Worse |
|---|---|---|---|---|---|
| Chronic relapsing osteofolliculitis | 3 | — | — | — | — |
| Chronic relapsing folliculitis gravis | 1 | — | — | — | — |
| Papular-pustular acne | 4 | 3 | — | — | — |
| Abscess and indurative acne | 4 | 1 | 1 | — | — |
| Chronic furunculitis | 10 | — | — | — | — |
| Chronic abscess pyoderma | 5 | 2 | — | — | — |
| Chronic ulcerative pyoderma | — | 2 | — | — | — |
| Totals: | 27 | 8 | 1 | 0 | 0 |

Long term follow-up:

Combination therapy with L-Glu-L-Trp and antibiotics resulted in clinical recovery in 27 patients with chronic pyoderma who previously had recurrently failed conventional broad-spectrum antibiotic therapy. In addition, considerable improvement was noted in 8 patients and improvement was observed in 1 case. In the 24 latter patients, recovery was stable over a six month period, and in the remaining 3 patients (of the trial) the recurrences of infection were much more mild than those previously documented in the patients' medical histories. Clinical recovery was attained in all patients with chronic recurring osteofolliculitis and folliculitis as well as those with chronic furunculosis. Of 7 patients with papulous pustular acne, clinical recovery was achieved in 4. Of 10 patients with abscessing and indurative acne, clinical recovery was achieved in 6. Of 7 patients with chronic abscessing pyoderma, complete clinical recovery with resolution of infiltrates and cicatrization of ulcers was achieved in 5. During 6–12 months follow-up, relapses were observed in 2 patients with acne vulgaris and 1 with chronic abscessive pyoderma. No recurrences of disease activity were noted in patients with chronic recurrent osteofolliculitis, folliculitis, and furunculosis. Aggravation of the disease process was observed in one patient with an ulcerative form of chronic pyoderma, ie., manifested as an increase in the quantity of purulent discharge. No side effects or allergic reactions were observed in these studies.

Summary:

The three step method of treatment, i.e., 1) treating with L-Glu-L-Trp assessing antibiotic sensitivity of isolates from patients, and 3) selecting and administering an antibiotic to which the bacteria is sensitive, permitted the attending physician to choose for each patient an individual antibiotic with highest anti-bacterial activity. Seventy-eight percent of patients (78%) at the conclusion of Stage 1 showed a marked and reliable decrease in the microbial inhibitory concentration (MIC) of antibiotic required to inhibit growth of the isolated bacteria in vitro. In vivo, increased antibiotic sensitivity was clinically manifested in 55–75% of the patients studied. At the conclusion of Stage 2 the combined treatment regimen with antibiotic and L-Glu-L-Trp resulted in complete recovery of 27 previously incurable patients. In addition, 8 patients showed significant improvement and I showed moderate improvement.

While somewhat unexpected and provocative, the clinical outcome is not without a variety of possible scientific explanations. At least the following possibilities come to mind: i) stimulation of cell mediated immunity in chronic staphylococcal infection leads to immune elimination, or slower growth, of the more resistant populations of bacteria; or, ii) L-Glu-L-Trp treatment induces production of a cytokine such as ASF (supra) or of lysozyme release at sites of infection; or, iii) immune mechanisms stimulated by L-Glu-L-Trp induce a down-regulation of the multiple drug resistant phenotype permitting a shift to more antibiotic sensitive bacteria in patients; or, iv) L-Glu-L-Trp may exert a direct antibacterial effect on Staphylococci.

Protocol A2: Chronic Staphylococcal Infection:

Summary Overview:

L-Glu-L-Trp was administered to 52 patients suffering from chronic skin diseases caused by antibiotic-resistant Staphylococci. 42 patients with the same pathology but not treated with the immunomodulator were the control group. L-Glu-L-Trp was administered im to 27 patients single daily at 100 μg for 5 days and intranasally to 25 patients with the same daily and total dose. Differences between these two methods of application were not noticed. The results of antibiotic sensitivity testing showed that in all the patients with signs of secondary T-immunodeficiency, the antibiotic-sensitivity of the patients' Staphylococci to one, a few, or all antibiotics was increased sharply (more than 100-fold). The increased antibiotic sensitivity permitted the physician to choose an antibiotic for each patient that had a high level of activity for the bacteria. As a whole, within each group of patients there was a marked and reliable increase in antibiotic sensitivity, ie, decreased microbial inhibitory concentration (MIC) for all antibiotics studied. The treatment regimen with L-Glu-L-Trp, followed by antibiotic sensitivity testing, and then administration of an individualized antibiotic provided complete recovery in all patients with previously incurable antibiotic resistant staphylococcal infections.

Protocol A3: Chronic Staphylococcal Infection and Systemic Lupus Erythematosus:

Patient Groups:

Group I constituted 50 patients with diagnosed pyoderma: i.e., 29 males and 21 females ranging from 17 to 59 years of age. All patients in this trial had recurrent episodes of pyoderma and all had previously received conventional therapy including use of antibiotics, without effect. Length of illness was from 6 months to 16 years. Twenty-four ofthe patients had one (or several) intermittent opportunistic and infectious diseases including: chronic tonsillitis (2), chronic maxillofacial sinusitis and sinusitis (2), dental granuloma (2), parodontitis (2), chronic cholestitis and pancreatitis (7), chronic gastritis and gastroenteritis (6), chronic bronchitis (1), chronic prostatitis (1), chronic lymphadenitis (2), chronic otitis (1), and focal pulmonary tuberculosis (1).

Group 1A (a subgroup of Group 1) consisted of 32 patients (17 males and 15 females ranging from 17 to 42 years of age) with chronic pyococcal skin diseases including furunculosis, disseminated impetigo, multiple ecthymas, recurring osteofolliculitis, seborrhea adiposa, and concrete seborrhea complicated by vulgar or abscessing acne. Diseases were characterized by a chronic course or frequent relapses, and at the time of presentation for entry into the trial, all patients had received several prior courses of antibiotic therapy, none of which led to any detectable clinical improvement. Patients in Group 1A were randomly divided into two treatment groups, the first consisting of 16 patients treated with L-Glu-L-Trp according to Therapy A, below, and the second consisting of 16 patients treated (as a control) according to conventional therapeutic methods- i.e., Therapy B (below). The results obtained with this patient population are summarized in the Tables, below.

Group 1B consisted of 18 patients (12 males and 6 females ranging in age from 27 to 62 years of age) having atypical forms of pyoderma persisting over 2–15 years and marked by chronic and recurrent courses with extreme resistance to therapy. Patients in Group 1B were randomly divided into two treatment groups, the first consisting of 10 patients (7 males and 3 females) treated with L-Glu-L-Trp according to Therapy A, below, and the second consisting of 8 patients (5 males and 3 females) treated (as a control) according to conventional therapeutic methods; i.e., Therapy B (below). The results obtained with this patient population are summarized in the Tables, below.

Group 2 constituted 22 patients with diagnosed forms of systemic lupus erythematosus (SLE): ie., 14 males and 8 females ranging in age from 21 to 62 years of age. The time since presentation with a diagnosis of SLE in this patient population ranged from several months to 18 years. All SLE patients in this trial had dermal manifestations of lupus erythematosus that included discoid disseminated forms of the disease. All patients had experienced chronic and recurrent episodes of pyoderma, and all had previously received conventional therapy, including use of antibiotics, delagil, and external corticosteroid ointments without effect. Patients in Group 2 were randomly divided into two treatment groups, the first consisting of 13 patients (9 men and 4 women) treated with L-Glu-L-Trp according to Therapy A, below, and the second consisting of 9 patients (5 men and 4 women) treated (as a control) according to Therapy B, ie., conventional therapeutic methods using anti-malarial preparations and vasoactive agents according to standard dosages and schedules.

Treatment Protocols

Therapy A: L-Glu-L-Trp was administered im to all patients at a dosage of 100 µg in a volume of 1 mL daily for 5 days. In treatment Protocol A, all patients received L-Glu-L-Trp in combination with antibiotics.

Therapy B (conventional therapy control): All patients in this protocol received the same antibiotics as in Therapy A and a nonspecific stimulatory agent, i.e., Thymogenin instead of L-Glu-L-Trp.

Laboratoy Tests:

Clinical and laboratory parameters of disease activity were monitored including morning body temperature, leukocyte and differential blood cell count, hematology measurements and blood chemistry and immunology determinations including the percentages and absolute numbers of B- and T-lymphocytes, T-helper and T-suppressor cells, and in vitro blast responsiveness of the cells to staphylococcal protein antigen, Concanavalin A mitogen, and staphylococcal protein A. Antibiotic sensitivity of Staphylococci was evaluated in patients before and after treatment with L-Glu-L-Trp or conventional antibiotics including penicillin (1), Ampicillin (5), oxacillin (13), Monomycin (1), Cisomycin (1), tetracycline (9), erythromycin (3), Garamycin (1), Lincomycin (1), cephalosporin (2), Kefzol (1), Keflin (1), and cephalex (1). Local antibiotics were administered as follows: Ampicillin (4), oxacillin (4), Levomycetin (1), tetracycline (9), Rondomycin (2), deoxycycline (8), cephalexin (2), and Rifampicin (1).

The hematology and clinical chemistry laboratory test results obtained with the patients in Group 1A, Group 1B, and Group 2 may be summarized as follows:

1. Hematology values were within the normal range of values prior to treatment and no significant differences were observed between the pre- and post-treatment values (i.e., either conventional therapy or L-Glu-L-Trp treatment) for clotting time of citrated whole blood that was recalcified; prothrombin clotting time; Thrombotest units; or, fibrinogen concentration in plasma; and, 2. Blood protein values were within the normal range prior to and after therapy for complement protein C3, alkaline phosphatase, bilirubin, creatinine, glucose, total protein, and concentrations of chloride, calcium, and sodium.

The results of laboratory tests of immune parameters of Groups 1A and 1B are presented in TABLE 26.

TABLE 26

Differential Cell Counts and Immunology Values:
Group 1A- Chronic Pyoderma; Group 1B- Atypical Pyoderma

| | | Group 1A | | | Group 1B | | |
|---|---|---|---|---|---|---|---|
| Index | Normal Healthy Values | Before Therapy (n = 32) | Control Therapy (n = 16) | L-Glu-L-Trp Therapy (n = 16) | Before Therapy (n = 18) | Control Therapy (n = 8) | L-Glu-L-Trp Therapy (n = 10) |
| Leukocytes (×10⁹/L): | 6.7 ± 2 | 7.7 ± 1 | 7.9 ± 1 | 8.7 ± 0.5 | 6.5 ± 1 | 6.4 ± 1 | 6.2 ± 1 |
| % Normal Value: | (100%) | (115%) | (118%) | (130%) | (97%) | (96%) | (93%) |
| Lymphocytes %: | 41.1 ± 12 | 27.3 ± 2 | 25.7 ± 2 | 25.9 ± 2.2 | 34.8 ± 3 | 34.7 ± 4 | 34.5 ± 4 |
| (×10⁹/L): | 2.8 ± 1 | 1.9 ± 0.1 | 2.2 ± 0.1 | 2.0 ± 0.2 | 2.26 ± 0 | 2.26 ± 0 | 2.14 ± 0 |
| % Normal Value: | (100%) | (68%) | (79%) | (71%) | (81%) | (81%) | (76%) |
| T-Lymphocytes (%): | 61.4 ± 13 | 49.9 ± 7 | 55.9 ± 4 | 52.3 ± 5 | 63.5 ± 7 | 61.4 ± 7 | 55.1 ± 6 |
| (×10⁹/L): | 1.7 ± 1 | 1.13 ± 0 | 1.32 ± 0 | 1.15 ± 0 | 1.12 ± 0 | 1.21 ± 0 | 0.87 ± 0 |
| % Normal Value: | (100%) | (66%) | (78%) | (68%) | (66%) | (71%) | (51%) |
| T-helper (%): | 47.1 ± 16 | 55.3 ± 6 | 48.3 ± 5 | 45.4 ± 4.9 | 39 ± 0 | 36.2 ± 6 | 32.1 ± 3 |
| (×10⁹/L): | 1.32 ± 1 | 1.07 ± 0 | 1.03 ± 0 | 0.92 ± 0.09 | 0.68 ± 0 | 0.65 ± 0 | 0.53 ± 0 |
| % Normal Value: | (100%) | (81%) | (78%) | (70%) | (52%) | (49%) | (40%) |
| T-suppressor (%): | 14.3 ± 12 | 13.7 ± 3 | 21.3 ± 4 | 28.2 ± 4 | 24.5 ± 5 | 24.5 ± 5 | 23.1 ± 5 |
| (×10⁹/L): | 0.39 ± 0 | 0.31 ± 0 | 0.36 ± 0 | 0.51 ± 0 | 0.55 ± 0 | 0.54 ± 0 | 0.49 ± 0 |
| % Normal Value: | (100%) | (79%) | (92%) | (131%) | (141%) | (138%) | (126%) |
| B-Lymphocytes (%): | 18 ± 11 | 7 ± 3 | 8 ± 2 | 7 ± 3 | 15 ± 3 | 11 ± 7 | 8.5 ± 1 |
| (×10⁹/L): | 0.49 ± 0 | 0.15 ± 0 | 0.14 ± 0 | 0.15 ± 0 | 0.25 ± 0 | 0.21 ± 0 | 0.14 ± 0 |
| % Normal Value: | (100%) | (31%) | (29%) | (31%) | (51%) | (43%) | (29%) |
| IgG (g/L) | 11 ± 2 | 15.1 ± 1 | 16.8 ± 1 | 16.2 ± 1 | 15 ± 4 | 15 ± 2 | 16.6 ± 2 |

TABLE 26-continued

Differential Cell Counts and Immunology Values:
Group 1A- Chronic Pyoderma; Group 1B- Atypical Pyoderma

|  | Normal Healthy Values | Group 1A ||| Group 1B |||
|---|---|---|---|---|---|---|---|
|  |  | Before Therapy (n = 32) | Control Therapy (n = 16) | L-Glu-L-Trp Therapy (n = 16) | Before Therapy (n = 18) | Control Therapy (n = 8) | L-Glu-L-Trp Therapy (n = 10) |
| Index |  |  |  |  |  |  |  |
| % Normal Value: | (100%) | (140%) | (156%) | (150%) | (141%) | (142%) | (154%) |
| IgA (g/L) | 2 ± 1 | 3 ± 0 | 3 ± 0 | 2.7 ± 1 | 2 ± 0 | 2 ± 0 | 2.21 ± 0 |
| % Normal Value: | (100%) | (156%) | (141%) | (143%) | (114%) | (124%) | (117%) |
| IgM (g/L) | 2 ± 0 | 1 ± 0 | 1 ± 0 | 1 ± 0 | 1 ± 1 | 1 ± 0 | 1.64 ± 0 |
| % Normal Value: | (100%) | (67%) | (58%) | (65%) | (84%) | (89%) | (104%) |
| Erythrocyte (sed. rate mm): | — | 11.2 ± 1 | 12.9 ± 1 | 13.1 ± 1 | — | — | — |
| Erythrocytes ($10^{12}$/L): | — | 4.3 ± 0.2 | 4.3 ± 0.2 | 4.2 ± 0.1 | 4.0 ± 0 | 4.0 ± 0 | 4.1 ± 0.1 |
| Neutrophils (%): | 49.9 ± 12 | 62.4 ± 5 | 62.8 ± 5 | 63.8 ± 4 | 65.1 ± 5 | 67.8 ± 5 | 66.5 ± 3.2 |
| Monocytes (%) | — | 5.9 ± 1 | 4.9 ± 2 | 4.5 ± 1 | 3.1 ± 2 | 2.9 ± 2 | 2.3 ± 1.6 |
| Basophils (%) | — | 0.2 ± 0 | 0.2 ± 0 | 0.01 ± 0 | 0.1 ± 0 | 0.1 ± 0 | 0.1 ± 0 |
| Eosinophils (%) | — | 3.1 ± 1 | 4.6 ± 1 | 4.2 ± 1 | 0.3 ± 2 | 0.4 ± 1 | 0.5 ± 1 |

†statistically significant when compared with the pre-treatment values, i.e. $p < 0.05$.

TABLE 27

Lymphocyte Functional Activity:
Group 1A-Chronic Pyoderma; Group 1B-Atypical Pyoderma

| Blast Transform. (Antigen) | Normal Values | Group 1A ||| Group 1B |||
|---|---|---|---|---|---|---|---|
|  |  | Before Therapy | Control Therapy | L-Glu-L-Trp Therapy | Before Therapy | Control Therapy | L-Glu-L-Trp Therapy |
| PHA (% of PBL) | 35.9 ± 21 | 49.1 ± 7 | 43.8 ± 7 | 42.7 ± 7 | 61.2 ± 23 | 72.3 ± 12 | 87.5 ± 5 |
| Con-A (% of PBL) | 49.4 ± 21 | 72.9 ± 12 | 66.3 ± 12 | 62.8 ± 8 | 52.5 ± 25 | 69.4 ± 12 | 96.1 ± 4 |
| Staph-A (% of PBL) | 95.3 ± 22 | 75.3 ± 10 | 79.4 ± 10 | 85.6 ± 9 | 87.5 ± 4 | 82.5 ± 5 | 75.3 ± 1 |

(No mean values were significantly different than the Pre-treatment values, i.e. $p > 0.05$)

Summary of Clinical Disease Responses in the Patients in Group 1A-Chronic Pyoderma.

The results presented in TABLE 27 show that treatments with L-Glu-L-Trp increased the percentage of lymphocytes blast-transformed following in vitro incubation in media containing PHA or Con-A when isolated from patients with diagnosed atypical pyoderma, but not from patients with chronic pyoderma.

Summary of Clinical Disease Responses in the Patients in Group 1B-Atypical Pyoderma:

The clinical investigators conducting this trial concluded as follows: "A clinical analysis of the conducted treatment show that, in comparison with the traditional therapy methods, no important advantages in using L-Glu-L-Trp were found. Thus, L-Glu-L-Trp treatment did not cause normalization of the immunologic changes found in this group of patients with chronic atypical pyoderma and did not turn out to be effective clinically."

The results obtained in the patients of Group 2 are summarized below in TABLES 28–29.

TABLE 28

Differential Cell Counts and Immunology Values:
Group 2: Pyoderma in Patients with SLE

| Index | Normal Range | Before Therapy (n = 22) | Conventional Therapy (n = 9) | L-Glu-L-Trp Therapy (n = 13) |
|---|---|---|---|---|
| Leukocytes |  |  |  |  |
| (×$10^9$/L): | 6.7 ± 2.4 | 6.15 ± 0.23 | 6.75 ± 0.3 | 5.74 ± 0.12 |
| % Normal Value: | (100%) | (92%) | (101%) | (86%) |
| Lymphocytes |  |  |  |  |
| %: | 41.1 ± 11.9 | 33.1 ± 1.6 | 33.9 ± 1.7 | 36.4 ± 2.3 |
| (×$10^9$/L): | 2.8 ± 1.4 | 2.11 ± 0.12 | 2.13 ± 0.21 | 2.17 ± 0.21 |
| % Normal Value: | (100%) | (75%) | (76%) | (78%) |
| T-Lymphocytes |  |  |  |  |
| (%): | 61.4 ± 13.1 | 48.9 ± 4.3 | 42.5 ± 3.1 | 44.3 ± 2.7 |

TABLE 28-continued

Differential Cell Counts and Immunology Values:
Group 2: Pyoderma in Patients with SLE

| Index | Normal Range | Before Therapy (n = 22) | Conventional Therapy (n = 9) | L-Glu-L-Trp Therapy (n = 13) |
|---|---|---|---|---|
| ($\times 10^9$/L): | 1.7 ± 0.9 | 1.02 ± 0.08 | 0.63 ± 0.08 | 1.13 ± 0.07 |
| % Normal Value: | (100%) | (60%) | (37%) | (66%) |
| T-helper | | | | |
| (%): | 47.1 ± 16.2 | 53.2 ± 1.9 | 44.3 ± 3.4 | 26.5 ± 2.7 |
| ($\times 10^9$/L): | 1.32 ± 0.81 | 1.08 ± 0.15 | 1.26 ± 0.15 | 0.87 ± 0.12† |
| % Normal Value: | (100%) | (82%) | (95%) | (66%) |
| T-suppressor | | | | |
| (%): | 14.3 ± 12.3 | 12.4 ± 2.1 | 9.3 ± 5.1 | 21.2 ± 3.7 |
| ($\times 10^9$/L): | 0.39 ± 0.38 | 0.29 ± 0.06 | 0.26 ± 0.07 | 0.53 ± 0.03†† |
| % Normal Value: | (100%) | (74%) | (67%) | (136%) |
| B-Lymphocytes | | | | |
| (%): | 18.1 ± 11 | 13.5 ± 1.01 | 12.1 ± 0.8 | 6.8 ± 0.9 |
| ($\times 10^9$/L): | 0.49 ± 0.3 | 0.31 ± 0.02 | 0.26 ± 0.01 | 0.16 ± 0.01 |
| % Normal Value: | (100%) | (63%) | (53%) | (52%) |
| IgG (g/L) | 10.8 ± 2.13 | 13.9 ± 1.34 | 10.2 ± 1.39 | 14.8 ± 1.27 |
| % Normal Value: | (100%) | (128%) | (94%) | (137%) |
| IgA (g/L) | 1.90 ± 0.99 | 2.21 ± 0.41 | 1.54 ± 0.52 | 2.85 ± 0.32 |
| % Normal Value: | (100%) | (116%) | (81%) | (150%) |
| IgM (g/L) | 1.58 ± 0.47 | 1.28 ± 0.47 | 0.72 ± 0.26 | 0.92 ± 0.12 |
| % Normal Value: | (100%) | (81%) | (46%) | (58%) |
| Erythrocytes ($10^{12}$/L): | | 4.4 ± 0.1 | 4.3 ± 0.1 | 4.7 ± 0.1 |
| Neutrophils | | | | |
| (%): | 49.9 ± 11.9 | 56.8 ± 2.8 | 59.7 ± 3.7 | 55.3 ± 4.2 |
| ($\times 10^9$/L): | 3.3 ± 1.1 | 2.6 ± 1.1 | 1.8 ± 1.2 | 3.5 ± 0.7 |
| % Normal Value: | (100%) | (79%) | (55%) | (106%) |
| Monocytes (%) | | 6.0 ± 0.9 | 5.0 ± 0.8 | 8.0 ± 0.7 |
| Basophils (%) | | 0.1 ± 0.1 | 0.1 ± 0.1 | 0.1 ± 0.1 |
| Eosinophils (%) | | 2.7 ± 0.2 | 1.8 ± 0.2 | 2.2 ± 0.1 |

††statistically significant in comparison with the pre-treatment values, i.e., $p < 0.01$
†statistically significant in comparison with the pre-treatment values, i.e., $p < 0.05$

TABLE 29

Lymphocyte Functional Activity:
Group 2-Pyoderma in Patients with SLE

| Blast Transformation (Antigen) | Normal Healthy Values | Before Therapy (n = 22) | Conventional Therapy Control (n = 9) | L-Glu-L-Trp Therapy (n = 13) |
|---|---|---|---|---|
| PHA (% of PBL) | 35.9 ± 20.7 | 58.1 ± 4.0 | 47.1 ± 3.7 | 47.4 ± 3.5 |
| Con-A (% of PBL) | 49.4 ± 20.7 | 57.2 ± 7.9 | 58.1 ± 8.3 | 64.1 ± 6.5 |

(No mean values were significantly different than the Pre-treatment values, i.e. $p > 0.05$)

Summary of Clinical Disease Responses in the Patients in Group 2- SLE-Patients with Pyoderma The investigators conducting the trial concluded: L-Glu-L-Trp "treatment proved more rational and adequate in the plan of correcting the immune shift discovered. Treating with L-Glu-L-Trp leads to a positive clinical effect and resolution of dermal rashes. Treatment with delagil in combination with vascular agents" (i.e., traditional therapy) "leads to the appearance of additional deviations in the immunity system and requires mandatory external treatment with corticosteroids."

Protocol B: Psoriasis:
Summary Overview:

A total of 30 patients with psoriasis were treated with L-Glu-L-Trp (Group 1) and 30 other psoriasis patients were entered into a control group (Group 2) and treated using conventional treatment. All patients had at least a 5 year history of unsuccessful antibiotic therapy. The administration of 100 µg im or 1 µg/kg intranasally daily for a period of 10 days resulted in the improvement in 7% of the patients, significant improvement in 60% of patients, and total recovery in 33% of the patients. Patients with psoriasis in the progressive phase exhibited i) a depression of cell mediated immune parameters, ii) an increase in serum concentrations of IgG, IgA, and IgM, iii) hyper-coagulation, and, iv) depressed fibrinolytic activity.

Patient Groups:

Group 1 constituted 30 patients, aged 15–60 years and with length of illness in most patients being >5 years. In 28 of the 30 patients, the illness was of a progressive nature, and in 29 of the 30, relapses had been observed during the winter months. Group 2 constituted 30 patients with disseminated forms of psoriasis.

Trial Treatment

Treatment B1: Traditional therapy in combination with L-Glu-L-Trp was administered to all patients in Group 1: i.e., L-Glu-L-Trp was administered im at a dosage of 100 µg in a volume of 1 mL with 0.25% novocaine every other day for 10 days. Treatment B2: Traditional therapy only was administered to the patients in Group 2: i.e., sedative desensitizers, vitamins A, $B_6$, and $B_{12}$, and folic acid, pyrogenic preparations, sedatives, UFO, and local prescription of salidol ointment and 3–5% sulfur salicylic and/or corticosteroid (salidol) ointments. Some modifications of treatment regimens were required because of intolerance to B group vitamins in three cases which manifested itself in dermal puritus and urticarial eruptions.

Laboratory parameters of disease activity were monitored including morning body temperature, leukocyte and differential blood cell count, hematology measurements and blood chemistry, acute phase proteins, and immunology determinations including the percentages and absolute numbers of B- and T-lymphocytes. Comparisons were made to laboratory values obtained from normal healthy persons aged 18 to 40 years.

Clinical parameters of disease activity were monitored by grading dermal manifestations of disease as follows: "improvement" defined as stabilization of the dermal disease process and lightening and smoothing of papular, plaque, and rash eruptions; "considerable improvement" defined as indications of dermal locations having maculas, and/or solitary smooth papules having a pale color, or resembling "maternal plaques," i.e., birth marks; and, "recovery" defined as indications of dermal locations having eruptions or maculas that are depigmented or mildly pink in color.

The findings of laboratory investigations are summarized in TABLES 30–32.

Summary of Treatment Effects on Hemostatic Values:
Conventional Therapy:

Shifts in certain coagulation parameters after conventional therapy, although significant, were not pronounced. Slight changes were observed in patients treated with conventional therapy as follows: i) in positive reactions of clotting to ethanol (data not shown above), ii) a slower clotting time for recalcified plasma, and (iii) a slightly slower clotting time for kaolin-cephalin induced clotting (KCT). Fibrinopeptide (FDP) concentration, (an indicator of the level of ongoing fibrinolysis in patients), decreased insignificantly.

Patients receiving L-Glu-L-Trp exhibited the following changes in coagulation measurements: i) clotting time for recalcified plasma was slowed, ii) KCT was also decreased, iii) thrombin time (Thrombotest; PTT) was decreased, iv) FDP concentration dropped significantly, v) antithrombin III (ATIII) decreased to normal levels, and vi) Hagemann-factor-dependent fibrinolytic activity was returned to normal levels. Overall, the changes appeared to indicate a decrease in underlying thrombotic processes in the patients treated with L-Glu-L-Trp, possibly by activation of cellular fibrinolytic activities, e.g., release of mediators inducing Hagemann factor dependent fibrinolysis. (Similar effects on FDP and ATIII were recorded in studies with patients in Example 6, Protocol C3, below; and, in the malaria patients of Example 19, also below.)

TABLE 30

Hematology Values

| Index | Healthy Normal Controls (n = 20) | Patients Before Therapy (n = 40) | Conventional Therapy Group 2 (n = 30) | L-Glu-L-Trp Therapy Group 1 (n = 30) |
|---|---|---|---|---|
| Clotting time (citrated whole blood-recalcified) | 123 ± 2.1 | 102 ± 3.1** | 13.5 ± 3.3†† | 141 ± 2.4†† |
| Kaolin-Cephalin clotting time | 53.6 ± 0.72 | 49.8 ± 0.8** | 57 ± 0.4†† | 58 ± 0.3† |
| PT | 22 ± 0.3 | 21 ± 0.37 | 21.6 ± 0.4 | 23 ± 0.2 |
| Thrombotest (units) | 30.7 ± 0.56 | 29.8 ± 0.37 | 31 ± 0.7 | 33 ± 0.5†† |
| Fibrinogen Concentration (g/L) | 2.74 ± 0.56 | 3.2 ± 0.37 | 3.0 ± 0.36 | 3.4 ± 0.1 |
| FDP (μg/mL) | —a | 64 ± 2.2 | 45 ± 2.14†† | 23 ± 1.8†† |
| Fibrinolytic Activity (min.) | 154 ± 12.6 | 200 ± 7.0* | 196 ± 6.6 | 200 ± 2.7†† |

*Statistically different than the normal control values, i.e., $p < 0.05$;
**statistically different than the normal control values at the $p < 0.001$ level;
†statistically different than the pre-treatment values, i.e., $p < 0.05$,
††statistically different than the pre-treatment values, $p < 0.001$;
aFDP, fibrin degradation products are usually not detectable in normal plasma if clotting is properly inhibited.

TABLE 31

Blood Acute-Phase Protein Measurements

| Index | Normal Healthy Values (n = 20) | Before Therapy (n = 40) | Conventional Therapy Group 2 (n = 30) | L-Glu-L-Trp Therapy Group 1 (n = 30) |
|---|---|---|---|---|
| C3 complement (mcg/mL) | 814 ± 46 | 893 ± 14.6 | 945 ± 14.8 | 926 ± 28.4 |
| Prealbumin (mcg/mL) | 304 ± 11.5 | 224 ± 4.49** | 248 ± 3.62 | 357 ± 3.8†† |
| Ceruloplasmin (mcg/mL) | 255 ± 16 | 329 ± 3.3** | 350 ± 11†† | 366 ± 11.4†† |
| Orosomucoid (mcg/mL) | 706 ± 31 | 837 ± 12.8** | 977 ± 26.7†† | 829 ± 13.2 |

TABLE 31-continued

Blood Acute-Phase Protein Measurements

| Index | Normal Healthy Values (n = 20) | Before Therapy (n = 40) | Conventional Therapy Group 2 (n = 30) | L-Glu-L-Trp Therapy Group 1 (n = 30) |
|---|---|---|---|---|
| α2-macroglobulin (mcg/mL) | 2.3 ± 0.82 | 2.3 ± 0.3 | 2.5 ± 0.07 | 2.5 ± 0.01 |
| Transferrin (mcg/mL) | 3.11 ± 0.1 | 2.87 ± 0.06 | 2.74 ± 0.08 | 3.36 ± 0.08[††] |

*Statistically different than the normal control values, i.e., $p < 0.05$;
**statistically different than the normal control values at the $p < 0.001$ level;
[††]statistically different than the pre-treatment values, i.e., $p < 0.001$.

Acute Phase Reactants:

Acute phase reactants ceruloplasmin and orosomucoid were significantly elevated, and prealbumin was depressed, prior to treatment. Patients in Group 2 experienced a further increase in orosomucoid concentration during therapy, and other acute phase reactants, while not increasing significantly, did not drop significantly in this control group. In patients treated with L-Glu-L-Trp (Group 1) ceruloplasmin, transferrin, and prealbumin increased significantly.

TABLE 32

Differential Cell Counts and Immunology Values

| Index | Normal Healthy Values (n = 20) | Before Therapy (n = 40) | Conventional Therapy Control (n = 30) | Combination L-Glu-L-Trp Therapy (n = 30) |
|---|---|---|---|---|
| Leukocytes | | | | |
| (×10⁹/L): | 5.8 ± 0.25 | 6.6 ± 0.1** | 6.7 ± 0.1 | 9.0 ± 1.4[††] |
| % Normal Value: | (100%) | (114%) | (116%) | (155%) |
| Lymphocytes | | | | |
| (×10⁹/L): | 1.74 ± 0.12 | 1.9 ± 0.07 | 1.7 ± 0.03 | 2.5 ± 0.09[††] |
| % Normal Value: | (100%) | (109%) | (98%) | (144%) |
| T-Lymphocytes | | | | |
| (×10⁹/L): | 0.89 ± 0.06 | 0.55 ± 0.04** | 0.50 ± 0.01 | 0.94 ± 0.07[††] |
| % Normal Value: | (100%) | (62%) | (56%) | (106%) |
| B-Lymphocytes: | | | | |
| (×10⁹/L): | 0.46 ± 0.02 | 0.36 ± 0.01** | 0.32 ± 0.02 | 0.53 ± 0.02[††] |
| % Normal Value: | (100%) | (78%) | (69%) | (115%) |
| IgG (mg/mL) | 134 ± 5.6 | 143 ± 7.3 | 146 ± 4.4 | 187 ± 1.9[†] |
| % Normal Value: | (100%) | (107%) | (109%) | (140%) |
| IgA (mg/mL) | 98.3 ± 6.2 | 140 ± 5.1** | 159 ± 5.1 | 138 ± 6.8 |
| % Normal Value: | (100%) | (142%) | (162%) | (140%) |
| IgM (mg/mL) | 127 ± 9.7 | 153 ± 5.9* | 179 ± 4.0 | 193 ± 9.6 |
| % Normal Value: | (100%) | (120%) | (141%) | (152%) |

*Statistically different than the normal control values, i.e., $p < 0.05$;
**statistically different than the normal control values at the $p < 0.001$ level;
[†]statistically different than the pre-treatment values, i.e., $p < 0.001$.

Cellular Immune Parameters.

In the trial group of patients with psoriasis there was a slight increase in lymphocyte count and a significant ($p<0.001$) decrease in T- and B-lymphocytes. Serum immunoglobulins were also elevated, i.e., IgA, IgM, and to a lesser extent IgG. After L-Glu-L-Trp treatment, a considerable increase was observed in the number of leukocytes and lymphocytes. The quantity of T- and B-lymphocytes approached normal and the number of T-helper cells also increased. The number of T-suppressors increased less dramatically. The levels of IgG and IgM after therapy remained unchanged, and IgA decreased, yet did not reach normal. Thus, employing L-Glu-L-Trp in combined therapy led to significant increases in peripheral blood lymphocytes and T-lymphocytes in this psoriasis patient group.

Clinical Responses:

Both conventional and L-Glu-L-Trp treatments resulted in remission of disease activity by day 8–10 (TABLE 33) in approximately the same percentage of patients. However, patients in Group 1 showed improvement more rapidly, i.e., with only the second injection of L-Glu-L-Trp there was noted an apparent pallor of psoriatic eruptions as well as a gradual smoothing of eruptions. Overall, disease activity in the combination L-Glu-L-Trp-treated patients recovered 2–3 days earlier than in patients treated with only the conventional therapy, and this was most evident as i) a more rapid decrease in erythema of the skin eruptions (i.e., 2.8 days sooner than controls), ii) a more rapid smoothing of papules and plaques, and iii) a more rapid disappearance of psoriatic rash (i.e., 7.1 days sooner than controls). The length of hospital stay for patients in Group 1 was also an average of 4.2 days shorter than patients in Group 2. Clinical evaluation of patients' disease activity at day 8–10 is summarized in the following TABLE 33.

TABLE 33

Clinical Evaluation of Patients Response to Therapy

| Treatment Group | Number of Patients Having a Clinical Outcome as: | | | |
|---|---|---|---|---|
| | No Improvement | Improvement | Considerable Improvement | Recovery |
| Conventional Treatment (Group 2) | 1/30 (3%) | 6/30 (20%) | 16/30 (55%) | 7/30 (23%) |
| L-Glu-L-Trp Combination Therapy (Group 1) | 3/30 (10%) | 2/30 (7%) | 18/30 (60%) | 7/30 (23%) |

Dermatological Diseases (Continued)

Protocol C: Wound Healing

Summary Overview:

L-Glu-L-Trp was administered to 37 patients with wounds of various origins, types and localizations. Patients in the control group (24) received conventional treatments. L-Glu-L-Trp was administered daily im (or topically) on each of 10 consecutive days. The im dose was 100 μg. L-Glu-L-Trp accelerated wound healing (in comparison to the controls.), and L-Glu-L-Trp treatment reduced the duration of therapy and prevented development of infectious complications.

Protocol D: Burns

Summary Overview:

A total of 23 patients with cutaneous burns were treated with L-Glu-L-Trp either im or intranasally. Fourteen patients in a control group were treated using conventional methods. Individuals treated with L-Glu-L-Trp exhibited an accelerated rate of wound healing, a diminished frequency of infections, and less escar was observed.

Protocol E: Frostbite

Summary Overview:

Seventeen patients with frostbite of the extremities were treated with L-Glu-L-Trp either im or intranasally. Eleven patients constituted a control group. Rapid healing and restoration of tissue integrity was observed in patients receiving L-Glu-L-Trp treatment.

EXAMPLE 7

Obstetric and Gynecologic Diseases

Protocol A: Pelvic Inflammatory Diseases

Summary Overview:

Ninety-six female patients (96) were entered into a trial having a variety of different disorders, i.e., pelvic inflammatory diseases, cervicitis, vaginitis and various tubo-ovarian and adnexal abscesses. Forty-six patients (46) comprised the L-Glu-L-Trp treatment group, and 50 patients comprised a conventional treatment control group. L-Glu-L-Trp was administered daily im at a dose of 100 μg, or 1 μg/kg intranasally, on each of 5 consecutive days. Alternatively, 50 μg of L-Glu-L-Trp was injected intralymphatically on each of 5 consecutive days in conjunction with conventional therapy. L-Glu-L-Trp treatment alleviated pain, reduced fever, and decreased the duration of the medical treatment in comparison with the control group receiving conventional treatment. Normalization of immune parameters was correlated with the observed clinical improvements.

Patient Populations:

The patient population constituted 96 acutely ill patients (18 to 50 years of age): 46 were treated with L-Glu-L-Trp (Group 1), and 50 were treated using conventional antibiotic therapy (Group 2). Patients entered into Group 1 (aged 19–50) were separable into clinical subgroups as follows: Subgroup 1A, consisted of 18 patients having febrile endometriosis (body temperature 38–39° C.), and suppurative vaginal discharge after infected abortions performed outside hospitals (average age 24.4±4.2 years); Subgroup 1B, consisted of 16 patients with abdominal pains resulting from chronic nonspecific subfebrile (<38° C.) inflammatory disease of the fallopian tubes (average age 32.2±3.9 years; range of abortions in the patient population 2–8); and, Subgroup 1C consisted of 12 patients with inflammation of the fallopian tubes, (38% resulting from placement of an IUD in the uterus more than 4 years previously). All patients had previously proved unresponsive to a full course of broad spectrum antibiotic therapy (i.e., metronidazole, nitrofurans, and sulfanilamides) delivered on an in-patient basis (average age 34.5±5.3 years). Group 2 (control) was constituted of 50 patients (aged 18–44) presenting with analogous symptoms and diseases and the patients in this group were treated with traditional antibiotic therapy.

Treatment Protocols:

In all cases L-Glu-L-Trp was delivered im at a dose of 100 μg in 1 ml volume daily on each of five days.

Treatment A: Administered to patients in Group 1A: The course of L-Glu-L-Trp therapy was administered, remnants of fetal tissue were surgically removed, and an additional course of L-Glu-L-Trp therapy was administered.

Treatment B: Administered to patients in Group 1B: L-Glu-L-Trp therapy was administered immediately upon admission into the protocol.

Treatment C: Administered to patients in Group 1C: Infected uterine tissues were surgically removed, abdominal drainage was established, and L-Glu-L-Trp therapy was administered starting 2 days post-operatively.

Laboratory Tests and Clinical Monitoring:

Patients were evaluated by monitoring the following parameters before, during, and 5–7 days after therapy: i) clinical status of the patient (i.e., body temperature, abdominal pain, and physical examinations) and, ii) laboratory data (i.e., urinalysis, blood chemistry, and blood immunology). The following clinical chemistry values of the patients in Groups 1A, 1B, and 1C were all within the normal range before and after treatment: AST, ALT, creatinine, urea, glucose, protein, chloride, potassium, and sodium. Patients in Groups 1A–1C and Group 2 exhibited elevated levels of alkaline phosphatase (80±13 ED/ml) and bilirubin (1.0±0.05 mg %) prior to treatment, but the values were still within the normal range, i.e., normal alkaline phosphatase (30–85 ED/ml), and normal bilirubin (0.15–1.0 mg %). Treatment with L-Glu-L-Trp reduced the latter serum markers, i.e., alkaline phosphatase fell to 62.71±5.67 ED/mL and bilirubin to 0.50±0.03 mg %.

Laboratory immunology test results were not statistically different between Groups 1A, 1B, and 1C before or after receiving Treatment A, B, and C, respectively, so the data were pooled and presented together in TABLE 34.

TABLE 34

Immunology Values

| Index | Normal Value (Healthy) | Before Therapy | After Conventional Antibiotic Therapy | After L-Glu-L-Trp Therapy |
|---|---|---|---|---|
| Lymphocytes: | | | | |
| % of PBL: | 41.11 ± 1.54 | 14.70 ± 1.26† | 19.09 ± 1.21* | 36.61 ± 1.32* |
| No. ($10^9$/L): | 2.78 ± 0.14 | 1.36 ± 0.11† | 1.23 ± 0.09 | 2.26 ± 0.12* |
| % Normal Value: | (100%) | (49%) | (44%) | (81%) |
| T-Lymphocytes: | | | | |
| % of Lym: | 61.42 ± 1.98 | 76.44 ± 1.52 | 74.1 ± 1.68 | 71.57 ± 1.76 |
| No. ($10^9$/L): | 1.69 ± 0.12 | 1.02 ± 0.11† | 0.75 ± 0.08* | 1.67 ± 0.09* |
| % of Normal Value: | (100%) | (60%) | (38%) | (75%) |
| B-Lymphocytes: | | | | |
| % of PBL: | 18.14 ± 1.12 | 11.30 ± 1.06 | 8.91 ± 0.78 | 11.09 ± 0.87 |
| No. ($10^9$/L): | 0.49 ± 0.08 | 0.17 ± 0.02† | 0.14 ± 0.02 | 0.27 ± 0.03* |
| % of Normal Value: | (100%) | (35%) | (28%) | (55%) |
| Phagocytes: | | | | |
| % PBL: | 64.43 ± 1.94 | 76.30 ± 2.39 | 73.36 ± 2.38 | 74.78 ± 2.35 |
| IgM (g/L) | 1.50 ± 0.17 | 1.90 ± 0.20 | 1.39 ± 0.10 | 2.64 ± 0.36* |
| % Normal Value: | (100%) | (126%) | (93%) | (176%) |
| IgG (g/L) | 10.84 ± 0.59 | 12.32 ± 0.75 | 12.91 ± 0 | 13.73 ± 0.51 |
| % Normal Value: | (100%) | (114%) | (119%) | (126%) |
| IgA (g/L) | 1.91 ± 0.15 | 1.89 ± 0.13 | 1.86 ± 0.1 | 2.61 ± 0.33* |
| % Normal Value: | (100%) | (99%) | (97%) | (137%) |
| Blastogenic Response: | | | | |
| % Lym blast w/PHA: | 35.83 ± 2.82 | 64.13 ± 4.90† | 54.84 ± 4.4 | 37.22 ± 2.81* |
| % Lym blast w/Con A | 49.4 ± 3.81 | 72.65 ± 5.61 | 62.89 ± 5.1 | 68.70 ± 5.32 |

†a p value of <0.05 was recorded in these studies after mathematical comparisons of Normal values with the Pre-treatment values;
*a p value of <0.05 was recorded in these studies after mathematical comparisons of Normal values with the Pre-treatment values.

The results presented in TABLE 34, above, show that prior to therapy the patients in this trial population had decreased absolute levels of lymphocytes (49% of normal), decreased T-lymphocytes (60% of normal), and decreased B-lymphocytes (35% of normal). On conventional therapy, the levels of all three monitors of immune function continued to deteriorate. In patients treated with L-Glu-L-Trp, the levels of lymphocytes increased to about 81% of normal, with T- and B-lymphocytes increasing to about 75% and 55%, respectively.

Protocol B: Complications of Pregnancy

Summary Overview:

One hundred fifty one patients (151) exhibiting toxemia in the first or second half of pregnancy were treated with either L-Glu-L-Trp (97 patients) or with conventional therapy (54 patients). L-Glu-L-Trp was administered im at 100 µg daily, or 1 µg/kg intranasally, for 5–10 days. L-Glu-L-Trp treatment normalized blood pressure, peripheral edema was reduced, abnormal blood chemistry values prior to treatment returned to within the normal range, and immune indices that were altered prior to treatment were returned to within the normal range.

Protocol C

Complications of Pregnancy

Summary Overview:

L-Glu-L-Trp was administered to 34 pregnant women and 27 pregnant women receiving conventional treatment served as a control group. L-Glu-L-Trp was administered daily at a dosage of 100 µg im, or 1 µg/kg intranasally, on each of 5–10 days. Signs of clinical improvement were resolution of weakness and dizziness, increased appetite, and the normalization of the immunological and hematological indices. Decreased fetal hypoxia was also observed in women treated with L-Glu-L-Trp.

Protocol D: Post-Partem Infections

Summary Overview:

Nineteen patients (19 women) post-term were treated with L-Glu-L-Trp and 48 women received conventional post-term treatment as a control group. Administration of 100 µg L-Glu-L-Trp im (or 1 µg/kg intranasally), over a period of 3–5 days resulted in the effacement of the cervix with thinning of the cervix and the descent of the fetus, resulting in a normal delivery.

Protocol E: Uterine Infections

Summary Overview:

Glu-L-Trp was administered in combination with antibiotic therapy to twelve female patients (average age 34) with chronic uterine infections caused by placement of I.U.D.'s (i.e., mean length of infection 4–5 years; maximum 15 years). All patients had received more than one previous course of antibiotic therapy during the course of their illness, and most patients had received several courses of therapy. Conventional treatment consisted of surgical removal of the I.U.D. followed by a course of antibiotic therapy. The control group consisted of 50 patients with uterine infections, (same cause), treated using conventional therapy. L-Glu-L-Trp was administered with conventional therapy by injecting 100 µg im daily on each of five consecutive days. Differences between the symptoms of post-operative recovery of the patients in the L-Glu-L-Trp treatment group (i.e., in comparison with the control group) were noted within as little as 3–4 days as increased appetite, and normalization of sleep and body temperature. Eleven of the 12 patients in the L-Glu-L-Trp treatment group healed more rapidly than the patients in the control group and physical therapy was started sooner than with the patients in the control group. Intramuscular injections of L-Glu-L-Trp did not induce any visible side effect or allergic reaction.

EXAMPLE 8

Herpes Virus Infections

Protocol A: Herpes vulgaris
Summary Overview:
Patients treated with L-Glu-L-Trp either topically, im, or intranasally experienced marked reduction of recurrence of herpetic lesions, with substantial reduction in the period between outbreaks. In one trial, individuals who experienced 7–10 outbreaks per year experienced less than one outbreak per year after treatment with L-Glu-L-Trp in combination with interferon.

Protocol B: Herpes Zoster
Summary Overview:
A total of 37 patients with Herpes Zoster were treated with L-Glu-L-Trp in combination with conventional interferon treatment. Twenty-five control patients (25) were treated with interferon alone. Administration of L-Glu-L-Trp was as a single daily injection of 100 μg im, or 1 μg/kg intranasally, over a period of 10 days. Treatment with L-Glu-L-Trp resulted in accelerated clearing of foci of herpes infection. Recurrence of lesions was prevented and healing occurred on the average 40% earlier in the L-Glu-L-Trp treated group than in the control group. Changes in immunological indices in the L-Glu-L-Trp treated patients were correlated with the favorable clinical outcome.

EXAMPLE 9

Dental Diseases

Protocol A: Gingivitis
Summary Overview:
Patients were treated for gingival disease by subcutaneous administration of L-Glu-L-Trp into the area of the gingiva. The treatment resulted in an arrest of gingival disease. Approximately 160 patients were studied, 80 patients were treated with L-Glu-L-Trp and an equal number were treated using conventional therapy (control). Administration of 100 μg L-Glu-L-Trp im, subcutaneously, or by electrophoresis (whereby a small voltage charge to the gums results in a rapid transfer of medication through the gum epithelium) resulted in a more rapid arrest of bleeding, eliminated of inflammation, and decrease in purulent discharge. L-Glu-L-Trp treatment resulted in fewer recurrences of gingival disease. Normalization of immunologic indices and coagulation in the L-Glu-L-Trp treated patients was correlated with favorable clinical outcome.

Protocol B: Dental Caries, Odontogenic Infections, Periapical Granulomas
Summary Overview:
Treatment of dental caries with toothpaste containing L-Glu-L-Trp will result in a reduction of caries. The use of dental toothpaste containing L-Glu-L-Trp will have the secondary effect of reducing incidence and severity of gingival disease. Patients with odontogenic infections and periapical granulomas can be treated with 100 μg of L-Glu-L-Trp instilled into the foramen at the base of the tooth, or alternatively, L-Glu-L-Trp can be compounded in a filling paste which is packed into the base of the tooth.

Protocol C: Odontogenic Infections—Periapical Granulomas
Summary Overview:
Forty-six patients (46; aged 3–14 years) with periapical granulomas and limited, focal, and diffuse forms of purulent odontogenic osteomyelitis were treated with L-Glu-L-Trp. Twenty-eight patients (15) having the same disease profile and under conventional treatment formed a control group.
Patent Population:
Forty-six children (aged 3–14 years; 29 boys and 17 girls) were entered into a combination L-Glu-L-Trp treatment group. The patients presented with the following diagnosed odontogenic infections: 18 with limited purulent infection(s), 7 with focal infection(s), 3 with diffuse infection(s). In addition, 3 patients presented with destructive osteomyelitis and 15 with plegmons mandible.
Fifteen children, with similar demographics and infectious odontogenic diseases, were entered into a control group treated with conventional antibiotic therapy.
Treatment Protocol:
L-Glu-L-Trp was administered im at a dosage of 2 μg/kg body mass daily for 3–7 days, depending upon the severity of the infection.
Evaluations included X-ray, clinical chemistry and serum protein testing, and immunological testing.
Laboratory Tests:
Pre-treatment measurements were performed with peripheral blood samples collected from 20 of the 46 L-Glu-L-Trp treated children to establish baseline values (Before Therapy). All 15 children in the conventional treatment group were evaluated before therapy. Post-treatment measurements were performed with peripheral blood samples that were collected from all the conventional and L-Glu-L-Trp treated children. Fifteen healthy normal children were also evaluated to determine the normal mean values in the respective assays (Normal Healthy Control). The results of these determinations are summarized in TABLE 35.

TABLE 35

| | Immunology Values: Periapical Ganulomas | | | | |
| --- | --- | --- | --- | --- | --- |
| | Normal | Conventional Antibiotic | | L-Glu-L-Trp Combination | |
| Index | Healthy Control | Before Therapy | After Therapy | Before Therapy | After Therapy |
| Leukocytes: No. (10$^9$/L): | 6.81 ± 0.26 | 9.20 ± 0.26$^†$ | 5.96 ± 0.47 | 10.0 ± 0.72$^†$ | 6.60 ± 0.39* |
| % Normal Value: | (100%) | (135%) | (88%) | (147%) | (97%) |

TABLE 35-continued

Immunology Values: Periapical Ganulomas

| | Normal | Conventional Antibiotic | | L-Glu-L-Trp Combination | |
|---|---|---|---|---|---|
| Index | Healthy Control | Before Therapy | After Therapy | Before Therapy | After Therapy |
| Lymphocytes: No. (10⁹/L): | 2.62 ± 0.28 | 2.14 ± 0.52 | 1.87 ± 0.43 | 2.98 ± 0.30 | 2.37 ± 0.21 |
| % Normal Value: | (100%) | (82%) | (71%) | (114%) | (36%) |
| T-Lymphocytes: No. (10⁹/L): | 1.26 ± 0.13 | 0.63 ± 0.12† | 0.77 ± 0.09 | 0.70 ± 0.08† | 1.24 ± 0.11* |
| % of Normal Value: | (100%) | (50%) | (61%) | (56%) | (98%) |
| B-Lymphocytes: No. (10⁹/L): | 0.62 ± 0.11 | 0.49 ± 0.09 | 0.58 ± 0.12 | 0.64 ± 0.10 | 0.67 ± 0.05 |
| % of Normal Value: | (100%) | (79%) | (94%) | (103%) | (108%) |
| IgM (g/L) | 0.98 ± 0.21 | 1.21 ± 0.18 | 1.11 ± 0.11 | 1.02 ± 0.08 | 0.93 ± 0.07 |
| % Normal Value: | (100%) | (123%) | (113%) | (105%) | (95%) |
| IgG (g/L) | 9.21 ± 0.16 | 1306 ± 0.42† | 12.14 ± 0.63 | 12.05 ± 0.71 | 10.78 ± 0.83 |
| % Normal Value: | (100%) | (142%) | (132%) | (131%) | (117%) |
| IgA (g/L) | 1.05 ± 0.11 | 1.91 ± 0.18 | 1.82 ± 0.12 | 1.88 ± 0.05 | 1.09 ± 0.04 |
| % Normal Value: | (100%) | (182%) | (173%) | (179%) | (104%) |
| LMIR Response: % w/PHA: | 11.60 ± 2.20 | 34.20 ± 2.42† | 24.27 ± 2.89 | 33.20 ± 3.23† | 14.65 ± 3.11* |

†$p < 0.05$ was recorded in these studies after mathematical comparisons of Normal values with the Pre-treatment values;
*$p < 0.05$ was recorded in these studies after mathematical comparisons of Pre-treatment values with the Post-treatment values.

The results in TABLE 35, show that prior to treatment the patients in the trial population exhibited a statistically significant elevation in total peripheral blood leukocytes and a decrease in T-lymphocytes (i.e., 50% and 56% of normal) but not in B-lymphocytes. Following L-Glu-L-Trp combination therapy, T-lymphocyte counts were increased to 98% of normal levels, while conventional therapy only increased the T-cell counts to about 61% of normal. Leukocyte counts decreased with both the conventional and L-Glu-L-Trp treatments.

EXAMPLE 10

Lymphatic Infections

L-Glu-L-Trp administered at a dosage of 100 µg im, or 1 µg/kg intranasally, or injected intralymphatically, controls the progression of lymphangitis.

EXAMPLE 11

Ear/Eye/Nose and Throat Infections

Protocol A: Ophthalmic Diseases:
Summary Overview:

Forty one patients (41; 17 men and 24 women; ranging in age from 17 to 68 years) with various eye diseases of infectious and non-infectious origin were treated with L-Glu-L-Trp. Patients having the following infectious, and non-infectious, ophthalmic diseases were entered into the trial: a) nonviral conjunctivitis, keratitis, chronic uveitis, persistent sties, and, focal chorioretinitis; and, b) retinal pigment dystrophy, Grenblad-Stranberg syndrome, and maculophathy, respectively. Five patients were Class II invalids due to vision impairment, 4 were Class III, and 32 were impaired but not invalid. L-Glu-L-Trp was administered as an adjunct to ongoing conventional treatment with antibiotics, eye drops, anti-inflammatory agents, and the like. L-Glu-L-Trp was administered daily in a single 0.1 mL (10 µg) dose by the parabulbar route (Group 1; n=21), or alternatively one drop of the dipeptide solution (5 µg) was delivered into the conjunctival cavity twice daily on each of 5 consecutive days (Group 2; n=20). Thirty six patients undergoing conventional therapy served as a control group (Group 3; n=36).

Clinical diagnoses of patients entered into Group 1 were as follows: 4 subjects had diagnosed adenoviral conjunctivitis; 2 subjects, recurring eyelid sties; 3 subjects, chronic serous-plastic uveitis; 3 subjects, central chorioretinitis; 5 subjects, central retinal dystrophy in both eyes; 4 subjects, pigment degeneration of the retina.

Clinical diagnoses of patients entered into Group 2 were as follows: namely, 7 subjects had diagnosed chronic serous-plastic uveitis, and 13 subjects adenoviral conjunctivitis.

Vision was assessed using standard measurements: i.e., field of vision, visual acuity, electrophysiological indices. Ophthalmascopic examination was used to evaluate and score corneal epithelial integrity, extent of edema and infiltration of the cornea (all strata), uveitis, retinal inflammation (edema, focal and peripheral changes, exudation, hemorrhage, plasmohemorrhagia), and expansion in the vitreous body. Immune parameters in peripheral blood were also assessed. Following treatment, the trial subjects were followed for not less than 12 months.

Laboratory Effects:

Treatment with L-Glu-L-Trp induced an increase in the number of circulating peripheral blood B- and T-lymphocytes, and in the numbers of CD4⁺- and CD8⁺-lymphocytes. Lymphokine production (i.e., measured by LMIR in response to Con-A stimulation) was increased in all patients in Group 1 and 2 immediately following the 5 days of L-Glu-L-Trp treatment.

Clinical Effects:

Treatment with L-Glu-L-Trp resulted in a more rapid arresting of the inflammatory process and the increase in visual acuity, with a decrease being observed in the time over which medical treatment was required. No unfavorable response to therapy was observed.

Group 1: A "marked favorable response" to L-Glu-L-Trp therapy was observed (as described further below) in 9 patients (4 men; 5 women; 19–52 years of age) having the following diagnosed infectious eye diseases: adenoviral keratoconjunctivitis and conjunctivitis (n=3), chronic serous-plastic uveitis (n=3), and central chorioretinitis unresponsive to conventional treatment (n=3). A "good response" to L-Glu-L-Trp therapy was observed (as described further below) in 9 patients (4 men; women; 17–68 years of age) having the following diagnosed infectious eye diseases: recurring eyelid sties (n=2); adenoviral conjunctivitis (n=1); pigment degeneration of the retina (n=2; Class II invalid vision disability); central retinal dystrophy (n=8; including 2 Class II and 1 Class III invalids for vision disability).

Group 2: A "marked favorable response" to L-Glu-L-Trp therapy was observed (as described further below) in 18 patients (8 men; 10 women; 20–70 years of age) having the following diagnosed eye diseases: namely, chronic serous-plastic uveitis (n=6 including 1 invalid), and adenoviral conjunctivitis (n=12). A "good response" to L-Glu-L-Trp therapy was observed (as described further below) in 2 patients (1 man; 1 woman; 17 and 50 years of age, respectively) having the following diagnosed infectious eye diseases: namely, serous-plastic chronic uveitis (n=1) and adenovirus conjunctivitis (n=1). A "poor response" to L-Glu-L-Trp therapy was observed in 3 patients with infectious eye diseases (2 men; 1 woman; 37–49 years of age) having the following diagnosed infectious eye diseases: central retinal dystrophy (n=1); pigment degeneration in the retina (n=2; including a class II and a class III invalid for vision impairment).

Group 3: As expected, since patients were selected based on their failure to respond to conventional therapy, response to conventional therapy varied between poor and nonexistent.

"Marked responses" to therapy with L-Glu-L-Trp in Groups 1 and 2 were manifested clinically in the following objective manner: patients with adenoviral conjunctivitis recovered faster (i.e., 10–13 days) than subjects in the control group. Patients with chronic serous-plastic uveitis experienced: i) disappearance of new eruptions; ii) complete resolution of established foci; iii) a rise in visual acuity by >0.1; and, iv) no recurrence of disease activity in the >12 month follow-up period. Patients with central chorioretinitis (previously nonresponsive to conventional therapy) showed i) an increase in visual acuity; ii) increase in visual field and particularly acuity at the peripheral borders of the field; iii) disappearance of hemorrhagic foci, edema, and other manifestations of inflammation in the fundus; iv) improvements in eletrophysiological properties of the retina, i.e., values recorded in the electroophthalmogram (EOG) recording approached normal values and STK values also increased.

"Good responses" to therapy with L-Glu-L-Trp in Groups 1 and 2 were manifested clinically in the following objective manner: all patients with recurring eyelid sties were disease free up to 6 months. Patients with adenoviral conjunctivitis were disease free for up to 6 months, recurring disease activity was observed thereafter, but the relapse was shorter and milder than previous episodes in the patient. Patients with pigment degeneration of the retina and central retinal dystrophy exhibited: i) an increase in visual acuity in the range of 0.05 to 0.09; ii) a broadening of the peripheral visual field borders by up to 109 meridians; iii) a decrease in the size of central scotomas; and, iv) improvements in electrophysiological indices (i.e., EOG values).

"Poor responses" to therapy with L-Glu-L-Trp in Group 1 were manifested clinically in the following objective manner: patients with pigment degeneration of the retina and central retinal dystrophy exhibited i) a change in visual acuity of less than 0.05; ii) an insignificant change in visual field; and, iii) no marked change in EOG values. Overall, a marked positive patient response was observed in 75% of patients with infectious eye diseases (e.g., adenoviral keratoconjunctivitis, recurring eyelid sties, recurring serous-plastic uveitis, and recurring chorioretinitis) following parabulbar introduction of L-Glu-L-Trp; and in 90% of the patients receiving L-Glu-L-Trp by instillation. A good response was obtained in 15% of patients following parabulbar introduction and 10% receiving L-Glu-L-Trp by instillation. In addition to the recorded changes in infectious and chronic diseases, L-Glu-L-Trp therapy reduced the incidence of disease recurrence and of complications. L-Glu-L-Trp treatment was found effective in 66.7% of the subjects in this trial with infectious eye diseases.

Protocol B: Ear Diseases

L-Glu-L-Trp administered im or by the intranasal route is used as an adjunctive therapy accompanying conventional antibiotic therapy. The latter route of L-Glu-L-Trp combination therapy results in accelerated healing of chronic and acute ear infections.

Protocol C: Corneal Diseases

L-Glu-L-Trp administered im, intranasally, or intraocularly stimulates regeneration of corneal epithelium and restoration of visual acuity with fewer infections and complications (e.g., escar) than conventional therapy.

EXAMPLE 12

Occupational Radiation Exposure

Protocol A: Exposure to 100–200 R

Summary Overview:

A total of 263 patients and 18 control patients sustained exposure to 100–200 Roentgens of occupational radiation over a period of several weeks. L-Glu-L-Trp was administered im at a dosage of 100 $\mu$g daily (or intranasally at 1 $\mu$g/kg), for 10 days. Repeated courses of therapy were prescribed (about every 4 to 6 months) for all patients who exhibited periodic decreases in immunological indices. Following each treatment, L-Glu-L-Trp induced a restoration of normal, or near normal, peripheral blood immune indices in all patients and functional lymphocyte activity. Clinically, treatment resulted in an arrest of asthenic syndrome, an arrest of the somatic pathological exacerbations, and a reduction in opportunistic infections.

Protocol B: Naval Specialists

A clinical trial was conducted of 152 naval specialists (aged 20–40 years) with evidence of occupational immunologic impairments resulting from their exposure to radiation and occupational toxins in the Kosomolets nuclear submarine sinking off the coast of Finland. L-Glu-L-Trp was evaluated for its possible effects on cellular and/or humoral immunity. Approximately 87% of the servicemen entered into the trial had moderate to severely impaired T-lymphocyte functional activity, (i.e., evidenced by decreased LMIR and blastogenesis with Con-A) and reduced neutrophil phagocytic activity (i.e., 30–40% of normal). Immune parameters were determined before and after a routine 21–24 day rest period, during a normal rest/recuperation and training rotation. Servicemen were divided into two groups, the first (control) group received no treatment, and the second (experimental) group of 88 servicemen received three consecutive daily intranasal doses of 100 mcg L-Glu-L-Trp.

L-Glu-L-Trp induced a pronounced increase in i) T-lymphocyte function (i.e., measured by LMIR and blastogenic response to mitogens); ii) the T-helper/T-suppressor ratio (i.e., T4/T8), which was normalized; and iii) the granulocyte lysosomal cation proteins levels, which were also normalized. Complement C3 levels were also returned to within the normal range. There were no observed side-effects or indications of any intolerance.

EXAMPLE 13

Opportunistic Infections in Transplantation

Summary Overview:

L-Glu-L-Trp was administered to 17 patients receiving allogeneic skin grafts. 27 patients receiving similar grafts and conventional care served as the control group. L-Glu-L-Trp was administered im as a single daily injection of 50–100 µg on each of 5 consecutive days, or alternatively, intranasally at a dose of 1 µg/kg daily for 5 days. Graft rejection was manifest in 8 of the control patients. L-Glu-L-Trp treatment prevented infectious complications and delayed graft rejection.

EXAMPLE 14

Allergies

Protocol A: Hayfever

Summary Overview:

Twenty nine patients (29) with various diagnosed allergies were treated on a daily basis for 5–7 days with L-Glu-L-Trp at a dose of 1 kg/kg delivered im or by the intranasal route. Seventeen patients (17) in the control group received conventional therapy. Treatment with L-Glu-L-Trp resulted in disappearance of allergic reactions.

Protocol B: Drug Allergies

Summary Overview:

L-Glu-L-Trp was administered to 76 patients having clinical histones of allergies to antibiotics, during the period of administration of the antibiotic. A control group consisted of 43 patients with similar antibiotic drug allergies. L-Glu-L-Trp was administered im on a daily basis for 5–10 days at a dosage of 100 µg, or alternatively, intranasally at a dosage of 1 µg/kg over the same 5–10 day period. L-Glu-L-Trp treatment prevented development of allergic reactions in the majority (i.e., 70%) of the patients, and in the remaining patients, the allergic disease course was less severe. Allergic reactions were pronounced in the control group with signs of drug intolerance.

EXAMPLE 15

Transfusion Reactions

Summary Overview:

Seventy-six patients (76) requiring hemotransfusion therapy with allogeneic blood were treated with L-Glu-L-Trp in the post-operative period, starting at day 4–6 post-op. Seventy-two patients (72) in a control group received conventional post-operative treatment. L-Glu-L-Trp treatment was administered as a single daily im dose of 100 µg on each of 5 consecutive days, or alternatively, at a dose of 1 µg/kg delivered on the same schedule by the intranasal route. None of L-Glu-L-Trp treated patients showed clinical manifestations of allogeneic hemotransfusion reactions. In contrast, a 17% rate of adverse reactions was observed in the control group.

EXAMPLE 16

Orthopedic Diseases

Protocol A: Fractures

Summary Overview:

L-Glu-L-Trp was applied to 44 patients with bone fractures of various origin. The control group comprised 28 patients. L-Glu-L-Trp was administered intramuscularly or intranasally in a single dose of 100 µg daily for 10 days. The use of L-Glu-L-Trp accelerated essentially (in comparison with the control group) the consolidation of fractures, prevented the development of infectious complications, reduced pain syndrome and treatment duration.

Protocol B: Chronic Osteomyelitis

Summary Overview:

L-Glu-L-Trp was administered to 176 patients with chronic osteomyelitis of various etiology and bone localizations. The control group consisted of 88 patients receiving conventional treatment. L-Glu-L-Trp was administered im as a single daily dosage of 100 µg, or intranasally at a dose of 1 µg/kg daily, over a period of 10 days. L-Glu-L-Trp treatment resulted in a pronounced positive effect on clinical course that was expressed as a significant decrease in systemic toxicity and pain, disappearance of purulent inflammation, accelerated wound healing, decreased size of the areas of bone destruction, and decreased incidence of clinical relapse.

Protocol C: Acute Osteomyelitis

Trial Population:

Seventeen hospitalized children (10 boys and 7 girls) were entered into this protocol: 6 with acute inflammatory diseases of soft tissues (abscesses, phlegmons), 4 with odotogenous osteomyelitis of the jaw, and 7 with hematogenous osteomyelitis of the flat and tubular bones. In 11 children, the course of the illness was acute and in 6 it was subacute and chronic.

Treatment Protocol:

L-Glu-L-Trp was administered in combination therapy with conventional antibiotic therapies. Where necessary, surgery was performed to drain infectious foci in the jaw or soft tissues, affected teeth were extracted, and for osteomyelitis a port was drilled for infusion of antibiotics. Physical examination and laboratory testing was conducted before administering L-Glu-L-Trp and 2–3 days after the treatment.

Laboratory tests were conducted to determine clinical chemistry and protein values prior to and after therapy (i.e., including the concentrations of bilirubin, creatinine, albumin, cholesterol, urea nitrogen, glucose, protein, chloride, potassium, phosphorus, calcium, sodium, alkaline phosphatase, $\alpha_1$-orosomucoid, $\alpha_2$-macroglobulin, prealbumin, ceruloplasmin, and transferrin). While urea nitrogen and cholesterol decreased slightly after therapy, these and all other changes observed after L-Glu-L-Trp treatment were not statistically significant. The results of differential cell counts and testing of immune parameters are summarized in TABLE 36.

TABLE 36

| | Immunology Values | |
|---|---|---|
| Index | Before Therapy | After L-Glu-L-Trp Therapy |
| Leukocytes: ($10^9$/L): B-Lymphocytes: | 8.7 ± 0.96 | 7.0 ± 0.4[†] |
| % of PBL: | 9.5 ± 1.24 | 15.1 ± 3.32[†] |
| No. ($10^9$/L): Null-Lymphocytes: | 0.29 ± 0.11 | 0.41 ± 0.11 |
| % of PBL: | 30.8 ± 4.94 | 18.7 ± 4.68[†] |
| No. ($10^9$/L): | 0.8 ± 0.18 | 0.42 ± 0.11[†] |

TABLE 36-continued

Immunology Values

| Index | Before Therapy | After L-Glu-L-Trp Therapy |
|---|---|---|
| Neutrophils: | | |
| % PBL: | 63 ± 4.63 | 50 ± 4.8† |
| ×10⁹/L: | 5.8 ± 0.93 | 3.4 ± 0.33† |
| LMIR: % PHA: | 93.7 ± 29.2 | 47.7 ± 11.2† |
| IgM (g/L) | 2.19 ± 0.65 | 1.64 ± 0.26† |
| IgA (g/L) | 1.63 ± 0.2 | 1.68 ± 0.18 |
| Lymphocytes: | | |
| % of PBL: | 29 ± 3.7 | 43 ± 3.61† |
| No. (10⁹/L): | 2.3 ± 0.33 | 3.15 ± 0.41 |
| T-Lymphocytes: | | |
| % of Lym: | 59.6 ± 5.12 | 66.2 ± 2.57 |
| No. (10⁹/L): | 1.6 ± 0.36 | 1.7 ± 0.3 |
| T-helper ($E_{tr}$-RFC): | | |
| % of Lym: | 50 ± 6.71 | 57.3 ± 6.34 |
| No. (10⁹/L): | 1.2 ± 0.3 | 1.4 ± 0.24 |
| T-suppressor: | | |
| % of Lym: | 9.5 ± 3.18 | 8.8 ± 5.4 |
| No. (10⁹/L): | 0.26 ± 0.09 | 0.3 ± 0.2 |
| LMIR: % Con A | 79 ± 5.85 | 49.7 ± 13.7† |
| IgG (g/L) | 14.3 ± 2.42 | 14.4 ± 1.31 |
| C3 (g/L) | 0.82 ± 0.03 | 0.72 ± 0.05 |

†a p value of <0.05 was recorded in these studies after mathematical comparisons of Pre-treatment and Post-treatment values.

The results presented in TABLE 36 show that prior to treatment the patients in the trial population had decreased levels of B- and T-lymphocyte mitogen responsiveness to PHA and Con-A, (i.e, as measured by cytokine production in LMIR assay). Prior to treatment, the patients also showed possible decreases in the percentages of T-helper lymphocytes and increases in T-suppressor lymphocytes, i.e., as determined using a trypsin-treated erythrocyte rosette forming cell ($E_{tr}$-RFC) assay, wherein T-helper cells are trypsin resistant ($E_{tr}$-RFC) and T-suppressor cells are trypsin sensitive ($E_{ts}$-RFC). Following treatment with L-Glu-L-Trp the following changes were observed: i) leukocyte counts and neutrophil counts dropped significantly; ii) Null lymphocyte counts dropped; and, iii) B-lymphocyte counts and serum IgM levels dropped significantly. While not statistically significant, lymphocyte counts in peripheral blood increased with T-helper rising and T-suppressor percent falling. T-lymphocyte function increased as measured by cytokine production in vitro in the LMIR assay in response to PHA and Con-A mitogens and staphylococcal and streptococcal antigens.

Clinical Response:

Children in the treatment group reported feeling better, and according to the report of the attending physician "wounds cleaned themselves of necrotic tissue and developed granulation tissue 2–3 days earlier than usual."

Protocol D: Acute Osteomyelitis

In 29 adolescents with osteomyelitis, 2 μg/kg L-Glu-L-Trp was administered im daily on each of 3–7 consecutive days, depending upon the severity of the infection. The control group consisted of 13 children who received conventional therapy with antibiotics. Clinical improvement was noted in the 3 days following L-Glu-L-Trp treatment with an arrest in the inflammatory process, a reduction in pain, and an increased stability of the underlying dental structures as evidenced by X-ray studies. Fevers reportedly resolved on the average 1–2 days sooner in the L-Glu-L-Trp treated group, and all wounds and purulent discharge were observed to close with healing 2–3 days earlier than children the control group. In only 1 child (i.e., having purulent osteomyelitis), out of the 29 L-Glu-L-Trp-treated, did the wounds failed to heal (i.e., a 3% failure rate), as compared with failure in 2 of the 13 children in the control group (i.e., a 15% failure rate). Clinical improvements in the L-Glu-L-Trp treated children were accompanied by decreases in the total leukocyte counts, and the T-cell counts nearly doubled.

EXAMPLE 17

Sidney and Prostate Diseases

Protocol A Pyelonephritis in Pregnancy

Summary Overview:

Twenty-seven pregnant female patients (27) with pyelonephritis were treated with L-Glu-L-Trp as a single daily dose of 100 μg on each of 5–10 consecutive days and in combination with ongoing conventional therapy. A control group was constituted of 19 control patients with pyelonephritis receiving the conventional therapy. Treatment with L-Glu-L-Trp resulted in reduction of fever, the normalization of urinary output, and overall clinical improvement with resolution of infection. Women treated with L-Glu-L-Trp experienced normal delivery without complications.

Protocol B

Prostatitis

Trial Population:

Thirty four patients (aged 22 to 45 years) with chronic prostatitis were entered into Group 1 of this trial during the acute phase of their disease. Diagnosis was based on medical history, and physical examination of the prostate (palpated through the rectum). Laboratory testing included microscopic examination of prostate gland secretions, spermography and urinalysis. All patients had previously received full courses of unsuccessful therapy with antibacterial agents, and additional individualized therapy including uroantiseptics, spasmolytic, ganglion blockers, novocain paraprostate and presacral blocks, ultrasound, and prostate gland massage. Success of any individualized therapy was only partial and short-term.

A control group (Group 2) constituted 14 patients (aged 23–45), also having chronic prostatitis, and enrolled during the active phase of the patients' disease. All patients in the control group had also failed previously one or more full courses of antibiotic and conventional therapy.

Treatment Protocol:

L-Glu-L -Trp was administered im daily at 100 μg/dose for 5 (500 μg total treatment course) in combination with conventional individualized therapy including antibacterial preparations and uroantiseptics (e.g., oletrin, and bisepton), physical procedures (e.g., ultrasound; using a Sterzhen 1 instrument), prostate gland massage, and exercise Patients in Group 2 received only conventional therapy with antibacterial agents and individualized treatments, (i.e., as above).

Laboratory Tests:

Peripheral blood samples were collected for laboratory testing 10 days after the last injection of L-Glu-L-Trp. The results of the laboratory testing for immune parameters are presented in TABLE 37.

TABLE 37

Immunology Values (X ± S.D.)

| Index | Normal ± SD or Range | Conventional Before | Conventional After | L-Glu-L-Trp Before | L-Glu-L-Trp After |
|---|---|---|---|---|---|
| T-Lymphocytes: % of Lym: | 54.0 ± 2.1 | 43.4 ± 4.4 | 41.7 ± 5.8 | 45.8 ± 2.3 | 44.4 ± 2.3 |
| No. ($10^9$/L): | — | 0.96 ± 0.01 | 0.92 ± 0.03 | 0.91 ± 0.02 | 0.88 ± 0.1 |
| B-Lymphocytes: % of PBL: | 24.0 ± 0.6 | 23.2 ± 2.3 | 24.8 ± 2.3 | 24.3 ± 1.5 | 27.2 ± 1.4 |
| No. ($10^9$/L): | — | 0.46 ± 0.03 | 0.5 ± 0.1 | 0.48 ± 0.1 | 0.54 ± 0.1 |
| Phagocytes: % PBL: | 23.3 ± 0.4 | 32.4 ± 2.6 | 29.7 ± 2.7 | 41.1 ± 3.8 | 39.4 ± 3.5 |
| Complement ($CH_{50}$) | 30.3 ± 0.2 | 29.2 ± 1.1 | 28.5 ± 1.1 | 29.5 ± 0.6 | 29.4 ± 0.5 |
| Immune Complexes (units) | 0.06–0.08 | 0.09 ± 0.01 | 0.08 ± 0.01 | 0.86 ± 0.01 | 0.80 ± 0.004 |
| IgM (g/L) % Normal Value: | 0.6–3.8 | 2.1 ± 0.9 | 2.3 ± 4.1 | 2.1 ± 0.2 | 2.1 ± 0.1 |
| IgG (g/L) % Normal Value: | 6–18 | 12.8 ± 1.2 | 12.5 ± 1.3 | 12.6 ± 0.2 | 12.5 ± 0.6 |
| IgA (g/L) % Normal Value: | 0.8–5.2 | 2.5 ± 0.3 | 2.4 ± 0.2 | 2.5 ± 0.2 | 2.2 ± 0.1 |

†a p value of <0.05 was recorded in these studies after mathematical comparisons of Pre-treatment and Post-treatment values.

Considering that not all of the subjects receiving L-Glu-L-Trp (Group 1) responded to therapy with a change in immune parameters, the data were evaluated in an attempt to identify individual subgroups of patients responsive to therapy. Patients were grouped according to whether the pre-treatment immune parameter was i) normal, ii) decreased, or iii) increased (relative to the normal healthy range of values). The results of these analyses are presented in TABLE 38.

TABLE 38

Immunology Values:
Grouped by Putative Immune Parameter Defect (X ± S.D.)

| Index | L-Glu-L-Trp Before | L-Glu-L-Trp After |
|---|---|---|
| T-Lymphocytes (%): | | |
| Normal (n = 18): | 54.0 ± 2.1 | 50.0 ± 3.6 |
| Decreased (n = 14): | 31.1 ± 1.0 | 37.9 ± 2.2 |
| Increased (n = 2): | 74.5 ± 2.1 | 40.0 ± 15.5 |
| B-Lymphocytes: | | |
| Normal (n = 16): | 24.0 ± 0.6 | 29.2 ± 2.2 |
| Decreased (n = 10): | 15.0 ± 1.2 | 26.0 ± 2.9† |
| Increased (n = 8): | 36.5 ± 2.2 | 24.8 ± 2.9† |
| Phagocytes (% of PBL): | | |
| Normal (n = 3): | 23.3 ± 0.4 | 58.6 ± 18 |
| Decreased (n = 5): | 16.6 ± 4.2 | 36.6 ± 8.5† |
| Increased (n = 26): | 47.9 ± 4 | 37.7 ± 3.9 |
| Complement ($CH_{50}$) | | |
| Normal (n = 13): | 30.3 ± 0.2 | 29.3 ± 0.9 |
| Decreased (n = 14): | 26.3 ± 0.5 | 34.2 ± 0.9† |
| Increased (n = 7): | 34.2 ± 0.9 | 30.7 ± 0.9 |
| Imm. Cmplx. (units) | | |
| Normal (n = 7): | 0.07 ± 0.03 | 0.08 ± 0.01 |
| Decreased (n = 8): | 0.05 ± 0.001 | 0.07 ± 0.01 |
| Increased (n = 19): | 0.11 ± 0.01 | 0.08 ± 0.01† |
| IgM (g/L) | | |
| Normal (n = 33): | 2.01 ± 0.13 | 2.08 ± 0.12 |
| Increased (n = 1): | 6.0 | 3.44 |
| IgG (g/L) | | |
| Normal (n = 26): | 11.8 ± 0.6 | 12.5 ± 0.7 |
| Decreased (n = 2): | 3.7 ± 0.4 | 7.8 ± 1.1† |
| Increased (n = 6): | 19.1 ± 0.3 | 14.7 ± 1.4 |
| IgA (g/L) | | |
| Normal (n = 34): | 2.50 ± 0.15 | 2.2 ± 0.12 |

†p < 0.05 statistical difference between Pre- and Post-treatment values.

The results presented in TABLE 38, above, show that treatment of the patients in Group 1 with L-Glu-L-Trp i) did not significantly alter immune values in patients that had "normal" pre-treatment values; ii) significantly increased B-lymphocytes, phagocytes, and complement and IgG levels in patients that had "decreased" pre-treatment values; and, iii) significantly decreased B-lymphocytes and immune complex levels in patients that had "increased" pre-treatment values. The same analysis was conducted using the data collected following conventional therapy of the patients in Group 2, and none of the differences were statistically significant.

Clinical Results:

Clinical results were recorded according to accepted criteria for evaluating the efficacy of treatments for prostatitis: namely, i) disappearance of painful symptoms over a period of 1–1.5 months (e.g., absence of pain in perineum, sacrum, and scrotum); ii) size and elasticity of the prostate on physical examination; iii) volume of prostate gland secretions and ejaculate; iv) microscopic features of secretions and ejaculate (e.g., leukocytes, macrophages, phagocyte lecithin granules, spermatozoids, squamous epithelial cells, erythrocytes), v) volume of urine; and, vi) overall patient health. A "good" result was scored if laboratory values were normalized and the patient remained pain free during the 1–1.5 month follow-up period of examination. A "satisfactory" result was scored if laboratory values were normalized even if some pain remained. An "unsatisfactory" result was scored if laboratory values remained unchanged and pain persisted.

A "good" result was recorded in 26 patients (76.5%) in Group 1 following L-Glu-L-Trp treatment. After finishing the treatment course, patients noticed significant improvement in general physical condition with disappearance of painful symptoms and dysuria. All the laboratory indicia returned to within the normal range of values. A "satisfactory" result was recorded in the remaining 8 patients in Group 1 (23.5%). No "unsatisfactory" results were recorded with the patients in Group 1.

In contrast, following conventional treatment, the patient responses in Group 2 were scored as follows: 9 "good" (64.3%); 3 satisfactory (21.4%); and, 2 (14.3%) unsatisfactory

EXAMPLE 18

Clinical Studies: Leprosy

Overview:

A total of 45 patients with leprosy (Hansen's disease) were treated with L-Glu-L-Trp administered im daily at a dose of 100 µg, or intranasally daily at a dose of 1 µg/kg, on each of 5 consecutive days as an adjunct to ongoing conventional therapy. Twenty-seven other M. leprae infected individuals constituted the control group. The patients studied had previously documented antibiotic resistance to treatment by conventional methods. L-Glu-L-Trp treatment resulted in i) resolution of dermal leprotic lesions, ii) lower incidence of recurrence of dermal disease, and iii) accelerated healing of individual dermal ulcers.

Infection with M. leprae is well recognized to result in immunosuppression. The immune indices in the peripheral blood of L-Glu-L-Trp treated patients were normalized, and certain patients acquired skin test responsiveness to lepromin antigen.

Background:

Infection with *Mycobacterium leprae* generally proceeds in a slow inexorable and progressively debilitating manner through stages of tuberculoid leprosy to lepromatous leprosy and eventual death. The disease progression is gradual from non-differentiated leprosy (J) to borderline tuberculoid (BT) to polar tuberculoid (TT) to borderline (BB) to borderline lepromatous (BL) to polar lepromatous (Llp). The lepromatous stage of the disease is further subdivided into subpolar lepromatous (Lls). Histological features of acid fast bacteria in tissues, perivascular granulomas in skin and mucous membranes are well established, as are the general immune suppression evident as the absence of a delayed-type hypersensitivity skin reaction to lepromin antigen, decreased blast transformation of peripheral blood lymphocytes to PHA, an altered ratio of $CD4^+/CD8^+$ lymphocytes in peripheral blood, and decreased levels of IgM and IgG in serum. The therapy of choice most commonly employs several antileprotic preparations in optimally-tolerated doses, e.g., diaminodiphenylsulfone (DDS) taken internally at a dose of about 50 mg and sodium sulfone taken intramuscularly using a 50% sterile injection solution. The minimal time frame for therapy of TT leprosy is 3 years; for non-differentiated leprosy 5–7 years; and, for LL leprosy, patients must receive treatment over their entire lives. Treatment courses are commonly 6 months with an intermission of 1–1.5 months between courses, and to prevent the development of drug resistant bacteria, the drug preparation is preferably changed to a new drug (e.g., Rifampicin, ethionamide, prothionamide or Lampren-clofaximine) after each course of therapy.

Trial Protocol:

An assessment was made of disease progression prior to and after combination therapy involving physical examination of the skin, biochemical testing of blood and urine, bacteriologic testing of skin plaques, immunological tests of cellular and humoral immunity, and histologic and electron microscopic examination of cutaneous skin lesions.

Patient Population:

Efficacy of L-Glu-L-Trp in combined antibiotic therapy was evaluated in 45 patients (aged 18 to 83; 23 men and 22 women) with chronic debilitating infection with *Mycobacterium leprae*, i.e., Hansen's disease (the length of illness varied from 2 to 25 years). According to standard diagnostic criteria at clinical presentation: 18 patients had active leprosy; and in 27 the disease was regressive. Sixteen of the patients with active leprosy also presented with neurotrophic ulcers (NTU) and chronic osteomyelitis. According to the Ridley-Jopling diagnostic classification criteria, 37 patients were suffering from lepromatous leprosy, 6 from borderline-lepromatous leprosy, and 2 from borderline tuberculous leprosy. The length of disease in this patient population was 2 to 25 years. None of the patients in the trial had received previous treatment with an immunomodulator, and all were receiving conventional courses of sulfone-type antibiotic therapy and experiencing prolonged slow-disease progression.

L-Glu-L-Trp Treatment:

The 18 patients with active leprosy were treated with L-Glu-L-Trp administered im at a dosage of 1 µg once daily in about 1 mL for 5 days. In 10 of the patients with the regressive course of disease, the L-Glu-L-Trp was administered daily intranasally by drops at a dosage of 1 µg daily for 5 days (i.e., one treatment course). Four of the 16 patients with active leprosy and NTU were treated with additional localized intra-ulcer injections of about 1–20 µg/site L-Glu-L-Trp. While L-Glu-L-Trp was being administered, antibiotic therapy was discontinued.

Summary of Immunological Studies:

Parameters of cellular and humoral immunity were tested 5–7 days after concluding one treatment course in the 16 patients with active leprosy. Nonspecific immunosuppression of M. leprae infection was evident in the patient population prior to initiating therapy with only about 13–15% of patient lymphocytes capable of mitogen-induced blast transformation (TABLE 38). This contrasted with 40–60% blast cells in normal subjects following culture with PHA (polyvalent mitogen), or 20–40% blast cells with Con-A (T-cell mitogen; TABLE 39; control). After the 5–7 day course of L-Glu-L-Trp treatment, blast responsiveness of patient lymphocytes was increased 1.8-fold to PHA and 1.6-fold to Con-A, and after 6 months (and several treatment courses), responsiveness to Con-A was in the normal range (i.e., 20–40% of lymphocytes responsive).

TABLE 39

Percentage of Peripheral Blood Lymphocytes Responsiveness to PHA and Con A

| Treatment | PHA (%)[a] | Con-A (%)[a] |
| --- | --- | --- |
| Before L-Glu-L-Trp | 15.2 ± 4.5 | 13.9 ± 2.9 |
| 5–7 days | 28.7 ± 3.8 | 22.5 ± 4.0 |
| 6 months | 22.3 ± 1.43 | 36.9 ± 1.28 |
| None-healthy controls | 40–60* | 20–40* |

[a]Mean % responsive PBL (blast cells); patient values +/− S.D. (number of patients = 16);
*Normal range of values for lymphocytes from healthy control subjects (n = 50).

The percentage of antigen-specific patient lymphocytes responsive to synthetic leprosy antigen was also increased by about 1.6-fold on day 5–7 of treatment from a pre-treatment mean value of 1.78±0.7% blast cells to a value of 2.86±0.9%.

Lymphocyte sub-populations were evaluated in leprosy patients before and after treatment and the results are presented in TABLE 40.

TABLE 40

Peripheral Blood Lymphocyte Subpopulations in Leprosy Patients
Before and After 5–7 Days Treatment with L-Glu-L-Trp*

| Patient Group | Treatment | OKT 11 (%) | OKT 8 (%) | OKT 4 (%) | OKT 4/OKT 8 |
|---|---|---|---|---|---|
| Active Disease | Before | 72.13 ± 3.34 | 26.00 ± 1.49 | 45.71 ± 4.99 | 1.83 ± 0.26 |
| | After | 72.22 ± 1.52 | 25.56 ± 1.15 | 40.67 ± 1.44 | 1.61 ± 0.08 |
| Regressive Disease | Before | 76.25 ± 3/82 | 27.75 ± 2.69 | 37.00 ± 4.09 | 1.33 ± 0.05 |
| | After | 76.25 ± 0.87 | 27.25 ± 3.42 | 43.25 ± 1.91 | 1.68 ± 0.32 |
| Healthy controls** | None | 72.5 ± 1.42 | 23.55 ± 1.24 | 44.55 ± 1.67 | 1.88 ± 0.09 |

*Mean patient values % +/− S.D. (number of patients = 16);
**Normal percentage for lymphocytes from healthy control subjects (n = 50).

The results in TABLE 40 show that the total percentage of T-lymphocytes (OKT 11$^+$) in peripheral blood was not significantly altered after therapy; the percentage of OKT 4$^+$ T-helper cells in circulation in patients with active disease was slightly decreased (possibly by redistribution into infected tissues); and, in patients with regressive disease, the percentage of OKT 4$^+$ cells in circulation was slightly increased. Apparently, the observed increase in mitogen-induced blast responsiveness of lymphocytes in the leprosy patients after 5–7 days of L-Glu-L-Trp treatment was accomplished without a major bulk change in either the number or subpopulation composition of peripheral blood T-lymphocytes.

Summary of Histological Findings:

Three indices were used to score serial sections of biopsy samples obtained from patients before and after treatment with L-Glu-L-Trp, namely, i) bacterial index (BI), i.e., the relative saturation of the tissue with mycobacterial bacilli in tissue sections on a scale of 0 (low) to 1 (high); ii) histologic index (HI), i.e., scoring the area of granuloma and bacteria (Materials and Methods, below); and, iii) esterase index (EI), scoring the differentiative state of the granuloma (Materials and Methods, below). The results of these studies with patients with regressive-differentiated lepromatous leprosy ($LL_D$), undifferentiated-active lepromatous leprosy ($LL_S$), borderline lepromatous leprosy (BL), and borderline tuberculoid leprosy (BT) are summarized in TABLE 41.

TABLE 41

Histologic Examination at One Month of Dermal Lesions in
Leprous Patients Before and After L-Glu-L-Trp Treatment*.

| Disease State | Treatment | BI | HI | EI | Gross Pathology |
|---|---|---|---|---|---|
| $LL_D$ (n = 3) | Before | 0 | 1.83 ± 0.03 | 0.6 ± 0.01 | maculation; surface infiltration lepromas on torso and extremities |
| | 1 Month After | 0 | 1.35 ± 0.03 (↓26%) | 0.91 ± 0.2 (↑52%) | no visible change |
| | 3 Months After | 0 | 0.66 ± 0.1 (↓64%) | 1.9 ± 0.5 (↑217%) | pronounced decrease in surface infiltration and macules |
| | 6 Months After | 0 | 0.56 ± 0.05 (↓%) | 2.15 ± 0.45 (↑258%) | complete disappearance of surface infiltrate and partial disappearance of deep infiltrate |
| $LL_S$ (n = 10) | Before | 0.97 ± 0.03 | 3.37 ± 0.04 | 0.55 ± 0.01 | thickening and sensitivity of peripheral nerve stems |
| | 1 Month After | 0.63 ± 0.03 (↓35%) | 3.24 ± 0.04 | 0.79 ± 0.3 (↑44%) | decreased skin infiltration |
| | 3 Months After | 0.39 ± 0.09 (↓60%) | 0.07 ± 0.01 (↓70%) | 1.17 ± 0.6 (↑113%) | disappearance of deep infiltrations; resolution of surface; regression of deep lepromas |
| | 6 Months After | 0.38 ± 0.05 (↓61%) | 2.00 ± 0.02 (↓38.1%) | 0.55 ± 0.01 | decrease in size/regression of lepromas |
| BL (n = 4) | Before | 1.04 ± 0.5 | 3.37 ± 0.9 | 0.73 ± 0.3 | diffuse surface and deep infiltration; papules on skin torso and extremities |
| | 1 Month After | 0.99 ± 0.3 | 2.71 ± 0.1 (↓20%) | 2.03 ± 0.25 (↑178%) | signs of regression of papules and decreased infiltration of skin |
| | 3 Months After | 0.72 ± 0.05 (↓31%) | 0.53 ± 0.1 (↓84%) | 3.45 ± 0.3 (↑372%) | regression of papules; disappearance of surface and deep infiltrates |
| | 6 Months After | 0.53 ± 0.07 (↓46%) | 1.25 ± 0.1 (↓54%) | 1.37 ± 0.1 (↓33%) | disappearance of dermal macules; resolution of infiltrated |
| BT (n = 1) | Before | 0 | 2.9 | 0.15 | extensive plaques in the skin of extremities; hyperemia; edema |
| | 1 Month After | 0 | 2.05 | 0.51 | plaques, scaling of skin, dermal edema all disappearing |
| | 3 Months After | 0 | 2.05 (↓29%) | 0.51 (↑240%) | decrease in area of plaques, papules, and surface scaling |
| | 6 Months After | 0 | 0 | 0.06 (↑250%) | a few residual macules on the skin, atrophy/scarring |

The results presented in TABLE 41, showed decreases in the histological index, i.e., decreased areas involved with bacteria and granulomatous infiltration in the skin biopsy samples obtained from all the patients studied at one month post-treatment with L-Glu-L-Trp. The histologic findings also suggested a trend toward a higher level of macrophage activation and greater differentiated state of the existing granulomata in the tissues. The latter findings are highly suggestive of increased bactericidal activity in the residual granulomas. Consistent with this interpretation was a general improvement in the gross pathology of the skin in the treated patient population when compared with the pretreatment pathology. Dramatically, in the patients with disease in regression (i.e., $LL_D$) what was before treatment a homogeneous mycobacterial infection had virtually disappeared after therapy and there was a decrease in the area of granulomas and an increase in the number of lymphocytes, mononuclear cells, fibroblasts, mast cells, histiocytes, fibroblasts and fat cells in the skin. In patients with active disease (i.e., $LL_S$), the number of macrophages containing bacilli was greatly reduced and the number of lymphoid cells, histiocytes and fibroblasts increased. Histological measurements performed at 3 months were striking, with signs of disease regression in all patients in the trial as evidenced by decreased recognizable bacilli in the tissues (i.e., decreased BI), decreased granulomata and cellular infiltration in the tissues (i.e., decreased HI), and more activated macrophages and differentiated granulomata (i.e., increased EI). Histologic and electron microscopic examination confirmed degenerative changes in the residual bacteria in patients' tissues, as evidenced by an increase in fat content in the cytoplasm of the bacilli, an increase in fuchsinophilic granules in tissues (degenerative mycobacterial bodies), and an increase in degenerative forms of leprous bacilli and cell wall materials visible in phagolysosomes of tissue macrophages and histiocytes. Signs of tissue would healing were also evident as neovascularization of tissues at the former granuloma sites. By six months (the time at which potential efficacy of a leprosy drug is normally assessed) histologic signs of a granulomatous response were waning with very few bacteria being evident, and decreased tissue infiltrate of immune cells.

The results indicated that introduction of L-Glu-L-Trp into the treatment plan for *M. leprae* greatly accelerated the resolution of skin lesions in all patients in the trial group. Dramatically, four subjects with negative skin tests for lepromin at the beginning of therapy turned positive. Other clinical evidences of success are disclosed below.

Summary of Clinical Results:

Six to seven days after the completion of a single course of L-Glu-L-Trp therapy, no visible changes were clinically evident. However, after 1 month of therapy, the first clinical effects became evident as decreased sizes of measured cutaneous lesions in the 6 patients with borderline lepromatous leprosy and the 2 patients with borderline tuberculous leprosy, although the clinical effects varied from patient to patient. No change was noted in the patients with progressive lepromatous leprosy, but some improvements in cutaneous lesions were noted in a few of the patients with static lepromatous leprosy.

After three months of treatment pronounced signs of dermal improvement were clinically evident in responsive patients, i.e., lepromatous papules, plaques, lepromas, and infiltrates were decreased.

After 6 months of treatment with L-Glu-L-Trp, cutaneous lesions were nearly completely absent from responsive patients, and the size of the remaining leprous plaques was greatly decreased in size with lucid zones of scar tissue forming about the periphery of the plaques. In some patients leprous plaques were completely absent and replaced by atrophic maculas having a burgundy-like color. Remarkably, one patient previously classified as borderline lepromatous leprosy was down-graded to borderline tuberculous leprosy with nearly a 100% reduction in histological evidence of infection, and complete histological disappearance of cutaneous *M. leprae*. A second patient, previously classified with tuberculous leprosy showed a complete cessation of leprous infection and was discharged to out-patient care.

At 6 to 12 months, two additional patients classified at the beginning of the trial with lepromatous leprosy and borderline leprosy were released to out-patient ambulatory care, with cutaneous and histological evidence of their disease completely absent. In one case a perivascular lepromatous granuloma evident by gross pathology at the beginning of treatment was histologically examined and seen to be resolved to a diffuse lympho-histiocytic infiltrate completely devoid of mycobacteria. Histological examination of biopsy samples from skin (and nasal mucous membranes) and taken from the locations of previous lesions all revealed a complete absence of mycobacteria or perivascular leprous granulomata, and instead, there was evidence of diffuse infiltration with small lymphocytes and histiocytes (dendritic and Langerhans cells).

Within the treatment subgroup of 16 patients who had neurotrophic ulcers at the beginning of the trial (NTU; above), 4 patients initially had presented with primary disease, 9 with recurrent NTU, and 3 with chronic oscheal osteomyelitis of the lower extremities complicated with NTU. At the beginning of therapy, the ulcerative lesions were filled with purulent-necrotic material and no evidence of wound healing was present. Fifteen of the 16 patients showed clinical improvements while on L-Glu-L-Trp therapy. For primary NTU, the clinical improvements were obtained after about 3–6 weeks of L-Glu-L-Trp treatment, i.e., with secretions from the ulcer disappearing; for recurrent NTU the improvements were obtained at about 4–6 weeks (in both cases, the results obtained were dependent on the size of the ulcers). The ulcers were replaced for the most part by a dried crusty scab, and eventually a callous. At about the same time chronic osteomyelitis of the lower extremities was healed in the three patients so afflicted. Cytological examination of smears taken from the ulcers during treatment revealed a decrease in acid fast bacteria in the exudates, and after only one week of therapy, activated lymphocytes, monocytes, and neutrophils were observed in the exudates (TABLE 42). Histologic evidence of re-epithelialization of the ulcers was evident after only two weeks of L-Glu-L-Trp therapy.

TABLE 42

Cytology of Smears from Lepromatous Ulcers in Patients Treated with L-Glu-L-Trp

| Treatment | Romanovsky Staining | Lysosome Cation (OD units) | HCT-test (OD units) |
| --- | --- | --- | --- |
| Before | degenerative necrotic cells | 0 | 0 |
| Day 2 | degenerative cells & inflammatory cells | 0.33 ± 0.02 | 0.09 ± 0.01 |
| Day 4 | regenerative: 1st or 2nd phase | 0.42 ± 0.05 | 0.11 ± 0.1 |
| Day 7 | regenerative: 2nd or 3rd. phase, destructive cellular elements gone from smears and replaced by neutrophils | 0.58 ± 0.03 | 0.59 ± 0.2 |

TABLE 42-continued

Cytology of Smears from Lepromatous Ulcers in Patients Treated with L-Glu-L-Trp

| Treatment | Romanovsky Staining | Lysosome Cation (OD units) | HCT-test (OD units) |
|---|---|---|---|
| Day 14 | regenerative: 3rd. phase/healing; lymphoid and monocytoid cells; epithelial cells in smears | 0.84 ± 0.09 | 0.78 ± 0.3 |

In treating patients with NTU, clinical improvement was noted in 15 of the 16 patients. In patient #16, chronic osteomyelitis was not improved. Healing times for NTU in the treated patients were about 3–6 weeks for primary NTU (depending upon size), and about 4–6 weeks for secondary recurrent lesions. The measured rate of healing for primary NTU (from planimetry) was 6.34 mm$^2$/day, and for recurrent NTU the rate was 5.91 mm$^2$/day. The area of ulceration decreased over the first week of treatment by a mean value of 40% in patients with primary NTU, and by 22.6% in those with recurrent ulcers. By the end of the second week the additional decrease in area of ulceration was 22% and 29%, respectively; and, by the third week 23.2% and 8.2%.

While the trial was terminated at 6 months, at twelve months, four patients (3 with LL and 1 with BL) who received repeat courses of L-Glu-L-Trp over the period from 6–12 months continued to be observed and their condition continued to improve with further regression of the cutaneous lesions clinically and histologically (i.e., with dermal atrophy, re-epithelialization, and stable regression of disease). Four other patients (3 with $LL_S$ and 1 with BL) who did not receive follow-up treatment with L-Glu-L-Trp showed a worsening of disease from the 6 month to the 1 year observation with new papules and macules apparent in the skin, and new perivascular granulomas evident histologically. The HI and EI values for these patients showed deterioration from the 6 month values.

On long-term follow up, one of the four ambulatory patients experienced a relapse of disease, but as a borderline tuberculoid form of leprosy (not lepromatous) and at three weeks after termination of the L-Glu-L-Trp trial.

Both parenteral (im) and intranasal (drops) instillation appear effective. In certain patients nasal stuffiness was encountered with visible nasal edema, and nasal instillation was discontinued.

Materials and Methods

Patient Examination:

Examinations were conducted before treatment, and at time intervals of: i) 5–7 days after the L-Glu-L-Trp treatment, ii) 1 month, iii) 3 months, iv) 6 months, and v) 12 months. Methods for skin examination included general observation, morphometry and planimetry to quantify the size of cutaneous leprotic lesions (as well as infiltrates, macules, and lepromas). Patient blood samples (obtained at the latter observation points) were tested (using standard methods) to determine total protein, creatinine, urea, and hepatic function (i.e., bilirubin, thymol, sulem, and AST and ALT transaminases). When appropriate, urinalysis was also conducted.

Indices of Cellular Immunity:

Functional activity of T-lymphocytes was determined by microscopically assessing blast transformation of peripheral blood lymphocytes, i.e., prepared by Ficoll-Urotrast (or Ficoll-Paque, Pharmacia, Sweden) density gradient sedimentation. Lymphocytes capable of blast transformation with PHA, Con A, or synthetic *M. leprae* antigen were counted microscopically after 36–48 hrs. in vitro culture. Lymphocyte subpopulations were determined by immunofluorescence microscopy using OKT-specific monoclonal antibodies (Ortho, Piscataway, N.J.) and FITC-labeled swine and mouse Ig.

Indices of Humoral Immunity:

Humoral immunity to *M. leprae* was determined by testing for the presence of IgG or IgM in the patient serum using the immunofluorescence agglutination (IFA) method. Briefly, patient antibodies capable of cross-linking bacilli can induce agglutination and after washing the bound antibodies can be visualized by immunofluorescence microscopy using FITC-labeled anti-human IgG or IgM. Antibodies to *M. leprae* were also assessed using indirect hemagglutination (of bacilli), radial immunodiffusion in agarose (i.e., Mancini's), and ELISA assays for *M. leprae*-specific phenol glycolipid antigen (PGL-1).

Histologic Examination:

Lepromatous lesions in patient skin were microscopically examined in using cryostat sections or paraffin sections of formalin-fixed punch biopsy samples (1×0.5×0.5 cm) using Sudan III staining to reveal neutral lipids, hematoxylin and eosin to visualize immune cells, and Sil-Nilssen acid fast staining to reveal *M. leprae* bacilli. Non-specific acid esterase was determined by fixing biopsy samples with calcium formol (per Becker's method) and staining according to the Naohlas, Seligman modification of Gomori's method. An ocular micrometer was used to measure (in serial sections) the area occupied by leporatomous lesions, as well as the size of the cellular infiltrate. A scale from 1+ to 6+ was used to score the extent of the tissue section that was saturated with mycobacteria, referred to as the bacterial index (BI). Staging of granulomatous lesions was according to Ridley and Jopling: i.e., the histological index (HI)=X+ BIG, where X is the decimal logarithm of the granulomatous areas measured in 5–6 serial sections, and BIG is the mean bacterial index of the 5–6 serial sections. Non-specific acid esterase was used to identify activated macrophages in granulomas in tissue sections and the intensity of the reaction in the epidermis was used to score the stage of the leprous infection: i.e., an esterase index value <1.0 corresponded to a highly active poorly differentiated leprotic process; >1.0 to a more granulomatous (developed) mass in the tissue section. Electron microscopy was conducted on ultra-thin sections from seven selected patients before and after treatment with L-Glu-L-Trp. Biopsy tissues were fixed in glutaraldehyde and osmium, dehydrated in ethanol and propylene oxide, and embedded in epoxide resin. Leprous infection in skin lesions was assessed using wound exudates. Exudates were collected from the moist surface of ulcerative defects, smears on slides were fixed with methanol and stained with azure-eosin according to the method of Romanovsky-Giemsa. Neutrophil activity was histochemically identified using lysosome cation and HCT tests.

EXAMPLE 19

Malaria: Plasmodium falciparum

Summary Overview:

Fifty-four patients (54) with relapsing forms of tropical malaria were entered into the trial. The patients' symptoms ranged from moderate to severe. Thirty-three patients (33) were entered into the L-Glu-L-Trp treatment group and 21 patients into a control group. L-Glu-L-Trp was administered as a single daily im injection at a dose of 100 μg, or alternatively, in at 1 μg/kg body weight, on each of 5–10 consecutive days. The treatment resulted in a reduction of the patients' hepatolineal syndrome, a normalization of hematological and immunological indices, a reduction of fever, and a decreased incidence of disease relapses in the treated subjects relative to the controls. The clinical investigators report as follows: "A commission consisting of Asst. Chief of the 175th MH," (Medical Hospital; name omitted) "and the Chief of the Infection Dept. of the 175th MH," (name omitted) "and the physicians," (two names omitted) "confirms that L-Glu-L-Trp use (sic) in combination with basic therapy for treating patients with tropical malaria in recurring form with a moderate or severe degree of severity hinders the development of early (over the course of 28 days) relapses of disease, and makes for a decrease (normalization) of the measurements of liver and spleen, as well as an elevation (normalization of the number of leukocytes)." The hematological, immunologic, and clinical chemistry values recorded in these studies are summarized in TABLES 43–44.

abnormality (i.e., as measured by clotting time, PTT, and Thrombotest), but did exhibit elevated levels of fibrinopeptide (FDP) and slightly decreased levels of antithrombin III (ATIII) suggesting some level of underlying thrombosis. While L-Glu-L-Trp treatment did not alter coagulation values, the levels of FDP decreased and ATIII increased, suggesting an effect on the underlying thrombotic processes in these patients. (These findings are similar to those presented in Examples 4 and 6, above.)

The levels of the following acute phase reactant proteins were evaluated in the trial subjects before and after L-Glu-L-Trp, or control, treatment and comparisons were made to the levels in normal healthy subjects: complement C3, prealbumin, ceruloplasmin, orosomucoid, $a_2$-macroglobulin, and transferrin. The results showed that the patients in the trial population exhibited no elevation in acute phase reactants prior to treatment, and after L-Glu-L-

TABLE 43

Hematology Values

| Index | Normal Healthy Values (n = 20) | Before Therapy (n = 40) | Conventional Therapy Control (n = 21) | L-Glu-L-Trp Therapy (n = 33) |
|---|---|---|---|---|
| Clotting time (whole blood) | 123 ± 2.1 | 102 ± 3.1 | 135 ± 3.3 | 141 ± 2.4 |
| Kaolin clotting time | 53.6 ± 0.72 | 49.8 ± 0.8 | 57 ± 0.4 | 58 ± 0.3 |
| PTT | 22 ± 0.31 | 21 ± 0.37 | 21.6 ± 0.4 | 23 ± 0.2 |
| Thrombotest | 30.7 ± 0.56 | 29.8 ± 0.37 | 31 ± 0.7 | 33 ± 0.5 |
| Fibrinogen Concentration (g/L) | 2.74 ± 0.56 | 3.2 ± 0.37 | 3.0 ± 0.36 | 3.4 ± 0.1 |
| FDP (mcg/ml) | — | 64 ± 2.2 | 45 ± 2.14 | 23 ± 1.8 |
| ATIII (%) | 100 ± 1.2 | 81 ± 1.1 | 82 ± 0.4 | 98 ± 1.38 |
| Total Fibrinogen | 154 ± 12.6 | 200 ± 7.0 | 196 ± 6.6 | 200 ± 2.7 |
| Hagemann factor dependent fibrinolysis | 14.4 ± 1.2 | 39 ± 3.6 | 35.9 ± 2.6 | 25 ± 2.58 |

The results presented in TABLE 43 show that this malaria trial population exhibited no overt signs of a coagulation Trp (or control) treatments no statistically significant change in these parameters was observed.

TABLE 44

Immunology Values:

| Index | Normal Healthy Values (n = 20) | Before Therapy (n = 40) | Conventional Therapy Control (n = 21) | L-Glu-L-Trp Therapy (n = 33) |
|---|---|---|---|---|
| Leukocytes: | | | | |
| (×10$^9$/L): | 5.8 ± 0.25 | 6.6 ± 0.1 | 3.7 ± 0.1 | 9.0 ± 0.14 |
| % Normal Value: | (100%) | (114%) | (64%) | (155%) |
| Lymphocytes: | | | | |
| (×10$^9$/L): | 1.74 ± 0.1 | 1.90 ± 0.07 | 1.68 ± 0.03 | 2.57 ± 0.09 |
| % Normal Value: | (100%) | (109%) | (97%) | (148%) |
| T-Lymphocytes: | | | | |
| (×10$^9$/L): | 0.89 ± 0.1 | 0.55 ± 0.04 | 0.50 ± 0.01 | 0.94 ± 0.06 |
| % Normal Value: | (100%) | (62%) | (57%) | (106%) |
| B-Lymphocytes: | | | | |
| (×10$^9$/L): | 0.46 ± 0.02 | 0.36 ± 0.01 | 0.32 ± 0.02 | 0.53 ± 0.02 |
| % Normal Value: | (100%) | (77%) | (70%) | (115%) |
| IgG (mg/ml): | 134 ± 5.6 | 143 ± 7.3 | 146 ± 4.4 | 187 ± 1.9 |
| % Normal Value: | (100%) | (94%) | (109%) | (140%) |
| IgA (mg/ml): | 98.3 ± 6.2 | 140 ± 5.1 | 159 ± 5.11 | 138 ± 6.0 |
| % Normal Value: | (100%) | (143%) | (162%) | (140%) |
| IgM (mg/ml): | 127 ± 9.7 | 153 ± 5.9 | 179 ± 4.0 | 193 ± 9.0 |
| % Normal Value: | (100%) | (120%) | (141%) | (152%) |

The results presented in TABLE 44, show a slight elevation in total peripheral blood leukocytes, and T- and B-lymphocytes in this trial group prior to therapy, with still further decreased PBL counts (and T- and B-lymphocyte counts) being observed following conventional treatment with anti-malarial agents (e.g. quinine derivatives) that have bone marrow suppressive effects. Treatment with L-Glu-L-Trp increased PBL and T- and B-lymphocyte counts to normal or supra-normal values. The increases in B-lymphocyte counts in L-Glu-L-Trp treated patients were accompanied by increased serum levels of IgG and IgM.

EXAMPLE 20

Hemorrhagic Dengue Fever

Protocol A

Summary Overview:

L-Glu-L-Trp was administered to 21 patients with hemorrhagic Dengue Fever, and 28 patients receiving conventional therapy served as controls. L-Glu-L-Trp was administered im single daily doses of 100 μg on each of 5 consecutive days as an adjunct to ongoing conventional therapy. Treatment with L-Glu-L-Trp resulted in decrease in fever, reduction of toxic symptoms (i.e., chills, headache, etc.), significant decrease in hepato-lineal syndrome. The investigators also observed that L-Glu-L-Trp treated patients experienced a reduction in muscle and bone pain. Immunological indices in peripheral blood were also normalized.

Patient Population:

Forty nine patients (20–30 years of age; Kinh nationality) with diagnosed Dengue Fever were entered into the trial. The patients were referred to the 175th Military Hospital in Ho Chi Minh City at the time of an epidemic of Dengue fever in the South Soviet Republic of Vietnam. Diagnosis was based on the criteria recommended by the World Health Organization (1986) using medical histories, and clinical and laboratory data. Serological analyses were conducted at the Arbovirus Infectious Diseases Laboratory of the Pasteur Institute in Ho Chi Minh City. All patients had a first or second degree disease severity. Clinical indicia of disease activity included: fever, chills, headache (98.3% of patients), dizziness (95%), weakness (100%), loss of appetite (95%), sleep disturbance (90%), sensations of mouth and lip dryness (85%), constipation (48.3%), catarrh in the nasopharynx with cough (35%), hyperemic facial tissue with pain in the superior ocular orbit (58.6%), inflammation in scleral vessels (55.2%), light sensitivity (32.2%), and muffled heart tones (86.7%) or a functional systolic murmur auscultated on the apex cordis (5.7%). Dyspeptic toxicosis, i.e., nausea and vomiting were rarely encountered (15% and 11.7%, respectively). Joint and muscle pains were pronounced, most commonly involving the spinal joints in the lumbar region (96.6%), joints of the pelvic girdle (82.2%), the ulnar joints (53.4%), as well as, the muscles of the lumbar (69%) and abdominal regions (69%). Exanthema (40.7%) and lymphadenopathy (46.7%) were evident in certain patients. Dermal puritus with rash was seldom observed (6.1%), but hepatomegaly (65.5%) and splenomegaly (53.4%) were pronounced, as were leukopenia, thrombocytopenia, and changes in blood coagulation time (during periods of hemorrhaging induced by the virus). Leukocytes during peak episodes of disease were recorded to be $4.60 \pm 0.17 \times 10^9$/L, and the absolute number of lymphocytes varied widely from 0.95 to $4.29 \times 10^9$/L.

Patients were divided into two groups: Group 1; consisting of 28 patients ("Control") treated only with conventional maintenance therapy; and, Group 2, consisting of 21 patients treated with L-Glu-L-Trp in combination with conventional maintenance therapy.

Treatment Regimens:

Group 1 received conventional maintenance therapy consisting of detoxifying preparations and methods, e.g., fluids, fever control agents and the like. Group 2 received combination therapy, i.e., maintenance therapy and L-Glu-L-Trp, but only during periods of acute disease activity. L-Glu-L-Trp was administered at a dosage of 500 μg. The efficacy of the respective treatment protocols was evaluated by recording the most frequently used clinical indicia of Dengue disease activity: namely, the clinical indicia recorded in TABLE 45.

TABLE 45

Primary Symptoms of Hemorrhagic Dengue Fever in Patients Treated with Conventional Therapy in Combination with L-Glu-L-Trp-Protocol A

| | Duration of Symptom(s) in Hours: | |
| --- | --- | --- |
| Clinical Index | Conventional Therapy (n = 28) | Combination L-Glu-L-Trp Therapy (n = 21) |
| Fever: | | |
| At day 2–6 of illness: | 7.3 ± 0.6 | 5.2 ± 0.3†† |
| At day 2–4 of illness: | 7.3 ± 0.6 | 4.7 ± 0.2††† |
| Headache: | 12.2 ± 1.1 | 8.1 ± 0.9† |
| Weakness: | 11.6 ± 1.2 | 9.3 ± 0.8† |
| Loss of appetite: | 11.4 ± 1.1 | 7.5 ± 0.8†† |
| Insomnia: | 11.0 ± 1.3 | 7.1 ± 0.7† |
| Hepatomegally: | 15.8 ± 0.6 | 11.3 ± 0.8††† |
| Splenomegally: | 13.3 ± 0.7 | 9.6 ± 0.7†† |
| Lumbar pain: | 13.8 ± 1.4 | 8.7 ± 0.7†† |
| Joint pain: | 12.2 ± 1.5 | 7.4 ± 0.7†† |
| Waist/Pelvic girdle pain: | 12.7 ± 1.3 | 8.1 ± 0.8† |
| Skeletal muscle pain: | 11.2 ± 1.7 | 7.7 ± 1.1 |
| Eye muscle pain: | 11.0 ± 1.1 | 6.6 ± 0.8†† |

†$p < 0.05$;
††$p < 0.01$;
†††$p < 0.001$

Summary of Clinical Disease Responses in the Patients—Protocol A:

Therapeutic efficacy of L-Glu-L-Trp was subjectively observed in these studies even before the collation of the objective evidence (above). In most patients, the day after initiating L-Glu-L-Trp therapy, body temperature became normal, and those patients who did not normalize on the first day normalized on day 2. A direct correlation was noted between the length of fever and the disease free interval following fever. L-Glu-L-Trp treatment appeared to increase the absolute numbers of leukocytes and T-lymphocytes. No side effects or allergic effects were observed during L-Glu-L-Trp treatment. L-Glu-L-Trp treatment led to a more rapid convalescence and restoration of the subjects' ability to perform work.

Protocol B

Summary Overview:

Sixty Dengue virus infected patients (60) were entered into the trial; 36 were treated with L-Glu-L-Trp and 24 were treated using conventional therapy (i.e., controls). Administration of L-Glu-L-Trp at a dosage of 100 μg im, or alternatively 1 μg/kg in, on each of 5–10 consecutive days resulted in the reduction of fever, more rapid reduction of toxic symptoms (e.g., chills, fever, rash, headaches, muscle aches and pains) and the restoration of immunologic indices.

EXAMPLE 21

Infectious Disease: Tuberculosis

Early Results:

Sixty-three patients having pulmonary infection with Mycobacterium tuberculosis (TB) were entered into the trial: 37 patients were treated with L-Glu-L-Trp and 26 patients (controls) were treated using conventional treatments. L-Glu-L-Trp was administered five times at a dosage of 50 $\mu$g to 100 $\mu$g every other day and as an adjunct to treatments with conventional antibiotics. Clinical evaluation of the patients at 2 months post-treatment with L-Glu-L-Trp revealed a disappearance of toxic symptoms, a resorption of pulmonary infiltrates, and a resolution of pulmonary cavities. The disappearance of TB bacilli was noted in the sputum. Prior to treatment, immune parameters in peripheral blood were abnormal, i.e., decreased, and following treatment with L-Glu-L-Trp these parameters were normalized.

Expanded Results:

One hundred and five patients (105) were entered into the trial. The patients, aged 19 to 60 years, consisted of 73 men and 32 women who were presenting for the first time with active progressive pulmonary TB infection. All patients in the trial had been hospitalized because of the severity of their disease. According to standard diagnostic criteria at clinical presentation: 59 patients had signs of pulmonary infiltration; 11 showed evidence of disseminated lung disease; 10 exhibited at least one fibrous/cavernous foci of infection; 9 showed at least one cavernous foci; and 16 had tuberculomas. The 105 patients were divided into three groups as follows: namely, Group 1, 37 patients, treated with conventional therapy and L-Glu-L-Trp (i.e., 50–100 $\mu$g daily for 5 days); Group 2, 22 patients, treated with conventional therapy and the immunomodulator "decaris" (i.e., 150 $\mu$g, twice weekly, for 1.5–2 months); and, Group 3, consisted of 46 patients, who received only conventional therapy (i.e., no immunomodulators).

Clinical criteria used in evaluating patients' responses included i) "considerable improvement", ii) "improvement", and iii) "no change" which were objectively defined from patient examinations and evaluation of chest X-ray data as follows: "Considerable improvement" required that 1) wheezing and catarrhal phenomena disappear completely from the lungs; 2) mononuclear cell infiltration and degenerative foci in the lungs largely disappear; 3) cavities of tissue degeneration in the lung disappear; nd 4) expectoration of acid fast bacteria cease; "Improvement" required that 1) wheezing (only) disappear from the lungs; 2) a progressive resolution of cellular in filtration and degenerative foci in the lungs; and, 3) a partial consolidation of degenerative foci; and 4) a reduction in the size of cavities in the lung.

The results of clinical evaluation at 2 months of therapy are summarized in TABLE 46.

TABLE 46

Effects of Treatment with L-Glu-L-Trp on Clinical Parameters of Lung Disease in Patients of with Progressive Tuberculosis: 2 months

| Group | No. Patients | Conventional Treatment* in Combination with: | No Change No. | No Change % | Improvement No. | Improvement % | Considerable Improvement No. | Considerable Improvement % |
|---|---|---|---|---|---|---|---|---|
| 1 | 37 | L-Glu-L-Trp | 1 | 3 | 27 | 73 | 9 | 24 |
| 2 | 22 | decaris | 3 | 13 | 18 | 82 | 1 | 5 |
| 3 | 46 | none | 7 | 15 | 36 | 78 | 3 | 6 |

*C, conventional antibiotic therapy; d, "decaris" immunomodulator.

The results presented in TABLE 46 show the following: in Group 1 (combination therapy with L-Glu-L-Trp), "considerable improvement" was observed in 9 patients (24%) and an additional 27 patients showed "improvement", i.e., for a total response rate of 97% of the patients showing improvement. (Degeneration foci and cavities in the lung were closed in the 9 patients responding rapidly to therapy.); in Group 2 ("decaris" immunomodulator combined therapy), only one patient (5%) showed "considerable improvement" and "improvement" was observed in 18 patients, i.e., for a response rate of 86%; and, in Group 3 (conventional therapy only), "considerable improvement" was noted in 3 patients (6%) and "improvement" in 36, i.e., for a response rate of 84%.

At 4–6 months of in-hospital treatment: in Group 1, positive changes were noted in the lungs of 35 of the 37 patients, i., closure of degeneration foci and cavities. One patient was discharged from the trial for a procedural violation, and one patient exhibited disease progression of what was determined later to be an antibiotic resistant strain of M. tuberculosis. In Group 2, foci and cavities of degeneration in the lungs were closed in 10 patients of the 22 in the trial (45%). In Group 3, foci and cavities of degeneration in the lungs were closed in 14 patients of the 46 in the trial (48%). Patients tolerated L-Glu-L-Trp therapy well, and no toxicity or allergic reactions were observed.

EXAMPLE 22

Respiratory Disease: Asthma and Allergy

Protocol A

Summary Overview:

Sixty five patients (65) with bronchial asthma, including both adults and children, were entered into the trial: 37 patients were treated with L-Glu-L-Trp and 28 (controls) received conventional therapy alone. L-Glu-L-Trp was administered im in a single daily dose of 1 $\mu$g/kg on each of 5–10 consecutive days. Treatment with L-Glu-L-Trp resulted in less severe asthmatic clinical symptoms, a decrease in the requisite duration of medical treatment, and a significant reduction in the incidence of bronchial obstruction and laryngotracheitis relative to the control group. In certain patients it was possible to eliminate the use of prescribed steroids. In the year long follow-up period of clinical observation, a 4.2-fold decrease in the incidence of bronchial asthmatic attacks was observed in the L-Glu-L-Trp treated subjects. A disappearance of clinical symptoms of food and drug allergies was observed in more than half of the L-Glu-L-Trp treated patients.

Protocol B

The use of L-Glu-L-Trp as an ingredient or applicant in cosmetic formulations and preparations provides less allergenic materials and/or materials evoking a lesser degree of allergic reactions in sensitized subjects.

Protocol C

Patent Population:

Twenty-eight children (19 boys; 9 girls) were entered into the trial for treatment with L-Glu-L-Trp: 17 were aged 1–3 years; 8 were aged 4–7 years; and, 3 were aged >8 years. Patients presented with the following diagnoses: 14 with acute respiratory viral infections (ARVI) and bronchitis; 4 with acute respiratory infection (ARI) complicated with recurrent purulent otitis; 2 with ARI and prolonged subfebrile infection; and, 11 with ARI and lymph node enlargement and hyperplasia of the palatine and nasopharyngeal tonsils. Bronchial asthma was diagnosed in 6 children and obstructive bronchitis in 8. In 11 children there was evidence, or medical history of, exudative/catarrhal diathesis; in 4 there was lymphatic/hypoplastic diathesis. The patient population was also selected for medical history of allergy, and 6 patients had one or more medicinal allergies, 7 had food allergies, 5 had both a food and a medicinal allergy, and one child had a history of bronchospasms initiated by chrysanthemums. Of the children 15 had one or more family members with a history of allergy, asthma, hayfever, or medicinal allergy. All patients had a previous medical history of recurrent infections and had previously received repeated courses of antibacterial preparations, i.e., penicillin-based antibiotics, sulfanilamides (biseptol), gammaglobulins, and phytotherapy.

A comparison (control) group consisted of 73 frequently ill children aged 1–7 years and including 44 boys and 29 girls.

Treatment Protocol:

The dosage of L-Glu-L-Trp administered to these children was as follows: children 1–3 years of age received 20 μg; 4–5 years of age received 30 μg; 6–7 years of age received 40 μg; and, those >7 years of age received 50 μg. The L-Glu-L-Trp preparation was administered im daily for 5 days and a repeat course of therapy was administered at 3–4 months. Two treatment courses were required for successful therapy. (Two children with pronounced allergies received zaditen, and one of the two also received histoglobulin.)

Indicators Evaluated:

The patients' response to therapy was evaluated by monitoring: physical condition (i.e., by physical examination), body temperature, blood chemistry, proteins, hematology, and immunology.

Immunological examination showed lower T-lymphocyte cell counts in patients prior to treatment than in normal healthy children, with a decrease noted in "active" T-lymphocytes, i.e., as measured by a decrease in the number of theophylline resistant lymphocytes ("active") without a change in the number of theophylline sensitive lymphocytes ("quiescent").

In vitro incubation of lymphocytes, (prepared from thirty of the patients prior to treatment) with L-Glu-L-Trp showed an increase in the percentage of E-rosette forming (CD2$^+$) T-lymphocytes in the respective different patient lymphocyte populations. Parallel incubation with the immunomodulator T-activin did not effect a change in the percentage of positive cells.

Following the first course of L-Glu-L-Trp therapy a statistically significant increase was noted in both the absolute number and percentage of T-lymphocytes in peripheral blood. A increase in the number of theophylline-resistant lymphocytes was also observed, with a slight decrease in the number of theophyline-sensitive lymphocytes. After the second course of L-Glu-L-Trp immunologic parameters were in the normal range.

Clinical evaluation of patients over 6–12 months documented a decrease in the number of respiratory infections in 92.9% of the children treated with L-Glu-L-Trp, with an average reduction in the number of infections 3.6-fold, and reduction in attacks of bronchial asthma (in the asthma patients) by 4.2-fold. Courses of illness were also milder (than historically) and did not require hospitalization. Infections in the treated patients were not accompanied by complication with bronchial obstruction or otitis. The average length of illness was decreased by 4–5 days, and food allergies disappeared in 67.8% of the patients having this pre-existing condition at the beginning of therapy. Patients experienced an increase in physical activity and appetite, with decrease in subfebrile episodes and manifestations of lymphadenopathy.

EXAMPLE 23

Gastro-intestinal Disease

Protocol A Gastric Ulcers

Gastric ulceration is accompanied by a persistent immunodeficiency condition in the pre-ulcerative stage, i.e., as the ulcer is developing in patients with gastritis.

Patient Population:

Twenty two patients (all men aged 18–30 years) suffering from chronic primary gastritis and gastro-duodenitis were entered into the trial. Diagnosis was based on physical examination, and clinical and laboratory investigations including roentgenoscopy and endoscopic examination of the stomach and duodenum. Patient entry criteria was further conditioned on the results of laboratory tests for i) pre-treatment immune indices (i.e., numbers of lymphocytes, T-, and B-lymphocytes, etc.; TABLE 46) and ii) the in vitro sheep red blood cell rosette forming response of T-lymphocytes to L-Glu-L-Trp, (i.e., whether in vitro incubation of patient peripheral blood lymphocytes with L-Glu-L-Trp increased the percentage of E-RFC). Ten patients (45%) exhibited a negative in vitro response to L-Glu-L-Trp and also exhibited immune indices that were within the normal range, and these patients were excluded from the trial. Twelve patients (55%) exhibited a positive in vitro response to L-Glu-L-Trp and immune indices that were altered, and outside the normal range, i.e., low absolute T-lymphocyte counts and increased absolute numbers of Null-lymphocytes. These twelve patients were entered into the trial.

For determining normal values, the control group consisted of 28 normal healthy volunteers aged 17–23.

Treatment Protocol:

Patients received L-Glu-L-Trp im daily at a dosage of 100 μg for 5 days in combination with their conventional ongoing treatment.

Laboratory Tests:

Lymphocyte sub-populations before and after treatment are presented in TABLE 47, in comparison with the results recorded with normal healthy subjects.

TABLE 47

Immunology Values:

| Index | Normal Healthy Values | Before Therapy | After L-Glu-L-Trp Combination Therapy |
|---|---|---|---|
| T-Lymphocytes (%): | 59.3 ± 2.4 | 44.0 ± 2.2$^{\dagger\dagger}$ | 55.4 ± 2.1** |
| (×10$^9$/L): | 1.087 ± 0.07 | 0.869 ± 0.44$^\dagger$ | 1.04 ± 0.04* |
| % Normal Value: | (100%) | (80%) | (96%) |
| B-Lymphocytes (%): | 8.0 ± 1.0 | 7.5 ± 0.8 | 7.2 ± 1.5 |
| (×10$^9$/L): | 0.145 ± 0.02 | 0.153 ± 0.02 | 0.14 ± 0.02 |
| % Normal Value: | (100%) | (106%) | (97%) |
| Null Lymphocytes (%) | 31.5 ± 2.2 | 48.5 ± 1.9$^{\dagger\dagger}$ | 37.3 ± 2.0** |
| (×10$^9$/L): | 0.621 ± 0.07 | 0.95 ± 0.09$^\dagger$ | 0.9 ± 0.05* |
| % Normal Value: | (100%) | (153%) | (145%) |

$^\dagger$p < 0.05 in comparison with normal;
$^{\dagger\dagger}$p < 0.001 in comparison with normal;
*p < 0.01 in comparison with pre-treatment values;
**p < 0.001 in comparison with pre-treatment values.

The results presented in TABLE 47 show that treatment with L-Glu-L-Trp induced a statistically significant increase in the percentage and absolute numbers of T-lymphocytes, with a concomitant fall in the percentage and numbers of Null-lymphocytes.

Clinical Response:

Treatment of the patients in the trial population with L-Glu-L-Trp lead to a more rapid recovery and the patients achieved a stable remission of disease activity in these patients with chronic gastritis and gastroenteritis.

Protocol B

Infectious Disease: Shigella dysenterae

Summary Overview:

A total 125 patients infected with Shigella dysentery were examined. Fifty-three patients constituted the control group. L-Glu-L-Trp was administered im single doses of 100 ug for 10 consecutive days with resultant normalization of fever, reduction of toxemia, and normalization of gastrointestinal disorders and symptoms. Bacterial shedding in the GI track was observed to cease, and the immunological indices were normalized.

EXAMPLE 24

Acquired Immunodeficiency: Adult Thymectomy

Summary Overview:

A total of 12 thymectomized patients were treated with L-Glu-L-Trp. Prior to therapy, these individuals had experienced frequent serious infections including upper respiratory infections. L-Glu-L-Trp was administered in a single dose of 100 µg daily for 10 days and repeated every 4–6 months. The normalization of immunologic indices was observed, and there was a reduction of infectious disorders including cutaneous infections and other chronic exacerbations.

EXAMPLE 25

Hepatic Diseases

Protocol A Jaundice and Systemic Toxicity

Summary Overview:

Thirty four patients (34) with diagnosed chronic liver disease were treated with L-Glu-L-Trp (Group 1). Entry into the trial was established on the basis of clinical symptoms and serum biochemistry, i.e., levels of aminotransferase, bilirubin, gamma-globulins, and thymol test results, as well as the results of radioisotope and ultrasound scanning. In certain cases liver biopsy specimens were obtained, and confirmed the diagnosis. Patient entry into the trial was also occasioned by symptoms and either i) presence of an abnormal T-helper/T-suppressor ratio, or ii) detectable levels of Australia antigen in serum. Twenty seven patients (27) fulfilling the same diagnostic criteria were entered into a control group for conventional treatments (Group 2).

Immune status was assessed by collecting and testing samples of peripheral blood. The following immune parameters were tested: total number of T-lymphocytes (E-RFC), theophylline-resistant lymphocytes (T-helpers), and theophylline-sensitive lymphocytes (T-suppressors); activity of Fc-receptor lymphocytes in antibody-dependent cellular cytotoxicity assays; serum concentrations of IgA, IgM, IgG, and IgD; and, the level of circulating immune complexes.

L-Glu-L-Trp was administered daily im at a dose of 100 µg on each of 5 to 10 consecutive days.

At time of entry into the trial, patients in Group 1 presented with the following: 29 patients were seropositive for hepatitis virus (i.e., 26 patients had circulating Hepatitis B antigen and 3 had circulating autoantibodies); 5 patients had cirrhotic liver disease (3 of viral etiology and 2 or unknown origin) with micronodular and mixed initial stage forms of disease. (L-Glu-L-Trp was not prescribed to patients with dystrophic cirrhotic liver disease.) All patients presented with abnormally decreased levels of T-suppressor cells in peripheral blood.

Clinical Effects:

Treatment of the patients in Group 1 with L-Glu-L-Trp resulted in three different types of clinical responses: i) in 21 of the 29 patients with serological evidence of hepatitis virus infection (above) a positive response to therapy was observed; ii) in the remaining 8 patients (of the 29 seropositive patients) no change was detectable either in the clinical picture or in the serum biochemical markers; and, iii) in 4 patients, (2 having autoantibodies; and 2 with cryptogenic cirrhosis) illness was aggravated.

The 21 patients of Group 1 having a positive response to L-Glu-L-Trp treatments exhibited the following at the conclusion of the 5 days of therapy: i) decreased symptoms of cellular insufficiency, weakness, and headache; ii) improved serum biochemical markers (i.e., bilirubin and aminotransferase activity); iii) improved ability to sleep; and, iv) decreased pain in the hypochondrium. In 2 of the responsive patients, jaundice disappeared with noticeable lessening of telangiectasia in the face. Following treatment, responsive patients showed i) an increase in the number of peripheral blood T-lymphocytes, (primarily because of an increase in the number of suppressor T-cells); and, ii) a decrease in the numbers of undifferentiated Null lymphocytes. In the 3 patients with mixed cirrhotic liver disease of viral etiology, ALT levels in serum dropped, suggesting a positive effect on liver cytology.

The 8 patients in Group 1 having a negative response to L-Glu-L-Trp treatments (i.e., patients with less severe inmmunodeficiencies and lesser immunoregulatory impairments) exhibited the following at the conclusion of the 5 days of therapy: i) no significant changes in clinical symptoms; ii) no (or minimal) changes in serum biochemical markers, i.e., ALT and bilirubin levels dropped slightly but AST and thymol test results increased slightly); and iii) lymphocyte counts increased with increases in the number of Null and T-lymphocytes.

The 4 patients of Group 1 having aggravation of disease activity following the L-Glu-L-Trp treatments exhibited the following at the conclusion of the 5 days of therapy: i) increased serum transaminase levels (AST; ALT); ii) increased thymol assay values; iii) increased autoantibody levels; iv) increased levels of immunoglobulins; and, v) increased numbers of T-helper lymphocytes.

Patients in the control Group 2 were, as previously, relatively non-responsive to conventional therapy and showed few signs of clinical response to therapy or changes in serum biochemical markers.

Protocol B

Hepatitis

Chronic hepatitis is an urgent problem in pediatric medicine with 350 million people worldwide registered to be carriers of the virus, and 2 million new cases each year. In 1 out of 10 patients, the viral infection takes a chronic course with cirrhosis of the liver and ultimately a fatal outcome. In 80% of cases of primary hepatoma, a link with the hepatitis virus has been recorded.

Patient Population:

In accord with a USSR Ministry of Health decision 125 children suffering with chronic persistent hepatitis B were entered into this trial over a two month period. Group 1 consisted of 35 children who received decaris immunomodulatory therapy; Group 2, 38 children who received thymalin treatments; Group 3, 19 children who received L-Glu-L-Trp; and, Group 4, 32 children who received only conventional symptom specific therapy. All patients admitted to the trial exhibited signs of secondary immunosuppression, as evidenced by a decrease in the numbers of E-rosette forming T-lymphocytes.

Treatment Protocol:

L-Glu-L-Trp was administered at a dose of 2 µg/kg of body mass, im, daily for days, and a repeat (identical) course of treatment was administered 10 days after termination of the first course.

Observations:

In about 63% patients at the conclusion of L-Glu-L-Trp treatment, numbers of E-RFC T-lymphocytes were increased and the ADCC activity (measured in vitro with antibody-coated target cells) was decreased to normal levels. A retrospective analysis of the data revealed two classes of patients: namely, the 63% responders and the remaining non-responders, i.e., based on differences in clinical responses to therapy, serum levels of ALST, E-RFC, ADCC activity, and $T4^+/T8^+$ ratios. An association was noted between the percentage of non-responders (than responders) with detectable auto-lymphocytotoxic (ALCT) antibodies (a marker for autoimmune disease in the patients), the index of ALCT cytotoxic activity, and the failure of L-Glu-L-Trp treatment to influence these markers in non-responder subjects. L-Glu-L-Trp treatment apparently affected the latter markers in the subgroup of responders.

TABLE 49

| Group # | Pre-Treatment ALCT Activity | Percent of Subjects Disease Free at 6 Months After Treatment With: | | | |
|---|---|---|---|---|---|
| | | Conventional | Descaris | Thymalin | L-Glu-L-Trp |
| 1 | None | 75 | 100 | 100 | 100 |
| 2 | Moderate | 35 | 67 | 76 | 80 |
| 3 | High | 0 | 67 | 33 | 0 |

EXAMPLE 26

Effects of L-Glu-L-Trp Dipeptide on Expression of E-receptors on Thymocytes

Thymus cells were isolated from male guinea pigs (180–200 g) under standard conditions of tissue mincing and differential centrifugation in Medium 199. Isolated thymocytes were treated with trypsin to remove cell surface E-receptors capable of binding rabbit erythrocytes (E). The percentage of cells capable forming E-rosettes (E-RFC) was decreased by about two-fold under these conditions.

L-Glu-L-Trp has been reported to restore T-cell receptors and E-RFC following incubation at 37° C. Studies were conducted in which the activity of L-Glu-L-Trp dipeptide were compared in the latter assay.

Thymocytes were prepared from 48 guinea pigs, treated with trypsin, and tested for E-RFC. The results of these experiments are summarized in TABLE 50.

TABLE 48

| | Immunology Values: | | | | |
|---|---|---|---|---|---|
| | Normal | Non-Responders | | Responders | |
| Index | Healthy Values (n = 20) | Before Therapy (n = 7) | After L-Glu-L-Trp (n = 7) | Before Therapy (n = 12) | L-Glu-L-Trp Therapy (n = 12) |
| T-Lymphocytes | | | | | |
| (E-RFC) % of PBL: | 61.0 ± 2.70 | 42.17 ± 2.4 | 56.7 ± 3.24 | 34.57 ± 2.57 | 47.33 ± 2.2 |
| ($\times 10^9$/L): | 1624 ± 58 | 770 ± 71 | 1382 ± 76 | 779 ± 41 | 1227 ± 65 |
| % Normal Value: | (100%) | (47%) | (85%) | (48%) | (76%) |
| Ratio $OKT4^+/OKT8^+$: | 1.33 ± 0.05 | 0.82 ± 0.07 | 0.82 ± 0.07 | 0.90 ± 0.007 | 1.08 ± 0.07 |
| ALCT: % of subjects: | 0 | 85.4 ± 13.2 | 57.14 ± 18.7 | 41.67 ± 14 | 16.7 ± 13.2 |
| Cytotoxic Index: | 0 | 50.4 ± 5.5 | 44.55 ± 6.8 | 29.9 ± 1.9 | 50.4 ± 5.5 |

Clinical Responses:

In patient's lacking an autoimmune disease component (i.e., as measured by ALCT), their disease resolved, while the disease of those having an autoimmune component did not. Disease activity was tracked over the six months following therapy, and remission was found to negatively correlate with the presence of a pre-treatment autoimmune component (i.e., ALCT). One hundred percent of the patients lacking demonstrable ALCT in the pre-treatment interval exhibited stable remission over the 6 months of observation, as contrasted with rates of 80% stable remission in patients with moderate ALCT activity, and 0% stable remission in patients with the highest ALCT levels.

TABLE 50

Effects of L-Glu-L-Trp on Expression of E-receptors on Thymocytes (X ± S.D.)

| Trypsin Treatment | Addition | Conc. (mg/ml) | E-RFC (%) |
|---|---|---|---|
| − | None | 0 | 66.0 ± 5.4 |
| + | None | 0 | 26.0 ± 1.8* |
| + | L-Glu-L-Trp | 1 | 42.8 ± 3.5*† |
| + | L-Glu-L-Trp | 0.01 | 36.8 ± 2.4*† |
| + | L-Glu-L-Trp | 0.0001 | 30.3 ± 3.1* |

*indicates significance at the $p < 0.05$ level in comparison with the non-trypsin treated control values ("−"/None/0); and,
†indicates significance at the $p < 0.05$ level in comparison with the trypsin treated control values ("+"/None/0).

The results presented in TABLE 50 show that addition of L-Glu-L-Trp at 0.01–1 mg/mL increased the percentage of E-RFC in trypsin-treated thymocyte cultures. The results suggest that L-Glu-L-Trp stimulates expression of E-receptors on thymocytes over a wide range of concentrations, perhaps by direct ligand-receptor interaction of L-Glu-L-Trp with the E-rosette receptor.

EXAMPLE 27

Effects on Thymocytes from Aged Animals

Effects of L-Glu-L-Trp on expression of E-receptors on "aged" thymocytes was investigated in a manner similar to that in EXAMPLE 26, above, but using thymocytes obtained from old male guinea pigs (700–800 g). In aged animals it is recognized that the percentage of thymocytes forming rosettes with rabbit erythrocytes is reduced, and cell surface E-receptors are likewise reduced. For these studies aged thymocytes were isolated in Medium 199 from 42 guinea pigs, and E-RFC determined as described by Stadecker, M. J., et al., *J. Immunol.* 111(8):4061–4065 (1973), incorporated herein by reference. L-Glu-L-Trp was dissolved in 0.9% (w/v) NaCl and added to cultures of thymocytes at concentrations of 1, 0.01, and 0.0001 mg/ml. The results of these experiments are summarized in TABLE 51.

TABLE 51

Effects of L-Glu-L-Trp on Expression of E-receptors on Aged Thymocytes (X ± S.D.)

| Addition | Conc. (mg/ml) | E-RFC (%) |
|---|---|---|
| None | 0 | 45.3 ± 3.7 |
| L-Glu-L-Trp | 1 | 54.6 ± 4.2* |
| L-Glu-L-Trp | 0.01 | 47.8 ± 3.9 |
| L-Glu-L-Trp | 0.0001 | 50.3 ± 4.2 |

*indicates significance at the $p < 0.05$ level in comparison with the non-treated control values (None/0).

The results presented in TABLE 51 show, as expected, a reduction in the percentage of E-RFC in populations of aged thymocytes, i.e., from 66±5% (TABLE 62) to 45.3±3.7% (TABLE 51). L-Glu-L-Trp fostered a statistically significant increase in the percentage of E-RFC at 1 mg/mL.

EXAMPLE 28

Effects of Dipeptide L-Glu-L-Trp on T-Lymphocyte Subsets in Human Peripheral Blood The effects of L-Glu-L-Trp on human peripheral blood T-lymphocytes was investigated using indirect immunofluorescence microscopy and OKT4 and OKT8 monoclonal antibodies (Ortho, USA) directed to lymphocyte cell surface differentiation antigens. For these studies lymphocytes were isolated from heparinized peripheral blood (25 units heparin/mL) isolated from 18 different donors with inflammatory lung diseases and chronic purulent bronchitis accompanied by a secondary immunodeficiency state. Lymphocytes were prepared by centrifugation on Ficoll-Hypaque, washed, and then incubated in vitro for 45 minutes at 37° C. in the presence (or absence) of L-Glu-L-Trp at concentrations of 1 mg/mL, 0.01 mg/mL, 0.0001 mg/mL. Following incubation the cells were washed with Medium 199 and the percentage of OKT4$^+$ (T-helper) and OKT8$^+$ (T-suppressor) lymphocytes determined by indirect immunofluorescent microscopy. The results presented in TABLE 51 show the mean percentages of OKT4$^+$ and OKT8$^+$ cells in this group of patients after incubation with Medium 199 (Control), or with L-Glu-L-Trp. The OKT4$^+$/OKT8$^+$ ratios for this group of patients is also shown in TABLE 52.

TABLE 52

Effects of L-Glu-L-Trp on T-helper (OKT4$^+$) and T-suppressor (OKT8$^+$) Lymphocytes from Patients with Secondary Immunodeficiency (X ± S.D.)

| Dose (mg/ml) | Control | L-Glu-L-Trp |
|---|---|---|
| (OKT4$^+$) | | |
| 1 | 23.9 ± 2.1 | 39.7 ± 2.7* |
| 0.01 | 2.42 ± 1.7 | 39.8 ± 2.4* |
| 0.0001 | 25.1 ± 1.1 | 25.4 ± 2.3 |
| (OKT8$^+$) | | |
| 1 | 19.9 ± 1.9 | 21.4 ± 1.3 |
| 0.01 | 20.6 ± 1.5 | 22.7 ± 1.8 |
| 0.0001 | 20.8 ± 1.2 | 23.1 ± 2.1 |
| (OKT4$^+$/OKT8$^+$) | | |
| 1 | 1.2 | 1.9* |
| 0.01 | 1.2 | 1.8* |
| 0.0001 | 1.2 | 1.1 |

*statistically significant at the $p < 0.05$ level when compared with the control values.

The results presented in TABLE 52 show L-Glu-L-Trp increased the percentage of detectable T-helpers at concentrations of 1 and 0.01 mg/mL. L-Glu-L-Trp did not alter the percentage of detectable OKT 8$^+$ T-suppressor cells.

EXAMPLE 29

Effects of Dipeptide L-Glu-L-Trp on Immunity in Experimental Animals

Protocol A: Healthy Guinea Pigs

Immune parameters were investigated in healthy male guinea pigs (250–300×g) following administration of test or control agents. Each test and control group consisted of 10 animals. Test agents were administered to animals once daily by the intramuscular (im) route over a period of 5 days and at 1 mg/kg dipeptide L-Glu-L-Trp. Physiological saline was administered im to the animals of the control group. The affects of these treatments were determined on day 10 (i.e., 5 days after the last injection) by preparing cells from peripheral blood (PBL), thymus (TYM), lymph nodes (LN), spleen (SPL), and red pulp of bone marrow (BM). Cells were tested for antibody Fc receptors (EA-RFC), complement receptors (EAC-RFC), T-lymphocytes, "active" T-lymphocytes (E-RFC), B-lymphocytes (EA-RFC and EAC-RFC; according to the method of Bianco, C., et al., *J. Exp. Med.* 132(4):702–720 (1970). The results of these analyses are shown in TABLES 53–54, below, where data are expressed either as the number of RFC×10$^9$ per liter of blood, or RFC×10$^3$ per milligram (mg) of tissue.

TABLE 53

Effect of L-Glu-L-Trp on
Immune Indices: E-RFC (X ± S.D.)

| Cell Population | Index per $10^x$ cells | E-RFC (X ± S.D.) Control | E-RFC (X ± S.D.) L-Glu-L-Trp | EA-RFC (X ± S.D.) Control | EA-RFC (X ± S.D.) L-Glu-L-Trp |
|---|---|---|---|---|---|
| PBL | $10^9$/L | 0.53 ± 0.10 | 1.59 ± 0.78 | 0.50 ± 0.09 | 0.82 ± 0.09 |
| TYM | $10^3$/mg | 440.4 ± 82.3 | 448.1 ± 51.4 | 345.6 ± 63.2 | 542.6 ± 42.3 |
| LN | $10^3$/mg | 119.1 ± 19.3 | 81.4 ± 7.6* | 78.7 ± 8.3 | 61.7 ± 8.2 |
| SPL | $10^3$/mg | 69.5 ± 6.6 | 75.9 ± 6.8 | 48.5 ± 6.4 | 81.2 ± 7.4* |
| BM | $10^3$/mg | 22.5 ± 3.9 | 11.2 ± 2.3* | 19.1 ± 2.2 | 25.1 ± 1.9* |

*statistically significant at the $p < 0.05$ level in comparison with the indices in the control.

TABLE 54

Effect of L-Glu-L-Trp on
Immune Indices: EAC-RFC (X ± S.D.)

| Cell Population | Index per $10^x$ cells | Control | L-Glu-L-Trp |
|---|---|---|---|
| PBL | $10^9$/L | 0.30 ± 0.09 | 0.79 ± 0.08* |
| TYM | $10^3$/mg | 3.4 ± 0.7 | 0 |
| LN | $10^3$/mg | 146.5 ± 12.4 | 173.3 ± 12.7 |
| SPL | $10^3$/mg | 140.2 ± 15.6 | 141.5 ± 22.6 |
| BM | $10^3$/mg | 19.7 ± 3.2 | 13.9 ± 2.1 |

*statistically significant at the $p < 0.05$ level in comparison with the indices in the control.

The results presented in TABLES 53–54 show that animals treated for 5 days with the dipeptide L-Glu-L-Trp had 3-fold more T-lymphocytes in peripheral blood (i.e., PBL; E-RFC) than control animals treated with saline. T-lymphocytes in LN and BM decreased (i.e., 50%) while splenic and thymus T-cells increased 2–9% after L-Glu-L-Trp treatment. At 10 days, animals who received L-Glu-L-Trp showed an increased number of T-lymphocytes in peripheral blood, spleen, and bone marrow.

L-Glu-L-Trp increased Fc-receptor bearing cells in spleen and bone marrow (TABLE 53). Numbers of complement receptor bearing cells (EAC-RFC) were increased 2-fold in blood by L-Glu-L-Trp treatment (TABLE 54).

The results indicate that L-Glu-L-Trp stimulated proliferation, differentiation, or migration of T- and B-lymphocytes.

Protocol B: Gamma-Irradiated Guinea Pigs

X-irradiation an accepted experimental animal model for depressing cellular immune mechanisms operative in anti-bacterial, anti-viral, and anti-parasitic immunity. The levels of lymphocytes in thymus, spleen, and lymph node are decreased following sub-lethal radiation exposure, and the effects of L-Glu-L-Trp on recovery of immune function following radiation exposure were investigated in this model.

142 guinea pigs were exposed to 1 Gy of X-irradiation and then treated with L-Glu-L-Trp at a dose of 0.01 mg/kg daily for 5 days starting two days after the irradiation. Immunologic indices were determined at 5, 10, and 20 days by preparing samples of immune cells from thymus, spleen, lymph nodes, and peripheral blood. Cell preparations were analyzed to determine the content of lymphocytes, E-RFC (i.e., T-lymphocytes), EA-RFC ("activated" T-lymphocytes), and EAC-RFC (i.e., B-lymphocytes). (The materials and methods used in these analyses are presented following EXAMPLE 38, below. The results obtained in these experiments are summarized in TABLE 55.

TABLE 55

Effect of L-Glu-L-Trp on Recovery of Immune Cells
in Irradiated Guinea Pigs (X ± S.D.): Thymic Lymphocytes

| Cell Population | Lymphocytes × $10^9$/L (% Normal)[a] Normal Healthy Control I | | Irradiated Un-treated Control II | | Irradiated and L-Glu-L-Trp Treated | |
|---|---|---|---|---|---|---|
| *5 Days Post Irradiation* | | | | | | |
| Lymphocytes | 481 +/− 21 | (100%) | 270 +/− 32* | (56%) | 395 +/− 27** | (82%) |
| E-RFC | 378 +/− 26 | (100%) | 93 +/− 10* | (25%) | 252 +/− 26** | (67%) |
| EA-RFC | 290 +/− 28 | (100%) | 74 +/− 8* | (26%) | 150 +/− 16** | (52%) |
| EAC-RFC | 5 +/− 0.3 | (100%) | 7 +/− 1* | (140%) | 4 +/− 1** | (80%) |
| *10 Days Post Irradiation* | | | | | | |
| Lymphocytes | 481 +/− 21 | (100%) | 87 +/− 13* | (18%) | 276 +/− 26** | (57%) |
| E-RFC | 379 +/− 26 | (100%) | 50 +/− 6* | (13%) | 195 +/− 21** | (51%) |
| EA-RFC | 290 +/− 28 | (100%) | 31 +/− 3* | (11%) | 143 +/− 16** | (49%) |
| EAC-RFC | 5 +/− 0.3 | (100%) | 6 +/− 1 | (120%) | 3 +/− 0.4* | (60%) |

TABLE 55-continued

Effect of L-Glu-L-Trp on Recovery of Immune Cells
in Irradiated Guinea Pigs (X ± S.D.): Thymic Lymphocytes Lymphocytes × $10^9$/L (% Normal)[a]

| Cell Population | Normal Healthy Control I | | Irradiated Un-treated Control II | | Irradiated and L-Glu-L-Trp Treated | |
|---|---|---|---|---|---|---|
| 20 Days Post Irradiation | | | | | | |
| Lymphocytes | 481 +/− 21 | (100%) | 254 +/− 33* | (53%) | 423 +/− 40** | (88%) |
| E-RFC | 379 +/− 26 | (100%) | 71 +/− 6* | (19%) | 343 +/− 30** | (91%) |
| EA-RFC | 290 +/− 28 | (100%) | 106 +/− 13* | (37%) | 243 +/− 28** | (84%) |
| EAC-RFC | 5 +/− 0.3 | (100%) | 4 +/− 0.5 | (80%) | 4 +/− 0.4 | (80%) |

[a]Cell counts × $10^9$/L;
*statistically significant at the p < 0.05 level when compared with Control I;
**significant at the p < 0.05 level (compared with Control II).

The results presented in TABLE 55 show a drop in thymic lymphocyte counts in irradiated control animals (i.e., Control II), i.e., at 5 days and 10 the lymphocyte counts decreased to 56% and then 18%, respectively, of normal levels. A partial return of immune cells was observed at day 20 with 53% of normal lymphocyte levels. Lymphocyte subpopulations in irradiated control guinea pigs was paralleled by decreases in the number of T- (i.e., E-RFC) and B-lymphocytes (i.e., EAC-RFC). L-Glu-L-Trp treatments resulted in a statistically significant increase in the number of thymic lymphocytes, i.e., from 56% to 82% of normal, on day 5; and from 18% to 56% on day 10. Similarly, thymic T-lymphocyte counts were increased on day 5 from 25% to 67% and on day 10 from 13% to 51%. L-Glu-L-Trp treatment was found to exhibit similar effects on splenic and lymph node T- and B-lymphocytes, TABLE 56.

The results presented in TABLE 56 show a decrease in the number of splenic lymphocytes in irradiated control guinea pigs, dropping to 36% of normal levels on day 10. Predictably, the majority of the decrease was evident in the short-lived B-lymphocyte subpopulation, and splenic T-lymphocytes proved more radiation resistant. Treatment with L-Glu-L-Trp significantly increased the numbers of splenic B-lymphocytes (i.e., EAC-RFC) on days 5 and 10; with increases on day 5 from 49% to 82% of normal, and on day 10 from 70% to 100%.

TABLE 56

Effect of L-Glu-L-Trp on Recovery of Immune Cells
in Irradiated Guinea Pigs (X ± S.D.): Splenic Lymphocytes Lymphocytes × $10^9$/L (% Normal)[a]

| Cell Population | Normal Healthy Control I | | Irradiated Un-treated Control II | | Irradiated and L-Glu-L-Trp Treated | |
|---|---|---|---|---|---|---|
| 5 Days Post Irradiation | | | | | | |
| Lymphocytes | 409 +/− 26 | (100%) | 273 +/− 32* | (67%) | 378 +/− 36** | (92%) |
| E-RFC | 40 +/− 3 | (100%) | 93 +/− 10* | (230%) | 48 +/− 4** | (120%) |
| EA-RFC | 26 +/− 2 | (100%) | 8 +/− 1* | (31%) | 22 +/− 4** | (85%) |
| EAC-RFC | 73 +/− 5 | (100%) | 36 +/− 3* | (49%) | 60 +/− 5** | (82%) |
| 10 Days Post Irradiation | | | | | | |
| Lymphocytes | 409 +/− 26 | (100%) | 148 +/− 23* | (36%) | 147 +/− 18** | (36%) |
| E-RFC | 40 +/− 3 | (100%) | 30 +/− 3* | (75%) | 29 +/− 3* | (73%) |
| EA-RFC | 26 +/− 2 | (100%) | 15 +/− 2* | (58%) | 15 +/− 2* | (58%) |
| EAC-RFC | 73 +/− 5 | (100%) | 51 +/− 4* | (70%) | 73 +/− 5** | (100%) |
| 20 Days Post Irradiation | | | | | | |
| Lymphocytes | 409 +/− 26 | (100%) | 273 +/− 47* | (67%) | 260 +/− 32** | (64%) |
| E-RFC | 40 +/− 3 | (100%) | 30 +/− 3* | (75%) | 45 +/− 4** | (113%) |
| EA-RFC | 26 +/− 2 | (100%) | 20 +/− 3* | (77%) | 29 +/− 4** | (112%) |
| EAC-RFC | 73 +/− 5 | (100%) | 67 +/− 8 | (92%) | 82 +/− 9 | (112%) |

[a]Cell counts × $10^9$/L;
*statistically significant at the p < 0.05 level when compared with Control I;
**significant at the p < 0.05 level (compared with Control II).

TABLE 57

Effect of L-Glu-L-Trp on Recovery of Immune Cells
in Irradiated Guinea Pigs (X ± S.D.): Lymph Node Lymphocytes

| | Lymphocytes × 10⁹/L (% Normal)[a] | | | | | |
|---|---|---|---|---|---|---|
| Cell Population | Normal Healthy Control I | | Irradiated Un-treated Control II | | Irradiated and L-Glu-L-Trp Treated | |
| | 5 Days Post Irradiation | | | | | |
| Lymphocytes | 252 +/− 18 | (100%) | 171 +/− 22* | (68%) | 183 +/− 21* | (73%) |
| E-RFC | 33 +/− 2 | (100%) | 24 +/− 3* | (73%) | 40 +/− 4** | (122%) |
| EA-RFC | 18 +/− 1 | (100%) | 11 +/− 2 | (61%) | 20 +/− 3** | (111%) |
| EAC-RFC | 56 +/− 4 | (100%) | 9 +/− 1* | (16%) | 25 +/− 2** | (45%) |
| | 10 Days Post Irradiation | | | | | |
| Lymphocytes | 252 +/− 18 | (100%) | 57 +/− 11* | (23%) | 75 +/− 13* | (30%) |
| E-RFC | 33 +/− 2 | (100%) | 15 +/− 2* | (45%) | 29 +/− 3** | (88%) |
| EA-RFC | 18 +/− 1 | (100%) | 10 +/− 1* | (56%) | 17 +/− 2** | (94%) |
| EAC-RFC | 56 +/− 4 | (100%) | 8 +/− 1* | (14%) | 12 +/− 1* | (21%) |
| | 20 Days Post Irradiation | | | | | |
| Lymphocytes | 252 +/− 18 | (100%) | 109 +/− 47* | (67%) | 242 +/− 31** | (96%) |
| E-RFC | 33 +/− 2 | (100%) | 18 +/− 2* | (75%) | 30 +/− 2** | (91%) |
| EA-RFC | 18 +/− 1 | (100%) | 9 +/− 1* | (50%) | 25 +/− 4** | (139%) |
| EAC-RFC | 56 +/− 4 | (100%) | 8 +/− 1* | (14%) | 9 +/− 1* | (16%) |

[a]Cell counts × 10⁹/L;
*statistically significant at the $p < 0.05$ level when compared with Control I;
**significant at the $p < 0.05$ level (compared with Control II).

The results presented in TABLE 57 show that irradiated guinea pigs exhibited decreased numbers of T- and B-lymphocytes in lymph nodes, i.e., 23% of normal T-cell levels on day 10 and only 14% of normal B-cell levels. Treatment with L-Glu-L-Trp significantly increased T-lymphocyte counts in lymph nodes on days 5, 10 and 20 and B-lymphocyte counts were statistically elevated on day 5. On day 10 and day 20 B-cell counts in the lymph nodes of L-Glu-L-Trp treated animals remained low, presumably because afferent repopulation with immune cells requires antigen stimulation.

TABLE 58

Effect of L-Glu-L-Trp on Recovery of Functional Activity of Immune
Cells in the Peripheral Blood of Irradiated Guinea Pigs (X ± S.D.)

| Days Post-Irradiation | Normal Healthy Control I | Irradiated Un-Treated Control II | Irradiated and L-Glu-L-Trp Treated |
|---|---|---|---|
| | Lymphocyte Blastogenesis with Con-A (%) | | |
| 5 | 36 +/− 1 | 66 +/− 4* | 44 +/− 4** |
| 10 | 37 +/− 2 | 81 +/− 7* | 67 +/− 5** |
| 20 | 37 +/− 2 | 76 +/− 7* | 49 +/− 2** |
| | Neutrophil Cationic Protein Levels | | |
| 5 | 1.79 +/− 0.07 | 1.36 +/− 0.09* | 1.42 +/− 0.15* |
| 10 | 1.76 +/− 0.07 | 1.29 +/− 0.08* | 1.54 +/− 0.09** |
| 20 | 1.81 +/− 0.08 | 1.47 +/− 0.12* | 1.63 +/− 0.11** |

*$p < 0.05$ in comparison with Control I;
**$p < 0.05$ in comparison with Control II.

As expected, the results presented in TABLE 58 show that peripheral blood lymphocytes from irradiated guinea pigs exhibited increased non-specific radiation-induced responsive to Concanavalin-A mitogen, and decreased levels of neutrophil cationic proteins. (Increased non-specific mitogen responsiveness in irradiated animals is correlated with decreased lymphocyte responsiveness to specific antigens, e.g., pathogens.) Treatment with L-Glu-L-Trp resulted in a statistically significant decrease in Con-A responsiveness and increased levels of neutrophil cationic proteins. Both of these findings are consistent with the conclusion that L-Glu-L-Trp treatments increased neutrophil-mediated immunity to pathogens, and lymphocyte responsiveness to foreign agents.

EXAMPLE 30

Effects of L-Glu-L-Trp Dipeptide on Indices of
Innate Immunity

The effects of L-Glu-L-Trp on innate mechanisms of immunity were investigated in male CBA mice (18–20 g). Eighty mice were divided into 4 groups of 20 mice each. The animals in each of the groups were injected intraperitoneally (ip) once daily over a period of 6 days with either: i) 1 mg/kg L-Glu-L-Trp, ii) 0.01 mg/kg L-Glu-L-Trp, or iii) non-pyrogenic physiological saline. Next (on day 6), each group of animals was subdivided into two subgroups of 10 animals each: i.e., one subgroup of animals was injected ip with 10% sterile proteose peptone to induce neutrophils (induced), while the other subgroup were non-induced (non-induced). The animals of the four induced-subgroups were sacrificed 2.5 hours after the ip injection. Thymus and spleen weights were determined in the non-induced animals; cell suspensions were prepared from each thymus and spleen; and, resident peritoneal exudate cells (PEC) were harvested by lavage with Medium 199 from each animal. The percentage content of T- and B-lymphocytes in the splenic cell populations from the non-induced animals was determined by phase-contrast and indirect immunofluorescence Shtorkh, V., & Emmrikh, I. M., *Immunological methods, Medicine, Russia*. pp. 254–268 (1987)) using rabbit antisera specific for murine Thy-1 and immunoglobulin. (Rabbit anti-Thy-1 was raised by immunization with a murine brain homogenate (Jolyb, E. S., *Cell. Immunol.* 2:353–361 (1971)) and anti-Ig by immunization with an ammonium sulfate precipitate of murine serum. The percentage macrophages in the resident PEC populations were determined in Romanovsky stained smears of cells, the cells then collected by centrifugation at 150×g/10 minutes, and macrophage activity measured by reduction of nitroblue tetrazolium (NBT; see Jolyb, supra) before and after induction with complement-opsonized zymosan (guinea pig complement activated by zymosan;). NBT reduction was quantified spetrophotometrically at 540 nm. Pinocytic activity of the resident peritoneal macrophages was assessed by measuring uptake of neutral red dye (measured spectrophotometrically). The percentage of neutrophils in the PEC population was determined using phase contrast microscopy and complement-opsonized zymosan. Phagocytic activity of neutrophils was determined by incubating the cells with $2.5 \times 10^8$ *Staphylococcus aureus* per milliliter (*S. aureus* from a 24 hour culture). The data were expressed as both the percentage of phagocytic cells (% of the total cell population phagocytizing 1 or more Staphylococci) and the phagocytic index (expressed as the mean number of intracellular bacteria inside each of the phagocytically active neutrophils), both measurements being made by microscopic examination following Romanovsky-Giemsa staining of cell smears.

The results of these respective experimental measurements on cells contributing to innate mechanisms of immunity are summarized in TABLES 59–64.

TABLE 59

Effect of L-Glu-L-Trp on Thymic and Spleen Mass (X ± S.D.)

| Group | No. Animals | Dose (mg/kg) | Thymus (mg) | Thymus Change (%)† | Spleen (mg) | Splenic Change (%) |
|---|---|---|---|---|---|---|
| Saline Control | 10 | 0 | 25.4 ± 1.6 | 0 | 81.7 ± 3.4 | 0 |
| L-Glu-L-Trp | 10 | 1.0 | 14.1 ± 1.3* | ↓ 44 | 88.4 ± 4.4 | ↑ 8 |
|  | 10 | 0.01 | 14.8 ± 1.6* | ↓ 42 | 69.8 ± 2.6** | ↓ 15 |

*statistically significant at the p < 0.01 level when compared with saline control;
**significant at the p < 0.05 level (compared with saline controls);
†percentage change of the mean value (%) relative to the mean value of the saline control.

The results presented in TABLE 59 show L-Glu-L-Trp induced a statistically significant decrease in thymic weight at both dosages, and had opposing effects on splenic weight at the indicated dosages. Interestingly, the 1 mg/kg dosage of L-Glu-L-Trp administered in these studies approximates a clinically effective dosage in humans for immune stimulation.

The results presented in TABLES 60–65, show the effects of this agent on individual cell populations and their activities.

TABLE 60 demonstrates the effects of L-Glu-L-Trp on the mean percentage of T- and B-lymphocytes isolated in the cell populations from the spleens of treated animals

TABLE 60

Effects of L-Glu-L-Trp on the Percentage of Splenic T- and B-lymphocytes (X ± S.D.)

| Group | Dose ip (μg/ml) | Dose (mg/kg) | T cells (%) | Change† | B cells (%) | Change† |
|---|---|---|---|---|---|---|
| Saline Control | 0.1 | 0 | 37.0 ± 1.28 | 0.0 | 50.0 ± 1.71 | 0.0 |
| L-Glu-L-Trp | 10 | 1.0 | 34.8 ± 2.5 | ↓ 0.9 | 52.4 ± 1.71 | 1.0 |
|  | 0.1 | 0.01 | 41.2 ± 2.1* | ↑ 1.1 | 50.8 ± 3.0 | 1.0 |

*statistically significant at the p < 0.01 level in comparison with the saline control group results;
†Change = % peptide treated/% control.

The results presented in TABLE 60 show that L-Glu-L-Trp slightly altered the percentage of splenic T-lymphocytes. In these studies the B-lymphocyte content of the spleen did not seem to be affected by the agent.

TABLE 61 shows the results of studies with peritoneal macrophages and their state of activation as measured by the ability to reduce NBT.

TABLE 61

Effects of L-Glu-L-Trp on the Innate State of Activation of Resident Peritoneal Macrophages as Determined by NBT Reduction

| Group | Dose (mg/kg) | NBT Reduction ($OD_{540}$)* Spontaneous | Induced† |
|---|---|---|---|
| Saline Control | 0 | 0.055 ± 0.002 | 0.105 ± 0.005 |
| L-Glu-L-Trp | 1 | 0.059 ± 0.003 | 0.116 ± 0.008 |
|  | 0.01 | 0.101 ± 0.002** | 0.205 ± 0.012** |

*mean ± S.D. of four determinations for each group;

TABLE 61-continued

Effects of L-Glu-L-Trp on the Innate State of Activation of Resident Peritoneal Macrophages as Determined by NBT Reduction

| Group | Dose (mg/kg) | NBT Reduction ($OD_{540}$)* Spontaneous | Induced† |
|---|---|---|---|

**statistically significant at the p < 0.05 level from the values recorded in the control group;
†macrophages induced with complement opsonized zymosan.

The results presented in TABLE 61 show, i) as expected, complement-opsonized zymosan activated resident peritoneal macrophages (saline controls) by about 1.9-fold; ii) treatment of animals with a six day ip treatment course of L-Glu-L-Trp (0.01 mg/kg) resulted in a spontaneous level of macrophage activity that approximated the activity observed with the induced resident peritoneal macrophages (i.e., in the saline treated controls); iii) when macrophages from L-Glu-L-Trp (0.01 mg/kg) treated animals were induced with complement-opsonized zymosan, 1.75-fold and 2-fold increases, respectively, in NBT reducing activity were observed In TABLE 62 are shown the results of experiments designed to examine the pinocytic activity of resident peritoneal macrophages from the respective treatment groups.

TABLE 62

Effect of L-Glu-L-Trp on Uptake of Neutral Red
by Resident Peritoneal Macrophages (X ± S.D.)†

| Group | Dose (mg/kg) | Neutral Red Uptake | |
|---|---|---|---|
| | | No. of Assays | Absorbance |
| Saline Control | 0 | 5 | 0.488 ± 0.026 |
| L-Glu-L-Trp | 1 | 5 | 0.469 ± 0.016 |
| | 0.01 | 4 | 0.604 ± 0.031** |

†mean absorbance values ± standard deviation of the mean;
*statistically significant at the $p < 0.01$ level in comparison with the control values;
**$p < 0.05$ The results presented in TABLE 62 show a 75% increase in neutral red uptake by macrophages from L-Glu-L-Trp treated animals (0.01 mg/kg), however, this difference was not statistically different from the control values.

TABLE 63 shows the results of experiments designed to investigate the tissue response of neutrophils to an inflammatory agent, i.e., induced in the peritoneum by injection of sterile proteose peptone.

TABLE 63

Effects of L-Glu-L-Trp Intraperitoneal Pretreatment
on Neutrophil Response to Proteose Peptone (X ± S.D.)

| Group | Dose ip (µg/ml) | Dose (mg/kg) | Total Number of Cells Induced (×10$^6$) |
|---|---|---|---|
| Saline Control | 0.1 | 0 | 40 |
| L-Glu-L-Trp | 10 | 1 | 80* |
| | 0.1 | 0.01 | 50 |

*statistically significant at the $p < 0.05$ level compared with values recorded in the control group.

The results presented in TABLE 63 show that ip pretreatment with L-Glu-L-Trp (0.1 mg/kg) doubled the number of neutrophils that could be induced following injection of proteose peptone.

It is interesting that the total volume of exudate obtained from L-Glu-L-Trp treated animals (0.01 mg/kg) was increased relative to the volume obtained from controls and the cell concentration was correspondingly decreased, i.e., $0.9 \times 10^6$ for L-Glu-L-Trp versus $1.9 \times 10^6$ for control.

In TABLE 64, are shown the results of experiments designed to test the phagocytic activity of the neutrophils induced by the proteose peptone injection.

TABLE 64

Effect of L-Glu-L-Trp Pretreatment on
Phagocytic Activity of Neutrophils Responding to Induction

| Group | Dose ip (µg/ml) | Dose (mg/kg) | Phagocytic Activity | |
|---|---|---|---|---|
| | | | Phagocytes (%) | Phagocytic Index (No. bacteria/phagocyte) |
| Saline Control | 0 | 0 | 18.8 ± 0.29 | 2.05 ± 0.10 |
| L-Glu-L-Trp | 10 | 1 | 31.5 ± 0.4* | 1.89 ± 0.03 |
| | 0.1 | 0.1 | 17.8 ± 1.13 | 1.90 ± 0.05 |

*statistically significant at the $p < 0.01$ level in comparison with the values recorded in controls.

The results presented in TABLE 64 show that the six day ip pretreatment course of L-Glu-L-Trp (1 mg/kg) induced statistically significant 1.5-fold and 1.7-fold increases, respectively, in the percentage of phagocytic cells induced into the peritoneal cavity following injection of a sterile inflammatory challenge with proteose peptone. The phagocytic capacity of the neutrophils induced in this manner was finite, i.e., about two Staphylococci per neutrophil in saline control or peptide treated animals. L-Glu-L-Trp pretreatment at a dose of 0.01 mg/kg did not appear to stimulate neutrophil migration in response to the sterile proteose peptone inflammatory stimulus (TABLE 63), nor the phagocytic activity of the cells so induced (TABLE 64).

The results presented in EXAMPLES 26–29, above, indicate the following: i) L-Glu-L-Trp treatment can cause redistribution of lymphoid cell populations in animals; ii) L-Glu-L-Trp treatment did not alter the activity of resident peritoneal macrophages; iii) L-Glu-L-Trp treatment stimulated both the number of neutrophils entering the tissue in response to a sterile inflammatory challenge and the percentage of phagocytically active cells in the cell exudate population; iv) L-Glu-L-Trp appeared to exhibit dosage-dependent differential effects, i.e., at the 1 mg/kg dose neutrophils were stimulated, but at the lower 0.01 mg/kg dose, macrophages, and not neutrophils, were stimulated, with a possible mobilization of thymic and bone marrow lymphocytes and increased T-lymphocytes in the spleen at the conclusion of the 6 day ip treatment regimen.

The combined results indicate that treatment with L-Glu-L-Trp can induce changes in distribution of lymphocyte cell populations, and changes in distribution and activities of macrophages and neutrophils, both of which changes favor a heightened state of innate immunity in the treated animals. For these and other reasons L-Glu-L-Trp is termed an "immunomodulator".

EXAMPLE 31

Effects of L-Glu-L-Trp on Induction of Antibody Responses as Measured by Jerne Plaque Formation Thirteen male (CBAxC57B1/6) F1 mice, 10–12 weeks of age (22±0.2 g) were challenged with a single intraperitoneal (ip) injection of $2.5 \times 10^7$ sheep red blood cells (s-rbc) in 0.5 mL normal saline. Within 20 minutes after the injection of s-rbc an L-Glu-L-Trp treatment trial was initiated by injecting 0.2 mL of the dipeptide preparation at a concentration sufficient to deliver a unit dosage of 1.0 µg/kg, 10 µg/kg, or 100 µg/kg. The same dosage was delivered daily for the next three days. Control animals (13 per group) included: i) non-s-rbc-immunized and ii) s-rbc immunized but non L-Glu-L-Trp-treated. At day 5 (post-s-rbc challenge), the spleens of the animals were removed and splenocytes prepared by homogenizing the spleens in a loose fitting glass Dounce-type homogenizer, followed by screening of the cell suspension through a caprone filter, and differential centrifugation (yield about $10^8$ cells/spleen).

Antibody-producing cells (AbPC) in the splenocyte preparations were quantified using the well known method of Jerne and Nordin. Briefly, concentrations of $5 \times 10^4$ to $10^6$ splenocytes were mixed with a 2% solution of s-rbc (% volume packed cells/volume medium) and incorporated into an agarose layer in petri dishes. The dishes were incubated for 60 minutes at 37° C. (in a humidified incubator in an atmosphere of 5% $CO_2$), to allow APC to synthesize antibody capable of binding to the surrounding s-rbc in the agarose matrix. After the 60 minute incubation, a 1:20 dilution of guinea pig serum was added as a source of complement and clear zones of s-rbc lysis (surrounding the AbPCs) were recorded by microscopic observation after an additional 60 minutes incubation. The results are summarized in TABLE 65.

infection. The lethal dosage of *E. coli* gram negative rods in the experimental model was in a stepwise manner. First, the number of bacteria equivalent to the $LD_{50}$ dose (50% survival) was determined by injecting intraperitoneally different log dosages of bacteria and determining the percentage of animals surviving 72 hours later. The $LD_{100}$ dose (100% mortality) was calculated by multiplying the number of bacteria in the $LD_{50}$ dose times 10. Second, the mean effective dose (MED) of Ampicillin sufficient to effect 100% survival of animals receiving one $LD_{50}$ dose of antibiotic-sensitive bacteria was determined.

Mice were divided into five L-Glu-L-Trp treatment groups, five combined treatment groups (i.e., L-Glu-L-Trp+ antibiotic), an antibiotic treatment control group (Ampicillin), and a saline control group (Control), with eighteen animals in each group. In the L-Glu-L-Trp treatment groups, mice received a prophylactic L-Glu-L-Trp treatment administered daily beginning 3 days before bacterial challenge (i.e., day -3 through day 1) as intraperitoneal injections of 0.01 µg/kg, 0.1 µg/kg, 1.0 µg/kg, 10 µg/kg, or

TABLE 65

Effects of L-Glu-L-Trp on the Antibody Plaque Forming Cell Response of Mice to Sheep Red Blood Cells (X ± S.D.)

| Test Agent | Dose (µg/kg) | Spleen weight/ Body weight | Splenocytes per Spleen (x$10^6$) | PFC/Spleen | PFC/$10^6$ splenocytes |
|---|---|---|---|---|---|
| None | 0 | 0.44 ± 0.02 | 159.5 ± 0.1 | 80 ± 19 | 0.5 ± 0.1 |
| Saline control | 0 | 0.53 ± 0.05 | 184.2 ± 7.3* | 4284 ± 579* | 24.3 ± 4.2* |
| L-Glu-L-Trp | 1 | 0.42 ± 0.01* | 168.6 ± 3.6 | 11722 ± 2005*† | 69.2 ± 11.3*† |
|  | 10 | 0.43 ± 0.01 | 159 ± 8.5† | 7854 ± 1631* | 48.8 ± 9*† |
|  | 100 | 0.44 ± 0.02 | 162.6 ± 6† | 6731 ± 1027* | 41.7 ± 6*† |

*statistically significant at the $p < 0.05$ level (Student's t-test) relative to the values recorded in the Non-immunized control group of animals;
†statistically significant at the $p < 0.05$ level relative to the values recorded in the s-rbc immunized, saline treated, control group of animals.

The results presented in TABLE 65 show that 3 daily ip treatments with L-Glu-L-Trp at a dose of 1 µg/kg, when delivered after an ip challenge with s-rbc, significantly increased the number of PFC in spleen by 2.7-fold over the values recorded in the saline-treated control animals. The frequency of PFC's expressed per $10^6$ splenocytes also increased by 2.8-fold. Spleen weights of the animals treated with the 1 µg/kg dosage of L-Glu-L-Trp did not increase, and in fact, decreased slightly (but significantly), and total splenocytes harvested from the treated animals were also lower, but still within the range harvested from the saline control animals. Thus, treatment with 1 µg/kg L-Glu-L-Trp increased the number and frequency of antigen producing cells within the total spleen cell population but without increasing the total number of cells in the spleen. Interestingly, treatments at dosages of 10 µg/kg and 100 µg/kg L-Glu-L-Trp resulted in significantly fewer splenocytes being harvested than from the saline control animals, and although 1.8-fold and 1.6-fold more PFCs were recorded (on a per spleen basis) than in saline control animals, the possibility exists that the higher doses activated AbPCs at the local site (or in local lymph nodes), and that the cells so activated failed to traffic to the spleen.

EXAMPLE 32

Therapeutic Efficacy of L-Glu-L-Trp in an Experimental Animal Model of Acute Peritoneal Bacterial Infection as Determined by Survival Following Intraperitoneal Infection with an $LD_{100}$ dose of *E. coli*

Therapeutic efficacy of L-Glu-L-Trp was tested in a murine experimental animal model of acute gram negative 100 µg/kg. In the five combined treatment groups, mice received the same five intraperitoneal dosages of L-Glu-L-Trp and, in addition, Ampicillin equivalent to one MED. In the antibiotic control group, mice received only Ampicillin, and in the saline control group, an injection of saline administered under the same conditions.

On day 0, a number of bacteria equivalent to one $LD_{100}$ was administered to all animals. Survival was determined after 24, 48, and 72 hours. The results of these studies are summarized in TABLE 66.

TABLE 66

Effects of L-Glu-L-Trp on Survival Rate (%) of Mice as a Function of Time After Induction of Acute Peritonitis by Injection of *E. coli*

| Group | Glu-Trp Dose (µg/kg) | Percentage Survivors: Hours After Injection | | |
|---|---|---|---|---|
|  |  | 24 | 48 | 72 |
| Saline Control | 0 | 0 | 0 | 0 |
| L-Glu-L-Trp | 10 | 83.3* | 11.1 | 11.1 |
|  | 100 | 77.8*† | 38.9* | 38.9* |
|  | 1000 | 83.3*† | 44.4* | 44.4* |
| Ampicillin Control | 1 MED | 33.3* | 22.2* | 22.2* |

TABLE 66-continued

Effects of L-Glu-L-Trp on Survival Rate (%) of Mice as a Function of Time After Induction of Acute Peritonitis by Injection of *E. coli*

| Group | Glu-Trp Dose (μg/kg) | Percentage Survivors: Hours After Injection | | |
|---|---|---|---|---|
| | | 24 | 48 | 72 |
| L-Glu-L-Trp | 10 | 94.4*† | 44.4*‡ | 44.4*‡ |
| + | 100 | 94.4*† | 66.7* | 61.1*† |
| Ampicillin | 1000 | 100.0*† | 77.8*‡ | 77.8*†‡ |

*statistically significant at the p < 0.05 level in comparison with the saline control values;
†statistically significant as compared to the Ampicillin-treatment control;
‡statistically significant (p < 0.05) compared with the corresponding dosage of L-Glu-L-Trp without Ampicillin.

The Materials and Methods used in these studies appear immediately following EXAMPLE 46.

EXAMPLE 33

Therapeutic Efficacy of L-Glu-L-Trp in an Experimental Animal Model of Acute Peritoneal Bacterial Infection as Determined by Survival Following Intraperitoneal Infection with an $LD_{100}$ dose of *Pseudomonas aeruginosa*

Therapeutic efficacy of L-Glu-L-Trp was tested in a murine experimental animal model of acute gram negative infection. The lethal dosage of Pseudomonas bacilli in the experimental model was in a stepwise manner. First, the number of bacilli equivalent to the $LD_{50}$ dose (50% survival) was determined by injecting intraperitoneally different log dosages of bacilli and determining the percentage of animals surviving 96 hours later. The theoretical $LD_{100}$ dose (100% mortality) was calculated by multiplying the number of bacteria in the $LD_{50}$ dose times 10. Second, the mean effective dose (MED) of Ampicillin sufficient to effect 100% survival of animals receiving one $LD_{50}$ dose of antibiotic-sensitive bacilli was determined.

Mice were divided into five L-Glu-L-Trp treatment groups, five combined treatment groups (i.e., L-Glu-L-Trp+ antibiotic), an antibiotic treatment control group (Gentamycin), and a saline control group (Control), with eighteen animals in each group. In the L-Glu-L-Trp treatment groups, mice received a prophylactic L-Glu-L-Trp treatment administered daily for 3 days before bacterial challenge as a daily intraperitoneal injection of 0.01 μg/kg, 0.1 μg/kg, 1.0 μg/kg, 10 μg/kg, or 100 μg/kg. In the five combined treatment groups, mice received the same five intraperitoneal dosages of L-Glu-L-Trp and, in addition, Gentamycin equivalent to one MED. In the antibiotic control group, mice received only Gentamycin, and in the saline control group, an injection of saline administered under the same conditions. On day 0, a number of bacilli equivalent to one $LD_{100}$ was administered to all animals. Survival was determined after 24, 48, and 96 hours. The results of these studies are summarized in TABLE 67.

TABLE 67

Effects of L-Glu-L-Trp on Survival Rate (%) of Mice as a Function of Time After Induction of Acute Peritonitis by Injection of *Pseudomonas aeruginosa*

| Group | Glu-Trp Dose (μg/kg) | Percentage Survivors: Hours After Injection | | |
|---|---|---|---|---|
| | | 24 | 48 | 96 |
| Saline Control | 0 | 0 | 0 | 0 |
| L-Glu-L-Trp | 10 | 55.6* | 5.6 | 5.6 |
| | 100 | 66.7*† | 38.9* | 38.9 |
| | 1000 | 77.8*† | 44.4* | 44.4* |
| Gentamycin Control | 1 MED | 27.8* | 27.8* | 27.8* |
| L-Glu-L-Trp | 10 | 77.8*† | 61.1*†‡ | 61.1*†‡ |
| + | 100 | 83.3*† | 77.8*†‡ | 77.8*†‡ |
| Gentamycin | 1000 | 100*†‡ | 88.9*†‡ | 77.8*†‡ |

*statistically significant at the p < 0.05 level in comparison with the saline control values;
†statistically significant (p < 0.05) as compared to the Gentamycin-treatment control;
‡statistically significant (p < 0.05) compared with the corresponding dosage of L-Glu-L-Trp without Gentamycin.

The results presented in TABLE 67 show that L-Glu-L-Trp alone, or in combination therapy with Gentamycin, significantly increased the percentage of mice surviving a lethal challenge of Pseudomonas.

EXAMPLE 34

Therapeutic Efficacy of L-Glu-L-Trp in an Experimental Animal Model of Acute Peritoneal Bacterial Infection as Determined by Survival Following Intraperitoneal Infection with an $LD_{100}$ dose of Antibiotic-Resistant *Staphylococcus aureus*

Therapeutic efficacy of L-Glu-L-Trp was tested in a murine experimental animal model of acute gram positive infection. The lethal dosage of Staphylococci in the experimental model was in a stepwise manner. First, the number of bacteria equivalent to an $LD_{50}$ dose (50% survival) was determined by injecting intraperitoneally different log dosages of Staphylococci and determining the percentage of animals surviving 72 hours later. The theoretical $LD_{100}$ dose (100% mortality) was calculated by multiplying the number of bacteria in the $LD_{50}$ dose times 10. Second, the mean effective dose (MED) of Ampicillin sufficient to effect 100% survival of animals receiving one $LD_{50}$ dose of methicillin-sensitive staphylococci was determined, i.e., 100 mg/kg when administered ip one hour after bacterial challenge. (In this animal model, methicillin-resistant Staphylococci were used as the bacterial challenge and Ampicillin on its own was not sufficient to prevent mortality.)

Mice were divided into five L-Glu-L-Trp treatment groups, five combined treatment groups (i.e., L-Glu-L-Trp+ antibiotic), an antibiotic treatment control group, and a saline control treatment group, with eighteen animals in each group. In the L-Glu-L-Trp treatment groups, mice received a prophylactic L-Glu-L-Trp treatment administered daily for 3 days before bacterial challenge as daily intraperitoneal injections of 0.01 μg/kg, 0.1 μg/kg, 1.0 μg/kg, 10 μg/kg, or 100 μg/kg. In the five combined treatment groups, mice received the same five intraperitoneal dosages of L-Glu-L-Trp and, in addition, Ampicillin equivalent to one MED. In the antibiotic control group, mice received only Ampicillin, and in the saline control group, an injection of saline administered under the same conditions. On day 0, a number of bacteria equivalent to one $LD_{100}$ was administered to all animals. Survival was determined after 24, 48, and 72 hours. The results of these studies are summarized in TABLE 68.

TABLE 68

Effects of Intraperitoneal Prophylactic Treatment with L-Glu-L-Trp on Survival Rate (%) of Mice as a Function of Time After Induction of Acute Peritonitis by Injection of *Staphylococcus aureus*

| Group | Glu-Trp Dose (μg/kg) | Percentage Survivors: Hours After Injection | | |
|---|---|---|---|---|
| | | 24 | 48 | 72 |
| Saline Control | 0 | 0 | 0 | 0 |
| L-Glu-L-Trp | 0.01 | 31.5 | 3.7 | 0 |
| | 0.1 | 33.3 | 0 | 0 |
| | 1 | 50.0* | 27.8* | 5.6 |
| | 10 | 83.3* | 50.0* | 33.3* |
| | 100 | 88.9* | 61.1* | 50.0* |
| | | 83.3* | 72.2* | 55.6* |
| Ampicillin Control | 1 MED | 75* | 44.4* | 30.6* |
| L-Glu-L-Trp + Ampicillin | 0.01 | 75.0* | 44.4* | 30.6* |
| | 0.1 | 100.0*†‡ | 77.8*†‡ | 61.1*†‡ |
| | 1 | 100.0*†‡ | 77.8*†‡ | 66.7*†‡ |
| | 10 | 100.0*† | 83.3†‡ | 66.7*†‡ |
| | 10 | 100.0† | 83.3*†‡ | 72.2*†‡ |
| | 100 | 94.4* | 88.9*† | 88.9*†‡ |

*statistically significant at the p < 0.05 level in comparison with the saline control values;
†statistically significant (p < 0.05) as compared to the Ampicillin-treatment control;
‡statistically significant (p < 0.05) compared with corresponding dosage of L-Glu-L-Trp without Ampicillin.

Figure 3A:
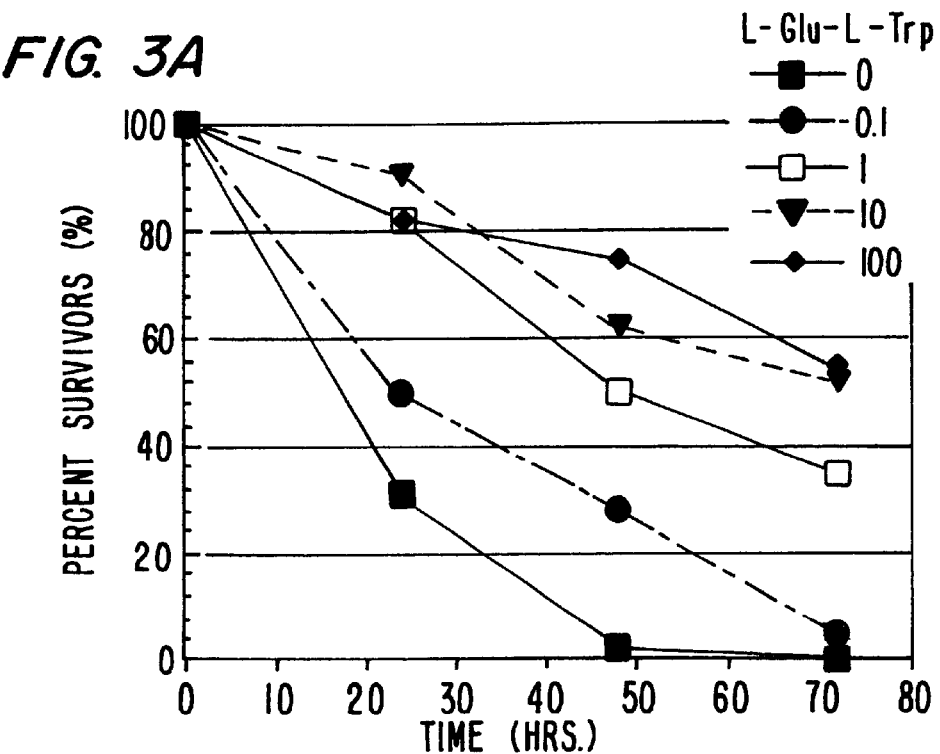
FIG. 3A graphically depicts the results of studies parallel to those described in regard to FIG. 1A, above, but using staphylococci. Mice in the experimental group received a prophylactic course of L-Glu-L-Trp treatment, while those in the control group did not.
Figure 3B:
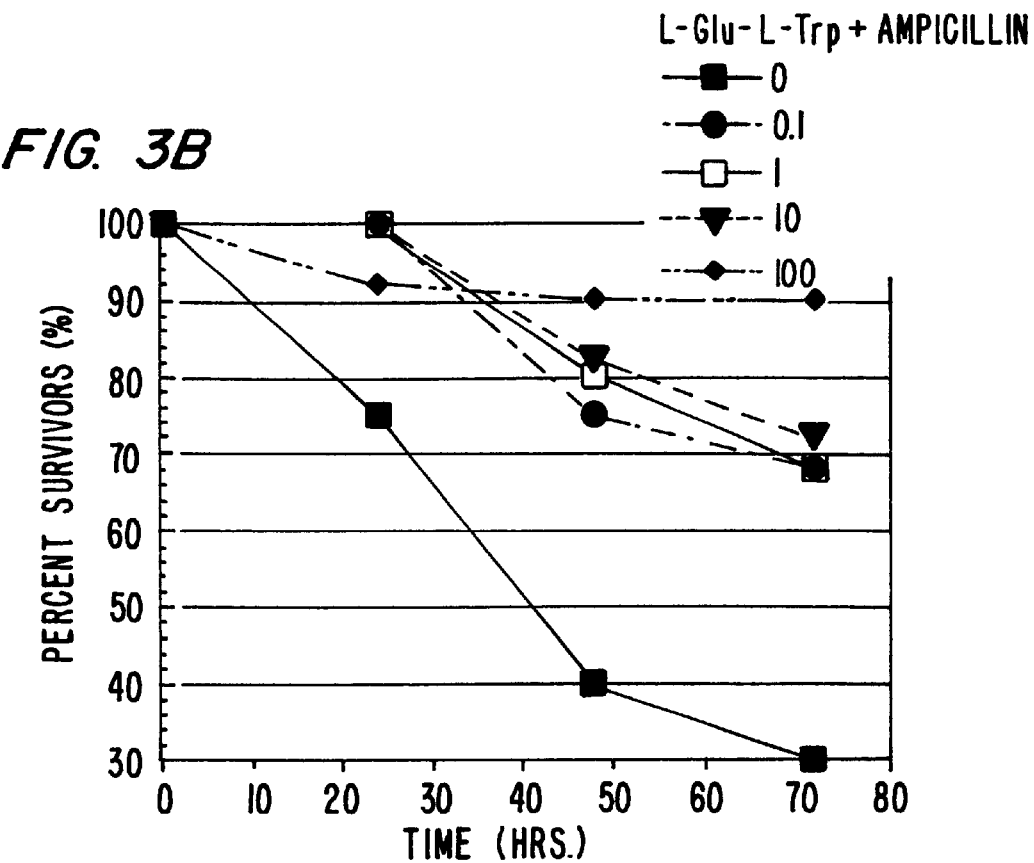
FIG. 3B graphically depicts the results of studies parallel to those described in regard to FIG. 1B, above, but using staphylococci. Mice in the experimental group received a prophylactic course of combination ip therapy using both L-Glu-L-Trp and ampicillin; mice in the control group were untreated; and, mice in the antibiotic control group were treated ip with only ampicillin (amp).
Figure 3C:
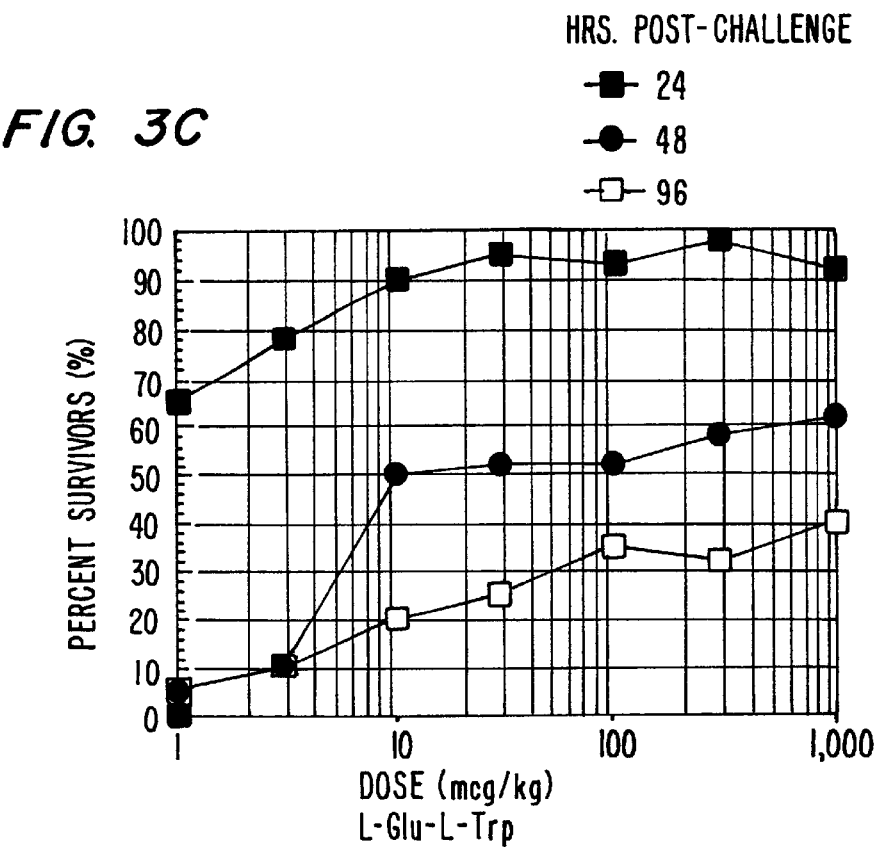
FIG. 3C graphically depicts data obtained in a parallel experiment to that of FIG. 3A, (but including additional dosages); plotted in a dose-response type fashion.
Figure 3D:
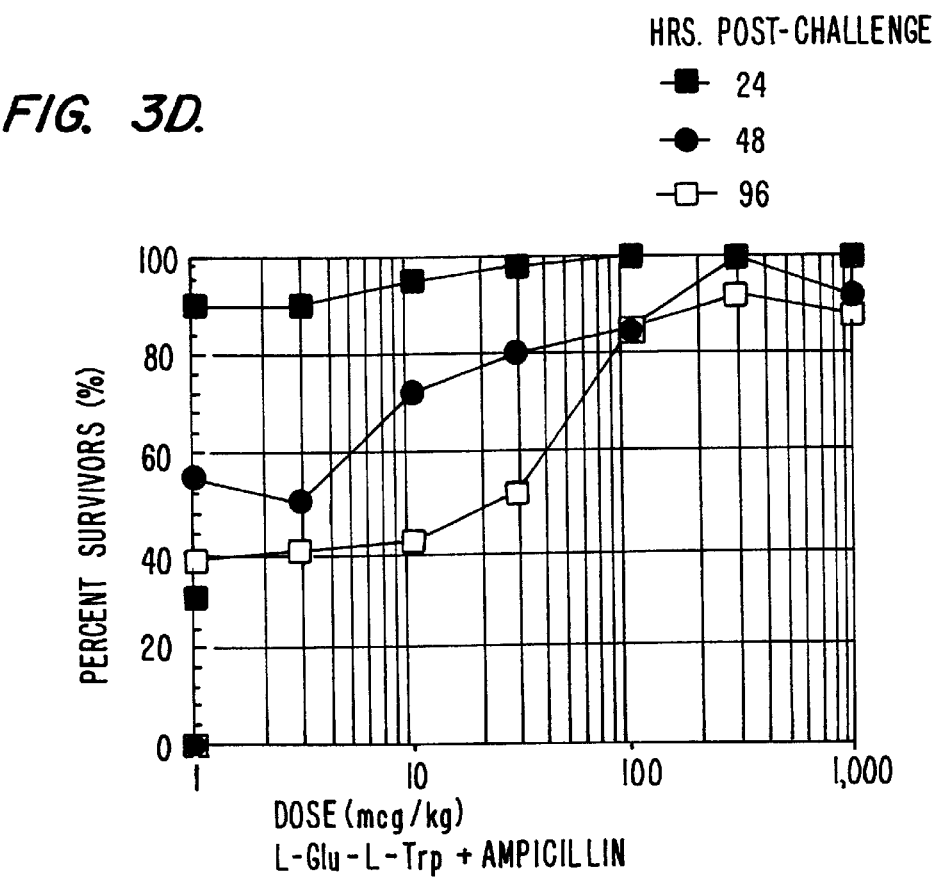
FIG. 3D graphically depicts data obtained in a parallel experiment to that of FIG. 3B, (but including additional dosages); plotted in a dose-response type fashion.

The results presented in TABLE 68 are presented graphically in FIGS. 3A–3D as a function of the i) time after injection of the bacterial challenge dose (i.e., hrs.); and, ii) the dose in mg/kg of single agent L-Glu-L-Trp or of combination therapy with L-Glu-L-Trp and Ampicillin.

Figure 3E:
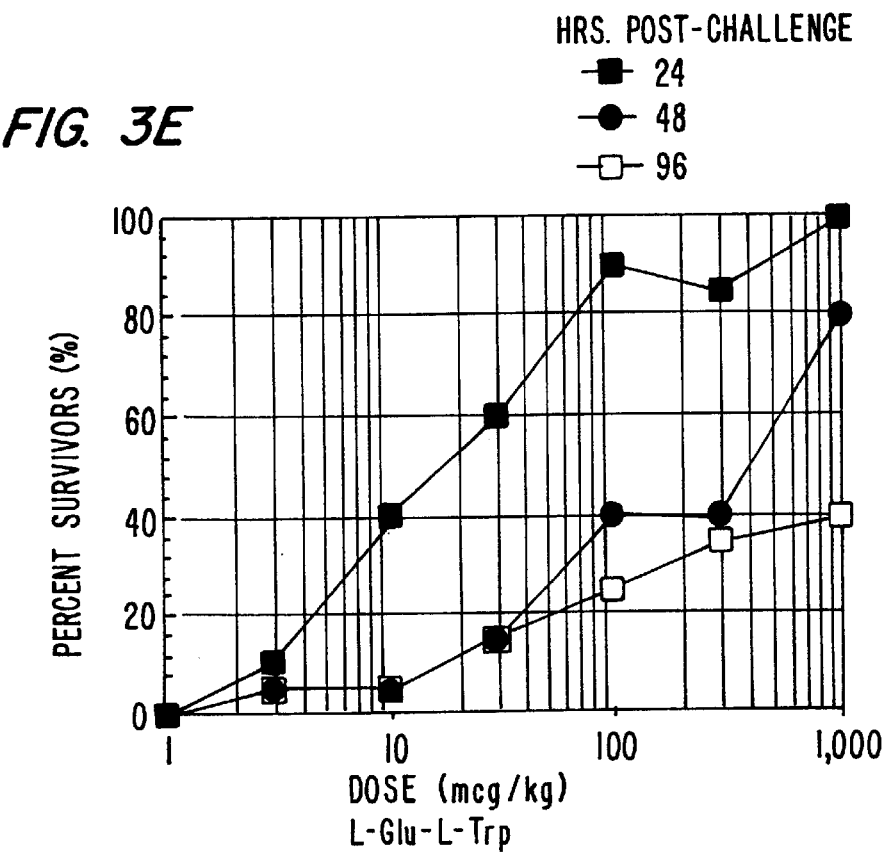
FIG. 3E graphically depicts data obtained in a dose-response experiment similar to that of FIG. 3C, but with L-Glu-L-Trp therapy administered intramuscularly (im) route of injection rather than ip.
Figure 3F:
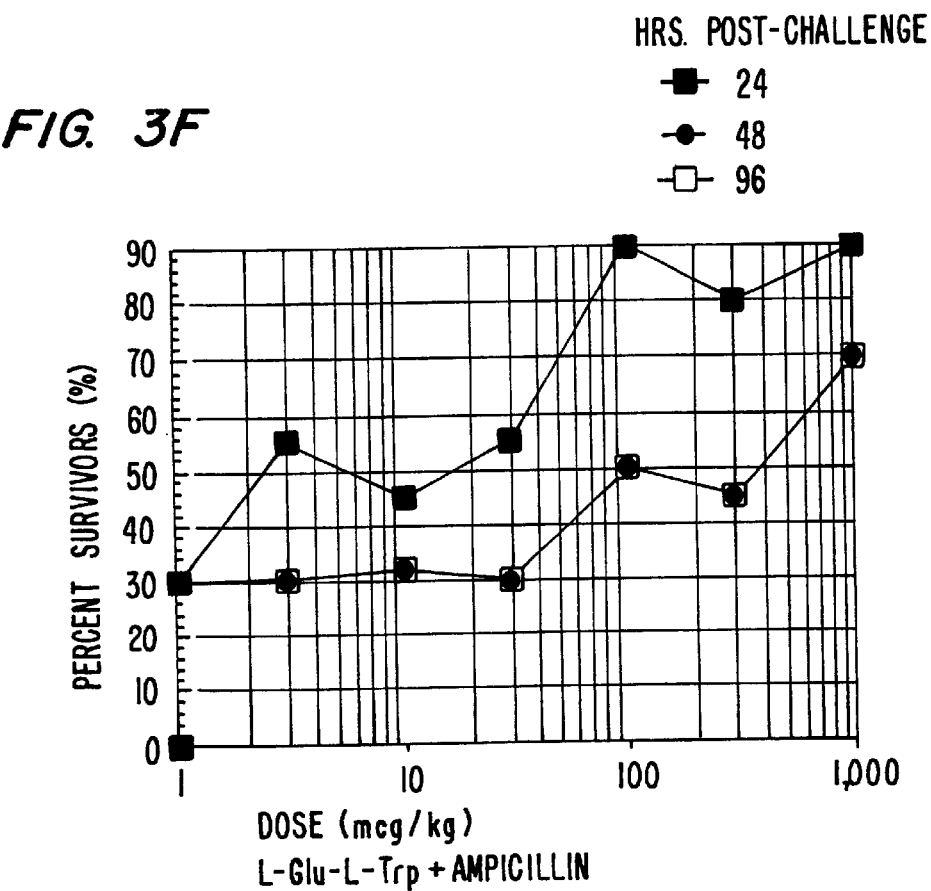
FIG. 3F graphically depicts data obtained in a dose-response experiment similar to that of FIG. 3D, but with combination therapy administered by the im route rather than ip.
Figure 4A:
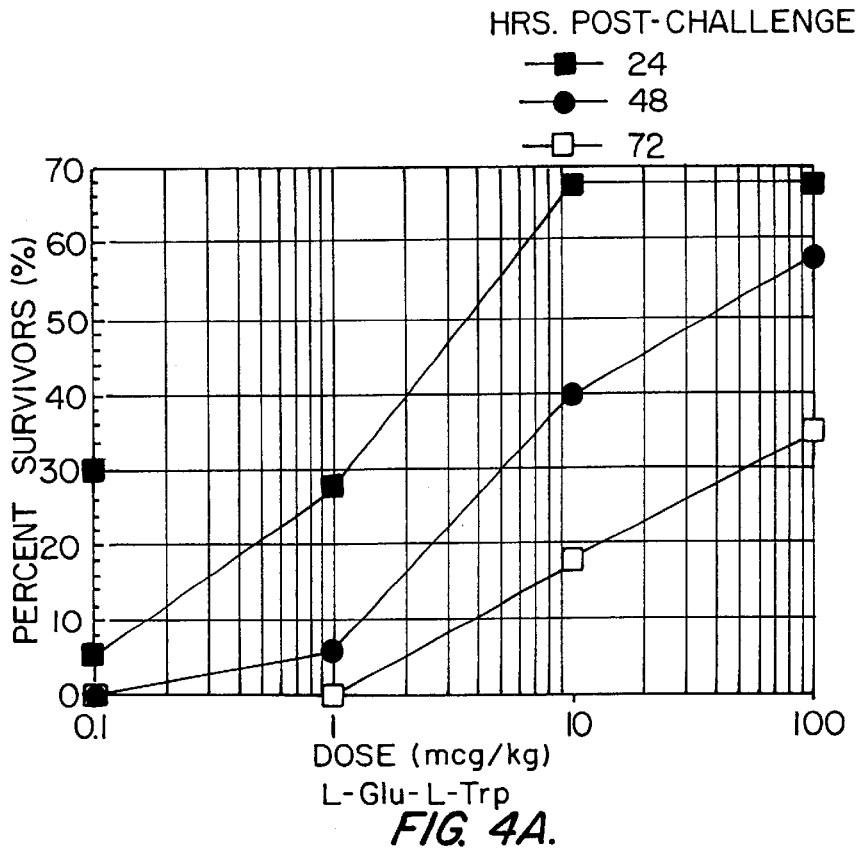
FIG. 4 graphically depicts the data shown in EXAMPLE 34, TABLE 70.
Figure 4B:
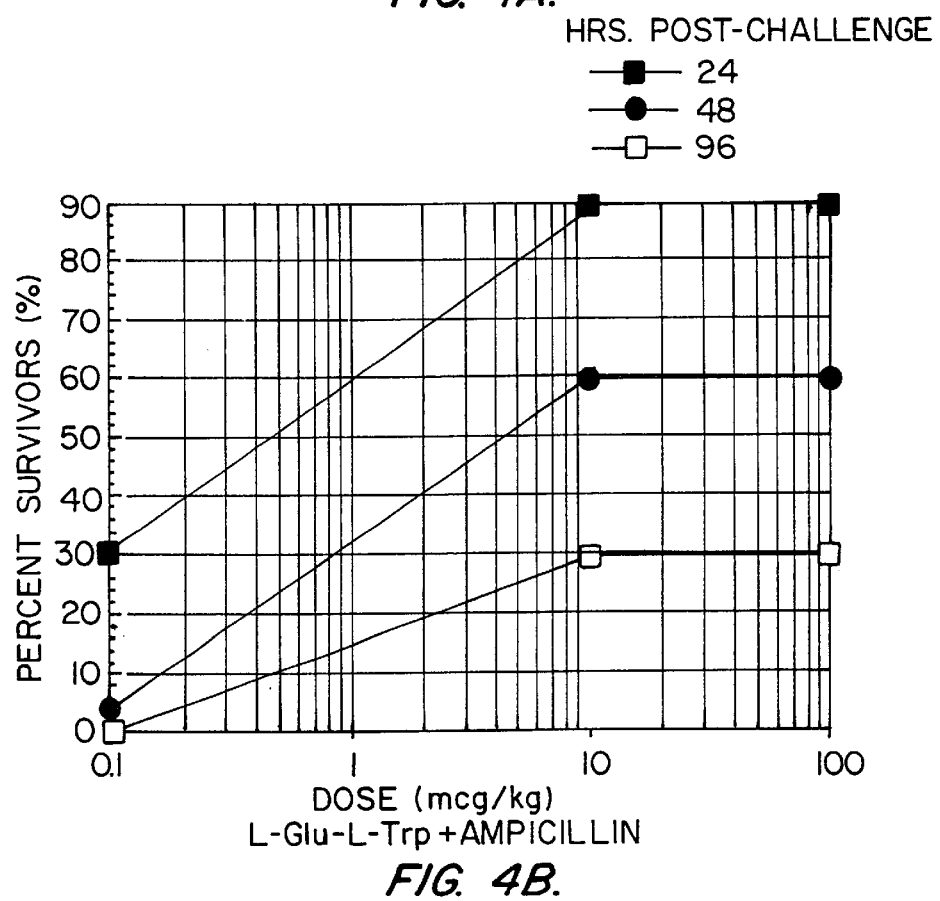

The results obtained in expanded dose-response studies of single agent and combined treatment with L-Glu-L-Trp ip and im are presented in FIGS. 3C, 3D, 3E, and 3F. The results confirm and extend those presented in TABLE 68. L-Glu-L-Trp administered by the ip or im routes increased the percentage of animals surviving challenge with a lethal number of *Staphylococcus aureus*. The experimental protocol disclosed in EXAMPLE 34 was repeated three times with substantially the same results. One of the three experimental iterations utilized *S. aureus* (ATCC 33593) to control for possible theoretical variations in the laboratory strain of Staphylococci used in the other studies. No difference was noted between the results obtained with ATCC 33593 and the laboratory staphylococcal strain. Additional studies of protection afforded to mice by different routes of delivery of L-Glu-L-Trp are summarized in TABLE 69.

TABLE 69

L-Glu-L-Trp Treatment: Survival Rate (%) as a Function of Time and Route of Delivery

| Group | Glu-Trp Dose (μg/kg) | Route of Therapy[a] | | | |
|---|---|---|---|---|---|
| | | ip | im | sc | in |
| Saline Control | 0 | ns | ns | ns | ns |
| L-Glu-L-Trp | 1 | * | ns | ns | — |
| | 3 | * | ns | ns | — |
| | 10 | † | * | * | — |
| | 30 | † | * | * | — |
| | 100 | † | † | † | — |
| | 300 | † | † | † | ns |
| | 1000 | † | † | † | * |
| | 2000 | — | — | — | * |
| | 4000 | — | — | — | * |
| | 8000 | — | — | — | ns |
| L-Glu-L-Trp + Ampicillin | 1 | * | ns | * | — |
| | 3 | * | * | ns | — |
| | 10 | * | ns | ns | — |
| | 30 | * | * | ns | — |
| | 100 | † | * | * | — |
| | 300 | † | * | * | * |
| | 1000 | † | † | * | * |
| | 2000 | — | — | — | ns |
| | 4000 | — | — | — | ns |
| | 8000 | — | — | — | ns |

[a]"ns", no statistically significant effect on mean survival time or death rate;
*statistically significant (p < 0.05) effect on mean survival time;
†statistically significant (p < 0.05) effect on death rate
— not tested.

The duration of the prophylactic effects of L-Glu-L-Trp were investigated by administering therapy ip at doses of 1 μg/kg, 10 μg/kg, 100 μg/kg, or 1000 μg/kg (alone or in combination with Ampicillin) at 120 hrs., 72 hrs., 48 hrs., 24 hrs., or 1 hr. before staphylococcal challenge. Survival was evaluated (as above) at 24, 48, and 72 hrs. after challenge with an $LD_{100}$ dose of Staphylococci. Administering L-Glu-L-Trp (alone) as a single injection ip 24 hours before bacterial challenge resulted in more surviving animals than if pretreatment was at 1, 48, or 72 hrs. Combination therapy with L-Glu-L-Trp and Ampicillin (ip) was also most effective when administered 24 hours before the bacterial challenge. When combination therapy (L-Glu-L-Trp+ Ampicillin) was administered im, rather than ip, at 120 hrs., 72 hrs., or 48 hrs. before bacterial challenge, a similar percentage of survival resulted, and this was greater than that achieved by administering the prophylactic treatment 1 hr before bacterial challenge.

The affects of administering multiple prophylactic doses of single agent (L-Glu-L-Trp) or combination therapy (i.e., Ampicillin) was investigated by treating ip (or im) at 72, 48, and 24 hrs. before bacterial challenge. Survival was assessed (as above) at 24, 48, and 72 hrs. after challenge with an $LD_{100}$ dose of Staphylococci. The multiple treatment regimen gave significantly higher (p<0.05) survival than a single treatment dose at 72, or 48, or 24 hrs. for either single agent or combined therapy, and multiple injections im resulted in higher survival that if the injections were administered ip.

The therapeutic efficacy of L-Glu-L-Trp was also investigated in the same experimental animal model of acute bacterial infection by initiating intraperitoneal infection in mice with an $LD_{100}$ dose of Staphylococci, and then initiating treatment 1 hour later with an ip injection of dipeptide, or dipeptide and antibiotic (i.e., ampicillin). The results of these studies are summarized in TABLE 70.

TABLE 70

Effects of Intraperitoneal Therapeutic Treatment with L-Glu-L-Trp on Survival Rate (%) of Mice as a Function of Time After Induction of Acute Peritonitis by Injection of *Staphylococcus aureus*

| Group | Glu-Trp Dose (µg/kg) | Percentage Survivors: Hours After Injection | | |
|---|---|---|---|---|
| | | 24 | 48 | 72 |
| Saline Control | 0 | 31.5 | 3.7 | 0 |
| L-Glu-L-Trp | 0.01 | 16.7 | 0 | 0 |
| | 0.1 | 5.6*† | 0† | 0 |
| | 1 | 27.8† | 5.6† | 0† |
| | 10 | 66.7* | 38.9* | 16.7* |
| | 100 | 66.7* | 55.6* | 33.3* |
| Ampicillin Control | 1 MED | 75.0* | 44.4* | 30.6* |
| L-Glu-L-Trp + | 10 | 88.3* | 61.1* | 33.3*† |
| Ampicillin | 100 | 88.9* | 61.1* | 50.0*† |

*statistically significant at the p < 0.05 level in comparison with the saline control values;
†statistically significant (p < 0.05) as compared to the Ampicillin-treatment control;
‡statistically significant (p < 0.05) compared with the corresponding dosage of L-Glu-L-Trp without Ampicillin.

The results presented in TABLE 70 shows a dose-response relationship between the amount of L-Glu-L-Trp administered ip and the survival of animals challenged with a lethal dose of *Staphylococcus aureus*. Combination therapy with L-Glu-L-Trp and antibiotic (i.e., Ampicillin) proved more effective than single agent therapy (i.e., L-Glu-L-Trp alone), and again exhibited a dose-response relationship between treatment dose and survival.

EXAMPLE 35

Effects of Synthetic Peptide L-Glu-L-Trp on Hematopoietic Activity of Bone Marrow The effects of L-Glu-L-Trp on bone marrow hematopoietic activity was investigated in 5-fluorouracil (5-FU) immunosuppressed CBA mice. Mice were treated with a dose schedule of 5-FU determined empirically to be sufficient to decrease the absolute number of bone marrow cells and peripheral blood leukocytes by about 50% on day 10–14. Treatment with L-Glu-L-Trp was initiated on day 10, and 1 µg/kg was administered ip daily on that day and each of the following 4 days. Bone marrow and peripheral blood cell populations were quantified on day 15.

TABLE 71

Effects of L-Glu-L-Trp Treatments on Bone Marrow Cells in 5-FU Immunosuppressed CBA Mice.

| Cell Type | Normal Control (untreated) | Negative Control (5-FU only) | Experimental (5-FU + L-Glu-L-Trp Therapy) |
|---|---|---|---|
| Myelokaryocytes: | | | |
| Total Cells x 10⁶/mg: | 2.44 | 1.38 | 1.41 |
| (% of Normal Control Value): | (100%) | (57%) | (58%) |
| Reticular cells:   %: | 0.8 | 0.6 | 0.7 |
| Total Cells x 10³/mg: | 19.6 | 8.3 | 9.8 |
| (% of Normal Control Value): | (100%) | (42%) | (50%) |
| Non-differentiated blast cells:   %: | 2.0 | 2.3 | 2.2 |
| Total Cells x 10³/mg: | 48.7 | 31.7 | 31.0 |
| (% of Normal Control Value): | (100%) | (65%) | (64%) |
| Myeloblasts:   %: | 3.9 | 6.7 | 5.0 |
| Total Cells x 10³/mg: | 95.3 | 92.4 | 70.6 |
| (% of Normal Control Value): | (100%) | (97%) | (74%) |
| Promyeloblasts:   %: | 2.8 | 4.9 | 3.6 |
| Total Cells x 10³/mg: | 68.3 | 67.6 | 50.8 |
| (% of Normal Control Value): | (100%) | (99%) | (74%) |
| Myelocytes + Neutrophil Metamyelocytes:   %: | 5.8 | 3.4 | 4.0 |
| Total Cells x 10³/mg: | 141.5 | 46.9 | 56.4 |
| (% of Normal Control Value): | (100%) | (33%) | (40%) |
| Stab + Seg. neutrophils:   %: | 41.9 | 13.1 | 24.9 |
| Total Cells x 10³/mg: | 1022.4 | 180.8 | 351.0 |
| (% of Normal Control Value): | (100%) | (18%) | (34%) |
| Eosinophils:   %: | 1.0 | 1.4 | 1.1 |
| Total Cells x 10³/mg: | 24.4 | 19.3 | 15.6 |
| (% of Normal Control Value): | (100%) | (79%) | (64%) |
| Lymphocytes:   %: | 28.8 | 52.5 | 43.9 |
| Total Cells x 10³/mg: | 702.8 | 717.6 | 618.9 |
| (% of Normal Control Value): | (100%) | (102%) | (88%) |
| Monocytes:   %: | 2.4 | 3.0 | 2.5 |
| Total Cells x 10³/mg: | 58.5 | 41.4 | 35.3 |
| (% of Normal Control Value): | (100%) | (71%) | (60%) |
| Megakaryocytes:   %: | 0.4 | 0.2 | 0.3 |
| Total Cells x 10³/mg: | 9.8 | 2.9 | 4.2 |
| (% of Normal Control Value): | (100%) | (29%) | (43%) |
| Erythroblasts:   %: | 1.9 | 2.3 | 2.1 |
| Total Cells x 10³/mg: | 46.4 | 31.7 | 29.6 |
| (% of Normal Control Value): | (100%) | (68%) | (64%) |
| Erythroid cells:   %: | 9.4 | 9.9 | 9.7 |
| Total Cells x 109³/mg: | 229.4 | 136.6 | 136.0 |
| (% of Normal Control Value): | (100%) | (60%) | (59%) |

The results presented in TABLE 71 show that the 5-FU dose schedule reduced the total number of all precursor cell types in the bone marrow except myeloblasts and promyeloblasts, and the results presented in TABLE 72 show that peripheral blood leukocytes were reduced to 44% of normal. In the bone marrow (TABLE 71), treatments with L-Glu-L-Trp resulted in: i) an increase in the numbers of myelocytes/neutrophils, stab and segmented neutrophils, and megakaryocytes; ii) no marked changes in the total numbers of myelokaryocytes, reticular cells, monocytes, erythroblasts, and erythroid cells; and, iii) a decrease in the absolute numbers of myeloblasts, promyeloblasts, eosinophils, and lymphocytes. In the peripheral blood (TABLE 72) the following observations were recorded: i) the total number of neutrophils increased (i.e., in parallel with the observed increase in bone marrow neutrophils); ii) the absolute number of monocytes dropped slightly, but insignificantly, since the percentage of monocytes in peripheral blood was about 2–3% before and after treatment; and, iii) the total number of peripheral blood lymphocytes increased (i.e., in parallel with the observed decrease in bone marrow lymphocytes). The observed decrease in bone marrow lymphocytes and increase in peripheral blood lymphocytes was consistent with L-Glu-L-Trp mobilization of these cells into the peripheral blood. The effects of the L-Glu-L-Trp treatment on other peripheral blood leukocyte populations in the 5-FU immunosuppressed mice are summarized in TABLE 72.

TABLE 72

Peripheral Blood Leukocyte Populations in 5-FU Suppressed CBA Mice Treated with L-Glu-L-Trp

| Cell Type | Normal Control (untreated) | Negative Control (5-FU only) | Experimental (5-FU + L-Glu-L-Trp Therapy) |
|---|---|---|---|
| Peripheral Blood Leukocytes: Total Cells × $10^9$/L: | 5.72 | 2.51 | 2.98 |
| (% of Normal Control Value): | (100%) | (44%) | (52%) |
| Lymphocytes: %: | 47.3 | 83.9 | 41.9 |
| Total Cells × $10^9$/L: | 2.71 | 2.10 | 2.52 |
| (% of Normal Control Value): | (100%) | (78%) | (93%) |
| Stab. Neutrophils: %: | 16.1 | 3.7 | 7.9 |
| Total Cells × $10^9$/L: | 0.92 | 0.09 | 0.24 |
| (% of Normal Control Value): | (100%) | (10%) | (26%) |
| Segmented Neutrophils: %: | 33.9 | 3.3 | 14.6 |
| Total Cells × $10^9$/L: | 1.93 | 0.08 | 0.43 |
| (% of Normal Control Value): | (100%) | (4%) | (22%) |
| Monocytes: %: | 1.86 | 3.35 | 2.5 |
| Total Cells × $10^9$/L: | 0.11 | 0.08 | 0.02 |
| (% of Normal Control Value): | (100%) | (73%) | (18%) |
| Eosinophils: %: | 0.2 | 0.2 | 0.3 |
| Total Cells × $10^9$/L: | 0.01 | 0.01 | 0.01 |
| (% of Normal Control Value): | (100%) | (100%) | (100%) |
| Blast Cells: %: | 0 | 5.2 | 0.3 |
| Total Cells × $10^9$/L: | 0 | 0.13 | 0.01 |

It is noteworthy that treatments with L-Glu-L-Trp were observed to increase the numbers of bone marrow megakaryocytes and neutrophils and also peripheral blood neutrophils, since these changes may provide an immunosuppressed subject an increased number of peripheral blood platelets and an increased measure of innate resistance to infection.

EXAMPLE 36

Effects of Synthetic Peptide L-Glu-L-Trp on Immune Status in Immunocompromised Rats An immunocompromised state was established over a period of 80 days in experimental rats by administration of cortisone acetate at a dosage of 25 mg/kg twice weekly with tetracycline hydrocholoride po in drinking water. In the experimental group, L-Glu-L-Trp was administered in three treatment courses, each course consisting of 10 daily im injections of 10 μg/kg or 100 μg/kg, and each course of treatment separated from the next course by a 1 month interval. In the control group, saline was administered in the same three treatment course schedule. Differential blood counts were conducted on day 0 (Normal Control), day 59, and day 79 of the study. L-Glu-L-Trp treatment at dosages of both 10 μg/kg and 100 μg/kg significantly p<0.05) increased the number of leukocytes, monocytes, and lymphocytes in the peripheral blood of cortisone-suppressed rats relative to the saline treated controls. Results obtained with the 10 μg/kg treatment dose (presented in TABLE 73) were not markedly different than those obtained with the 100 μg/kg dose.

TABLE 73

Effects of L-Glu-L-Trp Treatments on Peripheral Blood Leukocytes in Immunocompromised Cortisone Suppressed Rats.

| Cell Type | Saline Control Day 0 | Saline Control Day 59 | Saline Control Day 79 | L-Glu-L-Trp Treatment (10 μg/kg) Day 59 | L-Glu-L-Trp Treatment (10 μg/kg) Day 79 |
|---|---|---|---|---|---|
| Leukocytes: Total Cells × $10^9$/L: | 16.5 ± 1.3 | 10.5 ± 0.6* | 5.4 ± 0.6* | 12.4 ± 1.8 | 8.06 ± 0.9*† |
| (% of Normal Control Value): | (100%) | (64%) | (33%) | (75%) | (49%) |
| Stab Neutrophils: %: | 3.9 ± 0.9 | 6.9 ± 1.3 | 7.6 ± 1 | 4.7 ± 0.6 | 4.4 ± 0.7† |
| Total Cells × $10^9$/L: | 0.6 ± 0.2 | 0.7 ± 0.1 | 0.4 ± 0.1 | 0.6 ± 0.1 | 0.35 ± 0.1 |
| (% of Normal Control Value): | (100%) | (117%) | (67%) | (100%) | (58%) |
| Segmented Neutrophils: %: | 27 ± 0.6 | 57.7 ± 2* | 56 ± 2* | 26.7 ± 1† | 24.6 ± 1.3† |
| Total Cells × $10^9$/L: | 4.5 ± 0.4 | 6 ± 0.4 | 3 ± 0.3* | 3.3 ± 0.4† | 2 ± 2*† |
| (% of Normal Control Value): | (100%) | (133%) | (67%) | (73%) | (44%) |
| Eosinophils: %: | 2.6 ± 0.5 | 2.4 ± 0.6 | 6.4 ± 0.8* | 4.3 ± 0.4† | 4 ± 0.9 |
| Total Cells × $10^9$/L: | 0.4 ± 0.1 | 0.3 ± 0.1 | 0.3 ± 0.1 | 0.6 ± 0.1 | 0.3 ± 0.1 |
| (% of Normal Control Value): | (100%) | (75%) | (75%) | (150%) | (75%) |
| Basophils: %: | 0.4 ± 0.2 | 0.7 ± 0.2 | 0.3 ± 0.2 | 0.4 ± 0.2 | 0.3 ± 0.2 |
| Total Cells × $10^3$/mg: | 0.07 ± 0.04 | 0.07 ± 0.02 | 0.02 ± 0.01 | 0.05 ± 0.03 | 0.02 ± 0.02 |
| (% of Normal Control Value): | (100%) | (100%) | (29%) | (71%) | (29%) |
| Monocytes: %: | 4.7 ± 0.6 | 3.7 ± 0.6 | 8.7 ± 1.3* | 7 ± 0.9*† | 8 ± 0.8* |
| Total Cells × $10^9$/L: | 0.7 ± 0.1 | 0.4 ± 0.1* | 0.5 ± 0.1* | 0.92 ± 0.2† | 0.7 ± 0.1 |
| (% of Normal Control Value): | (100%) | (57%) | (71%) | (128%) | (100%) |
| Lymphocytes: %: | 61 ± 1.3 | 29 ± 2* | 21 ± 2* | 57 ± 1.5† | 59 ± 2† |
| Total Cells × $10^9$/L: | 10 ± 0.8 | 3 ± 0.3* | 1.1 ± 0.1* | 7 ± 1† | 4.7 ± 1† |
| (% of Normal Control Value): | (100%) | (30%) | (2%) | (11%) | (7.7%) |

*statistically significant difference (p < 0.05) from the values recorded on day 0;
†statistically significant difference (p < 0.05) from the values recorded in saline control group on day 59; day 0 values for animals in the L-Glu-L-Trp treated group were not statistically different from those in the saline treated group.

EXAMPLE 37

Stimulation of Natural Killer Cell Cytotoxic Activity by L-Glu-L-Trp Treatments Natural killer cells (i.e., NK lymphocytes) are considered by many to be one element of innate resistance to infection. L-Glu-L-Trp was tested under GLP conditions for its ability to effect a change in the activity of splenic natural killer (NK) lymphocytes. L-Glu-L-Trp was injected daily on each of 7 consecutive days ip into C3H/HeJ mice at a dose of 1, 10, or 1000 μg/kg (0.5 mL/mouse). Cyclophosphamide (50 μg/kg), or saline, were used as reference treatments. On day 8, spleen cells were prepared and diluted to $5 \times 10^6$ cells/ml. YAC-1 target cells were suspended at $5 \times 10^6$ cells/mL in Tris buffer containing 200 μCi/ml of $^{51}$Cr. After a 1 hour incubation at 37° C. the YAC-1 cells (target cells) were washed 3 times, and resuspended at a concentration of $1 \times 10^5$ cells/mL. Each 100 μL aliquot of target cells was mixed with a 100 μL aliquot of splenocytes (effector cells) in a well of a 96 well microtiter plate. Spontaneous release from the target cells was determined by incubating without effector cells; maximal release was determined by lysing target cells with 1 N HCl. Cytotoxic killing of target cells was determined after 4 hours incubation at 37° C. Specific $^{51}$Cr-release was calculated according to the following formula:

$$\frac{(CPM \text{ experimental release}) - (CPM \text{ spontaneous release})}{(CPM \text{ max. release}) - (CPM \text{ spontaneous release})} \times 100\%$$

The mean value for each group of 10 animals. The results are presented in TABLE 74.

TABLE 74

NK Activity of Splenocytes from L-Glu-L-Trp Treated Mice.

| Group | Treatment | Dose | % Cytotoxicity (mean +/- S.D.) | Change (%)* |
|---|---|---|---|---|
| 1 | Saline | 0 | 8.5 ± 2.0 | — |
| 2 | Glu-Trp | 1 | 10.7 ± 14 | 25 ↑ |
| 3 | | 10 | 14.3 ± 1.7 | 67 ↑ |
| 4 | | 1000 | 14.9 ± 2.9 | 75* ↑ |
| 5 | Cyclophosphamide | 50 | 6.4 ± 0.7 | −25 ↓ |

*statistically significant compared to saline control; $p < 0.05$

The results presented in TABLE 74 show that 7 days treatment with L-Glu-L-Trp increased the apparent NK cytotoxic activity of murine splenocytes by 25 to 75%. As expected, cyclophosphamide treatment decreased NK activity.

EXAMPLE 38

Stimulation of Anti-Viral Activity by Treatments with L-Glu-L-Trp

Innate mechanisms of anti-viral immunity are important to survival of the host. The Rauscher murine leukemia virus (MuLV) is an example of a highly virulent animal retrovirus infection, first isolated and characterized by Dr. Rauscher from BALB/c mouse tissues in 1962. Although anti-viral agents may exhibit viricidal activity in this model, many (if not most) immunomodulatory compounds lack significant activity in this animal model. The virus employed in present GLP/blinded study was a murine leukemia complex known to induce progressive erythroleukemia in mice (i.e., Rauscher MuLV and replication-defective Rauscher spleen focus-forming virus). Disease manifested within about 6 days with death by about 50 days. Measurements of splenomegaly, blood reverse transcriptase, virus plaque assays (i.e., XC-plaque assay for viremia using SC-1 host cells) and serum anti-viral antibody titers were used to assess infection. Spleens achieved about 2.0 grams in weight within 21 days of infection, as compared with a normal spleen weights in an uninfected animals of about 0.1 gram.

Mice were inoculated with Rauscher MuLV complex (0.1 ml/$7.8 \times 10^4$ PFU/mL) on day 0 and sacrificed on day 21. Test groups were comprised of 10 mice and control groups 6 mice. Control articles included saline and AZT (in drinking water at about 1.25 mg/mouse/day≈63 mg/kg/day/mouse). L-Glu-L-Trp was administered ip on each of 5 consecutive days to different groups of animals at doses of either 1, 10, 50, 100 or 500 μg/kg. A non-infected group of mice was also sacrificed on day 21 to provide normal control values.

TABLE 75

Stimulation of an Anti-Viral Response to Rauscher MuLV in Mice Treated with L-Glu-L-Trp

| | | | | Anti-Viral Activity | |
|---|---|---|---|---|---|
| Group | Treatment* | Dose (mg/kg) | Spleen Weight (mean ± SD)* | Reduction Splenomegaly (%) | Viremia ($\log_{10}$PFU/ml ± SEM) |
| 1 (non-infected) | None | 0 | 0.13 ± 0.02 | — | — |
| 2 | None | 0 | 0.35 ± 0.1 | — | — |
| 3 | Saline | 0 | 0.4 ± 0.15 | — | — |
| 4 | AZT | 200 | 0.31 ± 0.09 | 46 | ND |
| 5 | | 100 | 0.29 ± 0.02 | 52 | ND |
| 6 | | 50 | 0.35 ± 0.17 | 33 | ND |
| 7 | | 25 | 0.31 ± 0.05 | 46 | ND |
| 8 | Poly(IC) | 20 | 0.37 ± 0.22 | 27 | ND |
| 9 | Saline | 0 | 0.62 ± 0.36 | — | 4.06 ± 0.369 |

TABLE 75-continued

Stimulation of an Anti-Viral Response to Rauscher MuLV
in Mice Treated with L-Glu-L-Trp

| | | | | Anti-Viral Activity | |
|---|---|---|---|---|---|
| Group | Treatment* | Dose (mg/kg) | Spleen Weight (mean ± SD)* | Reduction Splenomegaly (%) | Viremia ($log_{10}$PFU/ml ± SEM) |
| 10 | Poly(IC) | 20 | 0.72 ± 0.29 | −78 | ND |
| 11 | Glu-Trp | 5 | 0.44 ± 0.15 | 6 | 3.43 ± 0.368[†] |
| 12 | | 1.75 | 0.45 ± 0.39 | 3 | ND |
| 13 | | 0.5 | 0.48 ± 0.3 | −12 | 3.31 ± 0.39[†] |
| 14 | | 0.17 | 0.42 ± 0.26 | 12 | ND |
| 15 | | 0.05 | 0.36 ± 0.11 | 30 | 2.99 ± 0.28[†]** |
| 16 | | 0.02 | 0.42 ± 0.32 | 12 | ND |
| 17 | | 0.005 | 0.47 ± 0.29 | −3 | 3.25 ± 0.27[†] |
| 18 | | 0.002 | 0.49 ± 0.31 | −9 | ND |

*Groups 4–8 were treated with AZT or poly(IC) on days 0, 1, 2, 3, and 4; Groups 10–18 were treated on days −2, −1, 0, +1, and +2 with the indicated compounds;
**1 log reduction in virus titer is about 99% virus kill;
[†]Probability Mann-Whitney U Test as follows: namely, group 11 ($P^3$ = 0.315); group 13 ($P^3$ = 0.315); group 15 ($P^3$ = 0.036); group 16 ($P^3$ = 0.143).

The results presented in TABLE 75 show that treatment with L-Glu-L-Trp significantly decreased viremia (i.e., at a dosage of 50 µg/kg), even in animals exhibiting splenomegaly.

EXAMPLE 39

Stimulation of Changes in Cyclic Nucleotides (cAMP/cGMP) Following Treatments with L-Glu-L-Trp Normal guinea pigs (10/group) were treated with 10 µg/kg L-Glu-L-Trp daily on each of five consecutive days and then spleens were removed, lymphocytes isolated, and cyclic AMP and GMP levels determined. To evaluate the effects of L-Glu-L-Trp on immune cells in the face of an ongoing anaphylactic response, splenic lymphocytes were isolated from guinea pigs sensitized for anaphylaxis, or following induction of anaphylactic shock.

tized animals (Group 3) as well as anaphylactic animals (Group 5). The results suggest a significant stimulatory effect of L-Glu-L-Trp on lymphocytes in anaphylactic animals. Anaphylaxis is known to be accompanied by release of negative regulators of lymphocyte and macrophage function. Evidence of a stimulatory effect of L-Glu-L-Trp treatments in this model is presently considered highly suggestive of a possible therapeutic efficacy in a variety of acute and chronic disease settings where lymphocyte and monocyte function is known to be down-regulated, e.g., septic shock, acute respiratory distress syndrome, asthma, and tuberculosis infection. Direct testing of efficacy in a tuberculosis animal model follows in Example 40, below.

EXAMPLE 40

Treatment of Murine *Mycobacterium bovis* Infection with L-Glu-L-Trp

The effects of L-Glu-L-Trp treatments on anti-bacterial cellular immunity were evaluated using a murine model of

TABLE 76

L-Glu-L-Trp Induced Increases in Splenic cAMP and cGMP

| | | | | Dose | Cyclic Nucleotide Content (pmole/$10^7$ cells) | | |
|---|---|---|---|---|---|---|---|
| Group | Sensitized | Anaphylaxis | EW* | (µg/kg) | cAMP | cGMP | cAMP/cGMP |
| 1 | − | − | − | 0 | 56 ± 6 | 1.8 ± 0.2− | 31 ± 3 |
| 2 | + | − | − | 0 | 157 ± 13* | 5.7 ± 0.3* | 27 ± 3 |
| 3 | + | − | + | 10 | 250 ± 30** | 11.2 ± 0.9** | 22 ± 2 |
| 4 | + | + | − | 0 | 117 ± 10* | 4.2 ± 0.3* | 28 ± 2 |
| 5 | + | + | + | 10 | 210 ± 30** | 7.9 ± 0.5** | 26 ± 3 |

*p < 0.05 compared with Group #1;
**p < 0.05 compared with Group #2;
†p < 0.05 compared with Group #4

The results presented in TABLE 76 show, on a macroscopic level, that: (a) the intensive immunization scheme required to induce sensitization for anaphylaxis induced a significant increase in the total levels of cAMP and cGMP in splenic lymphocytes, i.e., control animals in Group 2; and, (b) induction of anaphylaxis (Group 4) significantly decreased the levels of cAMP from the levels in the sensitized animals (Group 2). Treatments with L-Glu-L-Trp significantly elevated the levels of cAMP and cGMP in sensimycobacterial infection. Mice were inoculated iv with 0.1 mg (dry weight) of a mouse-passaged and adapted virulent laboratory strain of *M. bovis*. L-Glu-L-Trp was administered daily and the effects compared with those achieved with isoniazid (INH; also administered daily). Doses of L-Glu-L-Trp were 1, 10 and 100 µg/kg ip and INH was administered at 5 mg/kg sc. Survival was assessed out to 62 days post-infection. The treatment schedule included prophylactic and therapeutic regimens as follows: (i) prophylactic/ therapeutic treatments with L-Glu-L-Trp consisted of administering the test dose ip daily on each of 5 consecutive days of each week of the study starting 3 days before infecting the animals; and, (ii) therapeutic treatments with L-Glu-L-Trp consisted of administering the test dose ip daily on each of 5 consecutive days of each week starting at week 3 of the study. The survival statistics at 27 days are presented in TABLE 77.

hours before inoculating the yeast. At least 300 yeast cells (about 10 microscopic fields) were evaluated. The total number of fungal cell, number of non-germinated forms, and number of cells were germ tubes were all determined. Results are expressed as the mean percentage of yeast cells with germ tubes±SEM for each group of animals. A value (Student's t-test) of $p<0.05$ was considered statistically significance.

TABLE 77

Survival of Mice after Infection with a Lethal Dose of *M. bovis* and L-Glu-L-Trp Therapy

| Group | Isoniazid | Therapy[a] | EW[b] | D

TABLE 79

Effects of L-Glu-L-Trp on Mean Survival Time in Mice with Disseminated Candidiasis

| Group | Ampho-tericin | Therapy[a] | EW[b] | Dose (µg/kg) | No./grp[c] | Survival (days)[d] | | | | | Kidney Infection |
|---|---|---|---|---|---|---|---|---|---|---|---|
| | | | | | | Mean | % 6d | $X^2$ | % 8d | $X^2$ | |
| 1 | – | None | – | 0 | 20 | 5.4 ± 1.6 | 30 | – | 0 | – | 100% |
| 2 | – | PDR | + | 1 | 10 | 6.2 ± 2.0 | 50 | ns | 20 | <0.05 | 58% |
| 3 | – | PDR | + | 10 | 10 | 6.4 ± 2.2 | 60 | ns | 20 | <0.05 | 58% |
| 4 | – | PDR | + | 100 | 10 | 7.9 ± 1.9 | 80 | <0.05 | 40 | <0.05 | 75% |
| 5 | – | PDR | + | 300 | 10 | 7.8 ± 2.1 | 80 | <0.05 | 50 | <0.05 | 58% |
| 6 | – | TDR | + | 1 | 10 | 7.3 ± 2.7 | 60 | ns | 50 | <0.05 | 67% |
| 7 | – | TDR | + | 10 | 10 | 6.2 ± 2.2 | 50 | ns | 30 | <0.05 | 50% |
| 8 | – | TDR | + | 100 | 10 | 7.8 ± 1.9 | 80 | <0.05 | 50 | <0.05 | 75% |
| 9 | – | TDR | + | 300 | 10 | 7.8 ± 2.1 | 80 | <0.05 | 40 | <0.05 | 67% |

[a]PDR, prophylactic treatment regimen; TDR, therapeutic treatment regimen;
[b]EW = L-Glu-L-Trp.;
[c]No./Tot. = number of survivors/total evaluable animals;
[d]$X^2$ = Chi square significance for Groups 2–8 as compared with Control Group 1;
[e]kidney infection = greater than 8 logs of C. albicans cultured from kidney samples removed from mice in a parallel group of 12 animals on day 5.

The results presented in TABLE 79 show that prophylactic and therapeutic treatments with L-Glu-L-Trp significantly increased the number of animals surviving at days 6 and 8, and reduced the incidence of kidney infection at day 5.

EXAMPLE 42

Treatment of Rat *Pneumocystis carinii* Infection with L-Glu-L-Trp

Corticosteroids were administered to rats to induce an immunocompromised state in which an opportunistic infection with *Pneumocystis carinii* could be established. The immunocompromised state was induced by administering cortisone acetate im twice weekly at a dose of 25 mg/kg over the entire 12 week course of the study. *Pneumocystis carinii* lung infection was initiated by intranasal instillation on day 0. Prophylactic tetracycline was administered po in the drinking water (500 mg/mL), and peripheral blood differential counts were monitored over the next 12 weeks. In control (untreated) Pneumocystis-infected animals, differential counts, body weight, and lymphocyte counts began dropping at about 30–39 days and lung infection was evident histologically by about day 60–69. At day 80, tetracycline treatment was discontinued in all groups. By day 80 in this animal model, mean body weight of the animals had dropped by approximately 30% from the values recorded on day 0. Groups were comprised of 15 rats each.

L-Glu-L-Trp treatments were administered according to the following protocol: 10 consecutive daily im injections of 10 µg/kg or 100 µg/kg of L-Glu-L-Trp on days 0 through 9, 30 through 39, and 60 through 69 of the study. Differential cell counts in peripheral blood (TABLE 80) and lung histology (i.e., with enumeration of the number of *P. carinii*/10 microscopic fields—at 400x magnification) were used to monitor the course of the opportunistic infection.

TABLE 80

Differential Cell Counts on Peripheral blood obtained from Mice at 79 Days after Lung Infection with a Lethal Dose pf *Pneumocystis carinii* and Treatments with L-Glu-L-Trp.

| Group | EW[a] | Dose (µg/kg) | Total Leukocytes | | Lymphocytes | | Neutrophils | | Lung |
|---|---|---|---|---|---|---|---|---|---|
| | | | (×10⁶/ml) | (% normal)[b] | (×10⁶/ml) | (% normal)[b] | (×10⁶/ml) | (% normal)[b] | (bacteria)[c] |
| 1 | – | 0 | 5.4 ± 1.5 | 31 | 1.1 ± 0.4 | 11 | 3.0 ± 0.9 | 62 | 160 ± 80 |
| 2 | + | 10 | 8.1 ± 2.3 | 47 | 4.7 ± 1.2 | 45 | 2.0 ± 0.7 | 41 | 53 ± 32 |
| 3 | + | 100 | 7.8 ± 1.8 | 45 | 4.7 ± 1.4 | 45 | 1.5 ± 0.5 | 31 | 70 ± 33 |

[a]EW = L-Glu-L-Trp treatment;
[b]% normal = % of normal leukocyte values recorded on day 0;
[c]Lung bacteria = mean ± S.E. number of *P. carinii* bacteria per 10 sections (i.e., at a magnification of 400X).

The results presented in TABLE 80 show that long-term cortisone administration induced the desired reduction in peripheral blood leukocytes (i.e., 31% of normal), lymphocytes (i.e., 47% of normal) and neutrophils (i.e., 62% of normal), and resulted in establishment of an opportunistic lung infection. Treatments with L-Glu-L-Trp helped maintain leukocyte (i.e., 45–47% of normal) and lymphocyte counts (i.e., 45% of normal), but not systemic neutrophil counts. Numbers of lung bacteria were reduced by L-Glu-L-Trp treatments at the 10 µg/kg and 100 µg/kg doses (i.e., to about 33% and 43%, respectively, of the saline treated control Group 1).

EXAMPLE 43

Stimulation of Anti-Tumor Immunity by Treatment with L-Glu-L-Trp

Anti-tumor activity of L-Glu-L-Trp was evaluated using the murine Sarcoma 180 tumor (ATCC CCL-8 CCRF S-180 II) injected at $2\times10^6$ cells/0.1 mL im into each rear flank of Swiss-Webster mice. Groups consisted of 10 animals. L-Glu-L-Trp was administered in a single 0.1 mL dose of either 10 µg/kg, 75 µg/kg, 250 µg/kg or 1000 µg/kg. Tumor size was evaluated by surgically removing and weighing the affected limbs, and comparing the weight with the weight of normal control (non-tumor) limbs. The first prophylactic drug regimen (PDR-1) consisted of 5 consecutive daily ip injections commencing on day -5 and ending of day -1. The second prophylactic drug regimen (PDR-2) consisted of 5 consecutive daily im injections to the left rear flank (tumor site) beginning on day -5 and ending on day -1. Sarcoma 180 cells were injected im on day 0. Saline 0.1 mL served as the negative control.

TABLE 81

Effect of L-Glu-L-Trp Treatments on Sarcoma 180 Bilateral Tumor Size

| Group | Treatment Regimen | Dose (µg/kg) | Leg Weight (g) Left | Leg Weight (g) Right | Mean Tumor Weight[a] Left | Mean Tumor Weight[a] Right | Percent of Control Tumor Weight[b] | |
|---|---|---|---|---|---|---|---|---|
| 1A (normal) | None | 0 | 1.2 ± 0.1 | 1.2 ± 0.2 | 0 | 0 | — | — |
| 1B (tumor) | None | 0 | 3.7 ± 0.6 | 3.5 ± 0.7 | 2.5 | 2.3 | 0 | 0 |
| 2 | PDR-1 | 10 | 4.2 ± 0.9 | 4.1 ± 0.7 | 3.0 | 2.9 | 120 | 126 |
| 3 | PDR-1 | 75 | 4.2 ± 0.8 | 4.2 ± 0.8 | 3.0 | 3.0 | 120 | 130 |
| 4 | PDR-1 | 250 | 3.5 ± 1.0 | 3.1 ± 0.6 | 2.3 | 1.9 | 92 | 83 |
| 5 | PDR-1 | 1000 | 2.5 ± 0.7 | 2.2 ± 0.5 | 1.3 | 1.0 | 52 | 43 |
| 6 | PDR-2 | 10 | 3.6 ± 0.7 | 3.8 ± 0.7 | 2.4 | 2.6 | 96 | 113 |
| 7 | PDR-2 | 75 | 3.6 ± 0.7 | 3.5 ± 0.3 | 2.4 | 3.3 | 96 | 132 |
| 8 | PDR-2 | 250 | 3.0 ± 0.1 | 2.3 ± 0.5 | 1.8 | 1.1 | 72 | 48 |
| 9 | PDR-2 | 1000 | 2.4 ± 0.5 | 2.5 ± 0.5 | 1.2 | 1.3 | 48 | 57 |

[a]Mean Tumor weight = (mean leg weight treated - mean leg weight normal control);
[b]Inhibition = (tumor weight treated/tumor weight control) × 100%

The results presented in TABLE 81 show that prophylactic treatments with L-Glu-L-Trp ip or im at doses of 250 µg/kg and 1000 µg/kg inhibited subsequent im tumor growth. Interestingly, it appeared possible to invoke systemic inhibitor effects from treatments delivered at a local im site, because the im treatments delivered into the left flank inhibited subsequent tumor growth in the right flank (i.e., groups 8 and 9). The results are consistent with stimulation of systemic cell-mediated tumor immune mechanisms.

EXAMPLE 44

Stimulation of DTH Sensitization by Treatment with L-Glu-L-Trp

Effects of L-Glu-L-Trp treatments on cell mediated immunity were evaluated by testing its effects on induction of a delayed-type hypersensitivity response in two different studies involving sensitization of mice to Oxazolone and guinea pigs to tuberculin.

In the first study L-Glu-L-Trp was administered ip at a dose of 10 µg/kg, or 1000 µg/kg one hour before a sensitizing dose of Oxazolone (0.1 mL of a 5% solution) was applied to the abdominal surface of a mouse. Seven days later skin sensitivity was measured by administering 25 µL of a 2% oxazolone solution to the right mouse ear and a sample of the diluent solution, as a control, to the left ear. Ear thickness was measured at 24 hours using a Dyer Model micrometer. Three groups of 10 animals each were tested and the results are summarized in TABLE 82.

TABLE 82

L-Glu-L-Trp Induced DTH Sensitivity to Oxazolone in Mice

| Group | Sensitized | Oxazolone | EW* | Dose (µg/kg) | Mean Ear Thickness ± S.D. (µm) |
|---|---|---|---|---|---|
| 1 | − | + | − | 0 | 17 ± 2 |
| 2 | + | + | + | 10 | 17 ± 1 |
| 3 | + | + | + | 1000 | 24 ± 1 |

The results presented in TABLE 82 show an increase in DTH sensitivity to oxazolone in the group of mice treated with the 1000 µg/mL dose of L-Glu-L-Trp one hour prior to administering antigen.

In the second study, affects of L-Glu-L-Trp on DTH sensitivity were investigated in guinea pigs sensitized to tuberculin. L-Glu-L-Trp was administered ip at 10 µg/kg or 1000 µg/kg on the day of an intradermal sensitization with tuberculin antigen. DTH skin sensitivity was measured on day 10 and day 20, and the results are summarized in TABLE 83.

TABLE 83

L-Glu-L-Trp Induced DTH Sensitivity to Oxazolone in Mice

| Group | tuberculin Sensitized | skin test tuberculin | EW* | Dose (µg/kg) | Mean Skin Test Diameter ± S.D. (mm) Day 10 | Mean Skin Test Diameter ± S.D. (mm) Day 20 |
|---|---|---|---|---|---|---|
| 1 | + | + | − | 0 | 8.7 ± 0.7 | 7.4 ± 0.7 |
| 2 | + | + | + | 10 | 14.4 ± 1.3* | 15.1 ± 1.4* |
| 3 | + | + | + | 1000 | 15.2 ± 1.3* | 13.9 ± 1.1* |

*p < 0.05 compared with Group #1

The results presented in TABLE 83 show that L-Glu-L-Trp induced a statistically significant increase in the DTH response measured to tuberculin antigen as measured on day 10 or day 20 after immunization, and as compared with control tuberculin-sensitized animals.

EXAMPLE 45

Effects of L-Glu-L-Trp on Survival in a Model of LPS Shock

The $LD_{99}$ and $LD_{50}$ values for LPS-induced endotoxic shock (a.k.a. "septic shock") were determined in 8 groups of CBA mice (10 animals per group), using a single ip injection of 1–70 mg/kg LPS (Sigma Chemical Co., St. Louis, Mo.) and a record of mortality at 2 hr. intervals from 0 hrs. to 48 hrs. The mortality results were evaluated using the Litchfield-Wilcoxon's probit analysis method and a computer program written to conduct probit analyses. Having determined these lethal dose values, a prophylactic test regimen was conducted using L-Glu-L-Trp at doses of 10 μg/kg and 100 μg/kg ip delivered daily on each of three consecutive days prior to the ip LPS injection, with the last of the 3 injections being 24 hrs. prior to the LPS challenge. LPS was administered in different groups of animals (10 animals/control group and 11/experimental group) at either the $LD_{50}$ (58 mg/kg) or $LD_{99}$ (153 mg/kg) dose. The results presented in TABLE 84 show the survival of animals at 24 and 48 hrs.

TABLE 84

Survival at 24 hrs. and 30 hrs. After an ip Injection of an $LD_{99}$ Dose of LPS

| Group | Time (hrs.) | Test | Dose (μg/kg) | No. Animals | Survivors | Survivors (%) |
|---|---|---|---|---|---|---|
| 1 | 24 | Saline | 0 | 10 | 1 | 10 |
| 2 | 24 | Glu-Trp | 10 | 11 | 4 | 36 |
| 3 | 24 | Glu-Trp | 100 | 10 | 8 | 80* |
| 1 | 30 | Saline | 0 | 10 | 0 | 0 |
| 2 | 30 | Glu-Trp | 10 | 11 | 1 | 9 |
| 3 | 30 | Glu-Trp | 100 | 10 | 4 | 40* |

*$p < 0.05$

The results presented in TABLE 84 show that there was a statistically significant difference in the number of survivors at the 24 hr. and 30 hr. time points in the animals prophylactically treated with 100 μg/kg of L-Glu-L-Trp.

EXAMPLE 46

Preparation of Analogues, Antagonists and Agonists

The R'-Glu-Trp-R" pharmaceutical compositions of the present invention comprise a therapeutically effective amount of a dipeptide having the general formula R'-X-Tryptophan-R" or a pharmaceutically acceptable salt thereof, wherein X is any naturally-occurring amino acid; and a pharmaceutically acceptable carrier. Generally, X is glutamine, glutamate, leucine, or isoleucine, R' is a free amino group or amide, and R" is a carboxyl, hydroxyl or carbonyl group. Cyclic and polymeric forms of tryptophan-containing dipeptides may also be prepared and tested for activity according to any of the in vitro or in vivo assays identified above.

Up to three R'-X-Trp-R" dipeptide subunits may be joined (e.g., through peptide bonds) to form polymers that can be tested as described above. Polymers having the following formulas are synthesized and tested:

X—Trp—Y—Trp, or

X—Trp—Y—Trp—Z—Trp, or pharmaceutically acceptable salts thereof, wherein "X", "Y", and "Z" may be any naturally-occurring amino acids. X, Y, and Z may be the same or different amino acids. Generally, at least one of X, Y, and Z will be glutamic acid, glutamine, glutamate, or a derivative or analogue thereof.

R'-X-Trp-R" dipeptides and dipeptide polymers may also cyclized and tested. The cyclic forms so synthesized may have 1, 2, or 3 dipeptide subunits, e.g., of the general formula X—Trp, X—Trp—Y—Trp, or X—Trp—Y—Trp—Z—Trp or pharmaceutically acceptable salts thereof, wherein X, Y, and Z is any naturally-occurring amino acid. X, Y, and Z may be the same or different amino acids. Generally, at least one of X, Y, and Z will be glutamic acid, glutamine, glutamate, or a derivative or analogue thereof.

Derivatives of any of the aforementioned dipeptides may also be prepared and tested, e.g., acylated derivatives, amidated derivatives and methylated derivatives.

Other forms of the dipeptide may also be synthesized and tested, including cyclized monomers such as that representatively depicted in Formula I, below:

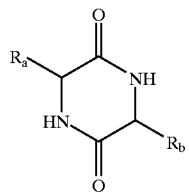

Formula I wherein $R_a$ and $R_b$ are, respectively, the alpha-side chains of Glu and Trp, or linear and/or cyclic polymers of EW dipeptide. The linear polymer is made by conventional peptide synthesis, including Merrifield solid-state peptide methodology (described below). The cyclic monomer and polymers is then prepared by cyclizing the linear peptides using peptide linking agents, e.g., in dilute solutions.

Easily hydrolyzable polypeptides with multimeric repeats of the EW dipeptide, (e.g., di-dipeptides or tri-dipeptides), can also be prepared and tested for activity according to any of the in vitro or in vivo assays identified above. The hydrolyzable polypeptides include e.g., anhydrous chlorides or fluorides. When introduced into aqueous solution the monomeric EW dipeptides are released from the polypeptides by hydrolysis. Multimers include molecules in which two or more EW covalently bonded to a common linker, or in which the two or more EW dipeptides are non-covalently linked together through the linker (e.g., through ion or hydrophobic interactions).

"Molecular mimics" can also be synthesized and tested for activity according to any of the in vitro or in vivo assays identified above., i.e., compounds mimicking and/or exceeding the biological activities of an R'-Glu-Trp-R" dipeptide. The subject molecular mimics generally conform to Formula II, below:

Formula II

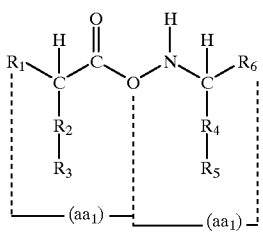

wherein, $R_1$ is a neutral polar, neutral nonpolar, or basic residue selected from a functional group containing a halogen atom such as an amine, amide, amido- and the like, or alternatively, $R_1$ is selected from a functional group containing a straight or branched peptide chain, or straight or branched chain alkyl-, alkoxy-, or cyclic hydrocarbon, such as methyl-, ethyl-, propyl-, isopropyl-, butyl-, isobutyl-, pentyl-, cyclohexyl-, phenoxy-, glycol- and the like, or alternatively, $R_1$ is selected from a hydrophobic or amphipathic residue such as a glycerol-phosphatide or fatty-acyl chain (e.g., phosphatidyl-ehtanolamine, phosphatidyl-choline, phosphatidyl-inositol, butyryl-, lauryl-, myristyl-, undecyl-, and the like) or a glycolipid (e.g., cerebroside, ceramide dihexoside and the like), or one or more hexosyl-residues, (e.g., sucrosyl-, glucosyl-, glucosaminyl-, galactosyl-, galactosaminyl-, lactosyl-, mannosyl-, sorbitolyl-, glycerolyl-, amylosyl- and the like).

One illustrative example of a glycerol-phosphatide multimer is provided in Formula III, below, as a phosphatidyl fatty acid of glycerol: namely, wherein a first EW dipeptide is depicted "$aa_1aa_2$" and a second EW dipeptide "$aa_3aa_4$"; $R_1$ and $R_2$ are "non-interfering residues". The non-interfering residues $R_1$ and $R_2$ may used to stabilize and/or enhance the biological activity of compound of Formula III.

$R_3$ is a negatively charged residue such as a modified carbonyl- residues such as carboxylic acids, carboxylic acid amides, acyl-modified carboxylic acids, carbamates, di-alcohols, aldehydes, and the like.

$R_5$ is an 3-indolyl-like residue such as 3-indolyl-, 3-indolinyl-, 9-purinyl-, 1H-indazole-3yl-, 3-isoindolyl-, 3-indolizinyl-, 3-isoquinolyl-, 3-quinolyl-, and the like.

$R_6$ is an electron donor residues such as acetyl-, alkyl-, or modified carbonyl- residues such as carboxylic acids, carboxylic acid amides, acyl-modified carboxylic acids, carbamates, di-alcohols, aldehydes, or alternatively, one or more cyclic or heterocyclic hydrocarbon rings such as phenyl-, phenoxy-.

Derivatives of R'-Glu-Trp-R" may also be constructed such as lipopeptides having multiple EW residues (e.g., di-, tri-, and tetra-lipopeptides and the like). One illustrative example of a glycerol-phosphatide multimer is provided in Formula III, below, as a phosphatidyl fatty acid of glycerol:

Formula III

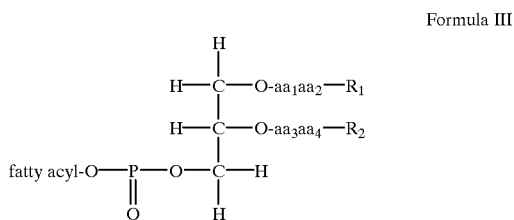

wherein a first EW dipeptide is depicted "$aa_1aa_2$" and a second EW dipeptide "$aa_3aa_4$"; $R_1$ and $R_2$ are "non-interfering residues." The non-interfering residues $R_1$ and $R_2$ may used to stabilize and/or enhance the biological activity of compound of Formula III. "Non-interfering residue" as used herein means any chemical residue that when present in position $R_1$ or $R_6$ of Formula II, or position $R_1$ or $R_2$ of Formula III does not interfere with binding of the subject ligand of the respective formula to a ligand receptor. For example, non-interfering amino acid residues or glycosyl residues may be useful in positions $R_1$ and $R_6$ of Formula I (or positions $R_1$ or $R_2$ of Formula III) to stabilize or enhance the biological activity of the synthetic compound.

Materials and Methods for Examples 1–45
Staphylococcal strains:
Laboratory strains of penicillin-sensitive and -resistant Staphylococci were used in the peritonitis experiments. The resistant strain was methicillin resistant. Penicillin-resistant staphylococcal strain ATCC 33593 was obtained from the American Type Culture Collection, Bethesda, Md.

Antibiotic sensitivity of Staphylococci were determined by doubling-dilution methods with the aid of the semiautomatic MIC-2000 system (Dynatech, USA).

Indices of humoral immunity (e.g., IgG, IgA, IgM) were determined in accordance with the methods recommended by the World Health Organization in 1976. Indices of cellular immunity were determined in accordance with accepted methods published in the Western scientific literature, and in some cases as translated and modified for use with reagents commonly available in the former Soviet Union. Peripheral blood cell differential cell counts were conducted according to routine methods. Lymphocytes were isolated from heparinized peripheral blood on Ficoll-Hypaque ($\delta$1.077; Ficoll-Paque, Pharmacia, Switzerland) or Ficoll-Urotrast. Total T cells were determined by E-rosette formation with ram erythrocytes, and T-helper and T-suppressor subpopulations were determined using indirect immunofluorescence and monoclonal antibodies OKT4 and OKT8 (Ortho, USA). B-lymphocytes were quantitated by EAC-rosetting and surface expression of IgG, IgA, or IgM determined using direct immunofluorescence microscopy and monospecific antibodies (Sevas, Czechoslovakia, (former)). Immunoglobulin (IgG, IgA, and IgM) and C3 concentrations in peripheral blood were determined using radial immunodiffusion in agarose and using monospecific antisera (Sevas, supra). Neutrophil phagocytic activity (% phagocytic cells) and phagocytic index (number of bacteria per cell) was determined using S. aureus strain Oxford 209P. Natural Killer (NK) lymphocyte activity was determined at a 50:1 E:T (effector:target) ratio with $^3$Uridine labeled K-562 target cells: i.e., % cytotoxicity (% C.I.) was calculated as follows: [% C.I.=1−CPM test/CPM control×100%]. Production of MIF cytokine was measured in vitro using a modification of the method described in "Evaluation of the Body's Immune Status in Therapeutic Institutions of the Soviet Army and Navy, Ministry of Defense, U.S.S.R., Center of Military Medicine, 1987 (L. A. Kozhemia, ed). MIF production was measured following stimulation of Ficoll-Hypaque-purified lymphocytes with mitogens, i.e., PHA, (phytohemagglutinin, Serva, West Germany (former); ConA, (Concanavalin-A, Serva), and antigens, i.e., hemolytic staphylococcal allergen (HSA; Kazanskii, SRI of Epidemiology and Microbiology, U.S.S.R.).

Periphery Blood and Serum Samples:
Patient and animal samples of peripheral blood were collected into heparin and serum was obtained from separate blood samples collected and clotted in glass tubes.

Thymus, Lymph Node, Bone Marrow and Spleen Samples:
Thymus, left paratracheal lymph node, and spleen were surgically removed, weighed, and homogenized in a glass Dounce homogenizer in Medium 199. Tissue fragments were removed by filtration through a chaperon. Bone marrow cell suspensions were prepared by irrigating the bone marrow canal of the pelvis with Medium 199 and homogenizing the irrigated solution. Suspensions from the different respective sources were purified by centrifuging the different cell samples on different aliquots of δ1.077 Ficoll-Urotrast for 40 minutes at 1500–1800 rpm. The lymphocyte interfaces from the gradients were collected into a siliconized test tube and washed in Medium 199. Residual red cells in the lymphocyte suspensions were lysed using 3% acetic acid in the presence of 0.05% Hessian-violet as a viability marker. Cell concentrations were determined microscopically using a Goryaev counting chamber. Cell concentrations were adjusted to $2.5 \times 10^6$/mL.

Differential Cell Counts:

Differential cell counts were performed by lysing erythrocytes in peripheral blood with 3% acetic acid, washing, and preparing smears of cells on a slide. After air-drying the cells in the smear were stained using the method of Romanovsky-Geimsa. Percentages of the different cell types were determined by counting a minimum of 100 cells in each sample.

Lymphocyte Preparations:

Lymphocytes were prepared by density gradient centrifugation on δ1.077 Ficoll-Urotrast (Pharmacia).

E-RFC:

Ram erythrocytes (E) were washed 4× in saline (2000 rpm/10 min.) and suspended at a final concentration of 1% in Medium 199. For determinations of the percentage of E-rosette forming T-lymphocytes (E-RFC) in a sample, 0.1 mL of a prepared lymphocyte suspension ($2.5 \times 10^6$/ml) was incubated with 0.1 mL of the 1% ram erythrocyte suspension at 37° C. for 10 min., centrifuged at 800–1000 rpm for 5 min., maintained at 4° C. for 2 hrs., and finally resuspended and counted in a Goryaev chamber. Activated T-lymphocytes (i.e., having increased E-RFC capacity) were determined by mixing the test lymphocyte suspension with E, immediately centrifuging for 5 min. at 800–1000 rpm, resuspending the cells and counting the rosettes formed in a Goryaev chamber.

EA-RFC:

Antibody-coated rabbit erythrocytes were used for determinations of EA-RFC (i.e., "activated" T-lymphocytes) according to the method of Stadecker, M. J., et al., *J. Immunol.* 11(6):1834–1837 (1973). Erythrocytes were prepared, incubated with an optimal dilution of anti-rabbit IgG, washed, and prepared as a 1% cell suspension in a manner analogous to those above (E-RFC, supra). EA-RFC assays were performed in a manner analogous to the description above, i.e., E-RFC, supra.

EAC-RFC:

Determinations of EAC-RFC (i.e., B-lymphocytes) were performed according to the method described by Bianco, C., et al., *J. Exp. Med.* 132(4):702–720 (1970).

$CD3^+$, $CD4^+$, $CD19^+$, and $CD8^+$ Lymphocytes:

To enumerate populations of lymphocytes, indirect immunofluorescence, (using Ortho OKT monoclonal antibodies according to the manufacturers instructions), and a direct fluorescence microscope equipped with phase contrast optics, employed. Cells having "ring" or "point" luminescence were counted. Diffuse staining was not counted. Determinations of the percentages of T- and B-lymphocytes were made by counting a minimum of 200–300 cells.

Blastogenesis with PHA and Con-A: Lymphocyte blastogenic responsiveness to mitogens was evaluated using the method of Bach, J. F. et al. (*Proc. Ann. Leukocyte Culture Conf.* p. 271–283 (1971)).

LMIR:

Lymphocyte migration inhibition factor production was determined according to a modification of Bendixsen, G. et al. 1980 by: i) adding Concanavalin-A to a sample of a patient's heparinized blood (25 units/ml heparin) to achieve a final concentration of 80 µg/ml Con-A; ii) collecting 200 µl of the Con-A-heparinized blood into a smooth bore heparinized glass capillary tube; iii) sealing one end of the capillary tube with paraffin or plastylene; iv) centrifuging the capillary for 5 minutes at 1500–2000 rpm; v) incubating the capillary tube for 18–24 hrs. at 37° C. in tissue culture medium in a vertical orientation; vi) determining the diameter of the zone of leukocyte migration at the border of the erythrocyte mass using an ocular micrometer; and, vii) subtracting from the recorded values the migration area in control samples (i.e., packed blood lacking Con-A). The calculation of LMIR % was as follows:

Migration inhibition (LMIR) %=diameter of the migration zone in the presence of Con-A/diameter of the migration zone in the absence of Con-A X 100%.

Three capillary tubes were used for each determination, and the mean of the values recorded in the determinations +/−S.D. are presented above.

Lysosomal Cation Test:

The lysosomal cation test (LCT) characterizes oxygen-independent metabolic processes in neutrophils. Neutrophil degranulation results in release of proteases (and cationic proteins), increased permeability of neutrophil membranes, increased oxygen consumption, activation of the hexose monophosphate shunt, and formation of hydrogen peroxide in lysosomes. Neutrophil cationic proteins are a measure the activation state of neutrophils and levels of these proteins are correlated with the level of non-specific resistance to infection in an animal (or man).

Neutrophil cationic proteins were determined according to the method of V. E. Pigarevsky and Yu. A. Mazing (1981). Briefly, blood smears were air dried, stained for 20 minutes in a buffered methanol.-fast green solution, washed in distilled water, and stained for an additional 30 minutes with Azure 11. The percentage of cells containing green-colored granules was determined by microscopically counting a minimum of 100–200 of the cells in the smears, and cation protein concentration was recorded as the mean cytotoxic coefficient (MCC) according to a modified formula of Astold & Berg.

Immunoglobulin and Acute Phase Reactant Protein Levels:

Concentrations of IgG, IgM and IgA and acute phase reactant proteins (e.g., $a_2$-macroglobulin, orosomucoid, prealbumin, etc.) in serum were determined by radial immunodiffusion in agarose according to the method of Mancini (1965).

Bacterial Challenge:

To insure a uniform inoculum of bacteria in EXAMPLES 32–34, above, suspensions were shaken at 30° C. for 2 hours on a rotary platform shaker in 1.5× brain heart infusion broth. Dispersed single cells were collected by centrifugation 3000 rpm/20 min. and resuspended in 1× brain heart infusion broth at a cell number equivalent to 10 times the $LD_{50}$ dose of bacteria, and then 5% sterile mucin was added to stabilize the inoculum. Animals were injected ip with 10 times the $LD_{50}$ number of bacteria suspended in the brain-heart infusion broth containing the 5% mucin.

Therapeutic Treatment:

EXAMPLES 32–34, above, test substance (i.e., L-Glu-L-Trp alone or in combination with antibiotic, or antibiotic alone) was injected sc, ip, po one hour after the bacterial challenge.

Prophylactic Treatment:

In EXAMPLES 32–34, above, test substance (i.e., L-Glu-L-Trp alone or in combination with antibiotic, or antibiotic alone) was injected daily ip for the three days immediately prior to the bacterial challenge.

Viral Assays:

In EXAMPLE 38, SC-1 cells were originally derived from murine embryos, and XC cells (a rat tumor cell line induced by Rous Sarcoma Virus) were obtained from the ATCC in Rockville, Md.

Citations

1. Goldstein, A. L., Guha, A., Zatz, M. M. et al. 1972. Purification and biological activity of thymosin, a hormone of the thymus gland. Proc. Natl. Acad. Sci. USA 69 (7): 1800–1803.
2. Mashkovskii, M. D. 1988. "Medicinal Remedies, 2nd. Ed.", Chapter 9, Russia, pp. 168–175.
3. Arion, V. Y., Khavinson, V. Kh., Morozov, V. G. 1988. Comparative investigation of biological activity of Thymalin and synthetic peptide. Scientific conference "Biochemistry-Medicine", Russia, pp. 217–218.
4. Goldstein, A. I., Guha, A., Zatz, M. M., Hardy, M. K. and White. 1972. Proc. Natl. Acad. Sci. USA. 69: 1800.
5. Khavinson, V. K., Morozov, V. G., Sery, S. V. and Yakolev, G. M. Treatment of immune-deficiency, immunodepressed or hyperactive immune states using the peptide L-Glu-L-Trp (L-Glu-L-Trp) for allergies, inflammatory diseases, etc. WO 92/217,191 (921015).
6. Sigma, Catalog.
7. Nekam, K., H. H. Fudenberg, A. J. Strelkanskas. 1982. Identification of "active" T-lymphocytes among effector cells in guinea pigs. Immunopharmacol. 5 (1): 85–94.
8. Stadecker, M. J., Bishop, G., Wortis, H. H. 1973. Rosette formation by guinea pig thymocytes and thymus-derived lymphocytes with rabbit red blood cells. J. Immunol. 111(8): 4061–4065.
9. Reinherz, E. L., Kung, P. C., Goldstein, G., Schlossman, S. F. 1979. Separation of functional subsets of human T cells by a monoclonal antibody. Proc. Natl. Acad. Sci. USA 76 (8): 4061–4065.
10. Bianco, C., Patrick, R., Nussenzwieg, V. 1970. A population of lymphocytes bearing a membrane receptor for antigen-antibody complexes. I. Separation and characterization. J. Exp. Med. 132 (4): 702–720.
11. Shtorkh, V., Emmrikh, I. M. 1987. Determination of cell markers by the method of membrane immunofluorescence. Immunological methods, Medicine, Russia. pp. 254–268.
12. Jolyb, E. S. 1971. Brain-associated antigen: reactivity rabbit anti-mouse brain with mouse lymphoid cells. Cell. Immunol. 2: 353–361.
13. Rook, J. A. W. et al. 1985. J. Immunol. Methods 82: 161–167.
14. Methodological recommendations for evaluation of pharmaceutical preparations immunological properties. M., Russian Federation, 1992.
15. Methods of research with phagocytic cells during the evaluation of human Immune status. L., Russian Federation, 1986.
16. Laboratory methods of research in the clinic. M., Russian Federation, 1987, p. 310.

While the preferred embodiment of the invention has been illustrated and described, it will be appreciated that various changes can be made therein without departing from the spirit and scope of the invention.

What is claimed is:

1. A method for treating complications in a human subject suffering from an immunodepressed state resulting from HIV infection comprising the step of administering an effective amount of a compound selected from the group consisting of L-Glu-L-Trp, a cyclic form of L-Glu-L-Trp, a linear or cyclic dimer or trimer of L-Glu-L-Trp and pharmaceutically acceptable salts thereof to the subject.

2. The method of claim 1, wherein the compound is L-Glu-L-Trp or a pharmaceutically acceptable salt thereof.

3. The method of claim 2, wherein HIV is HIV-1.

4. The method of claim 2, wherein HIV is HIV-2.

5. The method of claim 2, further comprising co-administering an anti-viral agent.

6. The method of claim 2, wherein the complication is an opportunistic infection.

7. The method of claim 2 or 6, wherein the compound is administered in the form of a pharmaceutical preparation comprising a pharmaceutically acceptable carrier and a therapeutically effective amount of the compound.

8. The method of claim 7, wherein the compound is administered intranasally or intravenously.

9. The method of claim 7, wherein the therapeutically effective amount is about 10 µg/kg to about 1 mg/kg.

10. The method of claim 7, wherein the compound is administered daily for about 1 to about 30 days.

11. The method of claim 10, wherein the compound is administered daily for about 3 to about 10 days.

12. The method of claim 7, wherein the pharmaceutically acceptable carrier is normal saline.

13. The method of claim 7 wherein the compound is a pharmaceutically acceptable salt of L-Glu-L-Trp wherein the salt is selected from the group consisting of potassium, ammonium and zinc.

14. The method of claim 7 wherein the compound is a sodium salt of L-Glu-L-Trp.

* * * * *